United States Patent
Hossain et al.

(10) Patent No.: US 7,449,475 B2
(45) Date of Patent: Nov. 11, 2008

(54) TRICYCLIC SPIROPIPERIDINES OR SPIROPYRROLIDINES

(75) Inventors: Nafizal Hossain, Lund (SE); Svetlana Ivanova, Lund (SE); Marguerite Mensonides-Harsema, Lund (SE)

(73) Assignee: AstraZeneca AB, Södertälje (SE)

( * ) Notice: Subject to any disclaimer, the term of this patent is extended or adjusted under 35 U.S.C. 154(b) by 131 days.

(21) Appl. No.: 10/520,699

(22) PCT Filed: Jul. 7, 2003

(86) PCT No.: PCT/SE03/01185

§ 371 (c)(1),
(2), (4) Date: Jan. 7, 2005

(87) PCT Pub. No.: WO2004/005295

PCT Pub. Date: Jan. 15, 2004

(65) Prior Publication Data

US 2005/0245741 A1 Nov. 3, 2005

(30) Foreign Application Priority Data

Jul. 8, 2002 (SE) .................................... 0202133

(51) Int. Cl.
*A61K 31/438* (2006.01)
*C07D 491/107* (2006.01)
(52) U.S. Cl. .................. 514/278; 546/17; 548/409; 544/124; 514/232.8; 514/409
(58) Field of Classification Search ................. 514/278, 514/409, 232.8; 546/17; 548/409; 544/124
See application file for complete search history.

(56) References Cited

U.S. PATENT DOCUMENTS

| 4,010,201 A | 3/1977 | Lednicer |
| 4,263,317 A | 4/1981 | Martin et al. |
| 5,962,462 A | 10/1999 | Mills et al. |
| 2006/0252751 A1 | 11/2006 | Xue et al. |
| 2007/0021498 A1 | 1/2007 | Hossain |
| 2007/0203229 A1 | 8/2007 | Hossain |
| 2007/0203230 A1 | 8/2007 | Hossain |

FOREIGN PATENT DOCUMENTS

| EP | 0 004 951 | 10/1979 |
| EP | 0 004 952 | 10/1979 |
| EP | 0417631 A2 | 3/1991 |
| EP | 0 722 941 | 7/1996 |
| EP | 1061076 B1 | 12/2000 |
| WO | WO 92/10096 | 6/1992 |
| WO | WO 96/36625 | 11/1996 |
| WO | WO 98/25605 | 6/1998 |
| WO | WO 98/31364 | 7/1998 |
| WO | WO 00/14086 | 3/2000 |
| WO | WO 01/30780 A2 | 5/2001 |
| WO | WO 01/64213 | 9/2001 |
| WO | WO 01/98273 | 12/2001 |
| WO | WO 02/102387 A1 | 12/2002 |
| WO | WO03/037271 A2 | 5/2003 |
| WO | WO 2004/005295 A1 | 1/2004 |
| WO | WO 2004/041279 | 5/2004 |
| WO | WO 2005/037814 | 4/2005 |
| WO | WO 2005/040167 | 5/2005 |
| WO | WO 2005/049620 | 6/2005 |
| WO | WO 2005/054249 | 6/2005 |
| WO | WO 2005/061499 | 7/2005 |
| WO | WO 2005/092895 | 10/2005 |

OTHER PUBLICATIONS

Pujol et al., "Novel tricyclic spiropiperidines. Synthesis and adrenergic activity of spiro[1,3-benzodioxolopiperidines] and spiro[1,3-benzodioxanepiperidines]", *Eur J Med Chem* 31:889-894 (1996).

Mehrotra et al., "Spirocyclic Nonpeptide Glycoprotein IIb-IIIa Antagonists. Part 3: Synthesis and SAR of Potent and Specific 2,8-Diazaspiro[4.5]decanes", Bioorganic & Medicinal Chemistry Letters 12:1103-1107 (2002).

Chen et al., "Heterodimerization and cross-desensitization between the μ-opioid receptor and the chemokine CCR5 receptor", *Eur. J. Pharmacol.* 483:175-186 (2004).

Dorwald F.Z. *Side Reactions in Organic Synthesis*. Wiley: VCH, Weinheim, 2005. p. IX of Preface.

Godessart N., "Chemokine Receptors: Attractive Targets for Drug Discovery", *Ann. N.Y. Acad. Sci.* 1051:647-657 (2005).

Knochel et al., "Highly Functionalized Organomagnesium Reagents Prepared through Haolgen-Metal Exchange", *Angew. Chem. Intl. Ed.* 42:4302-4320 (2003).

(Continued)

*Primary Examiner*—Charanjit S Aulakh
(74) *Attorney, Agent, or Firm*—Fish & Richardson P.C.

(57) ABSTRACT

The invention provides compounds of formula (I)

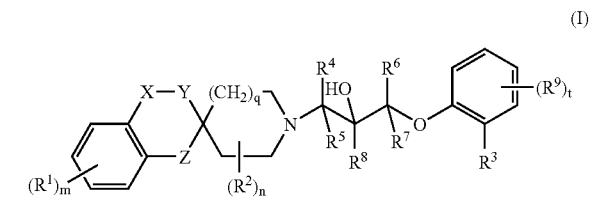

wherein m $R^1$, n, $R^2$, q, X, Y, Z, $R^3$, $R^4$, $R^5$, $R^6$, $R^7$, $R^8$, t, and $R^9$ are as defined in the specification, processes for their preparation, pharmaceutical compositions containing them and their use in therapy.

12 Claims, No Drawings

OTHER PUBLICATIONS

Li J.J. "Grignard reaction." in: *Name Reactions: A Collection of Detailed Reaction Mechanisms* Third Expanded Edition Springer 2006, pp. 271-272.

Brown et al., "Novel CCR1 antagonists with improved metabolic stability", *Bioorg. Med. Chem. Lett.* 14:2175-2179 (2004).

Martin et al., "Do Structurally Similar Molecules Have Similar Biological Activity?", *J. Med. Chem.* 45:4350-4358 (2002).

Pozharskii et al., *Heterocycles in Life and Society.* Wiley, 1997, pp. 1-6.

Thoma et al., "Orally Bioavailable Competitive CCR5 Antagonists", *J. Med. Chem.* 47:1939-1955 (2004).

Thomson et al., *The Cytokine Handbook*, 4th ed. New York, Academic Press, 2003, pp. 1084-1087.

Ting et al., "The synthesis of substituted bipiperidine amide compounds as CCR3 ligands: Antagonists versus agonists", *Bioorg. Med. Chem. Lett.* 15:3020-3023 (2005).

Xie et al., "Identification of novel series of human CCR1 antagonists", *Bioorg. Med. Chem. Lett.* 18:2215-2221 (2008).

TRICYCLIC SPIROPIPERIDINES OR SPIROPYRROLIDINES

CROSS-REFERENCE TO RELATED APPLICATIONS

This application is the national phase application under 35 U.S.C. § 371 of PCT International Application No. PCT/SE2003/001185, filed Jul. 7, 2003, which claims priority to Swedish Application Serial No. 0202133-5, filed Jul. 8, 2002.

The present invention relates to novel compounds, processes for their preparation, pharmaceutical compositions containing them and their use in therapy.

Chemokines play an important role in immune and inflammatory responses in various diseases and disorders, including asthma and allergic diseases, as well as autoimmune pathologies such as rheumatoid arthritis and atherosclerosis. These small secreted molecules are a growing superfamily of 8-14 kDa proteins characterised by a conserved four cysteine motif The chemokine superfamily can be divided into two main groups exhibiting characteristic structural motifs, the Cys-X-Cys (C-X-C) and Cys-Cys (C-C) families. These are distinguished on the basis of a single amino acid insertion between the NH-proximal pair of cysteine residues and sequence similarity.

The C-X-C chemokines include several potent chemoattractants and activators of neutrophils such as interleukin-8 (IL-8) and neutrophil-activating peptide 2 (NAP-2).

The C-C chemokines include potent chemoattractants of monocytes and lymphocytes but not neutrophils such as human monocyte chemotactic proteins 1-3 (MCP-1, MCP-2 and MCP-3), RANTES (Regulated on Activation, Normal T Expressed and Secreted), eotaxin and the macrophage inflammatory proteins 1α and 1β (MIP-1α and MIP-1β).

Studies have demonstrated that the actions of the chemokines are mediated by subfamilies of G protein-coupled receptors, among which are the receptors designated CCR1, CCR2, CCR2A, CCR2B, CCR3, CCR4, CCR5, CCR6, CCR7, CCR8, CCR9, CCR10, CXCR1, CXCR2, CXCR3 and CXCR4. These receptors represent good targets for drug development since agents which modulate these receptors would be useful in the treatment of disorders and diseases such as those mentioned above.

In accordance with the present invention, there is therefore provided a compound of formula

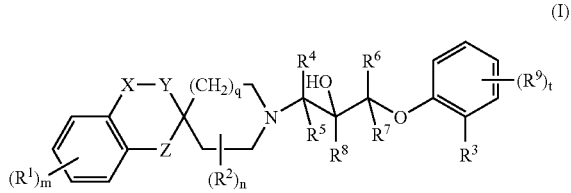

(I)

wherein
m is 0, 1, 2, 3 or 4;
each $R^1$ independently represents halogen, cyano, hydroxyl, $C_1$-$C_6$ alkyl, $C_1$-$C_6$ haloalkyl, $C_1$-$C_6$ alkoxy or sulphonamido (—$SO_2NH_2$);
either X represents a bond, —$CH_2$—, —O— or —C(O)— and Y represents a bond, —$CH_2$—, —O— or —C(O)—, or X and Y together represent a group —CH═C(CH$_3$)— or —C(CH$_3$)═CH—, and Z represents a bond, —O—, —NH— or —CH$_2$—, provided that only one of X, Y and Z can represent a bond at any one time and provided that X and Y do not both simultaneously represent —O— or —C(O)—;
n is 0, 1 or 2;
each $R^2$ independently represents halogen or $C_1$-$C_6$ alkyl;
q is 0 or 1;
$R^3$ represents —NHC(O)$R^{10}$, —C(O)N$R^{11}R^{12}$ or —COO$R^{12a}$;
$R^4$, $R^5$, $R^6$, $R^7$ and $R^8$ each independently represent a hydrogen atom or a $C_1$-$C_6$ alkyl group;
t is 0, 1 or 2;
each $R^9$ independently represents halogen, cyano, hydroxyl, carboxyl, $C_1$-$C_6$ alkoxy, $C_1$-$C_6$ alkoxycarbonyl, $C_1$-$C_6$ haloalkyl, or $C_1$-$C_6$ alkyl optionally substituted by at least one substituent selected from carboxyl and $C_1$-$C_6$ alkoxycarbonyl;
$R^{10}$ represents a group $C_1$-$C_6$ alkyl, $C_2$-$C_6$ alkenyl, $C_3$-$C_6$ cycloalkyl, adamantyl, $C_5$-$C_6$ cycloalkenyl, phenyl or a saturated or unsaturated 5- to 10-membered heterocyclic ring system comprising at least one ring heteroatom selected from nitrogen, oxygen and sulphur, each of which may be optionally substituted by one or more substituents independently selected from nitro, hydroxyl, oxo, halogen, carboxyl, $C_1$-$C_6$ alkyl, $C_1$-$C_6$ alkoxy, $C_1$-$C_6$ alkylthio, $C_1$-$C_6$ alkylcarbonyl, $C_1$-$C_6$ alkoxycarbonyl, phenyl and —NHC(O)—$R^{13}$, or
$R^{10}$ represents a group —N$R^{14}R^{15}$ or O—$R^{16}$;
$R^{11}$ and $R^{12}$ each independently represent (i) a hydrogen atom, (ii) a 3- to 6-membered saturated or unsaturated ring optionally comprising at least one ring heteroatom selected from nitrogen, oxygen and sulphur and optionally further comprising a bridging group, the ring being optionally substituted with at least one substituent selected from halogen, hydroxyl, $C_1$-$C_6$ alkyl, $C_1$-$C_6$ hydroxyalkyl and $C_1$-$C_6$ haloalkyl,
(iii) a $C_1$-$C_6$ alkyl group optionally substituted by at least one substituent selected from halogen, amino (—$NH_2$), hydroxyl, $C_1$-$C_6$ haloalkyl, carboxyl, $C_1$-$C_6$ alkoxy, $C_1$-$C_6$ alkoxycarbonyl, $C_1$-$C_6$ alkylcarbonylamino and a 3- to 6-membered saturated or unsaturated ring optionally comprising at least one ring heteroatom selected from nitrogen, oxygen and sulphur and optionally further comprising a bridging group, the ring being optionally substituted with at least one substituent selected from halogen, hydroxyl, oxo (═O), $C_1$-$C_6$ alkyl, $C_1$-$C_6$ hydroxyalkyl and $C_1$-$C_6$ haloalkyl, or
(iv) $C_1$-$C_6$ alkylsulphonyl, or
$R^{11}$ and $R^{12}$ together with the nitrogen atom to which they are attached form a 4- to 7-membered saturated heterocyclic ring that optionally further comprises a ring nitrogen, oxygen or sulphur atom and that is optionally fused to a benzene ring to form a 8- to 11-membered ring system, the heterocyclic ring or ring system being optionally substituted with at least one substituent selected from halogen, hydroxyl, amido (—$CONH_2$), $C_1$-$C_6$ alkyl, $C_1$-$C_6$ hydroxyalkyl, $C_1$-$C_6$ alkoxy, $C_1$-$C_6$ alkoxycarbonyl, $C_1$-$C_6$ haloalkyl, $C_1$-$C_6$ alkylamino, di-$C_1$-$C_6$ alkylamino, $C_1$-$C_6$ alkylcarbonyl, $C_1$-$C_6$ alkylcarbonylamino, $C_1$-$C_6$ alkylaminocarbonyl, di-$C_1$-$C_6$ alkylaminocarbonyl, phenyl, halophenyl, phenylcarbonyl, phenylcarbonyloxy and hydroxydiphenylmethyl;
$R^{12a}$ represents a hydrogen atom or a $C_1$-$C_6$ alkyl group;
$R^{13}$ represents a $C_1$-$C_6$ alkyl, amino (—$NH_2$) or phenyl group;
$R^{14}$ and $R^{15}$ each independently represent a hydrogen atom, or a group $C_1$-$C_6$ alkyl, $C_1$-$C_6$ alkylsulphonyl, phenyl or a saturated or unsaturated 5- to 10-membered heterocyclic ring system comprising at least one ring heteroatom selected from nitrogen, oxygen and sulphur, each group being optionally substituted as defined above for $R^{10}$, or $R^{14}$ and $R^{15}$ together with the nitrogen atom to which they are attached form a 4- to 7-membered saturated heterocyclic ring that optionally further comprises a ring nitrogen, oxygen or sulphur atom, the heterocyclic ring being optionally substituted by at least one hydroxyl; and $R^{16}$ represents a hydrogen atom, or a group $C_1$-$C_6$ alkyl, phenyl or a saturated or unsaturated 5- to 10-membered heterocyclic ring system comprising at least one ring heteroatom selected from nitrogen, oxygen and sulphur, each group being optionally substituted as defined above for $R^{10}$;

or a pharmaceutically acceptable salt or solvate thereof.

In the context of the present specification, unless otherwise stated, an alkyl or alkenyl substituent group or an alkyl moiety in a substituent group may be linear or branched. The alkyl moieties in a di-alkylamino or di-alkylaminocarbonyl substituent group may be the same or different. A haloalkyl or halophenyl substituent group will comprise at least one halogen atom, e.g. one, two, three or four halogen atoms. A hydroxyalkyl substituent may contain one or more hydroxyl groups but preferably contains one or two hydroxyl groups. In the ring substituted by $R^2$, $R^2$ may be attached to any suitable ring carbon atom including the carbon atom of $(CH_2)_q$. When $R^{11}$ and $R^{12}$ or $R^{14}$ and $R^{15}$ represent a 4- to 7-membered saturated heterocycle, it should be understood that the heterocycle will contain no more than two ring heteroatoms: the nitrogen ring atom to which $R^{11}$ and $R^{12}$ or $R^{14}$ and $R^{15}$ are attached and optionally a nitrogen, oxygen or sulphur ring atom. In the definition of $R^{10}$ (or $R^{14}$, $R^{15}$ or $R^{16}$) it should be noted that the saturated or unsaturated 5- to 10-membered heterocyclic ring system may have alicyclic or aromatic properties. Similarly, in the definition of $R^{11}$ or $R^{12}$, a 3- to 6-membered saturated or unsaturated ring optionally comprising at least one ring heteroatom may have alicyclic or aromatic properties. An unsaturated ring system will be partially or fully unsaturated.

In an embodiment of the invention, m is 0 or 1.

Each $R^1$ independently represents halogen (e.g. chlorine, fluorine, bromine or iodine), cyano, hydroxyl, $C_1$-$C_6$, preferably $C_1$-$C_4$, alkyl (e.g. methyl, ethyl, n-propyl, isopropyl, n-butyl, isobutyl, tert-butyl, n-pentyl or n-hexyl), $C_1$-$C_6$, preferably $C_1$-$C_4$, haloalkyl (e.g. trifluoromethyl), $C_1$-$C_6$, preferably $C_1$-$C_4$, alkoxy (e.g. methoxy, ethoxy, n-propoxy or n-butoxy) or sulphonamido.

In an embodiment of the invention, each $R^1$ independently represents halogen, $C_1$-$C_6$, preferably $C_1$-$C_4$, alkyl or $C_1$-$C_6$, preferably $C_1$-$C_4$, haloalkyl.

In another embodiment, each $R^1$ independently represents fluorine, chlorine, methyl or trifluoromethyl.

Combinations of X and Y of particular interest include any one or more of the following:

| X | Y |
|---|---|
| bond | O |
| O | bond |
| $CH_2$ | bond |
| bond | $CH_2$ |
| $CH_2$ | O |
| O | $CH_2$ |
| C(O) | O |
| O | C(O) |
| $CH_2$ | $CH_2$ |
| —CH=C($CH_3$)— | |

In an embodiment of the invention, X and Y have the meanings shown below:

| X | Y |
|---|---|
| bond | O |
| O | bond |
| $CH_2$ | O |
| O | $CH_2$ |
| C(O) | O |
| O | C(O) |
| $CH_2$ | $CH_2$ |
| —CH=C($CH_3$)— | |

In an embodiment of the invention, Z represents a bond, —O— or —$CH_2$—.

Combinations of X, Y and Z of particular interest include any one or more of the following:

| X | Y | Z |
|---|---|---|
| bond | O | $CH_2$ |
| O | bond | $CH_2$ |
| $CH_2$ | bond | O |
| bond | $CH_2$ | O |
| $CH_2$ | O | bond |
| C(O) | O | bond |
| O | C(O) | bond |
| $CH_2$ | $CH_2$ | bond |
| O | bond | O |
| bond | O | O |
| $CH_2$ | $CH_2$ | O |
| O | $CH_2$ | $CH_2$ |
| —CH=C($CH_3$)— | | bond |

In an embodiment of the invention, X, Y and Z have the meanings shown below:

| X | Y | Z |
|---|---|---|
| bond | O | $CH_2$ |
| O | bond | $CH_2$ |
| $CH_2$ | O | bond |
| O | $CH_2$ | bond |
| C(O) | O | bond |
| O | C(O) | bond |
| $CH_2$ | $CH_2$ | bond |
| bond | O | O |
| O | bond | O |
| —CH=C($CH_3$)— | | bond |

In another embodiment of the invention, X, Y and Z have the meanings shown below:

| X | Y | Z |
|---|---|---|
| bond | O | $CH_2$ |
| O | bond | $CH_2$ |
| $CH_2$ | bond | O |
| bond | $CH_2$ | O |
| $CH_2$ | O | bond |

In still another embodiment of the invention, X, Y and Z have the following meanings:

| X | Y | Z |
|---|---|---|
| bond | O | $CH_2$ |
| O | bond | $CH_2$ |
| $CH_2$ | O | bond |

Each $R^2$ independently represents halogen (e.g. chlorine, fluorine, bromine or iodine) or $C_1$-$C_6$, preferably $C_1$-$C_4$, alkyl (e.g. methyl, ethyl, n-propyl, isopropyl, n-butyl, isobutyl, tert-butyl, n-pentyl or n-hexyl).

In an embodiment of the invention, n is 1 and $R^2$ represents halogen, particularly fluorine.

In an embodiment of the invention, $R^3$ represents —NHC(O)$R^{10}$.

In another embodiment of the invention, $R^3$ represents —C(O)$NR^{11}R^{12}$.

$R^4$, $R^5$, $R^6$, $R^7$ and $R^8$ each independently represent a hydrogen atom or a $C_1$-$C_6$, preferably $C_1$-$C_4$, alkyl group (e.g. methyl, ethyl, n-propyl, isopropyl, n-butyl, isobutyl, tert-butyl, n-pentyl or n-hexyl).

In an embodiment of the invention, $R^4$, $R^5$, $R^6$, $R^7$ and $R^8$ each independently represent a hydrogen atom or a methyl group.

In another embodiment of the invention, $R^4$, $R^5$, $R^6$ and $R^7$ each represent a hydrogen atom and $R^8$ represents a methyl group.

In an embodiment of the invention, $R^4$, $R^5$, $R^6$, $R^7$ and $R^8$ each represent a hydrogen atom.

In an embodiment of the invention, t is 0, 1 or 2.

Each $R^9$ independently represents halogen (e.g. chlorine, fluorine, bromine or iodine), cyano, hydroxyl, carboxyl, $C_1$-$C_6$, preferably $C_1$-$C_4$, alkoxy (e.g. methoxy, ethoxy, n-propoxy or n-butoxy), $C_1$-$C_6$, preferably $C_1$-$C_4$, alkoxycarbonyl (e.g. methoxycarbonyl, ethoxycarbonyl, n-propoxycarbonyl or n-butoxycarbonyl), $C_1$-$C_6$, preferably $C_1$-$C_4$, haloalkyl (e.g. trifluoromethyl), or $C_1$-$C_6$, preferably $C_1$-$C_4$, alkyl (e.g. methyl, ethyl, n-propyl, isopropyl, n-butyl, isobutyl, tert-butyl, n-pentyl or n-hexyl) optionally substituted by at least one substituent (e.g. one, two or three substituents) independently selected from carboxyl and $C_1$-$C_6$, preferably $C_1$-$C_4$, alkoxycarbonyl (e.g. methoxycarbonyl, ethoxycarbonyl, n-propoxycarbonyl or n-butoxycarbonyl).

In an embodiment of the invention, each $R^9$ independently represents halogen, cyano, hydroxyl, carboxyl, $C_1$-$C_6$, preferably $C_1$-$C_4$, alkoxy, $C_1$-$C_6$, preferably $C_1$-$C_4$, alkoxycarbonyl, $C_1$-$C_6$, preferably $C_1$-$C_4$, haloalkyl or $C_1$-$C_6$, preferably $C_1$-$C_4$, alkyl.

In another embodiment of the invention, each $R^9$ independently represents halogen, hydroxyl, carboxyl, methyl, methoxy, methoxycarbonyl or trifluoromethyl.

$R^9$ is preferably bound to a carbon atom located in the para position with respect to the carbon atom to which either the oxygen atom or the group $R^3$ is bound, as indicated by the asterisks in the partial structure shown below:

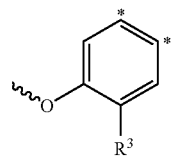

$R^{10}$ may represent a group $C_1$-$C_6$, preferably $C_1$-$C_4$, alkyl group (e.g. methyl, ethyl, n-propyl, isopropyl, n-butyl, isobutyl, tert-butyl, n-pentyl or n-hexyl), $C_2$-$C_6$, preferably $C_2$-$C_4$, alkenyl, $C_3$-$C_6$ cycloalkyl(cyclopropyl, cyclobutyl, cyclopentyl or cyclohexyl), adamantyl, $C_5$-$C_6$ cycloalkenyl, phenyl or a saturated or unsaturated 5- to 10-membered heterocyclic ring system comprising at least one ring heteroatom (e.g. one, two, three or four ring heteroatoms independently) selected from nitrogen, oxygen and sulphur, each of which (i.e. each of the recited groups and the ring system) may be optionally substituted by one or more (e.g. one, two, three or four) substituents independently selected from nitro, hydroxyl, oxo, halogen (e.g. fluorine, chlorine, bromine or iodine), carboxyl, $C_1$-$C_6$, preferably $C_1$-$C_4$, alkyl (e.g. methyl, ethyl, n-propyl, isopropyl, n-butyl, isobutyl, tert-butyl, n-pentyl or n-hexyl), $C_1$-$C_6$, preferably $C_1$-$C_4$, alkoxy (e.g. methoxy, ethoxy, n-propoxy or n-butoxy), $C_1$-$C_6$, preferably $C_1$-$C_4$, alkylthio (e.g. methylthio or ethylthio), $C_1$-$C_6$, preferably $C_1$-$C_4$, alkylcarbonyl (e.g. methylcarbonyl, ethylcarbonyl, n-propylcarbonyl, isopropylcarbonyl, n-butylcarbonyl, n-pentylcarbonyl or n-hexylcarbonyl), $C_1$-$C_6$, preferably $C_1$-$C_4$, alkoxycarbonyl (e.g. methoxycarbonyl or ethoxycarbonyl), phenyl and —NHC(O)—$R^{13}$.

The saturated or unsaturated 5- to 10-membered heterocyclic ring system in $R^{10}$ may be monocyclic or polycyclic (e.g. bicyclic), examples of which include pyrrolidinyl, piperidinyl, pyrazolyl, thiazolidinyl, thienyl, isoxazolyl, thiadiazolyl, pyrrolyl, furanyl, thiazolyl, indolyl, quinolinyl, benzimidazolyl, triazolyl, tetrazolyl, pyridinyl and combinations of any two or more thereof.

In an embodiment of the invention, $R^{10}$ represents a group $C_1$-$C_6$ alkyl, $C_3$-$C_6$ cycloalkyl, phenyl or a saturated or unsaturated 5- to 6-membered heterocyclic ring system comprising at least one ring heteroatom (e.g. one or two ring heteroatoms independently) selected from nitrogen, oxygen and sulphur, each of which (i.e. each of the recited groups and the ring system) may be optionally substituted by one, two, three or four substituents independently selected from nitro, hydroxyl, oxo, halogen, carboxyl, $C_1$-$C_6$, preferably $C_1$-$C_4$, alkyl, $C_1$-$C_6$, preferably $C_1$-$C_4$, alkoxy, $C_1$-$C_6$, preferably $C_1$-$C_4$, alkylthio, $C_1$-$C_6$, preferably $C_1$-$C_4$, alkylcarbonyl, $C_1$-$C_6$, preferably $C_1$-$C_4$, alkoxycarbonyl, phenyl and —NHC(O)—$R^{13}$.

In another embodiment of the invention, $R^{10}$ represents a group $C_1$-$C_6$ alkyl, $C_3$-$C_6$ cycloalkyl or phenyl, each of which may be optionally substituted by one or two substituents independently selected from halogen, $C_1$-$C_6$, preferably $C_1$-$C_4$, alkyl and $C_1$-$C_6$, preferably $C_1$-$C_4$, alkoxy.

In still another embodiment of the invention, $R^{10}$ represents $C_1$-$C_6$ alkyl, cyclopentyl or phenyl.

Alternatively, $R^{10}$ may represent a group —$NR^{14}R^{15}$ or O—$R^{16}$ $R^{14}$ and $R^{15}$ each independently represent a hydrogen atom, or a group $C_1$-$C_6$, preferably $C_1$-$C_4$, alkyl (e.g. methyl, ethyl, n-propyl, isopropyl, n-butyl, isobutyl, tert-butyl, n-pentyl or n-hexyl), $C_1$-$C_6$, preferably $C_1$-$C_4$, alkylsulphonyl (e.g. methylsulphonyl, ethylsulphonyl, n-propylsulphonyl, isopropylsulphonyl, n-butylsulphonyl, isobutylsulphonyl, tert-butylsulphonyl, n-pentylsulphonyl or n-hexylsulphonyl), phenyl or a saturated or unsaturated 5- to 10-membered heterocyclic ring system comprising at least one ring heteroatom (e.g. one, two, three or four ring heteroatoms independently) selected from nitrogen, oxygen and sulphur, each group (i.e. each of the recited groups including the ring system) being optionally substituted as defined above for $R^{10}$ (that is, optionally substituted with one or more (e.g. one, two, three or four) substituents independently selected from nitro, hydroxyl, oxo, halogen (e.g. fluorine, chlorine, bromine or iodine), carboxyl, $C_1$-$C_6$, preferably $C_1$-$C_4$, alkyl (e.g. methyl, ethyl, n-propyl, isopropyl, n-butyl, isobutyl, tert-butyl, n-pentyl or n-hexyl), $C_1$-$C_6$, preferably $C_1$-$C_4$, alkoxy (e.g. methoxy, ethoxy, n-propoxy or n-butoxy), $C_1$-$C_6$, preferably $C_1$-$C_4$, alkylthio (e.g. methylthio or ethylthio), $C_1$-$C_6$, preferably $C_1$-$C_4$, alkylcarbonyl (e.g. methylcarbonyl, ethylcarbonyl, n-propylcarbonyl, isopropylcarbonyl, n-butylcarbonyl, n-pentylcarbonyl or n-hexylcarbonyl), $C_1$-$C_6$, preferably $C_1$-$C_4$, alkoxycarbonyl (e.g. methoxycarbonyl or ethoxycarbonyl), phenyl and —NHC(O)—$R^{13}$), or $R^{14}$ and $R^{15}$ together with the nitrogen atom to which they are attached form a 4- to 7-membered saturated heterocyclic ring that optionally further comprises a ring nitrogen, oxygen or sulphur atom (e.g. pyrrolidinyl, piperidinyl, morpholino, piperazinyl or thiomorpholinyl), the heterocyclic ring being optionally substituted by at least one hydroxyl (e.g. one or two hydroxyls).

In $R^{14}$ or $R^{15}$, the saturated or unsaturated 5- to 10-membered heterocyclic ring system may be monocyclic or polycyclic (e.g. bicyclic), examples of which include pyrrolidinyl, piperidinyl, pyrazolyl, thiazolidinyl, thienyl, isoxazolyl, thiadiazolyl, pyrrolyl, furanyl, thiazolyl, indolyl, quinolinyl, benzimidazolyl, triazolyl, tetrazolyl, pyridinyl and combinations of any two or more thereof.

In an embodiment of the invention, $R^{14}$ and $R^{15}$ each independently represent a hydrogen atom or a $C_1$-$C_6$ alkyl or $C_1$-$C_6$ alkylsulphonyl group, each group being optionally substituted as defined above for $R^{10}$, or $R^{14}$ and $R^{15}$ together with the nitrogen atom to which they are attached form a 5- to 6-membered saturated heterocyclic ring that optionally further comprises a ring nitrogen, oxygen or sulphur atom, the heterocyclic ring being optionally substituted by at least one hydroxyl.

In a further embodiment, $R^{14}$ and $R^{15}$ each independently represent a hydrogen atom or a $C_1$-$C_6$ alkylsulphonyl group, or $R^{14}$ and $R^{15}$ together with the nitrogen atom to which they are attached form a 5- to 6-membered saturated heterocyclic ring that is optionally substituted by at least one hydroxyl.

In a still further embodiment, $R^{14}$ and $R^{15}$ each independently represent a hydrogen atom or a methylsulphonyl group, or $R^{14}$ and $R^{15}$ together with the nitrogen atom to which they are attached form a pyrrolidinyl or piperidinyl ring optionally substituted by one hydroxyl group.

$R^{16}$ represents a hydrogen atom, or a group $C_1$-$C_6$, preferably $C_1$-$C_4$, alkyl (e.g. methyl, ethyl, n-propyl, isopropyl, n-butyl, isobutyl, tert-butyl, n-pentyl or n-hexyl), phenyl or a saturated or unsaturated 5- to 10-membered heterocyclic ring system comprising at least one ring heteroatom (e.g. one, two, three or four ring heteroatoms independently) selected from nitrogen, oxygen and sulphur, each group (i.e. each of the recited groups including the ring system) being optionally substituted as defined above for $R^{10}$ (that is, optionally substituted with one or more (e.g. one, two, three or four) substituents independently selected from nitro, hydroxyl, oxo, halogen (e.g. fluorine, chlorine, bromine or iodine), carboxyl, $C_1$-$C_6$, preferably $C_1$-$C_4$, alkyl (e.g. methyl, ethyl, n-propyl, isopropyl, n-butyl, isobutyl, tert-butyl, n-pentyl or n-hexyl), $C_1$-$C_6$, preferably $C_1$-$C_4$, alkoxy (e.g. methoxy, ethoxy, n-propoxy or n-butoxy), $C_1$-$C_6$, preferably $C_1$-$C_4$, alkylthio (e.g. methylthio or ethylthio), $C_1$-$C_6$, preferably $C_1$-$C_4$, alkylcarbonyl (e.g. methylcarbonyl, ethylcarbonyl, n-propylcarbonyl, isopropylcarbonyl, n-butylcarbonyl, n-pentylcarbonyl or n-hexylcarbonyl), $C_1$-$C_6$, preferably $C_1$-$C_4$, alkoxycarbonyl (e.g. methoxycarbonyl or ethoxycarbonyl), phenyl and —NHC(O)—$R^{13}$).

In $R^{16}$, the saturated or unsaturated 5- to 10-membered heterocyclic ring system may be monocyclic or polycyclic (e.g. bicyclic), examples of which include pyrrolidinyl, piperidinyl, pyrazolyl, thiazolidinyl, thienyl, isoxazolyl, thiadiazolyl, pyrrolyl, furanyl, thiazolyl, indolyl, quinolinyl, benzimidazolyl, triazolyl, tetrazolyl, pyridinyl and combinations of any two or more thereof.

$R^{11}$ and $R^{12}$ each independently represent (i) a hydrogen atom, (ii) a 3- to 6-membered saturated or unsaturated ring optionally comprising at least one ring heteroatom (e.g. one, two, three or four ring heteroatoms independently) selected from nitrogen, oxygen and sulphur and optionally further comprising a bridging group (examples of which include cyclopropyl, cyclobutyl, cyclopentyl, cyclohexyl, bicyclo[2.2.1]heptyl, phenyl, pyrolyl, imidazolyl, pyridinyl, pyrazinyl, pyridazinyl, tetrazolyl, pyrimidinyl, thienyl, furanyl, tetrahydrofuranyl and combinations of any two or more thereof), the ring being optionally substituted with at least one substituent (e.g. one, two or three substituents independently) selected from halogen (e.g. fluorine, chlorine, bromine or iodine), hydroxyl, $C_1$-$C_6$, preferably $C_1$-$C_5$, alkyl (e.g. methyl, ethyl, n-propyl, isopropyl, n-butyl, isobutyl, tert-butyl, n-pentyl, 1,1-dimethylpropyl or n-hexyl), $C_1$-$C_6$, preferably $C_1$-$C_4$, hydroxyalkyl (e.g. —$CH_2OH$, —$CH_2CH_2OH$, —$CH_2CH_2CH_2OH$ or —CH(OH)$CH_3$) and $C_1$-$C_6$, preferably $C_1$-$C_4$, haloalkyl (e.g. trifluoromethyl), (iii) a $C_1$-$C_6$ alkyl group optionally substituted by at least one substituent (e.g. one, two, three or four substituents independently) selected from halogen (e.g. fluorine, chlorine, bromine or iodine), amino (—$NH_2$), hydroxyl, $C_1$-$C_6$, preferably $C_1$-$C_4$, haloalkyl (e.g. trifluoromethyl), carboxyl, $C_1$-$C_6$, preferably $C_1$-$C_4$, alkoxy (e.g. methoxy, ethoxy, n-propoxy or n-butoxy), $C_1$-$C_6$, preferably $C_1$-$C_4$, alkoxycarbonyl (e.g. methoxycarbonyl or ethoxycarbonyl), $C_1$-$C_6$, preferably $C_1$-$C_4$, alkylcarbonylamino (e.g. methylcarbonylamino or ethylcarbonylamino) and a 3- to 6-membered saturated or unsaturated ring optionally comprising at least one ring heteroatom (e.g. one, two, three or four ring heteroatoms independently) selected from nitrogen, oxygen and sulphur and optionally further comprising a bridging group (examples of which include cyclopropyl, cyclobutyl, cyclopentyl, cyclohexyl, bicyclo[2.2.1]heptyl, phenyl, pyrolyl, imidazolyl, pyridinyl, pyrazinyl, pyridazinyl, tetrazolyl, pyrimidinyl, thienyl, furanyl, tetrahydrofuranyl and combinations of any two or more thereof), the ring being optionally substituted with at least one substituent (e.g. one, two or three substituents independently) selected from halogen (e.g. fluorine, chlorine, bromine or iodine), hydroxyl, oxo (═O), $C_1$-$C_6$, preferably $C_1$-$C_4$, alkyl (e.g. methyl, ethyl, n-propyl, isopropyl, n-butyl, isobutyl, tert-butyl, n-pentyl or n-hexyl), $C_1$-$C_6$, preferably $C_1$-$C_4$, hydroxyalkyl (e.g. —$CH_2OH$, —$CH_2CH_2OH$, —$CH_2CH_2CH_2OH$ or —CH(OH)$CH_3$) and $C_1$-$C_6$, preferably $C_1$-$C_4$, haloalkyl (e.g. trifluoromethyl), or (iv) $C_1$-$C_6$, preferably $C_1$-$C_4$, alkylsulphonyl (e.g. methylsulphonyl or ethylsulphonyl), or $R^{11}$ and $R^{12}$ together with the nitrogen atom to which they are attached form a 4- to 7-membered saturated heterocyclic ring that optionally further comprises a ring nitrogen, oxygen or sulphur atom (e.g. pyrrolidinyl, piperidinyl, piperazinyl, morpholinyl or thiomorpholinyl) and that is optionally fused to a benzene ring to form a 8- to 11-membered ring system (e.g. dihydroisoquinolinyl or dihydroisoindolyl), the heterocyclic ring or ring system being optionally substituted with at least one substituent (e.g. one, two, three or four substituents independently) selected from halogen (e.g. fluorine, chlorine, bromine or iodine), hydroxyl, amido (—CONH$_2$), C$_1$-C$_6$, preferably C$_1$-C$_4$, alkyl (e.g. methyl, ethyl, n-propyl, isopropyl, n-butyl, isobutyl, tert-butyl, n-pentyl or n-hexyl), C$_1$-C$_6$, preferably C$_1$-C$_4$, hydroxyalkyl (e.g. —CH$_2$OH, —CH$_2$CH$_2$OH, —CH$_2$CH$_2$CH$_2$OH is or —CH(OH)CH$_3$), C$_1$-C$_6$, preferably C$_1$-C$_4$, alkoxy (e.g. methoxy, ethoxy, n-propoxy or n-butoxy), C$_1$-C$_6$, preferably C$_1$-C$_4$, alkoxycarbonyl (e.g. methoxycarbonyl or ethoxycarbonyl), C$_1$-C$_6$, preferably C$_1$-C$_4$, haloalkyl (e.g. trifluoromethyl), C$_1$-C$_6$, preferably C$_1$-C$_4$, alkylamino (e.g. methylamino or ethylamino), di-C$_1$-C$_6$, preferably C$_1$-C$_4$, alkylamino (e.g. dimethylamino), C$_1$-C$_6$, preferably C$_1$-C$_4$, alkylcarbonyl (e.g. methylcarbonyl or ethylcarbonyl), C$_1$-C$_6$, preferably C$_1$-C$_4$, alkylcarbonylamino (e.g. methylcarbonylamino or ethylcarbonylamino), C$_1$-C$_6$, preferably C$_1$-C$_4$, alkylaminocarbonyl (e.g. methylaminocarbonyl or ethylaminocarbonyl), di-C$_1$-C$_6$, preferably C$_1$-C$_4$, alkylaminocarbonyl (e.g. dimethylaminocarbonyl), phenyl, halophenyl (e.g. fluorophenyl or chlorophenyl), phenylcarbonyl, phenylcarbonyloxy and hydroxydiphenylmethyl.

In an embodiment of the invention, R$^{11}$ and/or R$^{12}$ represents a 3- to 6-membered saturated or unsaturated ring optionally comprising at least one ring heteroatom (e.g. one, two, three or four ring heteroatoms independently) selected from nitrogen, oxygen and sulphur and optionally further comprising a bridging group, the ring being optionally substituted with at least one substituent (e.g. one, two or three substituents independently) selected from hydroxyl, C$_1$-C$_6$, preferably C$_1$-C$_5$, alkyl (e.g. methyl, ethyl, n-propyl, isopropyl, n-butyl, isobutyl, tert-butyl, n-pentyl, 1,1-dimethylpropyl or n-hexyl) and C$_1$-C$_6$, preferably C$_1$-C$_4$, hydroxyalkyl (e.g. —CH$_2$OH, —CH$_2$CH$_2$OH, —CH$_2$CH$_2$CH$_2$OH or —CH(OH)CH$_3$).

In a further embodiment of the invention, R$^{11}$ and/or R$^{12}$ represents a 3- to 6-membered saturated or unsaturated ring optionally comprising at least one ring nitrogen atom and optionally further comprising a bridging group (in particular, cyclopropyl, cyclopentyl, cyclohexyl, bicyclo[2.2.1]heptyl, phenyl, pyrrolidinyl and tetrazolyl), the ring being optionally substituted with at least one substituent (e.g. one, two or three substituents independently) selected from hydroxyl, C$_1$-C$_5$ alkyl and C$_1$-C$_2$ hydroxyalkyl.

In an embodiment of the invention, R$^{11}$ and/or R$^{12}$ represents a C$_1$-C$_6$ alkyl group optionally substituted by at least one substituent (e.g. one, two, three or four substituents independently) selected from amino, hydroxyl, C$_1$-C$_6$, preferably C$_1$-C$_4$, alkoxy (e.g. methoxy, ethoxy, n-propoxy or n-butoxy), C$_1$-C$_6$, preferably C$_1$-C$_4$, alkoxycarbonyl (e.g. methoxycarbonyl or ethoxycarbonyl), C$_1$-C$_6$, preferably C$_1$-C$_4$, alkylcarbonylamino (e.g. methylcarbonylamino or ethylcarbonylamino) and a 3- to 6-membered saturated or unsaturated ring optionally comprising at least one ring heteroatom (e.g. one, two, three or four ring heteroatoms independently) selected from nitrogen and oxygen and optionally further comprising a bridging group, the ring being optionally substituted with at least one substituent (e.g. one, two or three substituents independently) selected from halogen (e.g. fluorine, chlorine, bromine or iodine), hydroxyl, oxo, C$_1$-C$_6$, preferably C$_1$-C$_4$, alkyl (e.g. methyl, ethyl, n-propyl, isopropyl, n-butyl, isobutyl, tert-butyl, n-pentyl or n-hexyl), C$_1$-C$_6$, preferably C$_1$-C$_4$, hydroxyalkyl (e.g. —CH$_2$OH, —CH$_2$CH$_2$OH, —CH$_2$CH$_2$CH$_2$OH or —CH(OH)CH$_3$) and C$_1$-C$_6$, preferably C$_1$-C$_4$, haloalkyl (e.g. trifluoromethyl).

In another embodiment of the invention, R$^{11}$ and/or R$^{12}$ represents a C$_1$-C$_6$ alkyl group optionally substituted by at least one substituent (e.g. one, two, three or four substituents independently) selected from amino, hydroxyl, C$_1$-C$_4$ alkoxy, C$_1$-C$_2$ alkoxycarbonyl, C$_1$-C$_2$ alkylcarbonylamino and a 3- to 6-membered saturated or unsaturated ring optionally comprising one or two ring heteroatoms selected from nitrogen and oxygen and optionally further comprising a bridging group (in particular, cyclopropyl, bicyclo[2.2.1]heptyl, phenyl or tetrahydrofuranyl), the ring being optionally substituted with at least one substituent (e.g. one, two or three substituents independently) selected from oxo (e.g. to form a 2,5-dioxoimidazolidinyl ring) and C$_1$-C$_2$ alkyl.

In an embodiment of the invention, R$^{11}$ and R$^{12}$ together with the nitrogen atom to which they are attached form a 4- to 7-membered saturated heterocyclic ring that optionally further comprises a ring nitrogen, oxygen or sulphur atom (e.g. pyrrolidinyl, piperidinyl, piperazinyl, morpholinyl or thiomorpholinyl) and that is optionally fused to a benzene ring to form a 8- to 11-membered ring system (e.g. dihydroisoquinolinyl or dihydroisoindolyl), the heterocyclic ring or ring system being optionally substituted with at least one substituent (e.g. one, two, three or four substituents independently) selected from halogen (e.g. fluorine, chlorine, bromine or iodine), hydroxyl, amido, C$_1$-C$_6$, preferably C$_1$-C$_4$, alkyl (e.g. methyl, ethyl, n-propyl, isopropyl, n-butyl, isobutyl, tert-butyl, n-pentyl or n-hexyl), C$_1$-C$_6$, preferably C$_1$-C$_4$, hydroxyalkyl (e.g. —CH$_2$OH, —CH$_2$CH$_2$OH, —CH$_2$CH$_2$CH$_2$OH or —CH(OH)CH$_3$), C$_1$-C$_6$, preferably C$_1$-C$_4$, alkoxy (e.g. methoxy, ethoxy, n-propoxy or n-butoxy), C$_1$-C$_6$, preferably C$_1$-C$_4$, alkoxycarbonyl (e.g. methoxycarbonyl or ethoxycarbonyl), C$_1$-C$_6$, preferably C$_1$-C$_4$, haloalkyl (e.g. trifluoromethyl), di-C$_1$-C$_6$, preferably C$_1$-C$_4$, alkylamino (e.g. dimethylamino), C$_1$-C$_6$, preferably C$_1$-C$_4$, alkylcarbonylamino (e.g. methylcarbonylamino or ethylcarbonylamino), di-C$_1$-C$_6$, preferably C$_1$-C$_4$, alkylaminocarbonyl (e.g. dimethylaminocarbonyl), phenyl, halophenyl (e.g. fluorophenyl or chlorophenyl), phenylcarbonyloxy and hydroxydiphenylmethyl.

In an embodiment of the invention, R$^{11}$ and R$^{12}$ together with the nitrogen atom to which they are attached form a 5- to 6-membered saturated heterocyclic ring that optionally further comprises a ring nitrogen, oxygen or sulphur atom and that is optionally fused to a benzene ring to form a 9- to 10-membered ring system, the heterocyclic ring or ring system being optionally substituted with one or two substituents independently selected from fluorine, hydroxyl, amido, C$_1$-C$_2$ alkyl, C$_1$-C$_2$ hydroxyalkyl, C$_1$-C$_2$ alkoxy, C$_1$-C$_2$ alkoxycarbonyl, C$_1$-C$_2$ haloalkyl, di-C$_1$-C$_2$ alkylamino, C$_1$-C$_2$ alkylcarbonylamino, di-C$_1$-C$_2$ alkylaminocarbonyl, phenyl, chlorophenyl, phenylcarbonyloxy and hydroxydiphenylmethyl.

In another embodiment of the invention, R$^{11}$ and R$^{12}$ together with the nitrogen atom to which they are attached form a heterocyclic ring or ring system selected from pyrrolidinyl, piperidinyl, piperazinyl, morpholinyl, thiomorpholinyl, dihydroisoquinolinyl and dihydroisoindolyl, the heterocyclic ring or ring system being optionally substituted with one or two substituents independently selected from fluorine, hydroxyl, amido, methyl, hydroxymethyl, 2-hydroxyethyl, methoxy, methoxycarbonyl, trifluoromethyl, dimethylamino, methylcarbonylamino, dimethylaminocarbonyl, phenyl, chlorophenyl, phenylcarbonyloxy and hydroxydiphenylmethyl.

R$^{12a}$ represents a hydrogen atom or a C$_1$-C$_6$, preferably C$_1$-C$_4$, alkyl (e.g. methyl, ethyl, n-propyl, isopropyl, n-butyl, isobutyl, tert-butyl, n-pentyl or n-hexyl) group.

In an embodiment of the invention, R$^{12a}$ represents a hydrogen atom or methyl group.

$R^{13}$ represents a $C_1$-$C_6$, preferably $C_1$-$C_4$, alkyl group (e.g. methyl, ethyl, n-propyl, isopropyl, n-butyl, isobutyl, tert-butyl, n-pentyl or n-hexyl), amino or phenyl group.

In an embodiment of the invention:

each $R^1$ independently represents halogen or $C_1$-$C_6$ alkyl;

either one of X and Y represents a bond and the other of X and Y represents an oxygen atom and Z represents —$CH_2$—, or X represents —$CH_2$—, Y represents an oxygen atom and Z represents a bond;

$R^4$, $R^5$, $R^6$ and $R^7$ each represent a hydrogen atom and $R^8$ represents a hydrogen atom or a $C_1$-$C_6$ alkyl group;

t is 1 or 2; and each $R^9$ independently represents hydroxyl (e.g. in the para position with respect to $R^3$) or halogen (e.g. either in the para position with respect to $R^3$ or in the para position with respect to —O—).

In an embodiment of the invention:

m is 0 or 1;

each $R^1$ independently represents fluorine, chlorine, methyl or trifluoromethyl;

either X represents a bond, —$CH_2$—, —O— or —C(O)— and Y represents a bond, —$CH_2$—, —O— or —C(O)—, or X and Y together represent a group —CH=C($CH_3$)—, and Z represents a bond, —O—, or —$CH_2$—, provided that only one of X, Y and Z can represent a bond at any one time and provided that X and Y do not both simultaneously represent —O— or —C(O)—;

n is 0 or 1;

$R^2$ represents fluorine;

q is 0 or 1;

$R^3$ represents —NHC(O)$R^{10}$, —C(O)N$R^{11}R^{12}$ or —COO$R^{12a}$;

$R^4$, $R^5$, $R^6$, $R^7$ and $R^8$ each independently represent a hydrogen atom or a methyl group;

t is 0, 1 or 2;

each $R^9$ independently represents halogen, hydroxyl, carboxyl, methyl, methoxy, methoxycarbonyl or trifluoromethyl;

$R^{10}$ represents a methyl, cyclopentyl, phenyl or a group —N$R^{14}R^{15}$;

$R^{11}$ and $R^{12}$ each independently represent (i) a hydrogen atom, (ii) a 3- to 6-membered saturated or unsaturated ring optionally comprising at least one ring nitrogen atom and optionally further comprising a bridging group, the ring being optionally substituted with at least one substituent selected from hydroxyl, $C_1$-$C_5$ alkyl and $C_1$-$C_2$ hydroxyalkyl, (iii) $C_1$-$C_6$ alkyl group optionally substituted by at least one substituent selected from amino, hydroxyl, $C_1$-$C_4$ alkoxy, $C_1$-$C_2$ alkoxycarbonyl, $C_1$-$C_2$ alkylcarbonylamino and a 3- to 6-membered saturated or unsaturated ring optionally comprising one or two ring heteroatoms selected from nitrogen and oxygen and optionally further comprising a bridging group, the ring being optionally substituted with at least one substituent selected from oxo and $C_1$-$C_2$ alkyl, or (iv) methylsulphonyl, or $R^{11}$ and $R^{12}$ together with the nitrogen atom to which they are attached form a 5- to 6-membered saturated heterocyclic ring that optionally further comprises a ring nitrogen, oxygen or sulphur atom and that is optionally fused to a benzene ring to form a 9- to 10-membered ring system, the heterocyclic ring or ring system being optionally substituted with one or two substituents independently selected from fluorine, hydroxyl, amido, $C_1$-$C_2$ alkyl, $C_1$-$C_2$ hydroxyalkyl, $C_1$-$C_2$ alkoxy, $C_1$-$C_2$ alkoxycarbonyl, $C_1$-$C_2$ haloalkyl, di-$C_1$-$C_2$ alkylamino, $C_1$-$C_2$ alkylcarbonylamino, di-$C_1$-$C_2$ alkylaminocarbonyl, phenyl, chlorophenyl, phenylcarbonyloxy and hydroxydiphenylmethyl;

$R^{12a}$ represents a hydrogen atom or a methyl group; and $R^{14}$ and $R^{15}$ each independently represent a hydrogen atom or a $C_1$-$C_6$ alkylsulphonyl group, or $R^{14}$ and $R^{15}$ together with the nitrogen atom to which they are attached form a 5- to 6-membered saturated heterocyclic ring that is optionally substituted by at least one hydroxyl.

In an embodiment of the invention:

m is 0 or 1;

$R^1$ represents halogen;

either X represents a bond, —$CH_2$—, —O— or —C(O)— and Y represents a bond, —$CH_2$—, —O— or —C(O)—, or X and Y together represent a group —CH=C($CH_3$)—, and Z represents a bond, —O— or —$CH_2$—, provided that only one of X, Y and Z can represent a bond at any one time and provided that X and Y do not both simultaneously represent —O— or —C(O)—;

n is 0;

q is 0 or 1;

$R^3$ represents —NHC(O)$R^{10}$, C(O)N$R^{11}R^{12}$ or —COO$R^{12a}$;

$R^4$, $R^5$, $R^6$, $R^7$ and $R^8$ each independently represent a hydrogen atom or a methyl group;

t is 0 or 1;

$R^9$ represents halogen, hydroxyl, methoxy or trifluoromethyl;

$R^{10}$ represents methyl;

$R^{11}$ and $R^{12}$ each independently represent hydrogen, methyl, cyclopropyl, hydroxyethyl or aminoethyl, or $R^{11}$ and $R^{12}$ together with the nitrogen atom to which they are attached form a morpholinyl group, or form a piperidinyl group substituted by hydroxyl; and $R^{12a}$ represents a hydrogen atom.

Examples of compounds of the invention include:

N-(2-{[(2S)-3-(5-Chloro-1'H,3H-spiro[1-benzofuran-2,4'-piperidin]-1'-yl)-2-hydroxypropyl]oxy}phenyl)acetamide, N-(2-{[(2S)-3-(5-Chloro-1'H,3H-spiro[1-benzofuran-2,4'-piperidin]-1'-yl)-2-hydroxypropyl]oxy}-4-fluorophenyl)acetamide, N-(2-{[(2S)-3-(5-Chloro-1'H,3H-spiro[1-benzofuran-2,4'-piperidin]-1'-yl)-2-hydroxypropyl]oxy}-4-methoxyphenyl)acetamide, N-(2-{[(2S)-3-(5-Chloro-1'H,3H-spiro[1-benzofuran-2,4'-piperidin]-1'-yl)-2-hydroxypropyl]oxy}-4-hydroxyphenyl)acetamide, N-[2-{[(2S)-3-(5-Chloro-1'H,3H-spiro[1-benzofuran-2,4'-piperidin]-1'-yl)-2-hydroxypropyl]oxy}5-(trifluoromethyl)phenyl]acetamide, 2-{[(2S)-3-(5-Chloro-1'H,3H-spiro[1-benzofuran-2,4'-piperidin]-1'-yl)-2-hydroxypropyl]oxy}-N-cyclopropylbenzamide, 2-{[(2S)-3-(5-Chloro-1'H,3H-spiro[1-benzofuran-2,4'-piperidin]-1'-yl)-2-hydroxypropyl]oxy}-N-cyclopropyl-4-fluorobenzamide, 2-{[(2S)-3-(5-Chloro-1'H,3H-spiro[1-benzofuran-2,4'-piperidin]-1'-yl)-2-hydroxypropyl]oxy}-N-cyclopropyl-4-methoxybenzamide, N-(2-{[(2S)-3-(5-Chloro-1'H,3H-spiro[1-benzofuran-2,4'-piperidin]-1'-yl)-2-hydroxy-2-methylpropyl]oxy}-4-hydroxyphenyl)acetamide trifluoroacetate, N-(5-Chloro-2-{[(2S)-3-(6-chloro-1'H,3H-spiro[2-benzofuran-1,4'-piperidin]-1-yl)-2-hydroxypropyl]oxy}phenyl)acetamide, N-(2-{[(2S)-3-(6-Chloro-1'H,3H-spiro[2-benzofuran-1,4'-piperidin]-1'-yl)-2-hydroxypropyl]oxy}-4-fluorophenyl)acetamide, N-(2-{[(2S)-3-(6-Chloro-1'H,3H-spiro[2-benzofuran-1,4'-piperidin]-1'-yl)-2-hydroxypropyl]oxy}phenyl)acetamide, N-(2-{[(2S)-3-(6-Chloro-1'H,3H-spiro[2-benzofuran-1,4'-piperidin]-1'-yl)-2-hydroxypropyl]oxy)-4-methoxyphenyl)acetamide, 2-{[(2S)-3-(6-Chloro-1'H,3H-spiro[2-benzofuran-1,4'-piperidin]-1'-yl)-2-hydroxypropyl]oxy}-N-cyclopropyl-4-fluorobenzamide, N-(2-{[(2S)-3-(5-Fluoro-1'H,3H-spiro[2-benzofuran-1,4'-piperidin]-1'-yl)-2-hydroxypropyl]phenyl)acetamide, N-(4-Chloro-2-{[(2S)-2-hydroxy-3-(3-oxo-1'H,3H-spiro[2-benzofuran-1,4'-piperidin]-1'-yl)propyl]oxy}phenyl)acetamide, N-Cyclopropyl-2-{[(2S)-2-hydroxy-3-(1'H,3H-spiro[2-benzofuran-1,4'-piperidin]-1'-yl)propyl]oxy}benzamide, N-(4-Chloro-2-{[(2S)-2-hydroxy-3-(1'H,3H-spiro[2-benzofuran-1,4'-piperidin]-1'-yl)propyl]oxy}phenyl)acetamide, N-(5-Chloro-2-{[(2S)-2-hydroxy-3-(1'H,3H-spiro[2-benzofuran-1,4'-piperidin]-1'-yl)propyl]oxy}phenyl)acetamide, N-(2-{[(2S)-2-hydroxy-2-methyl-3-(1'H,3H-spiro[2-benzofuran-1,4'-piperidin]-1'-yl)propyl]oxy}-4-methoxyphenyl)acetamide, N-[2-{[(2S)-2-Hydroxy-3-(1'H,3H-spiro[2-benzofuran-1,4'-piperidin]-1'-yl)propyl]oxy}-5-(trifluoromethyl)phenyl]acetamide, N-(2-{[(2S)-2-Hydroxy-3-(2-methyl-1'H-spiro[indene-1,4'-piperidin]-1'-yl)propyl]oxy}phenyl)acetamide, N-(2-{[(2S)-3-(2,3-Dihydro-1'H-spiro[indene-1,4'-piperidin]-1'-yl)-2-hydroxypropyl]oxy}phenyl)acetamide, N-(2-{[(2S)-2-Hydroxy-3-(2-oxo-1'H-spiro[1-benzofuran-3,4'-piperidin]-1'-yl)propyl]oxy}phenyl)acetamide, 2-{[(2S)-3-(5-Chloro-1'H,3H-spiro[1-benzofuran-2,4'-piperidin]-1'-yl)-2-hydroxypropyl]oxy}-N-cyclopropyl-4-hydroxybenzamide, 2-{[(2S)-3-(5-Chloro-1'H,3H-spiro[1-benzofuran-2,4'-piperidin]-1'-yl)-2-hydroxy-2-methylpropyl]oxy}-N-cyclopropyl-4-hydroxybenzamide, N-(4-hydroxy-2-{[(2S)-2-hydroxy-3-(1'H,4H-spiro[chromene-3,4'-piperidin]-1'-yl)propyl]oxy}phenyl)acetamide, 2-{[(2S)-3-(5-Chloro-1'H,3H-spiro[1-benzofuran-2,4'-piperidin]-1'-yl)-2-hydroxy-2-methylpropyl]oxy}-4-hydroxy-N-methylbenzamide(trifluoroacetate), 2-{[(2S)-3-(5-Chloro-1'H,3H-spiro[1-benzofuran-2,4'-piperidin]-1'-yl)-2-hydroxy]oxy}-4-hydroxy-N-methylbenzamide, N-(2-{[(2S)-3-(5-Chloro-1'H-spiro[1,3-benzodioxole-2,4'-piperidin]-1'-yl)-2-hydroxypropyl]oxy}-4-hydroxyphenyl)acetamide trifluoroacetate, N-(2-{[(2S)-3-(5-Chloro-1'H-spiro[1,3-benzodioxole-2,4'-piperidin]-1'-yl)-2-hydroxy-2-methylpropyl]oxy}-4-hydroxyphenyl)acetamide trifluoroacetate, N-(4-Hydroxy-2-{[(2S)-2-hydroxy-3-(1'H-spiro[1,3-benzodioxole-2,4'-piperidin]-1'-yl)propyl]oxy}phenyl)acetamide trifluoroacetate, N-(4-Hydroxy-2-{[(2S)-2-hydroxy-2-methyl-3-(1'H-spiro[1,3-benzodioxole-2,4'-piperidin]-1'-yl)propyl]oxy}phenyl)acetamide trifluoroacetate, N-(2-{[(2S)-3-(5-Chloro-1'H,3H-spiro[2-benzofuran-1,4'-piperidin]-1'-yl)-2-hydroxypropyl]oxy}-4-hydroxyphenyl)acetamide, N-(2-{[(2S)-3-(5-Chloro-1'H,3H-spiro[2-benzofuran-1,4'-piperidin]-1'-yl)-2-hydroxypropyl]oxy}phenyl)acetamide, 2-{[(2S)-3-(5-Chloro-1'H,3H-spiro[2-benzofuran-1,4'-piperidin]-1'-yl)-2-hydroxypropyl]oxy}-4-hydroxy-N-methylbenzamide, 2-{[(2S)-3-(5-Chloro-1'H,3H-spiro[2-benzofuran-1,4'-piperidin]-1'-yl)-2-hydroxy-2-methoxypropyl]oxy}-N-cyclopropyl-4-hydroxybenzamide, 2-{[(2S)-3-(5-Chloro-1'H,3H-spiro[1-benzofuran-2,4'-piperidin]-1'-yl)-2-hydroxypropyl]oxy}-4-hydroxy-N-(2-hydroxyethyl)benzamide, N-(2-Aminoethyl)-2-{[(2S)-3-(5-chloro-1'H,3H-spiro[1-benzofuran-2,4'-piperidin]-1'-yl)-2-hydroxypropyl]oxy}-4-hydroxybenzamide, 2-{[(2S)-3-(5-Fluoro-1'H,3H-spiro[1-benzofuran-2,4'-piperidin]-1'-yl)-2-hydroxypropyl]oxy}-4-hydroxy-N-methylbenzamide, N-(2-{[(2S)-3-(5-Fluoro-1'H,3H-spiro[1-benzofuran-2,4'-piperidin]-1'-yl)-2-hydroxypropyl]oxy}-4-hydroxyphenyl)acetamide, N-(2-{[(2S)-3-(5-Fluoro-1'H,3H-spiro[1-benzofuran-2,4'-piperidin]-1'-yl)-2-hydroxypropyl]oxy}phenyl)acetamide, N-[2-({(2S)-3[(2S)-5-Chloro-1'H,3H-spiro[1-benzofuran-2,3'-pyrrolidin]-1'-yl]-2-hydroxypropyl}oxy)phenyl]acetamide, N-[2-({(2S)-3[(2R)-5-Chloro-1'H,3H-spiro[1-benzofuran-2,3'-pyrrolidin]-1'-yl]-2-hydroxypropyl}oxy)phenyl]acetamide, N-[2-({(2S)-3-[(2S)-5-Chloro-1'H,3H-spiro[1-benzofuran-2,3'-pyrrolidin]-1'-yl]-2-hydroxypropyl}oxy}-4-methoxyphenyl]acetamide, N-[2-({(2S)-3-[(2R)-5-Chloro-1'H,3H-spiro[1-benzofuran-2,3'-pyrrolidin]-1'-yl]-2-hydroxypropyl}oxy)-4-methoxyphenyl]acetamide, 2-{[(2S)-3-(5-Chloro-1'H,3H-spiro[1-benzofuran-2,3'-pyrrolidin]-1'-yl)-2-hydroxypropyl]oxy}-4-hydroxy-N-methylbenzamide, 2-{[(2S)-3-(5-Chloro-1'H,3H-spiro[1-benzofuran-2,4'-piperidin]-1'-yl)-2-hydroxypropyl]oxy}-4-hydroxybenzoic acid (trifluoroacetate), 3(S)-1-(2-{[(2S)-3-(5-Chloro-1'H,3H-spiro[1-benzofuran-2,4'-piperidin]-1'-yl)-2-hydroxypropyl]oxy}-4-hydroxybenzoyl)pyrrolidin-3-ol, 3(R)-1-(2-{[(2S)-3-(5-Chloro-1'H,3H-spiro[1-benzofuran-2,4'-piperidin]-1'-yl)-2-hydroxypropyl]oxy}-4-hydroxybenzoyl)pyrrolidin-3-ol, 3-{[(2S)-3-(5-Chloro-1'H,3H-spiro[1-benzofuran-2,4'-piperidin]-1'-yl)-2-hydroxypropyl]oxy}-4-(morpholin-4-ylcarbonyl)phenol, 2-{[(2S)-3-(5-chloro-1'H-spiro[1,3-benzodioxole-2,4'-piperidin]-1'-yl)-2-hydroxypropyl]oxy}-N-methylbenzamide trifluoroacetate, N-(2-{[(2S)-3-(6-chloro-3,4-dihydro-1'H-spiro[chromene-2,4'-piperidin]-1'-yl)-2-hydroxypropyl]oxy}phenyl)acetamide trifluoroacetate, N-(2-{[(2S)-3-(6-chloro-3,4-dihydro-1'H-spiro[chromene-2,4'-piperidin]-1'-yl)-2-hydroxypropyl]oxy}-4-fluorophenyl)acetamide trifluoroacetate, 2-{[(2S)-3-(6-chloro-3,4-dihydro-1'H-spiro[chromene-2,4'-piperidin]-1'-yl)-2-hydroxypropyl]oxy}-N-methylbenzamide trifluoroacetate, N-(2-{[(2S)-3-(6-chloro-3,4-dihydro-1'H-spiro[chromene-2,4'-piperidin]-1'-yl)-2-hydroxypropyl]oxy}-4-hydroxyphenyl)acetamide trifluoroacetate, N-(2-{[(2S)-3-(6-chloro-3,4-dihydro-1'H-spiro[chromene-2,4'-piperidin]-1'-yl)-2-hydroxy-2-methylpropyl]oxy}-4-hydroxyphenyl)acetamide trifluoroacetate, N-[2-({(2S)-3-[(2R)-5-chloro-1'H,3H-spiro[1-benzofuran-2,3'-pyrrolidin]-1'-yl]-2-hydroxypropyl}oxy)-4-hydroxyphenyl]acetamide, N-[2-({(2S)-3-[(2S)-5-chloro-1'H,3H-spiro[1-benzofuran-2,3'-pyrrolidin]-1'-yl]-2-hydroxypropyl}oxy)-4-hydroxyphenyl]acetamide, 3-{[(2S)-3-(5-Chloro-1'H,3H-spiro[1-benzofuran-2,4'-piperidin]-1'-yl)-2-hydroxypropyl]oxy}-4-(pyrrolidin-1-ylcarbonyl)phenol, 1-(2-{[(2S)-3-(5-Chloro-1'H,3H-spiro[1-benzofuran-2,4'-piperidin]-1'-yl)-2-hydroxypropyl]oxy}-4-hydroxybenzoyl)piperidin-4-ol, (3S)-1-(2-{[(2S)-3-(5-Chloro-1'H,3H-spiro[1-benzofuran-2,4'-piperidin]-1'-yl)-2-hydroxypropyl]oxy}benzoyl)pyrrolidin-3-ol, 3-{[(2S)-3-(5-Chloro-1'H,3H-spiro[1-benzofuran-2,4'-piperidin]-1'-yl)-2-hydroxypropyl]oxy}-4-(piperidin-1-ylcarbonyl)phenol, (3S)-1-(2-{[(2S)-3-(5-Chloro-1'H,3H-spiro[2-benzofuran-1,4'-piperidin]-1'-yl)-2-hydroxypropyl]oxy}-4-hydroxybenzoyl)pyrrolidin-3-ol, 1-(2-{[(2S)-3-(5-Chloro-1'H,3H-spiro[2-benzofuran-1,4'-piperidin]-1'-yl)-2-hydroxypropyl]oxy}-4-hydroxybenzoyl)piperidin-4-ol, N-[4-Hydroxy-2-({(2S)-2-hydroxy-3-[5-(trifluoromethyl)-1'H,3H-spiro[1-benzofuran-2,4'-piperidin]-1'-yl]propyl}oxy)phenyl]acetamide, (3S)-1-(2-{[(2S)-3-(5-Chloro-1'H,3H-spiro[1-benzofuran-2,4'-piperidin]-1'-yl)-2-hydroxypropyl]oxy}-4-hydroxybenzoyl)pyrrolidin-3-ylbenzoate, (3S)-1-(2-{[(2S)-3-(5-Chloro-1'H,3H-spiro[1-benzofuran-2,4'-piperidin]-1'-yl)-2-hydroxypropyl]oxy}-4-fluorobenzoyl)pyrrolidin-3-ol, (3S)-1-[4-Hydroxy-2-({(2S)-2-hydroxy-3-[5-(trifluoromethyl)-1'H,3H-spiro[1-benzofuran-2,4'-piperidin]-1'-yl]propyl}oxy)benzoyl]pyrrolidin-3-ol, (3S)-1-(4-Fluoro-2-{[(2S)-2-hydroxy-3-(1'H,3H-spiro[1-benzofuran-2,4'-piperidin]-1'-yl)propyl]oxy}benzoyl)pyrrolidin-3-ol, 4-Fluoro-2-{[(2S)-3-(5-fluoro-1'H,3H-spiro[1-benzofuran-2,4'-piperidin]-1'-yl)-2-hydroxypropyl]oxy}benzoic acid (hydrochloride), (3S)-1-(4-Fluoro-2-{[(2S)-3-(5-fluoro-1'H,3H-spiro[1-benzofuran-2,4'-piperidin]-1'-yl)-2-hydroxypropyl]oxy}benzoyl)pyrrolidin-3-ol, N-[(3S)-1-(2-{[(2S)-3-(5-Chloro-1'H,3H-spiro[1-benzofuran-2,4'-piperidin]-1'-yl)-2-hydroxypropyl]oxy}-4-hydroxybenzoyl)pyrrolidin-3-yl]acetamide, 2-{[(2S)-3-(5-Chloro-1'H,3H-spiro[1-benzofuran-2,4'-piperidin]-1'-yl)-2-hydroxypropyl]oxy}-4-methylbenzoic acid hydrochloride, (3S)-1-(2-{[(2S)-3-(5-Chloro-1'H,3H-spiro[1-benzofuran-2,4'-piperidin]-1'-yl)-2-hydroxypropyl]oxy}-4-methylbenzoyl)pyrrolidin-3-ol, 2-{[(2S)-3-(5-Fluoro-1'H,3H-spiro[1-benzofuran-2,4'-piperidin]-1'-yl)-2-hydroxypropyl]oxy}-4-methylbenzoic acid hydrochloride, (2S)-1-(5-Chloro-1'H,3H-spiro[1-benzofuran-2,4'-piperidin]-1'-yl)-3-(2-{[2-(hydroxymethyl)morpholin-4-yl]carbonyl}-5-methylphenoxy)propan-2-ol, (3S)-1-(2-{[(2S)-3-(5-Fluoro-1'H,3H-spiro[1-benzofuran-2,4'-piperidin]-1'-yl)-2-hydroxypropyl]oxy}-4-methylbenzoyl)pyrrolidin-3-ol, 2-{[(2S)-3-(5-Chloro-1'H,3H-spiro[1-benzofuran-2,4'-piperidin]-1'-yl)-2-hydroxypropyl]oxy}-N-{[(4R)-2,5-dioxoimidazolidin-4-yl]methyl}-4-hydroxybenzamide, 1-(2-{[(2S)-3-(5-Chloro-1'H,3H-spiro[1-benzofuran-2,4'-piperidin]-1'-yl)-2-hydroxypropyl]oxy}-4-hydroxybenzoyl)-3-(trifluoromethyl)pyrrolidin-3-ol, 3-{[(2S)-3-(5-Chloro-1'H,3H-spiro[1-benzofuran-2,4'-piperidin]-1'-yl)-2-hydroxypropyl]oxy}-4-{[3-(trifluoromethyl)pyrrolidin-1-yl]carbonyl}phenol, N-[2-(Acetylamino)ethyl]-2-{[(2S)-3-(5-chloro-1'H,3H-spiro[1-benzofuran-2,4'-piperidin]-1'-yl)-2-hydroxypropyl]oxy}-4-hydroxybenzamide, N-(5-chloro-2-{[(2S)-3-(5-chloro-1'H,3H-spiro[1-benzofuran-2,4'-piperidin]-1'-yl)-2-hydroxypropyl]oxy}-4-methoxyphenyl)acetamide, (3S)-N-(5-chloro-2-{[(2S)-3-(5-chloro-1'H,3H-spiro[1-benzofuran-2,4'-piperidin]-1'-yl)-2-hydroxypropyl]oxy}phenyl)-3-hydroxypyrrolidine-1-carboxamide, (3S)-N-(2-{[(2S)-3-(5-chloro-1'H,3H-spiro[1-benzofuran-2,4'-piperidin]-1'-yl)-2-hydroxypropyl]oxy}phenyl)-3-hydroxypyrrolidine-1-carboxamide, N-(2-{[(2S)-3-(5-chloro-1'H,3H-spiro[1-benzofuran-2,4'-piperidin]-1'-yl)-2-hydroxypropyl]oxy}phenyl)-4-hydroxypiperidine-1-carboxamide, N-(2-{[(2S)-3-(5-Chloro-1'H,3H-spiro[1-benzofuran-2,4'-piperidin]-1'-yl)-2-hydroxypropyl]oxy}phenyl)urea trifluoroacetate, N-(2-{[(2S)-3-(5-chloro-1'H,3H-spiro[1-benzofuran-2,4'-piperidin]-1'-yl)-2-hydroxypropyl]oxy}-4-hydroxyphenyl)urea trifluoroacetate, N-(2-{[(2S)-3-(5-Chloro-1'H,3H-spiro[1-benzofuran-2,4'-piperidin]-1'-yl)-2-hydroxypropyl]oxy)}-4-fluorophenyl)urea trifluoroacetate, N-{[(2-{[(2S)-3-(5-Chloro-1'H,3H-spiro[1-benzofuran-2,4'-piperidin]-1'-yl)-2-hydroxypropyl]oxy}-4-hydroxyphenyl)amino]carbonyl}methanesulfonamide trifluoroacetate, (4S)-2-(2-{[(2S)-3-(5-Chloro-1'H,3H-spiro[1-benzofuran-2,4'-piperidin]-1'-yl)-2-hydroxypropyl]oxy}-4-hydroxybenzoyl)isoxazolidin-4-ol trifluoroacetate, (4R)-2-(2-{[(2S)-3-(5-Chloro-1'H,3H-spiro[1-benzofuran-2,4'-piperidin]-1'-yl)-2-hydroxypropyl]oxy}-4-hydroxybenzoyl)isoxazolidin-4-ol trifluoroacetate, (4S)-2-(2-{[(2S)-3-(5-Chloro-1'H,3H-spiro[1-benzofuran-2,4'-piperidin]-1'-yl)-2-hydroxypropyl]oxy}-4-hydroxybenzoyl)-4-methylisoxazolidin-4-ol trifluoroacetate, (4R)-2-(2-{[(2S)-3-(5-Chloro-1'H,3H-spiro[1-benzofuran-2,4'-piperidin]-1'-yl)-2-hydroxypropyl]oxy}-4-hydroxybenzoyl)-4-methylisoxazolidin-4-ol trifluoroacetate, 2-{[(2S)-3-(5-chloro-1'H,3H-spiro[1-benzofuran-2,4'-piperidin]-1'-yl)-2-hydroxypropyl]oxy}-N-(methylsulfonyl)benzamide trifluoroacetate, 2-{[(2S)-3-(5-chloro-1'H,3H-spiro[1-benzofuran-2,4'-piperidin]-1'-yl)-2-hydroxypropyl]oxy}-N-1H-tetrazol-5-ylbenzamide bis(trifluoroacetate), 3-{[(2S)-3-(5-chloro-1'H,3H-spiro[1-benzofuran-2,4'-piperidin]-1'-yl)-2-hydroxypropyl]oxy}-4-{[(3R)-3-(dimethylamino)pyrrolidin-1-yl]carbonyl}phenol bis(trifluoroacetate), 3-{[(2S)-3-(5-chloro-1'H,3H-spiro[1-benzofuran-2,4'-piperidin]-1'-yl)-2-hydroxypropyl]oxy}-4-{[(3S)-3-(dimethylamino)pyrrolidin-1-yl]carbonyl}phenol bis(trifluoroacetate), (3S)-1-(5-chloro-2-{[(2S)-3-(5-chloro-1'H,3H-spiro[1-benzofuran-2,4'-piperidin]-1'-yl)-2-hydroxypropyl]oxy}-4-hydroxybenzoyl)pyrrolidin-3-ol trifluoroacetate, 3-{[(2S)-3-(5-chloro-1'H,3H-spiro[1-benzofuran-2,4'-piperidin]-1'-yl)-2-hydroxypropyl]oxy}-4-{[(3S)-3-methoxypyrrolidin-1-yl]carbonyl}phenol trifluoroacetate, 3-{[(2S)-3-(5-chloro-1'H,3H-spiro[1-benzofuran-2,4'-piperidin]-1'-yl)-2-hydroxypropyl]oxy}-4-{[(2R)-2-(hydroxymethyl)pyrrolidin-1-yl]carbonyl}phenol trifluoroacetate, 3-{[(2S)-3-(5-chloro-1'H,3H-spiro[1-benzofuran-2,4'-piperidin]-1'-yl)-2-hydroxypropyl]oxy}-4-{[(2S)-2-(hydroxymethyl)pyrrolidin-1-yl]carbonyl}phenol trifluoroacetate, 3-{[(2S)-3-(5-chloro-1'H,3H-spiro[1-benzofuran-2,4'-piperidin]-1'-yl)-2-hydroxypropyl]oxy}-4-{[3-(hydroxymethyl)pyrrolidin-1-yl]carbonyl}phenol trifluoroacetate, 1-(2-{[(2S)-3-(5-chloro-1'H,3H-spiro[1-benzofuran-2,4'-piperidin]-1'-yl)-2-hydroxypropyl]oxy}-4-hydroxybenzoyl)-D-prolinamide trifluoroacetate, N-(4-hydroxy-2-{[(2S)-2-hydroxy-3-(1'H,3H-spiro[1-benzofuran-2,4'-piperidin]-1'-yl)propyl]oxy}phenyl)acetamide trifluoroacetate, N-(4-hydroxy-2-{[(2S)-2-hydroxy-3-(5-methyl-1'H,3H-spiro[1-benzofuran-2,4'-piperidin]-1'-yl)propyl]oxy}phenyl)acetamide trifluoroacetate, N-(5-chloro-2-{[(2S)-2-hydroxy-3-(1'H,3H-spiro[1-benzofuran-2,4'-piperidin]-1'-yl)propyl]oxy}-4-methoxyphenyl)acetamide trifluoroacetate, N-(5-chloro-4-hydroxy-2-{[(2S)-2-hydroxy-3-(1'H,3H-spiro[1-benzofuran-2,4'-piperidin]-1'-yl)propyl]oxy}phenyl)acetamide trifluoroacetate, (3S)-N-(2-{[(2S)-3-(5-chloro-1'H,3H-spiro[1-benzofuran-2,4'-piperidin]-1'-yl)-2-hydroxypropyl]oxy}-4-methoxyphenyl)-3-hydroxypyrrolidine-1-carboxamide trifluoroacetate, (3S)-N-(2-{[(2S)-3-(5-chloro-1'H,3H-spiro[1-benzofuran-2,4'-piperidin]-1'-yl)-2-hydroxypropyl]oxy}-4-hydroxyphenyl)-3-hydroxypyrrolidine-1-carboxamide trifluoroacetate, (3S)-1-(4-hydroxy-2-{[(2S)-2-hydroxy-3-(1'H,3H-spiro[1-benzofuran-2,4'-piperidin]-1'-yl)propyl]oxy}benzoyl)pyrrolidin-3-ol trifluoroacetate, 2-{[(2S)-3-(5-chloro-1'H,3H-spiro[1-benzofuran-2,4'-piperidin]-1'-yl)-2-hydroxypropyl]oxy}-5-methylbenzoic acid hydrochloride, 2-{[(2S)-3-(5-chloro-1'H,3H-spiro[1-benzofuran-2,4'-piperidin]-1'-yl)-2-hydroxypropyl]oxy}-4-methoxybenzoic acid hydrochloride, (3S)-1-(2-{[(2S)-3-(5-chloro-1'H,3H-spiro[1-benzofuran-2,4'-piperidin]-1'-yl)-2-hydroxypropyl]oxy}-5-methylbenzoyl)pyrrolidin-3-ol trifluoroacetate, (3S)-1-(2-{[(2S)-3-(5-chloro-1'H,3H-spiro[1-benzofuran-2,4'-piperidin]-1'-yl)-2-hydroxypropyl]oxy}-4-methoxybenzoyl)pyrrolidin-3-ol trifluoroacetate, 5-chloro-2-{[(2S)-3-(5-chloro-1'H,3H-spiro[1-benzofuran-2,4'-piperidin]-1'-yl)-2-hydroxypropyl]oxy}benzoic acid hydrochloride, (3S)-1-(5-chloro-2-{[(2S)-3-(5-chloro-1'H,3H-spiro[1-benzofuran-2,4'-piperidin]-1'-yl)-2-hydroxypropyl]oxy}benzoyl)pyrrolidin-3-ol trifluoroacetate, 2-{[(2S)-3-(5-chloro-1'H,3H-spiro[1-benzofuran-2,4'-piperidin]-1'-yl)-2-hydroxypropyl]oxy}-5-fluorobenzoic acid hydrochloride, (3S)-1-(2-{[(2S)-3-(5-chloro-1'H,33H-spiro[1-benzofuran-2,4'-piperidin]-1'-yl)-2-hydroxypropyl]oxy}-5-fluorobenzoyl)pyrrolidin-3-ol trifluoroacetate, N-(2-{[(2S)-3-(5-chloro-1'H,3H-spiro[1-benzofuran-2,4'-piperidin]-1'-yl)-2-hydroxypropyl]oxy}phenyl)pyrrolidine-1-carboxamide trifluoroacetate, Methyl 4-(acetylamino)-3-{[(2S)-3-(5-chloro-1'H,3H-spiro[1-benzofuran-2,4'-piperidin]-1'-yl)-2-hydroxypropyl]oxy}benzoate trifluoroacetate, 4-(acetylamino)-3-{[(2S)-3-(5-chloro-1'H,3H-spiro[1-benzofuran-2,4'-piperidin]-1'-yl)-2-hydroxypropyl]oxy}benzoic acid trifluoroacetate, N-(2-{[(2S)-3-(5-chloro-3'-fluoro-1'H,3H-spiro[1-benzofuran-2,4'-piperidin]-1'-yl)-2-hydroxypropyl]oxy}-4-hydroxyphenyl)acetamide, 2-{[(2S)-3-(5-chloro-1'H,3H-spiro[1-benzofuran-2,4'-piperidin]-1'-yl)-2-hydroxypropyl]oxy}-4-hydroxy-N-(2-hydroxypropyl)benzamide, 2-{[(2S)-3-(5-chloro-1'H,3H-spiro[1-benzofuran-2,4'-piperidin]-1'-yl)-2-hydroxypropyl]oxy}-4-hydroxy-N-(2-hydroxy-1,1-dimethylethyl)benzamide, 2-{[(2S)-3-(5-chloro-1'H,3H-spiro[1-benzofuran-2,4'-piperidin]-1'-yl)-2-hydroxypropyl]oxy}-N-cyclopentyl-4-hydroxybenzamide, 2-{[(2S)-3-(5-chloro-1'H,3H-spiro[1-benzofuran-2,4'-piperidin]-1'-yl)-2-hydroxypropyl]oxy}-4-hydroxy-N-(2-methoxyethyl)benzamide, 2-{[(2S)-3-(5-chloro-1'H,3H-spiro[1-benzofuran-2,4'-piperidin]-1'-yl)-2-hydroxypropyl]oxy}-4-hydroxy-N-(2-hydroxyphenyl)benzamide, N-(tert-butyl)-2-{[(2S)-3-(5-chloro-1'H,3H-spiro[1-benzofuran-2,4'-piperidin]-1'-yl)-2-hydroxypropyl]oxy}-4-hydroxybenzamide, 2-{[(2S)-3-(5-chloro-1'H,3H-spiro[1-benzofuran-2,4'-piperidin]-1'-yl)-2-hydroxypropyl]oxy}-4-hydroxy-N-(2-hydroxy-1-methylethyl)benzamide, 2-{[(2S)-3-(5-chloro-1'H,3H-spiro[1-benzofuran-2,4'-piperidin]-1'-yl)-2-hydroxypropyl]oxy}-4-hydroxy-N-isobutylbenzamide, 2-{[(2S)-3-(5-chloro-1'H,3H-spiro[1-benzofuran-2,4'-piperidin]-1'-yl)-2-hydroxypropyl]oxy}-4-hydroxy-N-(4-hydroxycyclohexyl)benzamide, 2-{[(2S)-3-(5-chloro-1'H,3H-spiro[1-benzofuran-2,4'-piperidin]-1'-yl)-2-hydroxypropyl]oxy}-N-(2,3-dihydroxypropyl)-4-hydroxybenzamide, 2-{[(2S)-3-(5-chloro-1'H,3H-spiro[1-benzofuran-2,4'-piperidin]-1'-yl)-2-hydroxypropyl]oxy}-4-hydroxy-N-(2-hydroxyethyl)-N-methylbenzamide, Methyl N-(2-{[(2S)-3-(5-chloro-1'H,3H-spiro[1-benzofuran-2,4'-piperidin]-1'-yl)-2-hydroxypropyl]oxy}-4-hydroxybenzoyl)serinate, 2-{[(2S)-3-(5-chloro-1'H,3H-spiro[1-benzofuran-2,4'-piperidin]-1'-yl)-2-hydroxypropyl]oxy}-N-(1-ethylpropyl)-4-hydroxybenzamide, 2-{[(2S)-3-(5-chloro-1'H,3H-spiro[1-benzofuran-2,4'-piperidin]-1'-yl)-2-hydroxypropyl]oxy}-4-hydroxy-N-(tetrahydrofuran-2-ylmethyl)benzamide, 2-{[(2S)-3-(5-chloro-1'H,3H-spiro[1-benzofuran-2,4'-piperidin]-1'-yl)-2-hydroxypropyl]oxy}-4-hydroxy-N-[1-(hydroxymethyl)-2,2-dimethylpropyl]benzamide, 2-{[(2S)-3-(5-chloro-1'H,3H-spiro[1-benzofuran-2,4'-piperidin]-1'-yl)-2-hydroxypropyl]oxy}-N-{[(1S,2R,5S)-6,6-dimethylbicyclo[3.1.1]hept-2-yl]methyl}-4-hydroxybenzamide, 2-{[(2S)-3-(5-chloro-1'H,3H-spiro[1-benzofuran-2,4'-piperidin]-1'-yl)-2-hydroxypropyl]oxy}-4-hydroxy-N-[1-(hydroxymethyl)-2-methylpropyl]benzamide, 3-{[(2S)-3-(5-chloro-1'H,3H-spiro[1-benzofuran-2,4'-piperidin]-1'-yl)-2-hydroxypropyl]oxy}-4-{[4-(2-hydroxyethyl)piperazin-1-yl]carbonyl}phenol, 3-{[(2S)-3-(5-chloro-1'H,3H-spiro[1-benzofuran-2,4'-piperidin]-1'-yl)-2-hydroxypropyl]oxy}-4-{[3-(hydroxymethyl)piperidin-1-yl]carbonyl}phenol, 2-{[(2S)-3-(5-chloro-1'H,3H-spiro[1-benzofuran-2,4'-piperidin]-1'-yl)-2-hydroxypropyl]oxy}-N-[5-(1,1-dimethylpropyl)-2-hydroxyphenyl]4-hydroxybenzamide,
2-{[(2S)-3-(5-chloro-1'H,3H-spiro[1-benzofuran-2,4'-piperidin]-1'-yl)-2-hydroxypropyl]oxy}-4-hydroxy-N-[3-(1-hydroxyethyl)phenyl]benzamide,
2-{[(2S)-3-(5-chloro-1'H,3H-spiro[1-benzofuran-2,4'-piperidin]-1'-yl)-2-hydroxypropyl]oxy}-N-(cyclopropylmethyl)-4-hydroxybenzamide,
2-{[(2S)-3-(5-chloro-1'H,3H-spiro[1-benzofuran-2,4'-piperidin]-1'-yl)-2-hydroxypropyl]oxy}-4-hydroxy-N-pyrrolidin-1-ylbenzamide,
N-[(1R,4S)-bicyclo[2.2.1]hept-2-yl]-2-{[(2S)-3-(5-chloro-1'H,3H-spiro[1-benzofuran-2,4'-piperidin]-1'-yl)-2-hydroxypropyl]oxy}-4-hydroxybenzamide,
4-(4-chlorophenyl)-1-(2-{[(2S)-3-(5-chloro-1'H,3H-spiro[1-benzofuran-2,4'-piperidin]-1'-yl)-2-hydroxypropyl]oxy}-4-hydroxybenzoyl)piperidin-4-ol,
2-{[(2S)-3-(5-chloro-1'H,3H-spiro[1-benzofuran-2,4'-piperidin]-1'-yl)-2-hydroxypropyl]oxy}-4-hydroxy-N-(2-hydroxy-1-phenylethyl)benzamide,
1-(2-{[(2S)-3-(5-chloro-1'H,3H-spiro[1-benzofuran-2,4'-piperidin]-1'-yl)-2-hydroxypropyl]oxy}-4-hydroxybenzoyl)-4-phenylpiperidin-4-ol,
3-{[(2S)-3-(5-chloro-1'H,3H-spiro[1-benzofuran-2,4'-piperidin]-1'-yl)-2-hydroxypropyl]oxy}-4-(3,4-dihydroisoquinolin-2(1H)-ylcarbonyl)phenol,
3-{[(2S)-3-(5-chloro-1'H,3H-spiro[1-benzofuran-2,4'-piperidin]-1'-yl)-2-hydroxypropyl]oxy}-4-{[2-(hydroxymethyl)piperidin-1-yl]carbonyl}phenol,
1-(2-{[(2S)-3-(5-chloro-1'H,3H-spiro[1-benzofuran-2,4'-piperidin]-1'-yl)-2-hydroxypropyl]oxy}-4-hydroxybenzoyl)-N,N-dimethylprolinamide,
Methyl (4R)-1-(2-{[(2S)-3-(5-chloro-1'H,3H-spiro[1-benzofuran-2,4'-piperidin]-1'-yl)-2-hydroxypropyl]oxy}-4-hydroxybenzoyl)-4-hydroxyprolinate,
(3R)-1-(2-{[(2S)-3-(5-chloro-1'H,3H-spiro[1-benzofuran-2,4'-piperidin]-1'-yl)-2-hydroxypropyl]oxy}-4-hydroxybenzoyl)piperidin-3-ol,
2-{[(2S)-3-(5-chloro-1'H,3H-spiro[1-benzofuran-2,4'-piperidin]-1'-yl)-2-hydroxypropyl]oxy}-4-hydroxy-N-(2-hydroxycyclohexyl)benzamide,
3-{[(2S)-3-(5-chloro-1'H,3H-spiro[1-benzofuran-2,4'-piperidin]-1'-yl)-2-hydroxypropyl]oxy}-4-[(4-phenylpiperidin-1-yl)carbonyl]phenol,
3-{[(2S)-3-(5-chloro-1'H,3H-spiro 1-benzofuran-2,4'-piperidin]-1'-yl)-2-hydroxypropyl]oxy}-4-(thiomorpholin-4-ylcarbonyl)phenol,
1-(2-{[(2S)-3-(5-chloro-1'H,3H-spiro[1-benzofuran-2,4'-piperidin]-1'-yl)-2-hydroxypropyl]oxy}-4-hydroxybenzoyl)piperidin-3-ol,
2-{[(2S)-3-(5-chloro-1'H,3H-spiro[1-benzofuran-2,4'-piperidin]-1'-yl)-2-hydroxypropyl]oxy}-N-(cyclopropylmethyl)-4-hydroxy-N-propylbenzamide,
2-{[(2S)-3-(5-chloro-1'H,3H-spiro[1-benzofuran-2,4'-piperidin]-1'-yl)-2-hydroxypropyl]oxy}-4-hydroxy-N,N-diisobutylbenzamide,
3-{[(2S)-3-(5-chloro-1'H,3H-spiro[1-benzofuran-2,4'-piperidin]-1'-yl)-2-hydroxypropyl]oxy}-4-(1,3-dihydro-2H-isoindol-2-ylcarbonyl)phenol,
N-(2-tert-butoxyethyl)-2-{[(2S)-3-(5-chloro-1'H,3H-spiro[1-benzofuran-2,4'-piperidin]-1'-yl)-2-hydroxypropyl]oxy}-4-hydroxy-N-isobutylbenzamide,
3-{[(2S)-3-(5-chloro-1'H,3H-spiro[1-benzofuran-2,4'-piperidin]-1'-yl)-2-hydroxypropyl]oxy}-4-[(4-fluoropiperidin-1-yl)carbonyl]phenol,
3-{[(2S)-3-(5-chloro-1'H,3H-spiro[1-benzofuran-2,4'-piperidin]-1'-yl)-2-hydroxypropyl]oxy}-4-[(4,4-difluoropiperidin-1-yl)carbonyl]phenol,
2-{[(2S)-3-(5-chloro-1'H,3H-spiro[1-benzofuran-2,4'-piperidin]-1'-yl)-2-hydroxypropyl]oxy}-N-phenylbenzamide,
3-{[(2S)-3-(5-chloro-1'H,3H-spiro[2-benzofuran-1,4'-piperidin]-1-yl)-2-hydroxypropyl]oxy}-4-({(2R)-2-[hydroxy(diphenyl)methyl]pyrrolidin-1-yl}carbonyl)phenol,
2-{[(2S)-3-(5-chloro-1'H,3H-spiro[2-benzofuran-1,4'-piperidin]-1'-yl)-2-hydroxypropyl]oxy}-4-hydroxy-N-(2-hydroxyethyl)-N-methylbenzamide,
3-{[(2S)-3-(5-chloro-1'H,3H-spiro[2-benzofuran-1,4'-piperidin]-1'-yl)-2-hydroxypropyl]oxy}-4-(pyrrolidin-1-ylcarbonyl)phenol,
3-{[(2S)-3-(5-chloro-1'H,3H-spiro[2-benzofuran-1,4'-piperidin]1'-yl)-2-hydroxypropyl]oxy}-4-{[4-(2-hydroxyethyl)piperazin-1-yl]carbonyl}phenol,
3-{[(2S)-3-(5-chloro-1'H,3H-spiro[2-benzofuran-1,4'-piperidin]-1'-yl)-2-hydroxypropyl]oxy}-4-{[3-(hydroxymethyl)piperidin-1-yl]carbonyl}phenol,
4-(4-chlorophenyl)-1-(2-{[(2S)-3-(5-chloro-1'H,3H-spiro[2-benzofuran-1,4'-piperidin]-1'-yl)-2-hydroxypropyl]oxy}-4-hydroxybenzoyl)piperidin-4-ol,
3-{[(2S)-3-(5-chloro-1'H,3H-spiro[2-benzofuran-1,4'-piperidin]-1'-yl)-2-hydroxypropyl]oxy}-4-{[4-(hydroxymethyl)piperidin-1-yl]carbonyl}phenol,
1-(2-{[(2S)-3-(5-chloro-1'H,3H-spiro[2-benzofuran-1,4'-piperidin]-1'-yl)-2-hydroxypropyl]oxy}-4-hydroxybenzoyl)-4-phenylpiperidin-4-ol,
3-{[(2S)-3-(5-chloro-1'H,3H-spiro[2-benzofuran-1,4'-piperidin]-1'-yl)-2-hydroxypropyl]oxy}-4-(3,4-dihydroisoquinolin-2(1H)-ylcarbonyl)phenol,
3-{[(2S)-3-(5-chloro-1'H,3H-spiro[2-benzofuran-1,4'-piperidin]-1-yl)-2-hydroxypropyl]oxy}-4-{[2-(hydroxymethyl)piperidin-1-yl]carbonyl}phenol,
3-{[(2S)-3-(5-chloro-1'H,3H-spiro[2-benzofuran-1,4'-piperidin]-1'-yl)-2-hydroxypropyl]oxy}-4-{[3-(dimethylamino)pyrrolidin-1-yl]carbonyl}phenol,
1-(2-{[(2S)-3-(5-chloro-1'H,3H-spiro[2-benzofuran-1,4'-piperidin]-1'-yl)-2-hydroxypropyl]oxy}-4-hydroxybenzoyl)-N,N-dimethylprolinamide,
2-{[(2S)-3-(5-chloro-1'H,3H-spiro[2-benzofuran-1,4'-piperidin]-1'-yl)-2-hydroxypropyl]oxy}-N-cyclohexyl-4-hydroxy-N-(2-hydroxyethyl)benzamide,
Methyl(4R)-1-(2-{[(2S)-3-(5-chloro-1'H,3H-spiro[2-benzofuran-1,4'-piperidin]-1'-yl)-2-hydroxypropyl]oxy}-4-hydroxybenzoyl)-4-hydroxyprolinate,
(3R)-1-(2-{[(2S)-3-(5-chloro-1'H,3H-spiro[2-benzofuran-1,4'-piperidin]-1'-yl)-2-hydroxypropyl]oxy}-4-hydroxybenzoyl)piperidin-3-ol,
3-{[(2S)-3-(5-chloro-1'H,3H-spiro[2-benzofuran-1,4'-piperidin]-1'-yl)-2-hydroxypropyl]oxy}-4-[(4-phenylpiperidin-1-yl)carbonyl]phenol,
3-{[(2S)-3-(5-chloro-1'H,3H-spiro[2-benzofuran-1,4'-piperidin]-1'-yl)-2-hydroxypropyl]oxy}-4-(thiomorpholin-4-ylcarbonyl)phenol,
1-(2-{[(2S)-3-(5-chloro-1'H,3H-spiro[2-benzofuran-1,4'-piperidin]-1-yl)-2-hydroxypropyl]oxy}-4-hydroxybenzoyl)piperidin-3-ol,
2-{[(2S)-3-(5-chloro-1'H,3H-spiro[2-benzofuran-1,4'-piperidin]-1'-yl)-2-hydroxypropyl]oxy}-N-(cyclopropylmethyl)-4-hydroxy-N-propylbenzamide,
2-{[(2S)-3-(5-chloro-1'H,3H-spiro[2-benzofuran-1,4'-piperidin]-1'-yl)-2-hydroxypropyl]oxy}-4-hydroxy-N,N-diisobutylbenzamide, 3-{[(2S)-3-(5-chloro-1'H,3H-spiro[2-benzofuran-1,4'-piperidin]-1'-yl)-2-hydroxypropyl]oxy}-4-(1,3-dihydro-2H-isoindol-2-ylcarbonyl)phenol, N-(2-tert-butoxyethyl)-2-{[(2S)-3-(5-chloro-1'H,3H-spiro[2-benzofuran-1,4'-piperidin]-1'-yl)-2-hydroxypropyl]oxy}-4-hydroxy-N-isobutylbenzamide, 3-{[(2S)-3-(5-chloro-1'H,3H-spiro[2-benzofuran-1,4'-piperidin]-1'-yl)-2-hydroxypropyl]oxy}-4-[(4-fluoropiperidin-1-yl)carbonyl]phenol, 3-{[(2S)-3-(5-chloro-1'H,3H-spiro[2-benzofuran-1,4'-piperidin]-1'-yl)-2-hydroxypropyl]oxy}-4-[(4,4-difluoropiperidin-1-yl)carbonyl]phenol, 2-{[(2S)-3-(5-chloro-1'H,3H-spiro[2-benzofuran-1,4'-piperidin]-1'-yl)-2-hydroxypropyl]oxy}-4-hydroxy-N-(2-hydroxypropyl)benzamide, 2-{[(2S)-3-(5-chloro-1'H,3H-spiro[2-benzofuran-1,4'-piperidin]-1'-yl)-2-hydroxypropyl]oxy}-4-hydroxy-N-(2-hydroxy-1,1-dimethylethyl)benzamide, 2-{[(2S)-3-(5-chloro-1'H,3H-spiro[2-benzofuran-1,4'-piperidin]-1'-yl)-2-hydroxypropyl]oxy}-N-cyclopentyl-4-hydroxybenzamide, 2-{[(2S)-3-(5-chloro-1'H,3H-spiro[2-benzofuran-1,4'-piperidin]-1'-yl)-2-hydroxypropyl]oxy}-4-hydroxy-N-(2-methoxyethyl)benzamide, 2-{[(2S)-3-(5-chloro-1'H,3H-spiro[2-benzofuran-1,4'-piperidin]-1'-yl)-2-hydroxypropyl]oxy}-4-hydroxy-N-(2-hydroxyphenyl)benzamide, 2-{[(2S)-3-(5-chloro-1'H,3H-spiro[2-benzofuran-1,4'-piperidin]-1'-yl)-2-hydroxypropyl]oxy}-4-hydroxy-N-(2-hydroxy-1-methylethyl)benzamide, 2-{[(2S)-3-(5-chloro-1'H,3H-spiro[2-benzofuran-1,4'-piperidin]-1'-yl)-2-hydroxypropyl]oxy}-4-hydroxy-N-isobutylbenzamide, 2-{[(2S)-3-(5-chloro-1'H,3H-spiro[2-benzofuran-1,4'-piperidin]-1'-yl)-2-hydroxypropyl]oxy}-4-hydroxy-N-(2-hydroxyethyl)benzamide, 2-{[(2S)-3-(5-chloro-1'H,3H-spiro[2-benzofuran-1,4'-piperidin]-1'-yl)-2-hydroxypropyl]oxy}-4-hydroxy-N-(4-hydroxycyclohexyl)benzamide, 2-{[(2S)-3-(5-chloro-1'H,3H-spiro[2-benzofuran-1,4'-piperidin]-1'-yl)-2-hydroxypropyl]oxy}-N-(2,3-dihydroxypropyl)-4-hydroxybenzamide, Methyl N-(2-{[(2S)-3-(5-chloro-1'H,3H-spiro[2-benzofuran-1,4'-piperidin]-1'-yl)-2-hydroxypropyl]oxy}-4-hydroxybenzoyl)serinate, 2-{[(2S)-3-(5-chloro-1'H,3H-spiro[2-benzofuran-1,4'-piperidin]-1'-yl)-2-hydroxypropyl]oxy}-N-(1-ethylpropyl)-4-hydroxybenzamide, 2-{[(2S)-3-(5-chloro-1'H,3H-spiro[2-benzofuran-1,4'-piperidin]-1'-yl)-2-hydroxypropyl]oxy}-4-hydroxy-N-(tetrahydrofuran-2-ylmethyl)benzamide, 2-{[(2S)-3-(5-chloro-1'H,3H-spiro[2-benzofuran-1,4'-piperidin]-1'-yl)-2-hydroxypropyl]oxy}-4-hydroxy-N-[1-(hydroxymethyl)-2,2-dimethylpropyl]benzamide, 2-{[(2S)-3-(5-chloro-1'H,3H-spiro[2-benzofuran-1,4'-piperidin]-1'-yl)-2-hydroxypropyl]oxy}-4-hydroxy-N-[1-(hydroxymethyl)-2-methylpropyl]benzamide, 2-{[(2S)-3-(5-chloro-1'H,3H-spiro[2-benzofuran-1,4'-piperidin]-1'-yl)-2-hydroxypropyl]oxy}-4-hydroxy-N-[3-(1-hydroxyethyl)phenyl]benzamide, 2-{[(2S)-3-(5-chloro-1'H,3H-spiro[2-benzofuran-1,4'-piperidin]-1'-yl)-2-hydroxypropyl]oxy}-N-(cyclopropylmethyl)-4-hydroxybenzamide, 2-{[(2S)-3-(5-chloro-1'H,3H-spiro[2-benzofuran-1,4'-piperidin]-1'-yl)-2-hydroxypropyl]oxy}-4-hydroxy-N-pyrrolidin-1-ylbenzamide, N-[(1R,4S)-bicyclo[2.2.1]hept-2-yl]-2-{[(2S)-3-(5-chloro-1'H,3H-spiro[2-benzofuran-1,4'-piperidin]-1'-yl)-2-hydroxypropyl]oxy}-4-hydroxybenzamide, 2-{[(2S)-3-(5-chloro-1'H,3H-spiro[2-benzofuran-1,4'-piperidin]-1'-yl)-2-hydroxypropyl]oxy}-4-hydroxy-N-(2-hydroxy-1-phenylethyl)benzamide, 2-{[(2S)-3-(5-chloro-1'H,3H-spiro[2-benzofuran-1,4'-piperidin]-1'-yl)-2-hydroxypropyl]oxy}-4-hydroxy-N-(2-hydroxycyclohexyl)benzamide, 1-(2-{[(2S)-3-(5-chloro-1'H,3H-spiro[1-benzofuran-2,4'-piperidin]-1'-yl)-2-hydroxypropyl]oxy}-4-hydroxybenzoyl)pyrrolidine-3-carboxamide trifluoroacetate, 1-(2-{[(2S)-3-(5-chloro-1'H,3H-spiro[1-benzofuran-2,4'-piperidin]-1'-yl)-2-hydroxypropyl]oxy)}-4-hydroxybenzoyl)-L-prolinamide trifluoroacetate, 2-chloro-5-{[(2S)-3-(5-chloro-1'H,3H-spiro[1-benzofuran-2,4'-piperidin]-1'-yl)-2-hydroxypropyl]oxy}-4-{[(3R)-3-(dimethylamino)pyrrolidin-1-yl]carbonyl}phenol bis(trifluoroacetate), 2-chloro-5-{[(2S)-3-(5-chloro-1'H,3H-spiro[1-benzofuran-2,4'-piperidin]-1'-yl)-2-hydroxypropyl]oxy}-4-{[(3R)-3-(hydroxymethyl)pyrrolidin-1-yl]carbonyl}phenol trifluoroacetate, 2-chloro-5-{[(2S)-3-(5-chloro-1'H,3H-spiro[1-benzofuran-2,4'-piperidin)-1'-yl)-2-hydroxypropyl]oxy}-4-{[(3S)-3-(hydroxymethyl)pyrrolidin-1-yl]carbonyl}phenol trifluoroacetate, 2-chloro-5-{[(2S)-3-(5-fluoro-1'H,3H-spiro[1-benzofuran-2,4'-piperidin)-1'-yl)-2-hydroxypropyl]oxy}-4-(pyrrolidin-1-ylcarbonyl)phenol trifluoroacetate, N-(2-{[(2R)-3-(5-Fluoro-1'H,3H-spiro[1-benzofuran-2,4'-piperidin]-1'-yl)-2-hydroxypropyl]oxy}-4-methoxyphenyl)acetamide, Methyl 2-{[(2S)-3-(5-fluoro-1'H,3H-spiro[1-benzofuran-2,4'-piperidin]-1'-yl)-2-hydroxypropyl]oxy}benzoate, 2-{[(2S)-3-(5-Fluoro-1'H,3H-spiro[1-benzofuran-2,4'-piperidin]-1'-yl)-2-hydroxypropyl]oxy}benzoic acid (hydrochloride), (3S)-1-(2-{[(2S)-3-(5-Fluoro-1'H,3H-spiro[1-benzofuran-2,4'-piperidin]-1'-yl)-2-hydroxypropyl]oxy}benzoyl)pyrrolidin-3-ol, 3-{[(2S)-3-(5-Fluoro-1'H,3H-spiro[1-benzofuran-2,4'-piperidin]-1'-yl)-2-hydroxypropyl]oxy}-4-(pyrrolidin-1-ylcarbonyl)phenol, N-(4-fluoro-2-{[(2S)-3-(5-fluoro-1'H,3H-spiro[1-benzofuran-2,4'-piperidin]-1'-yl)-2-hydroxypropyl]oxy}phenyl)acetamide, N-{5-chloro-2-[3-(5-chloro-1'H, 3H-spiro[1-benzofuran-2,4'-piperidin]-1'-yl)-2-hydroxypropoxy]-4-hydroxyphenyl}cyclopentanecarboxamide, N-{5-chloro-2-[3-(5-fluoro-1'H, 3H-spiro[1-benzofuran-2,4'-piperidin]-1'-yl)-2-hydroxypropoxy]4-hydroxyphenyl}cyclopentanecarboxamide, N-{5-chloro-4-hydroxy-2-[2-hydroxy-3-(1'H, 3H-spiro[1-benzofuran-2,4'-piperidin]-1'-yl)propoxy]phenyl}cyclopentanecarboxamide, N-(5-Chloro-2-{[(2S)-3-(5-chloro-1'H,3H-spiro[1-benzofuran-2,4'-piperidin]-1'-yl)-2-hydroxypropyl]oxy}-4-hydroxyphenyl)benzamide trifluoroacetate, N-(5-Chloro-2-{[(2S)-3-(5-fluoro-1'H,3H-spiro[1-benzofuran-2,4'-piperidin]-1'-yl)-2-hydroxypropyl]oxy}-4-hydroxyphenyl)benzamide trifluoroacetate, N-(5-Chloro-2-{[(2S)-3-(5-chloro-1'H,3H-spiro[1-benzofuran-2,4'-piperidin]-1'-yl)-2-hydroxypropyl]oxy}-4-hydroxyphenyl)urea trifluoroacetate, N-(5-Chloro-2-{[(2S)-3-(5-fluoro-1'H,3H-spiro[1-benzofuran-2,4'-piperidin]-1'-yl)-2-hydroxypropyl]oxy}-4-hydroxyphenyl)urea trifluoroacetate, N-(5-chloro-2-{[(2S)-3-(5-fluoro-1'H,3H-spiro[1-benzofuran-2,4'-piperidin]-1'-yl)-2-hydroxypropyl]oxy}phenyl)urea, N-(5-chloro-2-{[(2S)-3-(5-chloro-1'H,3H-spiro[1-benzofuran-2,4'-piperidin]-1'-yl)-2-hydroxypropyl]oxy}phenyl)urea, N-(2-{[(2S)-3-(5-fluoro-1'H,3H-spiro[1-benzofuran-2,4'-piperidin]-1'-yl)-2-hydroxypropyl]oxy}phenyl)urea, N-(2-{[(2S)-2-hydroxy-3-(1'H,3H-spiro[1-benzofuran-2,4'-piperidin]-1'-yl)propyl]oxy}phenyl)urea, N-(4-fluoro-2-{[(2S)-3-(5-fluoro-1'H,3H-spiro[1-benzofuran-2,4'-piperidin]-1'-yl)-2-hydroxypropyl]oxy}phenyl)urea, N-(4-fluoro-2-{[(2S)-2-hydroxy-3-(1'H,3H-spiro[1-benzofuran-2,4'-piperidin]-1'-yl)propyl]oxy}phenyl)urea, and pharmaceutically acceptable salts and solvates of any one thereof.

The present invention further provides a process for the preparation of a compound of formula (I) or a pharmaceutically acceptable salt or solvate thereof as defined above which comprises, (a) reacting a compound of formula

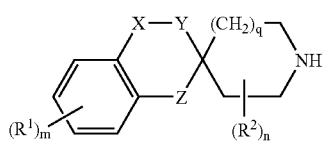

(II)

wherein m, $R^1$, n, $R^2$, q, X, Y and Z are as defined in formula (I), with a compound of formula

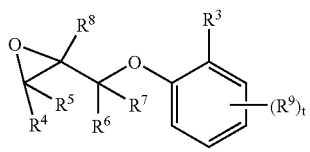

(III)

wherein $R^3$, $R^4$, $R^5$, $R^6$, $R^7$, $R^8$, t and $R^9$ are as defined in formula (I); or (b) reacting a compound of formula

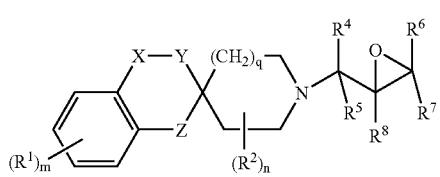

(IV)

wherein m, $R^1$, n, $R^2$, q, X, Y, Z, $R^4$, $R^5$, $R^6$, $R^7$ and $R^8$ are as defined in formula (I), with a compound of formula

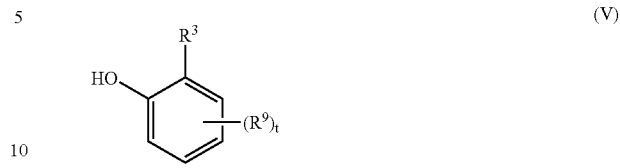

(V)

wherein $R^3$, t and $R^9$ are as defined in formula (I), in the presence of a suitable base; or (c) when $R^3$ represents —NHC(O)$R^{10}$, reacting a compound of formula

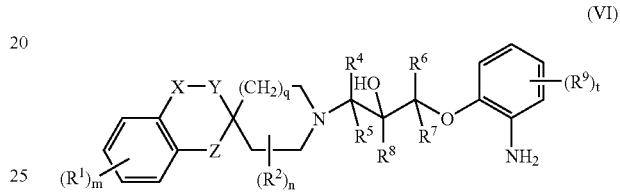

(VI)

wherein m, $R^1$, n, $R^2$, q, X, Y, Z, $R^4$, $R^5$, $R^6$, $R^7$, $R^8$, t and $R^9$ are as defined in formula (I), with a compound of formula

(VII)

wherein $L^1$ represents a leaving group (e.g. a hydroxyl group or a halogen atom such as chlorine) and $R^{10}$ is as defined in formula (I); or (d) when $R^3$ represents —C(O)N$R^{11}R^{12}$, reacting a compound of formula

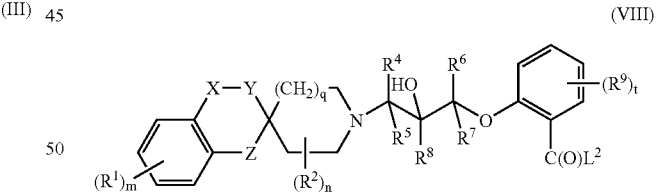

(VIII)

wherein $L^2$ represents a leaving group (e.g. a hydroxyl group or a halogen atom such as chlorine) and m, $R^1$, n, $R^2$, q, X, Y, Z, $R^4$, $R^5$, $R^6$, $R^7$, $R^8$, t and $R^9$ are as defined in formula (I), with a compound of formula (IX), NH$R^{11}R^{12}$, wherein $R^{11}$ and $R^{12}$ are as defined in formula (I); or (e) when $R^3$ represents —NHC(O)$R^{10}$, $R^{10}$ represents —N$R^{14}R^{15}$ and $R^{14}$ and $R^{15}$ both represent hydrogen, reacting a compound of formula (VI) as defined in (c) above with potassium cyanate;

and optionally after (a), (b), (c), (d) or (e) forming a pharmaceutically acceptable salt or solvate.

The processes of the invention may conveniently be carried out in a solvent, e.g. an organic solvent such as an alcohol (e.g.

methanol or ethanol), a hydrocarbon (e.g. toluene) or tetrahydrofuran, dimethylformamide, N-methylpyrrolidinone or acetonitrile at a temperature of, for example, 0° C. or above such as a temperature in the range from 0, 5, 10, 15 or 20° C. to 100, 110 or 120° C.

Certain compounds of formula (II) are novel. Thus, the present invention further provides an intermediate compound of formula

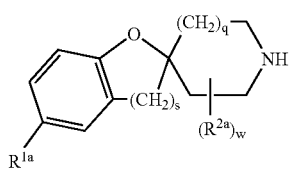
(IIA)

wherein $R^{1a}$ is selected from fluorine, chlorine, methyl and trifluoromethyl; s is 1 or 2; q is 0 or 1; w is 0 or 1; and $R^{2a}$ is fluorine.

Specific examples of compounds of formula (IIA) include:
5-fluoro-3H-spiro[1-benzofuran-2,4'-piperidine]

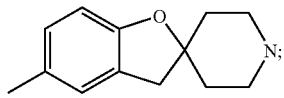

5-methyl-3H-spiro[1-benzofuran-2,4'-piperidine]

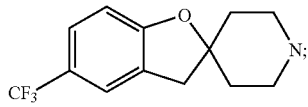

5-(trifluoromethyl)-3H-spiro[1-benzofuran-2,4'-piperidine]

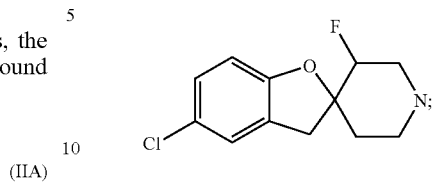

5-chloro-3'-fluoro-3H-spiro[1-benzofuran-2,4'-piperidine]

5-chloro-3H-spiro[1-benzofuran-2,3'-pyrrolidine]

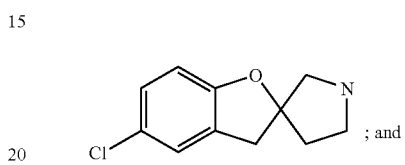
; and 6-chloro-3,4-dihydrospiro[chromene-2,4'-piperidine]

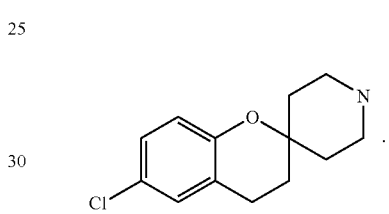

Other compounds of formula (II) and compounds of formulae (III), (IV), (V), (VI), (VII), (VIII) and (IX) are either commercially available, are known in the literature or may be prepared using known techniques.

For example, compounds of formula (II) in which m is 1, $R^1$ is chlorine or fluorine, n is 0, q is 1, one of X and Y represents a bond and the other of X and Y represents an oxygen atom and Z represents $CH_2$, may be prepared according to the following reaction schemes in which DMF denotes dimethylformamide, EtOH denotes ethanol, DME denotes 1,2-dimethoxyethane, i-Pr denotes isopropyl, THF denotes tetrahydrofuran, KOtBu denotes potassium tert butoxide and HOAc denotes acetic acid (A)

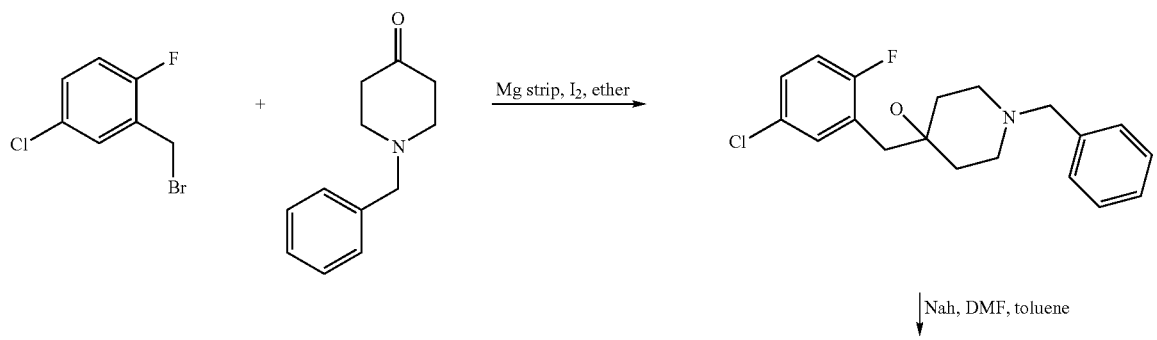

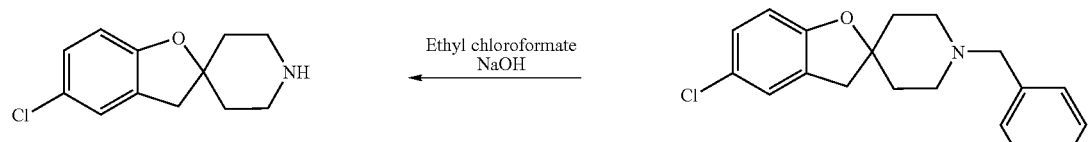
(B)
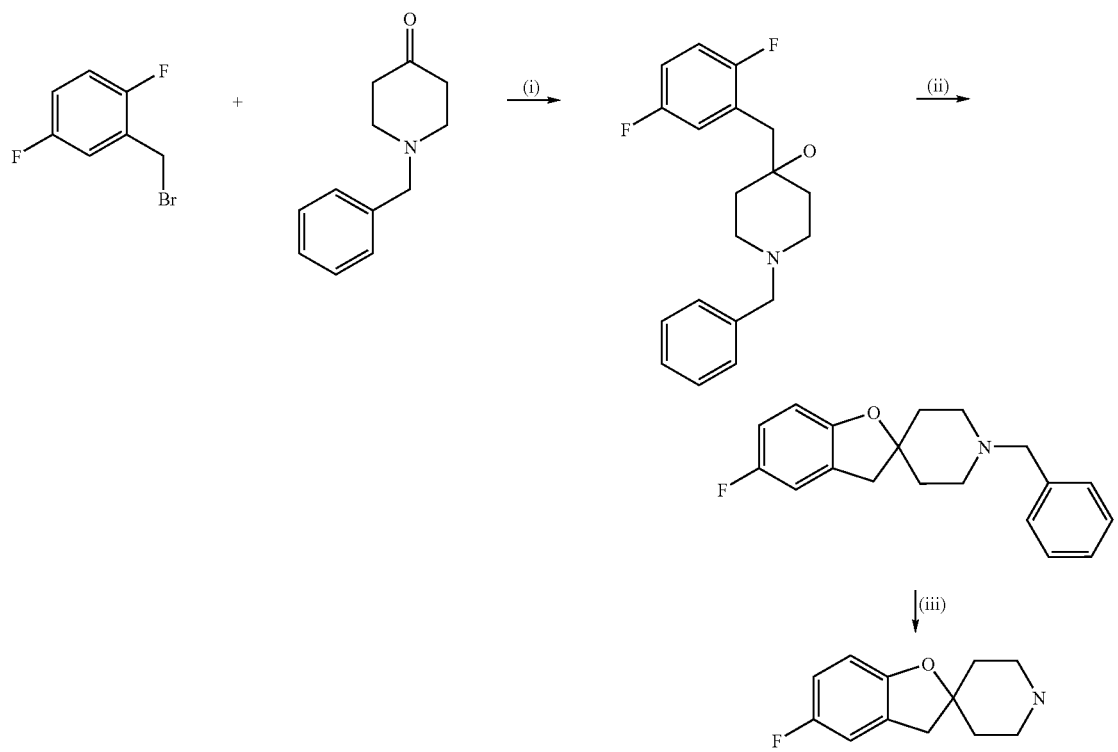
(i) Mg strip, diethyl ether (ii) NaH, toluene, DMF
(iii) ethyl chloroformate, toluene, aq. KOH, EtOH
(C)
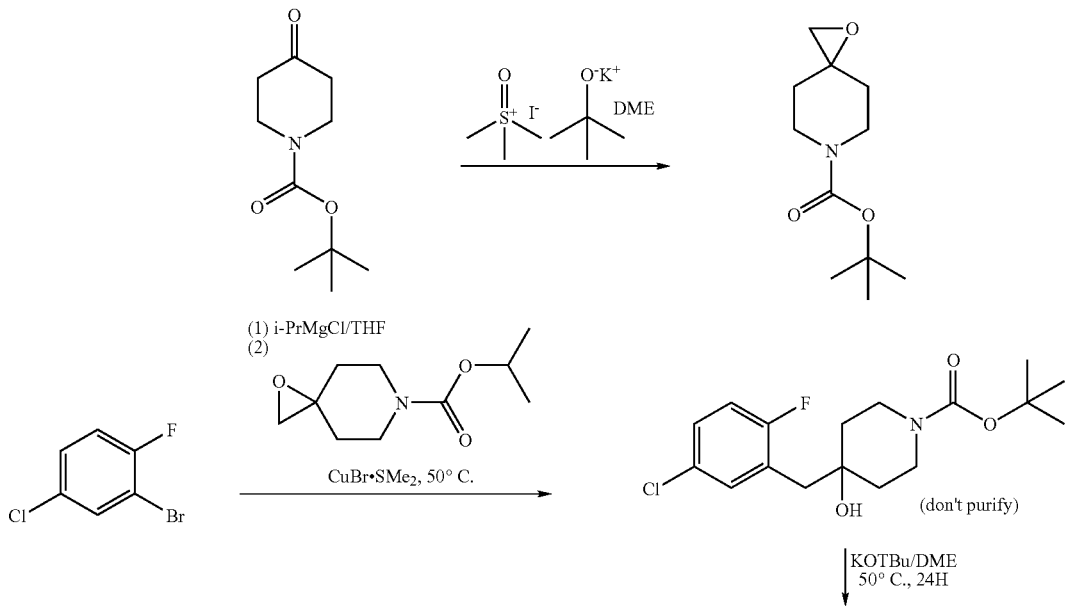

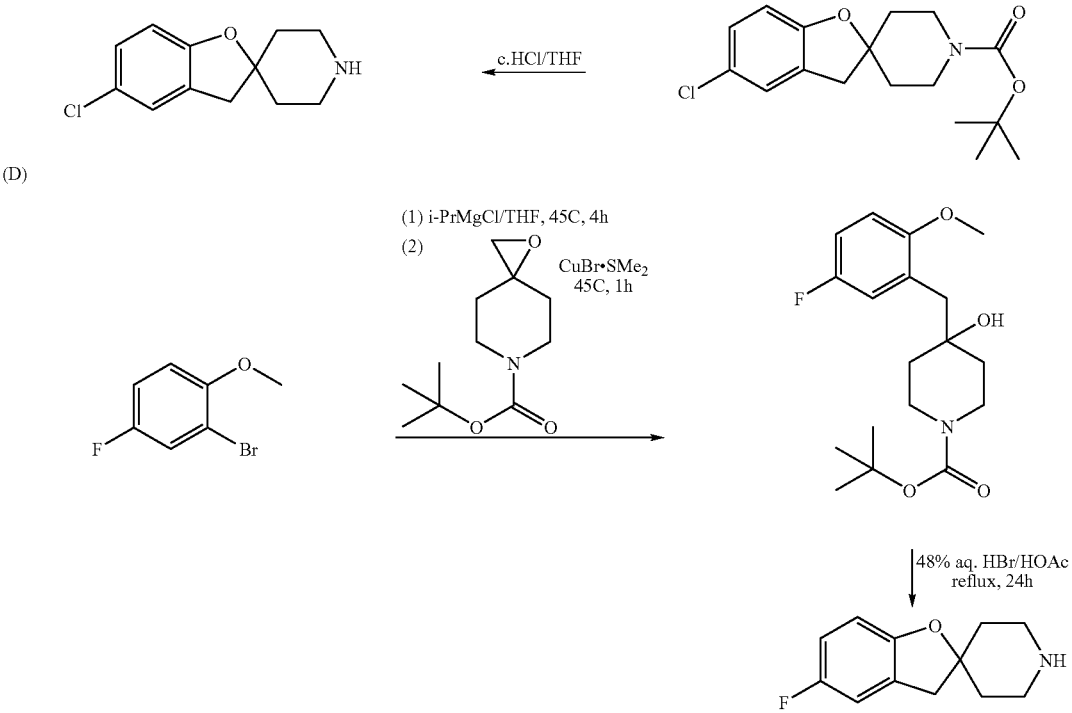
Compounds of formula (II) in which m is 1, $R^1$ is chlorine, n is 0, q is 1, X represents $CH_2$, Y represents an oxygen atom and Z represents a bond, may be prepared according to the following reaction schemes in which THF denotes tetrahydrofuran:
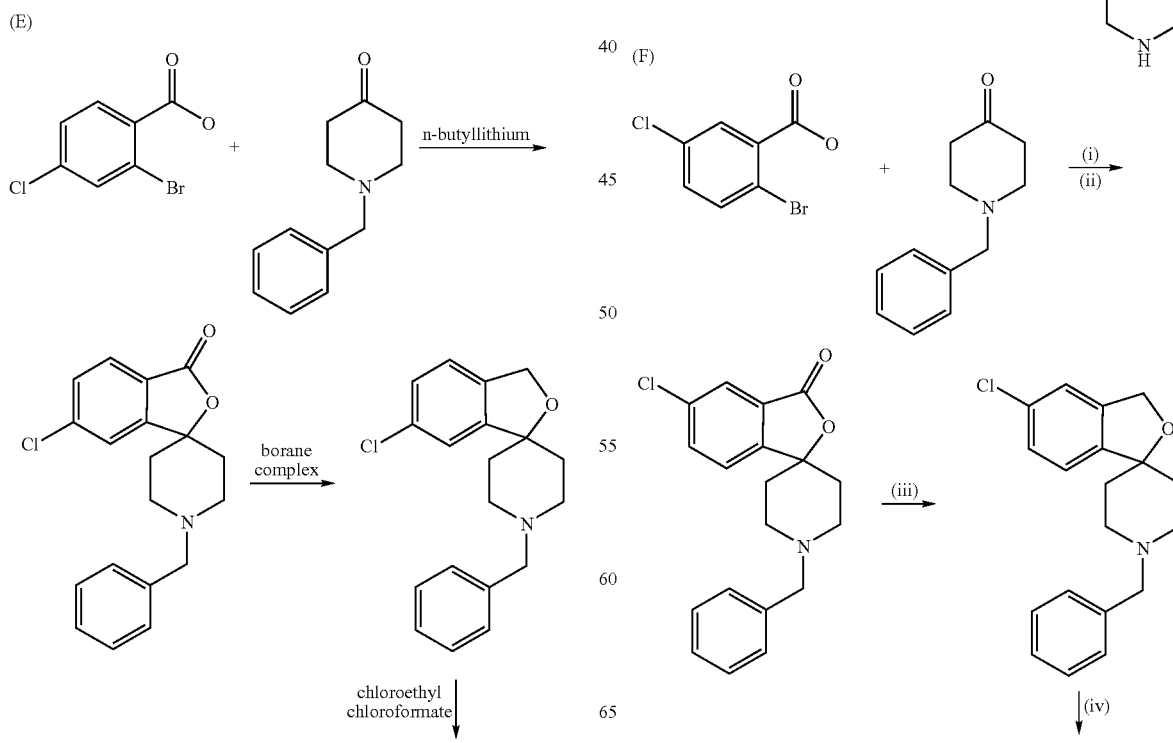

-continued

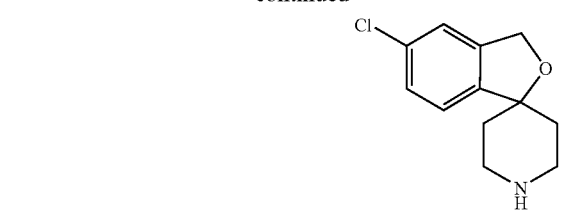

(i) n-BuLi, THF (ii) Aq. HCl (iii) Borane-THF complex, THF, aq. HCl (iv) 1-chloro ethylchloroformate, dichloromethane, methanol Compounds of formula (II) in which m is 1, $R^1$ is chlorine, n is 0, q is 0, one of X and Y represents a bond and the other of X and Y represents an oxygen atom and Z represents $CH_2$, may be prepared according to the following reaction scheme in which DMF denotes dimethylformamide and EtOH denotes ethanol:

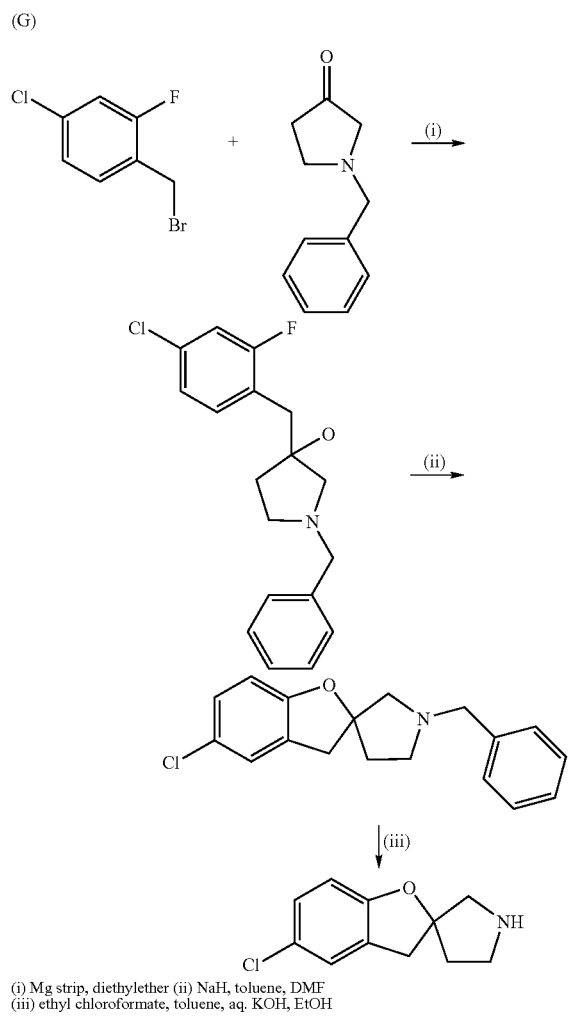

(i) Mg strip, diethylether (ii) NaH, toluene, DMF
(iii) ethyl chloroformate, toluene, aq. KOH, EtOH Compounds of formula (II) in which m is 1, $R^1$ is methyl, n is 0, q is 1, one of X and Y represents a bond and the other of X and Y represents an oxygen atom and Z represents $CH_2$, may be prepared according to the following reaction scheme in which DMSO denotes dimethylsulphoxide:

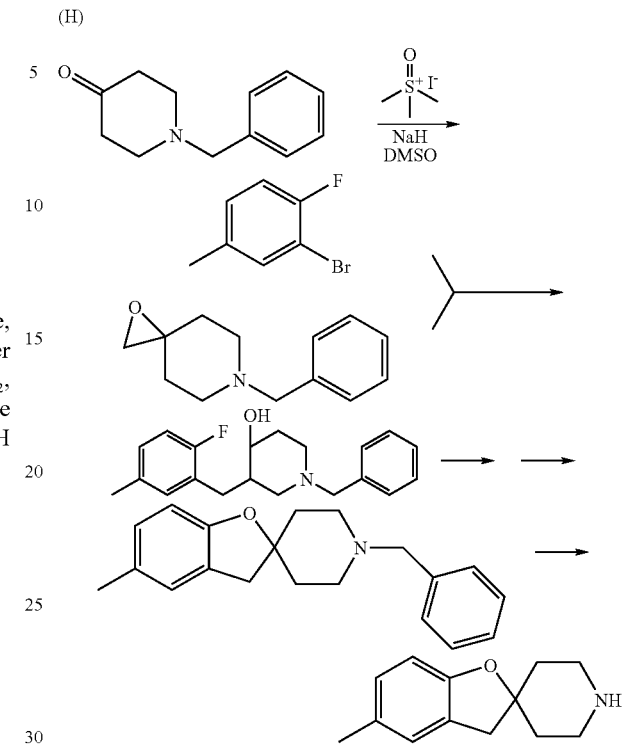

Process routes (C), (D) and (H) above are novel.

Thus, the present invention further provides a process for preparing a compound of formula (IIA) as defined above in which s is 1, which comprises reacting a compound of formula

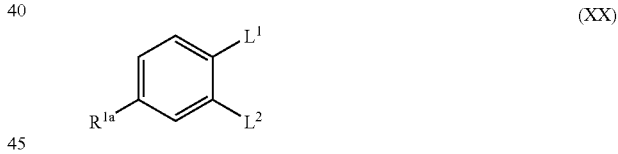

(XX)

wherein $L^1$ represents a suitable leaving group (e.g. an electron withdrawing group such as a halogen atom) or an alkoxy, particularly methoxy, group, $L^2$ represents a suitable leaving group such as a halogen atom and $R^{1a}$ is as defined in formula (IIA), with a compound of formula

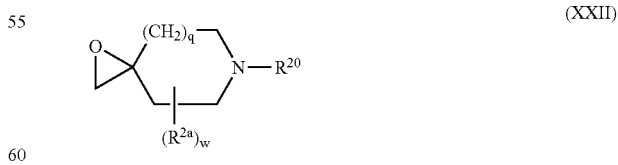

(XXII)

wherein $R^{20}$ represents a protecting group such as a benzyl group or a group —C(O)—O—$R^{21}$ in which $R^{21}$ represents an alkyl (e.g. $C_1$-$C_6$ alkyl, particularly tert-butyl) or aryl (e.g. phenyl) group and q, w and $R^{2a}$ are as defined in formula (IIA) to form a compound of formula

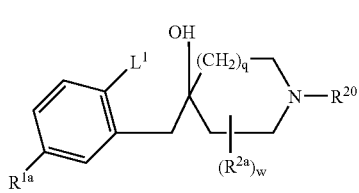

(XXIV)

followed by a cyclisation reaction and then removal of the protecting group $R^{20}$.

It will be appreciated by those skilled in the art that in the processes of the present invention certain functional groups such as hydroxyl or amino groups in the reagents may need to be protected by protecting groups. Thus, the preparation of the compounds of formula (I) may involve, at an appropriate stage, the removal of one or more protecting groups.

The protection and deprotection of functional groups is described in 'Protective Groups in Organic Chemistry', edited by J. W. F. McOmie, Plenum Press (1973) and 'Protective Groups in Organic Synthesis', $3^{rd}$ edition, T. W. Greene and P. G. M. Wuts, Wiley-Interscience (1999).

The compounds of formula (D) above may be converted to a pharmaceutically acceptable salt or solvate thereof, preferably an acid addition salt such as a hydrochloride, hydrobromide, phosphate, acetate, fumarate, maleate, tartrate, citrate, oxalate, methanesulphonate or p-toluenesulphonate.

Compounds of formula (I) are capable of existing in stereoisomeric forms. It will be understood that the invention encompasses the use of all geometric and optical isomers (including atropisomers) of the compounds of formula (I) and mixtures thereof including racemates. The use of tautomers and mixtures thereof also form an aspect of the present invention. Enantiomerically pure forms are particularly desired.

The compounds of formula (I) have activity as pharmaceuticals, in particular as modulators of chemokine receptor (especially MIP-1α chemokine receptor) activity, and may be used in the treatment of autoimmune, inflammatory, proliferative and hyperproliferative diseases and immunologically-mediated diseases including rejection of transplanted organs or tissues and Acquired Immunodeficiency Syndrome (AIDS).

Examples of these conditions are:

(1) (the respiratory tract) airways diseases including chronic obstructive pulmonary disease (COPD) such as irreversible COPD; asthma, such as bronchial, allergic, intrinsic, extrinsic and dust asthma, particularly chronic or inveterate asthma (e.g. late asthma and airways hyper-responsiveness); bronchitis; acute, allergic, atrophic rhinitis and chronic rhinitis including rhinitis caseosa, hypertrophic rhinitis, rhinitis purulenta, rhinitis sicca and rhinitis medicamentosa; membranous rhinitis including croupous, fibrinous and pseudomembranous rhinitis and scrofoulous rhinitis; seasonal rhinitis including rhinitis nervosa (hay fever) and vasomotor rhinitis; sarcoidosis, farmer's lung and related diseases, fibroid lung and idiopathic interstitial pneumonia;

(2) (bone and joints) rheumatoid arthritis, seronegative spondyloarthropathies (including ankylosing spondylitis, psoriatic arthritis and Reiter's disease), Behcet's disease, Sjogren's syndrome and systemic sclerosis;

(3) (skin) psoriasis, atopical dermatitis, contact dermatitis and other eczmatous dermitides, seborrhoetic dermatitis, Lichen planus, Pemphigus, bullous Pemphigus, Epidermolysis bullosa, urticaria, angiodermas, vasculitides, erythemas, cutaneous eosinophilias, uveitis, Alopecia greata and vernal conjunctivitis;

(4) (gastrointestinal tract) Coeliac disease, proctitis, eosinopilic gastro-enteritis, mastocytosis, Crohn's disease, ulcerative colitis, food-related allergies which have effects remote from the gut, e.g., migraine, rhinitis and eczema;

(5) (other tissues and systemic disease) multiple sclerosis, atherosclerosis, Acquired Immunodeficiency Syndrome (AIDS), lupus erythematosus, systemic lupus, erythematosus, Hashimoto's thyroiditis, myasthenia gravis, type I diabetes, nephrotic syndrome, eosinophilia fascitis, hyper IgE syndrome, lepromatous leprosy, sezary syndrome and idiopathic thrombocytopenia pupura;

(6) (allograft rejection) acute and chronic following, for example, transplantation of kidney, heart, liver, lung, bone marrow, skin and cornea; and chronic graft versus host disease;

(7) cancers, especially non-small cell lung cancer (NSCLC) and squamous sarcoma;

(8) diseases in which angiogenesis is associated with raised chemokine levels; and (9) cystic fibrosis, stroke, re-perfusion injury in the heart, brain, peripheral limbs and sepsis.

Thus, the present invention provides a compound of formula (I), or a pharmaceutically-acceptable salt or solvate thereof, as hereinbefore defined for use in therapy.

In a further aspect, the present invention provides the use of a compound of formula (I), or a pharmaceutically acceptable salt or solvate thereof, as hereinbefore defined in the manufacture of a medicament for use in therapy.

In the context of the present specification, the term "therapy" also includes "prophylaxis" unless there are specific indications to the contrary. The terms "therapeutic" and "therapeutically" should be construed accordingly.

The invention also provides a method of treating an inflammatory disease which comprises administering to a patient in need thereof a therapeutically effective amount of a compound of formula (I), or a pharmaceutically acceptable salt or solvate thereof, as hereinbefore defined.

The invention still further provides a method of treating an airways disease which comprises administering to a patient in need thereof a therapeutically effective amount of a compound of formula (I), or a pharmaceutically acceptable salt or solvate thereof, as hereinbefore defined.

For the above-mentioned therapeutic uses the dosage administered will, of course, vary with the compound employed, the mode of administration, the treatment desired and the disorder indicated. The daily dosage of the compound of formula (I) may be in the range from 0.001 mg/kg to 30 mg/kg.

The compounds of formula (I) and pharmaceutically acceptable salts and solvates thereof may be used on their own but will generally be administered in the form of a pharmaceutical composition in which the formula (I) compound/salt/solvate (active ingredient) is in association with a pharmaceutically acceptable adjuvant, diluent or carrier. Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The present invention also provides a pharmaceutical composition comprising a compound of formula (I), or a pharmaceutically acceptable salt or solvate thereof, as hereinbefore defined, in association with a pharmaceutically acceptable adjuvant, diluent or carrier.

The invention further provides a process for the preparation of a pharmaceutical composition of the invention which comprises mixing a compound of formula (1), or a pharmaceutically acceptable salt or solvate thereof, as hereinbefore defined, with a pharmaceutically acceptable adjuvant, diluent or carrier.

The pharmaceutical compositions may be administered topically (e.g. to the skin or to the lung and/or airways) in the form, e.g., of creams, solutions, suspensions, heptafluoroalkane aerosols and dry powder formulations; or systemically, e.g. by oral administration in the form of tablets, capsules, syrups, powders or granules; or by parenteral administration in the form of solutions or suspensions; or by subcutaneous administration; or by rectal administration in the form of suppositories; or transdermally.

The invention will now be further explained by reference to the following illustrative examples, in which $^1$H NMR spectra were recorded on Varian Unity Inova 400. The central solvent peak of chloroform-d$_6$ ($\delta_H$ 7.27 ppm), acetone-d$_6$ ($\delta_H$ 2.05 ppm), DMSO-d$_6$ ($\delta_H$ 2.50 ppm), or methanol-d$_4$ ($\delta_H$ 4.87 ppm) were used as internal standard. Low resolution mass spectra and accurate mass determination were recorded on a Hewlett-Packard 1100 LC-MS system equipped with APCI/ESI ionisation chambers. All solvents and commercial reagents were laboratory grade and used as received. The nomenclature used for the compounds was generated with ACD/IUPAC Name Pro.

The abbreviations or terms used in the examples have the following meanings:

| | |
|---|---|
| BuLi | butyllithium |
| DCM | dichloromethane |
| DEAD | diethyl azodicarboxylate |
| DMAP | 4-dimethylaminopyridine |
| DME | 1,2-dimethoxyethane |
| DMF | N,N-dimethylformamide |
| DMSO | dimethyl sulfoxide |
| Et$_2$O | diethyl ether |
| EtOAc | ethyl acetate |
| EtOH | ethanol |
| HOAc | acetic acid |
| KotBu | potassium tert butoxide |
| MeCN | acetonitrile |
| MeOH | methanol |
| NMP | 1-methyl-2-pyrrolidinone |
| TEA | triethylamine |
| TFA | thrifluoroacetic acid |
| THF | tetrahydrofuran |
| TMSCl | chlorotrimethylsilane |

SELECTFLUOR™ fluorinating reagent (Aldrich)
Chemical name: [1-(chloromethyl)-4-fluoro-1,4-diazoniabicyclo[2.2.2]octane bis(tetrafluoroborate)]
PS-Carbodiimide: a resin-bound coupling agent
Chemical name: N-cyclohexylcarbodiimide-N'-propyloxymethyl polystyrene

EXAMPLES

Intermediate Compound: 5-Chloro-3H-spiro[1-benzofuran-2,4'-piperidine]

Method A: This compound was prepared as described by Effland, R. C; Gardner, B. A; Strupczewski, J., *J. Heterocyclic Chem.*, 1981, 18,811-814.

Method B:

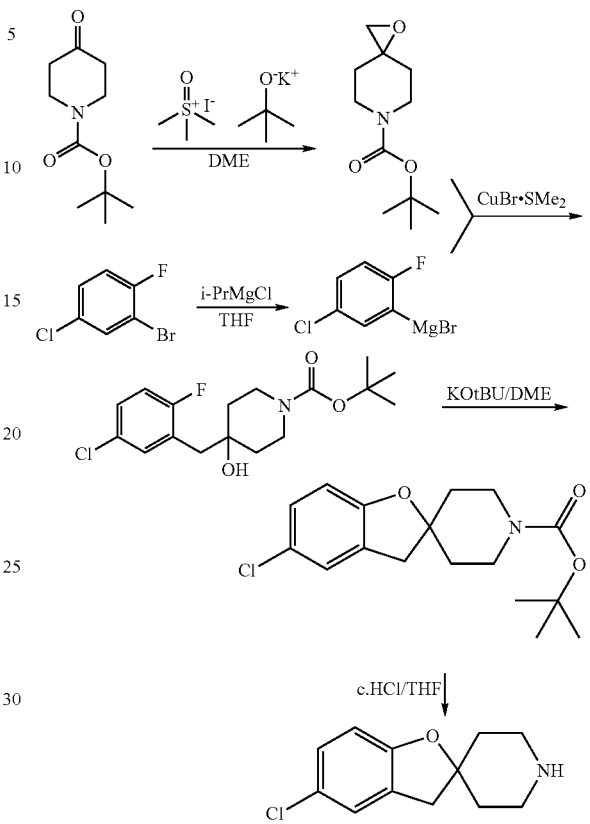

i) 1-Oxa-6-azaspiro[2,5]octane-6-carboxylic acid, 1,1-dimethylethyl ester

Potassium t-butoxide (31 g) was added to a stirred suspension of trimethylsulfoxonium iodide (60.8 g) in 1,2-dimethoxyethane (250 ml) at 20° C. After 1 hour, the mixture was added portionwise over 30 minutes to a stirred solution of 4-oxo-1-piperidinecarboxylic acid, 1,1-dimethylethyl ester (50 g) in 1,2-dimethoxyethane (50 ml) at 0° C. After a further 2 hours, water (500 ml) was added and the mixture extracted with tert.-butyl methyl ether (2×500 ml). The organic extracts were washed separately with saturated sodium bicarbonate solution (250 ml), combined, dried over anhydrous magnesium sulphate, filtered and evaporated under reduced pressure. The residual oil was co-evaoprated with toluene (100 ml) to give the sub-title compound (43.25 g, 81%) as a solid.

$^1$H-NMR (400 MHz, CDCl$_3$): δ 1.46 (9H, s), 1.43-1.48 (2H, m), 1.75-1.84 (2H, m), 2.69 (2H, s), 3.38-3.47 (2H, m), 3.70-3.75 (2H, m).

(ii) 5-Chlorospiro[1-benzofuran-2,4'-piperidine]-1'-carboxylic acid, 1,1-dimethyl ester A solution of iso-propylmagnesium chloride in tetrahydrofuran (2M, 106.6 ml) was added dropwise over 15 minutes to a stirred solution of 2-bromo-4-chloro-1-fluorobenzene (42.5 g) in anhydrous tetrahydrofuran (250 ml) at 0° C. under nitrogen. After a further 15 minutes; a solution of 1-oxa-6-azaspiro[2.5]octane-6-carboxylic acid, 1,1-dimethylethyl ester (43.2 g) in anhydrous tetrahydrofuran (50 ml) was added followed by copper(I) bromide dimethyl sulphide complex (0.4 g). The mixture was stirred at 40° C. for 18 hours, cooled to 20° C., diluted with water (300 ml) and extracted with with tert.-butyl methyl ether (2×300 ml). Organic extracts were dried over anhydrous magnesium sulphate, filtered and evaporated under reduced pressure. The residual oil was dissolved in 1,2-dimethoxypropane (200 ml). Potassium tert.-butoxide (22.8 g) was added and the mixture stirred at 40° C. for 16 hours then at 50° C. for 24 hours. Further potassium tert.-butoxide (5.7 g) was added and stirring continued at 50° C. for 2 hours then at 55° C. for 4 hours. Water (500 ml) was added and the mixture extracted with tert.-butyl methyl ether (2×300 ml). Organic extracts were dried over anhydrous magnesium sulphate, filtered and evaporated under reduced pressure to give the sub-title compound (47.45 g, 67%) as an oil.

$^1$H-NMR (400 MHz, CDCl$_3$): δ 1.47 (9h, s), 1.67 (2H, td), 1.85-1.93 (2H, m), 2.94 (2H, s), 3.39 (2H, td), 3.65-3.80 (2H, m), 6.67 (1H, d), 7.06 (1H, d), 7.10 (1H, s).

iii) 5-Chlorospiro[1-benzofuran-2,4'-piperidine]

Concentrated hydrochloric acid (23 ml) was added to a solution of 5-chlorospiro[1-benzofuran-2,4'-piperidine]-1'-carboxylic acid, 1,1-dimethyl ester (46.43 g) in tetrahydrofuran (230 ml). The mixture was stirred at 50° C. for 6 hours, cooled to 20° C., diluted with water (230 ml) and extracted with tert.-butyl methyl ether (2×230 ml). The aqueous phase was adjusted to pH >10 by addition of 50 wt. % sodium hydroxide solution and extracted with tert.-butyl methyl ether (3×300 ml). Organic extracts were dried over anhydrous magnesium sulphate, filtered and evaporated under reduced pressure. The residual oil was dissolved in tetrahydrofuran (240 ml), concentrated hydrochloric acid (12 ml) was added and the mixture stirred at 20° C. for 16 hours. Precipitated solid was filtered and dissolved in water (100 ml). The solution was adjusted to pH >10 by addition of 50 wt. % sodium hydroxide solution and extracted with tert.-butyl methyl ether (3×100 ml) to give the title compound (13.3 g, 45%) as a solid.

$^1$H-NMR (400 MHz, CDCl$_3$): δ 1.69-1.76 (2H, m), 1.83-1.87 (2H, m), 2.78-2.84 (2H, m), 2.98-3.03 (4H, m), 6.65 (1H, d), 7.04 (1H, d), 7.13 (1H, s). APCI-MS: m/z 224/6 [M+H]$^+$

Intermediate Compound: 5-Fluoro-3H-spiro[1-benzofuran-2,4'-piperidine]

Method A:

i) 1'-Benzyl-5-fluoro-3H-spiro[1-benzofuran-2,4'-piperidine]

To a stirring suspension of magnesium strip (763 mg) in diethyl ether (7 mL) was added a crystal of iodine followed by (0.4 mL of 2-(bromomethyl)-1,4-difluorobenzene under nitrogen. The reaction mixture was initiated with a high intensity heat gun, 2-(bromomethyl)-1,4-difluorobenzene 5.0 g, 24.25 mmol) in diethyl ether (7 mL) was added slowly maintaining gentle reflux. After addition was completed the reaction mixture was stirred at reflux for 100 min, cooled to room temperature. To this reaction mixture a solution of 1-benzylpiperidin-4-one (4.57 g, 24.25 mmol) in diethyl ether (12 mL) was added dropwise with vigorous stirring. After addition was completed the reaction mixture was left at room temperature overnight. Aqueous NH$_4$Cl solution was added and stirred at room temperature until hydrolysis was completed, extracted with diethyl ether. The organic layer was washed with H$_2$O, dried over Na$_2$SO$_4$, filtered and concentrated in vacuo. The residue was purified by silica gel flash chromatography (0-1% methanol in dichloromethane, 0.2% NH$_4$OH) to give intermediate 1-benzyl-4-(2,5-difluorobenzyl)piperidin-4-ol (2.74 g) containg large quantities of unknown impurities. To a suspension of NaH (55%, 1.12 g, 26.0 mmol) in toluene (10 mL) was slowly added a solution of 1-benzyl-4-(2,5-difluorobenzyl)piperidin-4-ol in toluene (15 mL). After addition was completed the reaction mixture was stirred at 110° C. (in a pre heated oil bath), after 5 min, DMF (9 mL) was added and stirring was continued at reflux temperature for 2 h. The reaction mixture was cooled to room temperature, H$_2$O (20 mL) was added and extracted with ethyl acetate. The organic layer was dried over Na$_2$SO$_4$, filtered and concentrated. The residue was purified by silica gel flash chromatography (0-1.5% methanol in dichloromethane, 0.2% NH$_4$OH) to give the subtitled compound (190 mg).

$^1$H-NMR (CDCl$_3$, 400 MHz): δ 7.39-7.26 (m, 5H); 6.88-6.76 (m, 2H); 6.67 (dd, J=4.2, 8.7 Hz, 1H); 3.59 (s, 2H); 2.99 (s, 2H); 2.68-2.47 (m, 4H); 2.03-1.94 (m, 2H); 1.86-1.76 (m, 2H). APCI-MS: m/z 298 (MH$^+$).

(ii) 5-Fluoro-3H-spiro[1-benzofuran-2,4'-piperidine]

Ethyl chloroformate (65.6 mg, 0.604 mmol) was added to a solution of 1'-benzyl-5-fluoro-3H-spiro[1-benzofuran-2,4'-piperidin](150 mg, 0.504 mmol) in toluene (2 mL) and the reaction mixture was refluxed overnight. The reaction mixture was cooled to room temperature, diluted by addition of toluene, washed successively with aqueous NaHCO$_3$ and H$_2$O. The organic layer was dried over Na$_2$SO$_4$, filtered and concentrated in vacuo. The residue was dissolved in ethanol (3.5 mL), aqueous KOH (800 mg, KOH in 0.8 mL H$_2$O) was added and the reaction mixture was stirred at reflux temperature overnight, cooled to room temperature, ethanol was removed in vacuo. Aqueous layer was extracted with Et$_2$O, combined ether layer was washed with 3N aqueous HCl. Combined aqueous layer was made pH 10 by addition of aqueous NaOH. The basic solution was extracted with ethyl acetate. The combined organic layer was washed with H$_2$O, dried over Na$_2$SO$_4$, filtered and concentrated. The residue was purified by HPLC (10-55% CH$_3$CN in H$_2$O, 0.1% NH$_4$OH) to give the titled compound (49 mg).

$^1$H-NMR (CD$_3$OD, 400 MHz): δ 6.92-6.87 (m, 1H); 6.81-6.75 (m, 1H); 6.64 (dd, J=4.2, 8.7 Hz, 1H); 3.08-2.98 (m, 4H); 2.89-2.81 (m, 2H); 1.91-1.83 (m, 2H); 1.78-1.71 (m, 2H). APCI-MS: m/z 208 (MH$^+$).

Method B:

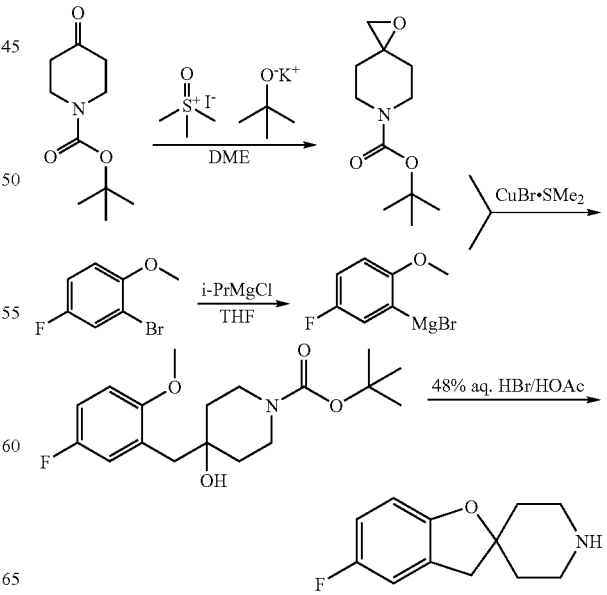

(i) 4-[(5-Fluoro-2-methoxyphenyl)methyl]-4-hydroxy-1-piperidinecarboxylic acid, 1,1-dimethylethyl ester A solution of iso-propylmagnesium chloride in tetrahydrofuran (2M, 130 ml) was added dropwise over 30 minutes to a stirred solution of 2-bromo-4-fluoroanisole (34.2 ml) in anhydrous tetrahydrofuran (400 ml) at 30° C. under nitrogen. After a further 16 hours at 30° C., copper(I) bromide dimethyl sulphide complex (0.4 g) was added followed by a solution of 1-oxa-6-azaspiro[2.5]octane-6-carboxylic acid, 1,1-dimethylethyl ester (56.2 g) in anhydrous tetrahydrofuran (I 10 ml). After a further 3 hours at 30° C., the solution was cooled to 20° C., diluted with water (600 ml) and extracted with tert.-butyl methyl ether (600 ml) then ethyl acetate (600 ml). Combined organic extracts were dried over anhydrous magnesium sulphate, filtered and evaporated under reduced pressure to give crude sub-title compound (86 g) as a solid.

APCI-MS: m/z 240 μM+H—(CH$_3$)$_2$CCH$_2$—CO$_2$]$^+$ (ii) 5-Fluorospiro[1-benzofuran-2,4'-piperidine]hydrochloride Hydrobromic acid (48%, 60 ml) was added to a solution of the crude 4-[(5-Fluoro-2-methoxyphenyl)methyl]4-hydroxy-1-piperidinecarboxylic acid, 1,1-dimethylethyl ester in acetic acid (300 ml). The mixture was heated at reflux for 5 hours. Further hydrobromic acid (48%, 60 ml) was added and reflux continued for 24 hours. The mixture was cooled to room temperature, added to water (2 l) and extracted with tert.-butyl methyl ether (2×500 ml). The aqueous phase was adjusted to pH >10 by addition of 50 wt. % sodium hydroxide solution and extracted with tert.-butyl methyl ether (21+11). Organic extracts were dried over anhydrous magnesium sulphate, filtered and evaporated under reduced pressure. The residual oil was dissolved in tetrahydrofuran (200 ml), concentrated hydrochloric acid (13 ml) was added and the solution evaporated under reduced pressure. The residual solid was crystallised from tetrahydrofuran/tert.-butyl methyl ether (4:1, 500 ml) to give the title compound (20.0 g, overall yield 31%).

$^1$H-NMR (CD$_3$OD, 400 MHz): δ 1.86-1.98 (2H, m), 2.03-2.07 (2H, m), 3.05 (2H, s), 3.16-3.27 (4H, m), 6.61 (1H, dd), 6.74 (1H, dt), 6.81 (1H, dd). APCI-MS: m/z 208 [M+H]$^+$

Intermediate Compound:
3H-Spiro[1-benzofuran-2,4'-piperidine]

This compound was prepared as described by Effland, R. C; Gardner, B. A; Strupczewski, J., *J. Heterocyclic Chem.*, 1981, 18, 811-814.

Intermediate compound: 5-Methyl-3H-spiro[1-benzofuran-2,4'-piperidine]

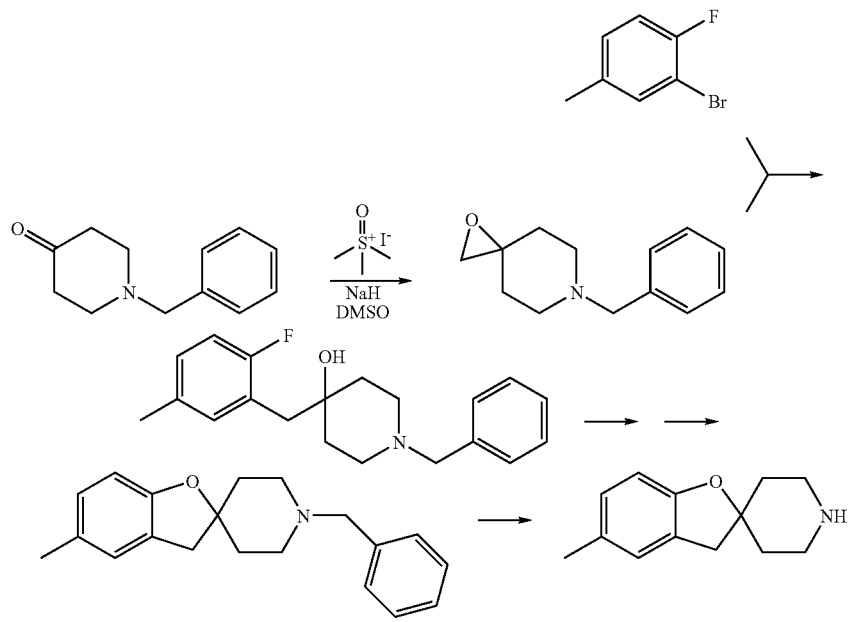

(i) 6-benzyl-1-oxa-6-azaspiro[2.5]octane

Sodium hydride (55% suspension in mineral oil, 1.57 g, 35 mmol) was washed with heptane, dried in the stream of nitrogen and suspended in dry DMSO (10 ml). A solution of trimethylsulfoxonium iodide (4.8 g, 22 mmol) in DMSO (45 ml) was added dropwise under nitrogen. After stirring for 20 min a solution of 1-benzylpiperidin-4-one (3.78 g, 20 mmol) was added dropwise. The mixture was stirred overnight at room temperature, then poured over ice (200 g), and extracted with dichloromethane (2×200 ml). The combined extracts were washed with water (3×100 ml) and dried over Na$_2$SO$_4$. The solvent was removed i. vacuo. The residue was dissolved in diethyl ether, and the insoluble material was removed by filtration. Evaporation of solven afforded pale-yellow oil (2.95 g, 73%).

$^1$H-NMR (CDCl$_3$, 400 MHz): δ 7.2-7.4 (m, 5H); 3.57 (s, 2H); 2.5-2.7 (m, 4H); 1.85 (m, 2H); 1.55 (m, 2H).

(ii) 1-benzyl-4-(2-fluoro-5-methylbenzyl)piperidin-4-ol

To a solution of 2-bromo-1-fluoro-4-methylbenzene (0.76 g, 4 mmol) in THF (15 ml) at −70° C. under Ar a solution of n-BuLi (1.6 M in hexane, 2.5 ml, 4 mmol) was added dropwise. The reaction mixture was stirrred at −70° C. for 1 h, then BF$_3$.Et$_2$O (0.5 ml, 4 mmol) was added. After stirring for 20 min at −70° C., a solution of 6-benzyl-1-oxa-6-azaspiro[2.5]

octane (0.41 g, 2 mmol) in dry THF (5 ml) was added dropwise. The stirring was continued for 2 h at −70° C., then the reaction mixture was quenched with sat. aq. NH₄Cl (20 ml). The layers were separated, the aqueous layer extracted with THF. The combined organic layers were dried over Na₂SO₄. The solvent was removed in vacuo. Diethyl ether (50 ml) was added to the residue, folowed by a 2 M HCl in Et₂O (5 ml). The precipitate was collected, washed with Et₂O, and dissolved in minimal volume of methanol (ca. 5 ml). Water (50 ml) was added, and pH adjusted to 10 by addition of 2 M aq. NaOH. The mixture was extracted with ethyl acetate (2×25 ml), and the combined organic extracts were dried with Na₂SO₄. Evaporation of solvent afforded brownish oil.

APCI-MS: m/z 314 [M+H]+

(iii) 1'-benzyl-5-methyl-3H-spiro[1-benzofuran-2,4'-piperidine]

To a suspension of NaH (55% in mineral oil, 200 mg, 5 mmol) in toluene (10 mL) was slowly added a solution of crude 1-benzyl-4-(2-fluoro-5-methylbenzyl)piperidin-4-ol in toluene (15 mL). After addition was completed, the reaction mixture was heated to 110° C. and stirred for 5 min. DMF (9 mL) was added and stirring was continued at reflux temperature for 10 h. The reaction mixture was cooled to room temperature, poured into water (50 ml), and extracted with ethyl acetate (2×25 ml). The organic layer was dried over Na₂SO₄, filtered and concentrated. The residue was purified by silica gel flash chromatography (ethyl acetate/n-heptane) to give the subtitle compound (240 mg, 41%).

¹H-NMR (CDCl₃, 400 MHz): δ 7.2-7.4 (m, 5H); 6.8-6.9 (m, 2H); 6.64 (d, J=10.8 Hz, 1H); 3.54 (s, 2H); 2.91 (s, 2H); 2.4-2.7 (m, 4H); 2.24 (s, 3H); 1.92 (m, 2H); 1.78 (m, 2H). APCI-MS: m/z 294 [M+H]⁺

(iv) 5-methyl-3H-spiro[1-benzofuran-2,4'-piperidine]

To a solution of 1'-benzyl-5-methyl-3H-spiro[1-benzofuran-2,4'-piperidine](0.12 g, 0.41 mol) in dichloromethane (3 ml) was added 1-chloroethyl chloroformate (87 mg, 0.61 mmol). The solution was stirred at room temperature overnight. The solvent was removed i. vacuo. The residue was dissolved in methanol (3 ml), and the solution was heated at 70° C. for 2 h. The solvent was eeporated, and the residue treated with diethyl ether. The precipitate formed was collected by filtration, washed with diethyl ether, and dissolved in methanol (1 ml). Water (25 ml) was added, and pH was adjusted to 10 by addition of 2 M aq. NaOH. The mixture was extracted with dichloromethane (2×25 ml), and the combined organic extracts were dried over Na₂SO₄. Evaporation of solvent afforded brownish oil (64 mg, 77%).

¹H-NMR (CDCl₃, 400 MHz): δ 6.95 (s, 1H); 6.90 (d, J=8 Hz, 1H); 6.64 (d, J=8 Hz, 1H); 3.11 (m, 2H); 2.95 (s, 2H); 2.85 (m, 2H); 2.26 (s, 3H); 1.88 (m, 2H); 1.72 (m, 2H). APCI-MS: m/z 204 [M+H]⁺

Intermediate Compound: 5-(Trifluoromethyl)-3H-spiro[1-benzofuran-2,4'-piperidine]

(i) 1-Benzyl-4-[2-fluoro-5-(trifluoromethyl)benzyl]piperidin-4-ol

To a stirring suspension of Mg strips (308 mg) in Et₂O (5 mL) was added a crystal of iodine followed by 0.3 mL of 2-(bromomethyl)-1-fluoro-4-(trifluoromethyl)benzene under argon. The reaction was initiated with a high intensity heat gun, then 2-(bromomethyl)-1-fluoro-4-(trifluoromethyl)benzene (2.5 g, 9.73 mmol) in Et₂O (5 mL) was added slowly (maintaining reflux). After addition was completed the reaction mixture was refluxed for 50 min, cooled to room temperature. A solution of 1-benzylpiperidin-4-one (1.84 g, 9.73 mmol) in Et₂O (10 mL) was added slowly with vigorous stirring. After addition was completed, the reaction mixture was left at room temperature for 50 min, saturated aqueous NH₄Cl solution was added and stirred at room temperature untill hydrolysis was finished, extracted with ethyl acetate. The combined organic layer was washed with water, dtied over Na₂SO₄, filtered and concentrated. The residue was purified by silica gel flash chromatography (0-1% methanol in dichloromethane, 0.2% NH₄OH) to give the subtitled compound (720 mg).

APCI-MS: m/z 368 (MH⁺).

(ii) 1'-Benzyl-S-(trifluoromethyl)-3H-spiro[1-benzofuran-2,4'-piperidine]

To a suspension of NaH (55%) (127 mg, 2.91 mmol) in toluene (4 mL) was slowly added a solution of 1-benzyl-4-[2-fluoro-5-(trifluoromethyl)benzyl]piperidin-4 (715 mg, 1.94 mmol) in toluene (5 mL) at room temperature. After addition was completed the reaction mixture was stirred at 110° C. for 5 min, then DMF (3 mL) was added and the reaction mixture was stirred at reflux temperature for 40 min, cooled to room temperature, H₂O (3 mL) was added, extracted with ethyl acetate. The organic layer was dried over Na₂SO₄, filtered and concentrated. The residue was purified by silica gel flash chromatography (0-1% methanol in dichloromethane, 0.2% NH₄OH) to give the subtitled compound (380 mg).

¹H-NMR (CDCl₃, 400 MHz): δ 7.45-7.23 (m, 6H); 6.82 (d, J=9.0 Hz, 1H); 3.60 (s, 2H); 3.02 (s, 2H); 2.70-2.45 (m, 4H); 2.00 (m, 2H); 1.85 (m, 2H). APCI-MS: m/z 348 (MH⁺).

(iii) 5-(Trifluoromethyl)-3H-spiro[1-benzofuran-2,4'-piperidine]

To a solution of 1'-benzyl-5-(trifluoromethyl)-3H-spiro[1-benzofuran-2,4'-piperidin] (280 mg, 0.806 mmol) in toluene (3 mL) was added ethylchloroformate (0.093 mL, 0.967 mmol) and the reaction mixture was stirred at reflux temperature overnight, cooled to room temperature, diluted by addition of toluene and washed with aqueous NaHCO₃ and water successively. The organic layer was dried over Na₂SO₄, filtered and concentrated. The residue was dissolved in ethanol ((4 mL), aqueous KOH (1.14 g KOH in 1.2 mL of H₂O) was added and the reaction mixture was refluxed overnight, cooled to room temperature, ethanol was removed in vacuo. Aqueous layer was extracted with Et₂O, combined ether layer was washed with 3N aqueous HCl. Combined acidic layer was made pH 10 by addition of aqueous NaOH. The basic solution was extracted with ethyl acetate. The combined organic layer was washed with water, dried over Na₂SO₄, filtered and concentrated. The residue was purified by silica gel flash chromatography (0-2% methanol in dichloromethane, 0.2% NH₄OH) to give the subtitled compound (156 mg).

¹H-NMR (CD₃OD, 400 MHz): δ 7.29 (s, 1H); 7.39 (d, J=8.4 Hz, 1H); 6.82 (d, J=8.4 Hz, 1H); 3.10-3.00 (m, 4H); 2.89-2.81 (m, 2H); 1.94-1.86 (m, 2H); 1.82-1.74 (m, 2H). APCI-MS: m/z 258 (MH⁺).

Intermediate Compound: 5-chloro-3'-fluoro-3H-spiro[1-benzofuran-2.4'-piperidine]

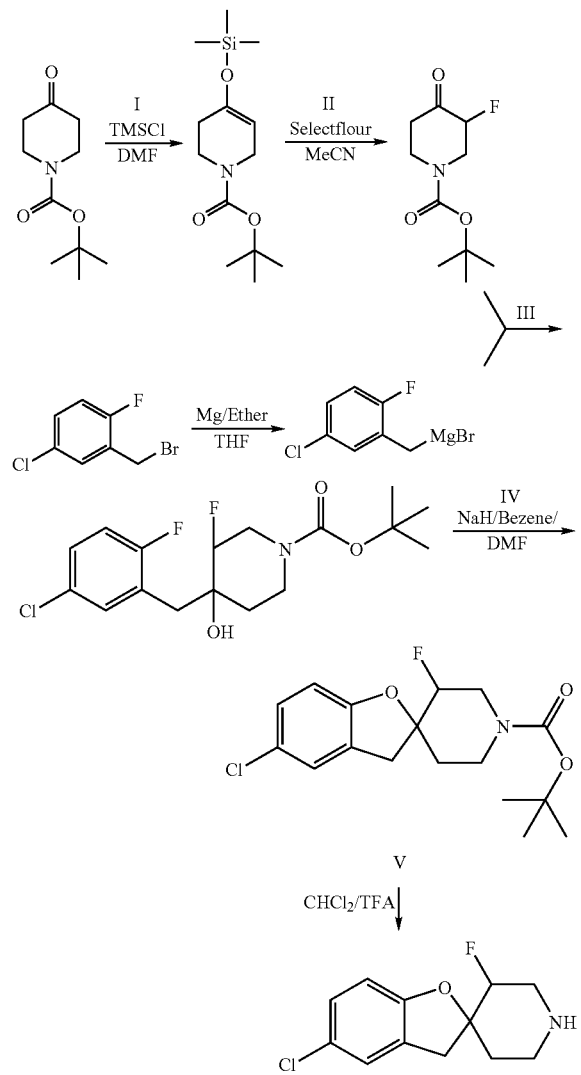

(i) tert-Butyl 4-[(trimethylsilyl)oxy]-3,6-dihydropyridine-[(2R)-carboxylate

To a solution of tert-butyl 4-oxopiperidine-1-carboxylate (10.13 g, 50.84 mmol) in DMF under argon was added TMSCl (7.74 ml, 61.27 mmol) followed by $Et_3N$ (17 ml). The mixture was stirred at 80° C. overnight. The solution was cooled to ambient temperature and then diluted with heptane, washed with conc. aq $NaHCO_3$ and water. The organic layer was then dried over sodium sulphate, filtered and concentrated. Chromatographic purification on silica gel (EtOAc: pethroleum ether 40-60 1:9) gave 9.6 g (69%) of an oil which solidified on standing.

$^1$H-NMR (CDCl$_3$, 300 MHz): δ 4.79 (m, 1H); 3.87 (m, 2H); 3,52 (t, J=5.8 Hz, 2H); 2.11 (m, 2H); 1.47 (s, 9H); 0.19 (s, 9H). APCI-MS: m/z 272 (M+H)$^+$.

(ii) tert-Butyl 3-fluoro-4-oxopiperidine-1-carboxylate

To a solution of tert-Butyl 4-[(trimethylsilyl)oxy]-3,6-dihydropyridine-[(2H)-carboxylate (9.52 g, 35.07 mmol) in $CH_3CN$ under argon was added selectfluor reagent (13.7 g, 38.6 mmol) and stirred at room temp. for 2 h. The reaction mixture was diluted with EtOAc (1000 ml), washed with dilute brine, water, dried over sodium sulphate, filtered and concentreated in vacuo. Chromatographic purification on silica gel (MeOH:EtOAc, from 0:1 to 2:98) gave 5.35 g (70%) of an oil, which solidified on standing.

$^1$H-NMR (CDCl$_3$, 300 MHz): δ 4.73-4.94 (m, 1H), 4.14-4.23 (m, 2H), 3.30-3.20 (m, 2H) 2.49-2.66 (m, 2H), 1.50 (s, 9H) APCI-MS: m/z 218 (M+H)$^+$ (iii) tert-Butyl 4-(5-chloro-2-fluorobenzyl)-3-fluoro-4-hydroxypiperidine-1-carboxylate To magnesium turnungs covered with ether was added a small amount of a solution of 2-(bromomethyl)-4-chloro-1-fluorobenzene in diethyl ether and the reaction was intiated by a high intesisty heat gun. To the refluxing mixture was added the remaining solution (150 ml) dropwise maintaining the reflux. After all the solution was added the mixture was stirred untill the reflux was ceased. A solution of tert-butyl 3-fluoro-4-oxopiperidne-1-carboxylate in diethylether (50 ml) was added slowly. The resulting mixture was sitirred for further 4 s at room temp., then it was quenched by slow addition sat. aq ammonium chloride (125 m). It was extracted with EtOAc (2×150 mml), washed with brine, water, dried over sodium sulphate, filtered and concentrated. The resulting residue was purified on silica gel (heptane-Et$_2$O 4:1-2:1) to give 1.61 g (18%) of subtitle compound.

$^1$H-NMR (CDCl$_3$300 MHz): δ 6.74 (s, 1H), 7.15 (s, 1H), 7.10-7.14 (m, 1H), 4.85-5.02 (m, 1H), 3.78-3.88 (m, 2H), 3.50 (m, 2H) 2.74 (s, 2H), 1.63-1.67 (m, 2H), 1.44 (s, 9H) APCI-MS: m/z 362 (M+H)$^+$ (iv) tert-Butyl 5-chloro-3'-fluoro-1'H,3H-spiro[1-benzofuran-2,4'-piperidine]-1'-carboxylate To a suspension of NaH (60% in mineral oil, 1.38 g, 4.35 mmol) in benzene (30 ml) was added a solution of tert-butyl 4-(5-chloro-2-fluorobenzyl)-3-fluoro-4-hydroxypiperidine-1-carboxylate in benzene (50 mml) and the mixture was heated to reflux. DMF 20 (mml) was added and refluxing continued for 6 hrs. The mixture was cooled to rt and poured into water and extracted with ETOAc. The organic layer was dried over sodium sulphate, filtered and concentrated. The residue was purified by chromatography on SiO$_2$ (ethylacetate: n-heptane) to give the product (10 mg, 26%).

APCI-MS m/z 342 [M+H]$^+$ (v) 5-Chloro-3'-fluoro-3H-spiro[1-benzofuran-2,4'-piperidine]

A solution of tert-butyl 5-chloro-3'-fluoro-1'H,3H-spiro[1-benzofuran-2,4'-piperidine]-1'-carboxylate in DCM/TFA (20 ml, 5:2) was stirred at room temp. for 2 h. the solvent was removed in vacuio, the residue diluted with EtOAc and washed with sat. aq. NaHCO$_3$, and water. The organic layer was dried over Na$_2$SO$_4$, filtered and concentrated to give the title compound (60 mg).

APCI-MS m/z 242 μM+H}$^+$

Intermediate Compound: 4H-spiro[chromene-3,4'-piperidine]

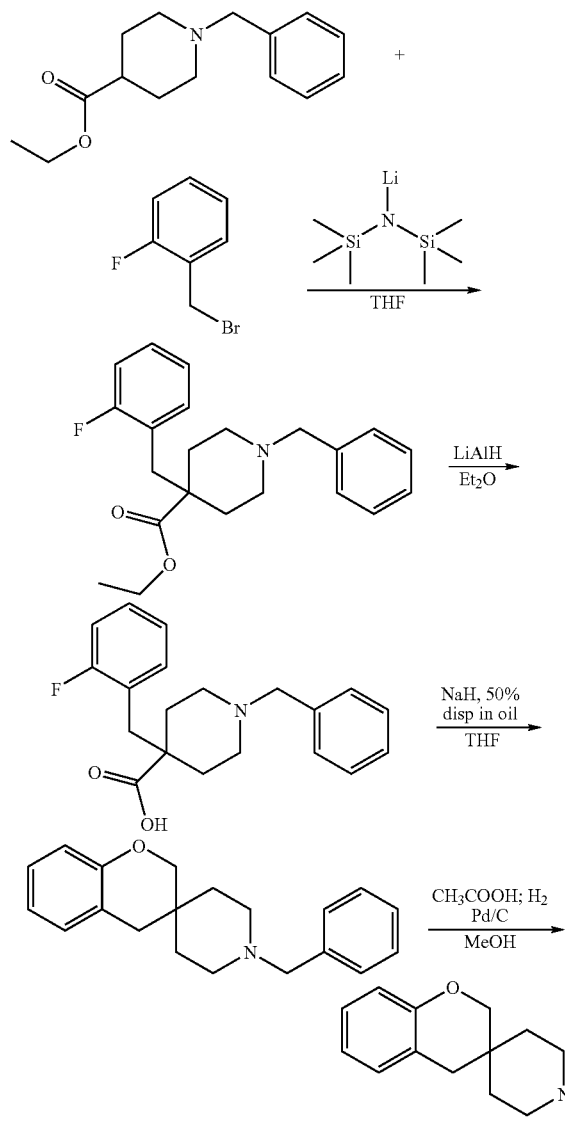

(i) Ethyl 1-benzyl-4-(2-fluorobenzyl)piperidine-4-carboxylate

Ethyl 1-benzylpiperidine-4-carboxylate (2.47 g, 10 mmol) was dissolved in tetrahydrofuran (20 mL) and cooled to −78° C. Lithium bis(trimethylsilyl)amide (11 mL, 1.0 M in tetrahydrofuran) was added slowly, and stirred for 30 minutes. 2-fluoro-benzylbromide (1.34 mL, 11 mmol) in 5 mL tetrahydrofuran was added slowly. The resulting solution was allowed to reach room temperature and stirred over night. The reaction was quenched with ammonium chloride (aq, sat) and partitioned between water and ethyl acetate. The organic layer was washed with brine and dried over magnesium sulphate, filtrated and concentrated. The crude material was purified on silica (heptane/ethyl acetate), to give 2.7 g (77%) the subtitle compound as a colourless oil.

APCI-MS: m/z 356 [MH+]

(ii) [1-Benzyl-4-(2-fluorobenzyl)piperidin-4-yl]methanol

A stirred solution of ethyl 1-benzyl-4-(2-fluorobenzyl)piperidine-4-carboxylate (1.85 g, 5.2 mmol) in diethyl ether was cooled on ice/sodium chloride. Lithium aluminium hydride (5.8 mL, 1.0 M in diethyl ether) was added drop wise. After stirring at room temperature for 2 hrs the mixture was re-cooled on ice, quenched with water/sodium hydroxide (10%) and stirred at room temperature for 1 hrs. The solids were filtered off, and the organic layer was dried over disodium sulphate, filtrated and concentrated. The crude material was purified on silica (dichloromethane/ethanol) to give 1.0 g (61%) the subtitle compound.

APCI-MS: m/z 314 [MH+]

(iii) 1'-Benzyl-4H-spiro[chromene-3,4'-piperidine]

Sodium hydride (350 mg, 7.0 mmol, 50% disp in oil) was washed three times with heptane, under nitrogen atmosphere, and then dissolved in tetrahydrofuran (50 mL). A solution of [1-benzyl-4-(2-fluorobenzyl)piperidin-4-yl]methanol (1 g, 3.2 mmol) in tetrahydrofuran (30 mL) was added and the resulting mixture was refluxed for 3 hrs. The cooled solution was partitioned between water and ethyl acetate and the organic layer was dried over magnesium sulphate and concentrated. The crude product was purified on silica (dichloromethane/methanol) to give 0.83 g (89%) of the subtitle compound.

APCI-MS: m/z 294 [MH+]

(iv) 4H-Spiro[chromene-3,4'-piperidine]

1'-benzyl-4H-spiro[chromene-3,4'-piperidine] (800 mg, 2.7 mmol) was dissolved in methanol (100 mL). Acetic acid (5 mL) and palladium on activated charcoal (cat amount, 10%) was added. Reaction in a Parr apparatus at 35 psi for 18 hrs, followed by filtration, evaporation and HPLC purification on C18 (acetonitrile/water) yielded 500 mg (92%) of the title compound.

$^1$H-NMR (400 MHz, DMSO-$d_6$) δ: 8.86 (1H, bs); 7.10-7.05 (2H, m); 6.85 (1H, dt); 6.76 (1H, d); 3.93 (2H, s); 3.15-3.01 (4H, m); 2.71 (2H, s); 1.66-1.51 (4H, m) APCI-MS: m/z 204 [MH$^+$]

Intermediate Compound: 6-Chloro-3,4-dihydrospiro[chromene-2,4'-piperidine]

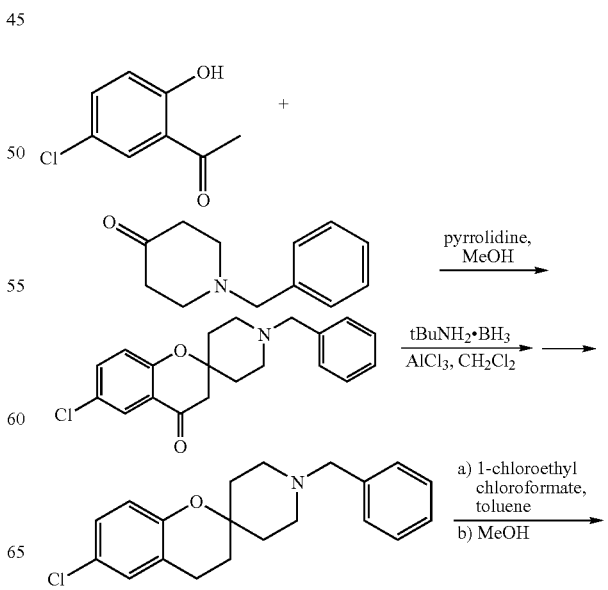

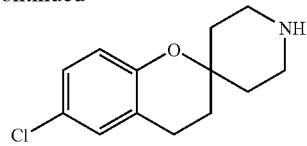

(i) 1'-Benzyl-6-chlorospiro[chromene-2,4'-piperidin]4(3R)-one

A solution of 1-(5-chloro-2-hydroxyphenyl)ethanone (1.7 g, 10 mmol), 1-benzylpiperidin-4-one (2.08 g, 11 mmol) and pyrrolidine (1.07 g, 15 mmol) in methanol (2 ml) was heated at 70° C. for 3 h. After cooling to room temperature, the reaction mixture was poured into water (20 ml), and extracted with ethyl acetate (50 ml). The organic layer was washed with 1 N aq. HCl (2×50 ml), 2 N aq. NaOH (50 ml), and water. Drying over $Na_2SO_4$ and evaporation of solvent afforded subtitle compound as orange-coloured oil (2.61 g, 77%).

APCI-MS: m/z 342 [M+H]$^+$ (ii) 1'-Benzyl-6-chloro-3,4-dihydrospiro[chromene-2,4'-piperidine]

To a stirred suspension of $AlCl_3$ (3.04 g, 22.8 mmol) in dichloromethane (75 ml) tert-butylamine-borane (1:1) (3.98 g, 45.8 mmol) was added at 0° C., and the stirring was continued for 15 min at this temperature to obtain a clear solution. A solution of 1'-benzyl-6-chlorospiro[chromene-2,4'-piperidin]-4(3H)-one (2.61 g, 7.6 mmol) in dichloromethane (15 ml) was added dropwise. The stirring was continued for 2 h at 0° C. and for 3 h at room temperature. The reaction mixture was quenched by dropwise addition of 0.1 N aq. HCl. After the gas evolution has ceased, the layers were separated. The organic layer was washed with 0.1 N HCl (2×50 ml) and brine (50 ml), and dried over $Na_2SO_4$. The solvent was removed in vacuo to afford subtitle compound as colourless solid (1.63 g, 65%).

APCI-MS: m/z 328 [M+H]$^+$ (iii) 6-Chloro-3,4-dihydrospiro[chromene-2,4'-piperidine] hydrochloride A solution of 1'-benzyl-6-chloro-3,4-dihydrospiro[chromene-2,4'-piperidine] (1.63 g, 5.0 mmol) and 1-chloroethyl chloroformate (1.07 g, 7.5 mmol) in toluene (5 ml) was heated with reflux overnight. The solvent was removed i. vacuo, the oily residue dissolved in methanol (10 ml) and heated with reflux overnight. The solvent was removed in vacuo, and the residue treated with diethyl ether (50 ml). The white precipitate was collected by filtration, washed with diethyl ether and dried to afford the subtitle compound as white powder (0.58 g, 49%).

$^1$H-NMR (CDCl$_3$, 400 MHz): δ 7.07 (d, J=10.0 Hz, 2H); 7.63 (d, J=8.4 Hz, 1H); 3.2-3.5 (m, 4H); 2.77 (t, J=6.6 Hz, 2H); 1.9-2.2 (m, 4H); 1.88 (t, J=6.6 Hz, 2H). APCI-MS: m/z 238 [M+H]$^+$

Intermediate Compound: 6-Chloro-3H-spiro[2-benzofuran-1,4'-piperidine]

(i) 1'-Benzyl-6-chloro-3H-spiro[2-benzofuran-1,4'-piperidin]-3-one

To a solution of 2-bromo-4-chlorobenzoic acid (2.35 g, 10.0 mmol) in tetrahydrofuran (THF) (15 mL) was added, a 1.6 M solution in hexane, n-butyllithium (Parham, W. E; Egberg, D. C.; Sayed, Y. A; Thraikill, R. W; Keyser, G. E; William, M. N; Montgomery, M. C; Jones, L. D., *J. Org. Chem.*, 1976, 41, 2628-2633) (20 mL, 32.0 mmol) slowly at −78° C. under nitrogen. After addition was complete the reaction mixture was stirred at −78° C. for 3 hours (h). Then a solution of 1-benzylpiperidin-4-one (3.78 g, 20.0 mmol) in THF (10 mL) was added slowly to the reaction mixture at −78° C. After addition was complete the reaction temperature was raised to room temperature and the reaction mixture was stirred at room temperature overnight. The reaction mixture was poured into a mixture of water ($H_2O$) (60 mL) and diethyl ether (60 mL), layers were separated. The aqueous layer was extracted with diethyl ether (2×20 mL). The aqueous layer was acidified with aq 6 M HCl to pH 2 and boiled for 1 h, cooled to 0° C., pH was adjusted to 10 by addition of aqueous sodium hydroxide (NaOH) (6M) and rapidly extracted with trichloromethane (CHCl$_3$). The organic layer was washed with $H_2O$, dried over sodium sulphate ($Na_2SO_4$), filtered and concentrated in vacuo to give sub-titled compound (1.22 g) and it was pure enough for the next step.

$^1$H-NMR (CDCl$_3$, 400 MHz): δ 7.84 (d, J=8.2 Hz, 1H); 7.51 (dd, J=1.7, 8.2 Hz, 1H); 7.45-7.25 (m, 6H); 3.67 (s, 2H); 3.00 (br.d; J=9.4 Hz, 2H); 2.61 (br.t, J=11.2 Hz, 2H); 2.32 (br, s, 2H); 1.74 (d, J=12.2 Hz, 2H). APCI-MS: m/z 328(MH$^+$).

(ii) 1'-Benzyl-6-chloro-3H-spiro[2-benzofuran-1,4'-piperidine]

To a solution of 1'-benzyl-6-chloro-3H-spiro[2-benzofuran-1,4'-piperidine]-3-one (1.1 g, 3.35 mmol) in THF (15 mL) was added 1 M solution of borane (Marxer, A; Rodriguez, H. R; McKenna, J. M; Tsai, H. M., *J. Org. Chem.*, 1975, 40, 1427-1430) complex in THF (7 mL, 7.0 mmol) slowly at 0° C. After addition was complete, the reaction mixture was kept at room temperature for 30 minutes (min), then kept at reflux overnight, cooled to 0° C. and 6M aqueous hydrochloric acid (HCl) (3.5 mL) was added slowly. The reaction mixture was kept at reflux for 5 h, cooled to 0° C., pH of the reaction mixture was adjusted to 10 by addition of aqueous NaOH 6M and the whole was extracted with ethyl acetate. The organic layer was washed with $H_2O$, dried over $Na_2SO_4$, filtered, and concentrated in vacuo. The residue was purified by silica gel flash chromatography (0-30% ethyl acetate in petroleum ether) to give the sub-titled compound (900 mg).

$^1$H-NMR (CDCl$_3$, 400 MHz): δ 7.44-7.22 (m, 6H); 7.18 (m, 2H); 5.03 (s, 2H); 3.60 (s, 2H) 2.87 (br.d, J=10.5 Hz, 2H); 2.45 (br.t, J=11.2 Hz, 2H); 2.00 (br.s, 2H); 1.79 (d, J=11.2 Hz, 2H). APCI-MS: m/z 314(MH$^+$).

(iii) 6-Chloro-3H-spiro[2-benzofuran-1,4'-piperidine]

To a solution of 1'-benzyl-6-chloro-3H-spiro[2-benzofuran-1,4'-piperidine] (850 mg, 2.7 mmol) in dichloromethane ($CH_2Cl_2$) (8 mL) was added chloroethyl chloroformate (Yang, B. V; o'Rourke, D; Li, J., *Synlett*, 1993, 195-196) (772 mg, 5.4 mmol) slowly at 0° C. After addition was complete the reaction mixture was stirred at 0° C. for 30 min. The volatiles were removed in vacuo, residue was dissolved in methanol (10 mL) and kept at reflux for 40 min. The volatiles were removed in vacuo and the residue was purified by silica gel flash chromatography (0-6% methanol in dichloromethane, 0.2% ammonium hydroxide (NH$_4$OH)) to give the titled compound (170 mg) and 1'-benzyl-6-chloro-3H-spiro[2-benzofuran-1,4'-piperidine] was recovered (200 mg).

$^1$H-NMR (CD$_3$OD, 400 MHz): δ 7.29-7.21 (m, 3H); 5.00 (s, 2H); 2.99 (m, 4H); 1.90-181 (m, 2H); 1.70 (m, 2H). APCI-MS: m/z 224(MH$^+$).

Intermediate Compound: 5-Fluoro-3H-spiro[2-benzofuran-1,4'-piperidine]

(iv) 1'-Benzyl-5-fluoro-3H-spiro[2-benzofuran-1,4'-piperidin]-3-one

This reaction was performed as described for (i) above using 2-bromo-5-fluorobenzoic acid (2.19 g, 10.0 mmol), 1-benzylpiperidin-4-one (3.78 g, 20.0 mmol), n-butyl lithium (n-BuLi) (20 mL) and THF (20 mL) to give the sub-titled compound.

$^1$H-NMR (CDCl$_3$, 400 MHz): δ 7.58-7.23 (m, 8H); 3.68 (s, 2H); 2.98 (m, 2H); 2.59 (m, 2H); 2.28 (m, 2H); 1.74 (m, 2H). APCI-MS: m/z 312(MH$^+$).

(v) 1'-Benzyl-5-fluoro-3H-spiro[2-benzofuran-1,4'-piperidine]

This reaction was performed as described for (ii) above using 1'-benzyl-5-fluoro-3H-spiro[2-benzofuran-1,4'-piperidin]-3-one (200 mg, 0.642 mmol), borane THF complex 1M solution (1.34 mL, 1.34 mmol) and THF (3 mL) to give the sub-titled compound (148 mg).

$^1$H-NMR (CDCl$_3$, 400 MHz): δ 7.41-7.27 (m, 5H); 7.08 (dd, J=4.8, 8.3 Hz, 1H); 6.97 (m, 1H); 6.89 (m, 1H); 5.08 (s, 2H); 3.60 (s, 2H); 2.87 (m, 2H); 2.46 (m, 2H); 1.97 (m, 2H); 1.88 (m, 2H). APCI-MS: m/z 298(MH$^+$).

(vi) 5-Fluoro-3H-spiro[2-benzofuran-1,4'-piperidine]

This reaction was performed as described for (iii) above using 1'-benzyl-5-fluoro-3H-spiro[2-benzofuran-1,4'-piperidine] (145 mg, 0.487 mmol), chloroethyl chloroformate (0.07 mL) to give the titled compound.

$^1$H-NMR (CD$_3$OD, 400 MHz): δ 7.18 (dd, J=4.9, 8.1 Hz, 1H); 7.03-6.96 (m, 2H); 5.01 (s, 2H); 3.09-2.93 (m, 4H); 1.91-1.81 (m, 2H); 1.73-1.66 (m 2H). APCI-MS: m/z 208 (MH$^+$).

Intermediate Compound: [(2S)-2-methyloxiran-2-yl]methyl 3-nitrobenzenesulfonate

Prepared as described by Eriksson, T.; Klingstedt, T.; Mussie, T., Published International Patent Application No. WO 01/98273.

Example 1

N-(2-{[(2S)-3-(5-Chloro-1'H,3H-spiro[1-benzofuran-2,4'-piperidin]-1'-yl)-2-hydroxypropyl]oxy}phenyl)acetamide Step I:

N-{2-[(2S)-Oxiran-2-ylmethoxy]phenyl}acetamide

A mixture of N-(2-hydroxyphenyl)acetamide (1.51 g, 10 mmol), (2S)-oxiran-2-ylmethyl-3-nitrobenzenesulfonate (2.59 g, 10 mmol) and cesium carbonate (Cs$_2$CO$_3$) (3.9 g, 12 mmol) in dimethylformamide (DMF) (30 mL) was stirred at room temperature overnight. The reaction mixture was partitioned between ethyl acetate and H$_2$O. The organic layer was dried over Na$_2$SO$_4$, filtered, concentrated and the residue was purified by silica gel flash chromatography to give the sub-titled compound (1.34 g).

$^1$H-NMR (CDCl$_3$, 400 MHz): δ 8.40 (m, 1H); 7.90 (br.,s, 1H); 7.05 (m, 2H); 6.92 (m, 1H); 4.37 (dd, J=2.5, 11.3 Hz, 1H); 3.98 (dd, J=5.9, 11.3 Hz, 1H); 3.40 (m, 1H); 2.97 (t, J=4.8 Hz, 1H); 2.81 (dd, J=2.7, 4.8 Hz, 1H); 2.20 (s, 3H).

Step II:

N-(2-{[(2S)-3-(5-Chloro-1'H,3H-spiro[1-benzofuran-2,4'-piperidin]-1'-yl)-2-hydroxypropyl]oxy}phenyl)acetamide A mixture of 5-chloro-3H-spiro[1-benzofuran-2,4'-piperidine] (36 mg, 0.16 mmol) and N-{2-[(2S)-oxiran-2-ylmethoxy]phenyl}acetamide (33 mg, 0.16 mmol) in ethanol (3 mL) was stirred at 80° C. overnight. The volatiles were removed in vacuo and the residue was purified by silica gel flash chromatography (0-3% methanol in dichloromethane containing 0.2% ammonium hydroxide) to give the titled compound (25 mg).

$^1$H-NMR (CDCl$_3$, 400 MHz): δ 7.82 (d, J=4.8 Hz, 1H); 7.22 (m, 1H); 7.13 (m, 2H); 7.05 (d, J=7.5 Hz, 1H); 6.98 (m, 1H); 6.74 (d, J=8.6 Hz, 1H); 4.49 (m, 1H); 4.08 (d, J=4.8 Hz, 2H); 3.70 (m, 2H); 3.43 (m, 4H); 3.12 (s, 2H); 2.20 (m, 7H). APCI-MS: m/z 433 (MH$^+$).

Example 2

N-(2-{[(2S)-3-(5-Chloro-1'H,3H-spiro[1-benzofuran-2,4'-piperidin]-1'-yl)-2-hydroxypropyl]oxy}-4-fluorophenyl)acetamide Step I:

N-(4-Fluoro-2-hydroxyphenyl)acetamide

A mixture of 5-fluoro-2-nitrophenol (5 g, 31.8 mmol), acetic anhydride (4.86 g, 47.7 mmol) and platinum on carbon (5%, 200 mg) in methanol was hydrogenated at 35 psi for 3 hours. The catalyst was filtered off and the residue was purified by silica gel flash chromatography to give the subtitled compound (4.7 g).

$^1$H-NMR (CD$_3$OD, 300 MHz): δ 7.56-7.51 (m, 1H); 6.61-6.50 (m, 2H); 2.15 (s, 3H). APCI-MS: m/z 170 (MH$^+$).

Step II:

N-{4-Fluoro-2-[(2S)-oxiran-2-ylmethoxy]phenyl)acetamide

A mixture of N-(4-fluoro-2-hydroxyphenyl)acetamide (1.69 g, 10.0 mmol), (2S)-oxiran-2-ylmethyl-3-nitrobenzenesulfonate (2.59 g, 10.0 mmol) and Cs$_2$CO$_3$ (4.87 g, 15.0 mmol) in DMF (15 mL) was stirred at room temperature for 2 h. The reaction mixture was partitioned between ethylacetate and H$_2$O. The organic layer was dried over Na$_2$SO$_4$ filtered and concentrated. The residue was purified by silica gel flash chromatography to give the subtitled compound (1.35 g).

$^1$H-NMR (CDCl$_3$, 400 MHz): δ 8.33-8.29 (m, 1H); 7.71 (br. S, 1H), 6.74-6.66 (m, 2H); 4.39-4.36 (m, 1H); 3.95-3.90 (m, 1H); 3.41-3.39 (m, 1H); 2.99-2.97 (m, 1H); 2.80-2.79 (m, 1H). APCI-MS: m/z 226 (MH$^+$).

Step III:

N-(2-{[(2S)-3-(5-Chloro-1'H,3H-spiro[1-benzofuran-2,4'-piperidin]-1'-yl}2-hydroxypropyl]oxy}-4-fluorophenyl)acetamide A mixture of 5-chloro-3H-spiro[1-benzofuran-2,4'-piperidine] (45 mg, 0.201 mmol) and N-{4-fluoro-2-[(2S)-oxiran-2-ylmethoxy]phenyl}acetamide (45.3 mg, 0.201 mmol) in ethanol (3 mL) was stirred at 80° C. overnight. The volatiles were removed in vacuo and the residue was purified by silica gel flash chromatography (0-3% methanol in dichloromethane, 0.2% NH$_4$OH) to give the titled compound (33 mg).

$^1$H-NMR (CDCl$_3$, 400 MHz): δ 8.52 (s, 1H); 8.20 (dd, J=6.4, 8.9 Hz, 1H); 7.18 (s, 1H); 7.13 (dd, J=2.0, 8.5 Hz, 1H);

6.74 (dd, J=2.6, 8.6 Hz, 1H); 6.69 (d, J=8.6 Hz, 1H); 6.59 (dd, J=2.6, 9.8 Hz, 1H); 4.48 (m, 1H); 4.17 (dd, J=3.7, 9.8 Hz, 1H); 4.00 (dd, J=2.2, 9.8 Hz, 1H); 3.79 (m, 2H); 3.59 (br.d, J=11.7 Hz, 1H); 3.38 (m, 1H); 3.27 (m, 1H); 3.12 (s, 2H); 3.05 (m, 1H); 2.48 (m, 1H); 2.37 (m, 1H); 2.24 (s, 3H); 2.17 (m, 2H). APCI-MS: m/z 451 (MH$^+$).

Example 3

N-(2-{[(2S)-3-(5-Chloro-1'H,3H-spiro[1-benzofuran-2,4'-piperidin]-1'-yl)-2-hydroxypropyl]oxy}-4-methoxyphenyl)acetamide Step I:

N-(2-Hydroxy-4 methoxyphenyl)acetamide

2-Nitro-5-methoxyphenol (prepared from 3-methoxyphenol, R. J. Maleski, *Synthetic Communications*, 1993, 23, 343-348) (48.5 g, 0.287 mol) dissolved in THF (1.5 L) was hydrogenated at ambient temperature over night with 10% palladium on carbon (10 g) until 20.3 L of hydrogen was consumed. After filtration and evaporation the residue was suspended in degased water (1.7 L) and acetic anhydride (42.5 mL) was added with stirring. The mixture was heated to 60° C. for 1 h and then cooled to room temperature. The volatiles were removed in vacuo and the solid was washed thoroughly with water and dried in vacuo to give brick-red crystals (41.7 g, 80%).

$^1$H-NMR (400 MHz, CDCl$_3$): δ 8.98 (s, 1H); 7.34 (br.s, 1H); 6.81 (d, 1H); 6.58 (d, 1H); 6.44 (dd, 1H); 3.78 (s, 3H); 2.26 (s, 3H)

Step II:

N-{4-Methoxy-2[(2S)-oxiran-2-ylmethoxy]phenyl}acetamide

N-(2-Hydroxy-4-methoxyphenyl)acetamide (18.12 g, 0.1 mol) and (2S)-oxiran-2-ylmethyl-3-nitrobenzenesulfonate (25.92 g, 0.1 mol) were dissolved in dry DMF (75 mL) and stirred under nitrogen (N$_2$) on an ice-bath. Cesium carbonate (35.8 g, 0.1 mol) was added and the stirring under N$_2$ was continued at ambient temperature overnight. The mixture was poured into ethyl acetate (1 L) and water (250 mL). The organic phase was washed with water (3×250 mL), dried over Na$_2$SO$_4$, filtered and concentrated in vacuo to give an orange solid crude product (29 g), which was recrystallized from ethanol (100 mL) and washed with ether to give white crystals. More white crystals were obtained from the mother liquor, after evaporation and recrystallazition from 2-propanol. Total yield 15 g is (63%).

$^1$H-NMR (CDCl$_3$): δ 8.22 (d, 1H); 7.64 (bs, 1H); 6.53 (dd, 1H); 6.50 (d, 1H); 4.34 (dd, 1H); 3.92 (dd, 1H); 3.79 (s, 3H); 3.38 (m, 1H); 2.96 (t, 1H); 2.78 (dd, 1H); 2.20 (s, 3H)

Step III:

N-(2-{[(2S)-3-(5-Chloro-1'H,3H-spiro[1-benzofuran-2,4'-piperidin]-1'-yl)-2-hydroxypropyl]oxy}-4-methoxyphenyl)acetamide A mixture of 5-chloro-3H-spiro[1-benzofuran-2,4'-piperidine] (200 mg, 0.894 mmol) and N-{4-methoxy-2[(2S)-oxiran-2-ylmethoxy]phenyl}acetamide (212 mg, 0.894 mmol) in ethanol (5 mL) was stirred at 80° C. overnight. The volatiles were removed in vacuo and the residue was purified by silica gel flash chromatography (0-2% methanol in dichloromethane, 0.2% NH$_4$OH) to give the titled compound (400 mg).

$^1$H-NMR (CD$_3$OD, 400 MHz): δ 7.74 (d, J=8.9 Hz, 1H); 7.13 (m, 1H); 7.04 (dd, J=2.3, 8.5 Hz, 1H); 6.65 (d, J=8.5 Hz, 1H); 6.61 (d, J=2.7 Hz, 1H); 6.51 (dd, J=2.7, 8.8 Hz, 1H); 4.17 (m, 1H); 4.08 (dd, J=3.4, 10.0 Hz, 1H); 3.98 (dd, J=6.3, 9.9 Hz, 1H); 3.79 (s, 3H); 3.03 (s, 2H); 2.72 (m, 4H); 2.62 (m, 2H); 2.15 (s, 3H); 1.95 (m, 2H); 1.84 (m, 2H). APCI-MS: m/z 461 (MH$^+$).

Example 4

N-(2-{[(2S)-3-(5-Chloro-1'H,3H-spiro[1-benzofuran-2,4'-piperidin]-1'-yl)-2-hydroxypropyl]oxy}-4-hydroxyphenyl)acetamide To a cold (0° C.) solution of N-(2-{[(2S)-3-(5-chloro-1'H,3H-spiro[1-benzofuran-2,4'-piperidin]-1'-yl)-2-hydroxypropyl]oxy}-4-methoxyphenyl)acetamide (380 mg, 0.82 mmol) in dichloromethane (8 mL) was added 1M solution of boron tribromide (BBr$_3$) in dichloromethane (2.47 mL, 2.47 mmol) slowly. After addition was complete the icebath was removed and the reaction mixture was stirred at room temperature for 2 h 30 min. The reaction mixture was cooled to 0° C. and methanol (2 mL) was added slowly with stirring for 10 min. The volatiles were removed in vacuo. The residue was dissolved in large volume of ethyl acetate, washed successively with aqueous sodium hydrogencarbonate (NaHCO$_3$) solution and water. The organic layer was dried over Na$_2$SO4, filtered, concentrated and the residue was purified by silica gel flash chromatography (0-3% methanol in dichloromethane, 0.2% NH$_4$OH) to give the titled compound (155 mg).

$^1$H-NMR (CD$_3$OD, 400 MHz): δ 7.57 (d, J=8.7 Hz, 1H); 7.14 (m, 1H); 7.04 (dd, J=2.3, 8.5 Hz, 1H); 6.66 (d, J=8.5 Hz, 1H); 6.48 (d, J=2.5 Hz, 1H); 6.32 (dd, J=2.5, 8.6 Hz, 1H); 4.17 (m, 1H); 4.06 (dd, J=3.4, 9.8 Hz, 1H); 3.93 (dd, J=6.2, 9.8 Hz, 1H); 3.03 (s, 2H); 2.70 (m, 4H); 2.59 (m, 2H); 2.13 (s, 3H); 1.95 (m, 2H); 1.84 (m, 2H). APCI-MS: m/z 447 (MH$^+$).

Example 5

N-[2-{[(2S)-3-(5-Chloro-1'H,3H-spiro[1-benzofuran-2,4'-piperidin]-1'-yl)-2-hydroxypropyl]oxy}-5-(trifluoromethyl)phenyl]acetamide Step I:

N-(2-{[(2S)-2-Methyloxiran-2-yl]methoxy}-5-(trifluoromethyl)phenyl] acetamide

A mixture of 2-nitro-4-(trifluoromethyl)phenol (310 mg, 1.5 mmol), palladium on carbon (10%, 125 mg) and acetic anhydride (306.3 mg, 3.0 mmol) in methanol was hydrogenated for 2 h at atmospheric pressure. The catalyst was filtered off, the filtrate was concentrated in vacuo to give crude N-[2-hydroxy-5-(trifluoromethyl)phenyl]acetamide (331 mg). A part (219.16 mg, 1.0 mmol) of N-[2-hydroxy-5-(trifluoromethyl)phenyl]acetamide was treated with [(2S)-2-methyloxiran-2-yl]methyl3-nitrobenzenesulfonate (273.27 mg, 1.0 mmol) in the presence of Cs$_2$CO$_3$ (406.25 mg, 1.25 mmol) in DMF (5 mL) at room temperature for 5 h. The reaction mixture was partitioned between ethyl acetate and water. The organic layer was dried over Na$_2$SO$_4$, filtered, concentrated. The residue was purified by silica gel flash chromatography (0-40% ethyl acetate in petroleum ether) to give the subtitled compound (230 mg).

$^1$H-NMR (CDCl$_3$, 400 MHz): δ 8.86 (s, 1H); 8.00 (br.s, 1H); 7.29 (m, 1H); 6.97 (d, J=8.5 Hz, 1H); 4.23 (d, J=11.0 Hz, 1H); 4.04 (d, J=11.03 Hz, 1H) 2.93 (m, 1H); 2.81 (d, J=4.6 Hz, 1H); 2.22 (s, 31H); 1.42 (s, 3H).

Step II:

N-[2-{[(2S)-3-(5-Chloro-1'H,3H-spiro[1-benzofuran-2,4'-piperidin]-1'-yl)-2-hydroxypropyl]oxy}-5-(trifluoromethyl)phenyl]acetamide A mixture of 5-chloro-3H-spiro[1-benzofuran-2,4'-piperidine] (35 mg, 0.155 mmol) and N-[2-{[(2S)-2-methyloxiran-2-yl]methoxy}-5-(trifluoromethyl)phenyl]acetamide (45 mg, 0.155 mmol) in ethanol (2 mL) was stirred at 80° C. overnight. The volatiles were removed in vacuo and the residue was purified by silica gel flash chromatography (0-1.5% methanol in dichloromethane, 0.2% NH$_4$OH) to give the titled compound (28 mg).

$^1$H-NMR (CD$_3$OD, 400 MHz): δ 8.40 (d, J=1.8 Hz, 1H); 7.40 (dd, J=1.4, 8.7 Hz, 1H); 7.18 (d, J=8.6 Hz, 1H); 7.13 (m, 1H); 7.03 (dd, J=2.2, 8.5 Hz, 1H); 6.63 (d, J=8.5 Hz, 1H); 4.13 (d, J=9.3 Hz, 1H); 3.98 (d, J=9.3 Hz, 1H); 2.99 (s, 2H); 2.78 (m, 1H); 2.68 (m, 3H); 2.58 (m, 1H); 2.22 (s, 3H); 1.88 (m, 2H); 1.78 (m, 2H); 1.32 (s, 3H). APCI-MS: m/z 513 (MH$^+$).

Example 6

2-{[(2S)-3-(5-Chloro-1'H,3H-spiro[1-benzofuran-2,4'-piperidin]-1'-yl)-2-hydroxypropyl]oxy}-N-cyclopropylbenzamide Step I:

N-Cyclopropyl-2-hydroxybenzamide

A mixture of of methyl salicylate (4.36 g, 28.69 mmol) and cyclopropylamine (1.64 g) was heated in a sealed tube at 80-100° C. for 3 h. An additional 0.5 g of cyclopropylamine was added and heated at 70° C. overnight. The volatiles were removed in vacuo and the residue was purified by silica gel flash chromatography to give the subtitled compound (2.71 g).

$^1$H-NMR (CDCl$_3$, 400 MHz): δ 12.40 (s, 1H); 7.40 (m, 1H); 7.38 (m, 1H); 7.01 (m, 1H); 6.81 (m, 1H); 6.48 (br.s, 1H); 2.85 (m, 1H); 0.98 (m, 2H); 0.82 (m, 2H).

Step II:

N-Cyclopropyl-2-[(2S)-oxiran-2-ylmethoxy]benzamide

A mixture of N-cyclopropyl-2-hydroxybenzamide (270 mg, 1.52 mmol), (2S)-oxiran-2-ylmethyl-3-nitrobenzenesulfonate (378 mg, 1.68 mmol) and cesium carbonate (645 mg, 1.98 mmol) in DMF (4 mL) was stirred at room temperature overnight. The reaction mixture was partitioned between ethyl acetate and water. The organic layer was dried over Na$_2$SO$_4$, filtered and concentrated. The residue was purified by silica gel flash chromatography (40% heptane in ethyl acetate) to give the subtitled compound (354 mg).

$^1$H-NMR (CDCl$_3$, 400 MHz): δ 8.22 (dd, J=1.8, 7.8 Hz, 1H); 7.95 (br.s, 1H); 7.42 (m, 1H); 7.10 (m, 1H); 6.93 (d, J=8.3 Hz, 1H); 4.44 (dd, J=2.5, 10.7 Hz, 1H); 4.08 (dd, J=5.1, 10.8 Hz, 1H); 3.40 (m, 1H); 3.04-2.95 (m, 2H); 2.83 (dd, J=2.7, 4.5 Hz, 1H); 0.86 (m, 2H); 0.65 (m, 2H).

Step III:

2-{[(2S)-3-(5-Chloro-1'H,3H-spiro[1-benzofuran-2,4'-piperidin]-1'-yl)-2-hydroxypropyl]oxy}-N-cyclopropylbenzamide A mixture of 5-chloro-3H-spiro[1-benzofuran-2,4'-piperidine] (9 mg, 0.04 mmol) and N-cyclopropyl-2-[(2S)-oxiran-2-ylmethoxy]benzamide (9.4 mg, 0.4 mmol) in ethanol (1.5 mL) was stirred at 80° C. overnight. The volatiles were removed in vacuo and the residue was purified by silica gel flash chromatography (0-1.5% methanol in dichloromethane, 0.2% NH$_4$OH) to give the titled compound (7 mg).

$^1$H-NMR (CD$_3$OD, 400 MHz): δ 7.92 (m, 1H); 7.47 (m, 1H); 7.13 (m, 2H); 7.05 (m, 2H); 6.65 (d, J=8.5 Hz, 1H); 4.23 (dd, J=3.0, 9.4 Hz, 1H); 4.16 (m, 1H); 4.09 (dd, J=5.5, 9.4 Hz, 1H); 3.03 (s, 2H); 2.93 (m, 1H); 2.70 (br. S, 4H); 2.60 (d, J=6.3 Hz, 1H); 1.96 (m, 2H); 1.85 (m, 2H); 0.81 (m, 2H); 0.69 (m, 2H). APCI-MS: m/z 457 (MH$^+$).

Example 7

2-{[(2S)-3-(5-Chloro-1'H,3H-spiro[1-benzofuran-2,4'-piperidin]-1'-yl)-2-hydroxypropyl]oxy}-N-cyclopropyl-4-fluorobenzamide Step I:

N-Cyclopropyl-4-fluoro-2-hydroxybenzamide

A suspension of methyl 4-fluoro-2-hydroxybenzoate (510 mg, 3.0 mmol) in cyclopropylamine (5 mL) was stirred at room temperature overnight when it became a clear solution. The volatiles were removed in vacuo and the residue was purified by silica gel flash chromatography (0-30% ethyl acetate in petroleum ether) to give the subtitled compound (493 mg).

$^1$H-NMR (CD$_3$OD, 400 MHz): δ 12.65 (s, 1H); 7.28 (m, 1H); 6.69 (dd, J=2.6, 10.4 Hz, 1H); 6.56 (ddd, J=2.6, 8.0, 10.4 Hz, 1H); 6.30 (br. S, 1H); 2.88 (m, 1H); 0.98 (m, 2H); 0.66 (m, 2H). APCI-MS: m/z 196 (MH$^+$).

Step II:

N-Cyclopropyl-4-fluoro-2-(oxiran-2-ylmethoxy)benzamide

A mixturte of N-cyclopropyl-4-fluoro-2-hydroxybenzamide (195 mg, 1.0 mmol), (2S)-oxiran-2-ylmethyl3-nitrobenzenesulfonate (259 mg, 1.0 mmol) and Cs$_2$CO$_3$ (390 mg, 1.2 mmol) in DMF (5 mL) was stirred at room temperature overnight. The reaction mixture was partitioned between ethyl acetate and water. The organic layer was dried over Na$_2$SO$_4$, filtered and concentrated. The residue was purified by silica gel flash chromatography (0-30% ethylacetate in petroleum ether) to give the subtitled compound (150 mg).

$^1$H-NMR (CDCl$_3$, 400 MHz): δ 8.24 (dd, J=7.0, 8.8 Hz, 1H); 7.80 (br. s, 1H); 6.82 (ddd, J=2.3, 7.6, 10.2 Hz, 1H); 6.66 (dd, J=2.3, 10.2 Hz, 1H); 4.45 (dd, J=2.4, 10.7 Hz, 1H); 4.05 (dd, J=5.1, 10.7 Hz, 1H); 3.40 (m, 1H); 3.00 (m, 2H); 2.84 (dd, J=2.6, 4.8 Hz, 1H); 0.86 (m, 2H); 0.65 (m, 2H). APCI-MS: m/z 252 (MH$^+$).

Step III:

2-{[(2S)-3-(5-Chloro-1'H,3H-spiro[1-benzofuran-2,4'-piperidin]-1'-yl)-2-hydroxypropyl]oxy}-N-cyclopropyl-4-fluorobenzamide A mixturte of 5-chloro-3H-spiro[1-benzofuran-2,4'-piperidine] (30 mg, 0.134 mmol) and N-cyclopropyl-4-fluoro-2-(oxiran-2-ylmethoxy)benzamide (33.6 mg, 0.134 mmol) in ethanol (2 mL) was stirred at 80° C. overnight. The volatiles were removed in vacuo and the residue was purified by silica gel flash chromatography (0-2% methanol in dichloromethane, 0.2% NH$_4$OH) to give the titled compound (36 mg).

$^1$H-NMR (CD$_3$OD, 400 MHz): δ 7.97 (dd, J=6.9, 8.7 Hz, 1H); 7.14 (m, 1H); 7.05 (dd, J=2.3, 8.5 Hz, 1H); 6.96 (dd, J=2.4, 10.4 Hz, 1H); 6.82 (ddd, J=2.4, 8.0, 10.4 Hz, 1H); 6.66 (d, J=8.5 Hz, 1H); 4.24 (dd, J=3.0, 9.4 Hz, 1H); 4.17 (m, 1H); 4.10 (dd, J=5.5, 9.4 Hz, 1H); 3.05 (s, 2H); 2.82 (m, 1H); 2.71 (br. s, 4H); 2.60 (d, J=6.3 Hz, 2H); 1.99 (m, 2H); 1.88 (m, 2H); 0.83 (m, 2H); 0.58 (m, 2H). APCI-MS: m/z 252 (MH$^+$).

Example 8

2-{[(2S)-3-(5-Chloro-1'H,3H-spiro[1-benzofuran-2, 4'-piperidin]-1'-yl)-2-hydroxypropyl]oxy}-N-cyclopropyl-4-methoxybenzamide Step I:

N-Cyclopropyl-2-hydroxy-4-methoxybenzamide

A suspension of methyl 2-hydroxy-4-methoxybenzoate (5.1 g, 28.0 mmol) in cyclopropyl amine 24 mL) was stirred at room temperature for 5 days. The volatiles were removed in vacuo and the residue was purified by silica gel flash chromatography (0-60% ethyl acetate in petroleum ether) to give the subtitled compound (1.8 g).

$^1$H-NMR (CD$_3$OD, 400 MHz): δ 7.61 (d, J=8.8 Hz, 1H); 6.42 (m, 2H); 3.80 (s, 3H); 2.80 (m, 1H); 0.80 (m, 2H); 0.62 (m, 2H). APCI-MS: m/z 208 (MH$^+$)

Step II:

N-Cyclopropyl-4-methoxy-2-[(2S)-oxiran-2-ylmethoxy]benzamide

A mixture of N-cyclopropyl-2-hydroxy-4-methoxybenzamide (700 mg, 3.38 mmol), (2S)-oxiran-2-ylmethyl3-nitrobenzenesulfonate (876 mg, 3.38 mmol) and Cs$_2$CO$_3$ (1.31 g, 4.05 mmol) in DMF (12 mL) was stirred at room temperature overnight. The reaction mixture was partitioned between ethyl acetate and water. The organic layer was dried over Na$_2$SO$_4$, filtered and concentrated. The residue was purified by silica gel flash chromatography (0-80% ethyl acetate in petroleum ether) to give the subtitled compound (1.0 g).

$^1$H-NMR (CDCl$_3$, 400 MHz): δ 8.20 (d, J=8.8 Hz, 1H); 7.85 (br.s, 1H), 6.63 (dd, J=2.3, 8.8 Hz, 1H); 6.45 (d, J=2.3 Hz, 1H); 4.42 (dd, J=2.5, 10.8 Hz, 1H); 4.05 (dd, J=5.2, 10.8 Hz, 1H); 3.82 (s, 3H); 3.40 (m, 1H); 3.00 (m, 2H); 2.83 (dd, J=2.6, 4.8 Hz, 1H); 0.88 (m, 2H); 0.68 (m, 2H). APCI-MS: m/z 264 (MH$^+$).

Step III:

2-{[(2S)-3-(5-Chloro-1'H,3H-spiro[1-benzofuran-2,4'-piperidin]-1'-yl)-2-hydroxypropyl]oxy}-N-cyclopropyl-4-methoxybenzamide A mixture of 5-chloro-3H-spiro[1-benzofuran-2,4'-piperidine] (100 mg, 0.447 mmol) and N-cyclopropyl-4-methoxy-2-[(2S)-oxiran-2-ylmethoxy]benzamide (117.7 mg, 0.447 mmol) in ethanol (3 mL) was stirred at 80° C. overnight. The volatiles were removed in vacuo and the residue was purified by silica gel flash chromatograpy (0-1.5% methanol in dichloromethane, 0.2% NH$_4$OH) to give the titled compound (145 mg).

$^1$H-NMR (CDCl$_3$, 400 MHz): δ 8.18 (m, 2H); 7.12 (m, 1H); 7.09 (dd, J=2.3, 8.5 Hz, 1H); 6.70 (d, J=8.5 Hz, 1H); 6.63 (dd, J=2.3, 8.8 Hz, 1H); 6.44 (d, J=2.3 Hz, 1H); 4.19 (dd, J=3.3, 9.4 Hz, 1H); 4.13 (m, 1H); 3.97 (dd, J=5.0, 9.4 Hz, 1H); 3.88 (s, 3H); 3.02 (m, 3H); 2.92 (m, 1H); 2.81 (m, 1H); 2.63 (m, 3H); 2.53 (dd, J=3.6, 12.4 Hz, 1H); 2.04 (m, 2H); 1.88 (m, 2H); 0.85 (m, 2H); 0.06 (m, 2H). APCI-MS: m/z 487 (MH$^+$).

Example 9

N-(2-{[(2S)-3-(5-Chloro-1'H,3H-spiro[1-benzofuran-2,4'-piperidin]-1'-yl)-2-hydroxy-2-methylpropyl]oxy}-4-hydroxyphenyl)acetamide trifluoroacetate Step I:

2-Methyl-1,3-benzoxazol-6-ol

To a stirred solution of 1-(2,4-dihydroxyphenyl)ethanone (20 g, 131 mmol) in pyridine (80 mL) hydroxylamine hydrochloride (9.1 g, 131 mmol) was added over a period of 15 min in small portions at room temperature. The reaction mixture was stirred for 20 h and then diluted with water (600 mL) and extracted with ethyl acetate (2×250 mL). The combined organic extracts were washed with water (2×250 mL) and 5% aqueous HCl (250 mL). The solvent was removed in vacuo. Water (200 mL) was addded to the residue and then concentrated in vacuo, then toluene (200 mL) was added and concentrated in vacuo. The residue was dissolved in a mixture of acetonitrile (150 mL) and dimethylacetamide (25 mL). The solution was cooled to 5° C., phosphorus oxychloride (20.4 g, 12.2 mL, 133 mmol) was added dropwise allowing the temperature to exceed 10° C. After the addition was complete, the reaction mixture was stirred at room temperature for 1 h and then it was slowly poured into a mixture of sodium carbonate (55 g) and ice (ca 800 g). After the ice melted, the resulting slurry was filtered and the solid collected was washed with water (2×150 mL). The product was dried in vacuo to afford a yellow powder (14.4 g, 97 mmol, 76%).

$^1$H-NMR (400 MHz, DMSO-d$_6$): δ 9.68 (br. s, 1H), 7.38 (d, J=8.5 Hz, 1H), 6.94 (d, J=2.2 Hz, 1H), 6.74 (dd, J=8.5, 2.2 Hz, 1H), 2.50 (s, 3H).

Step II:

2-Methyl-1,3-benzoxazol-6-yl benzoate

To a stirred suspension of 2-methyl-1,3-benzoxazol-6-ol (2.99 g, 20 mmol) in dichloromethane (50 mL) was added triethylamine (4.05 g, 5.58 mL, 40 mmol). A solution of benzoyl chloride (3.09 g, 2.56 mL, 22 mmol) in dichloromethane (20 mL) was added dropwise over ca. 10 min. The reaction mixture was stirred at room temperature for 2.5 h, then washed with water (2×50 mL), and dried over Na$_2$SO$_4$, filtered and concentrated in vacuo to give the subtitled compound as a colourless solid (5.05 g, 20 mmol).

$^1$H-NMR (400 MHz, CDCl$_3$): δ 8.22 (m, 2H), 7.66 (m, 2H), 7.53 (m, 2H), 7.40 (d, 1H), 7.16 (dd, 1H), 2.65 (s, 3H). APCI-MS: m/z 254 [MH$^+$].

Step III:

4-(Acetylamino)-3-hydroxyphenyl benzoate

To a solution of 2-methyl-1,3-benzoxazol-6-yl benzoate (5.05 g, 20 mmol) in THF (100 mL) a mixture trifluoroacetic acid/water (4 ml/10 mL) was added. The reaction mixture was stirred at room temperature for 16 h, then saurated aqueous NaHCO$_3$ (150 mL) was added. The mixture was extracted with ethyl acetate (150 mL), dried over Na$_2$SO$_4$, filtered and concentrated in vacuo to give the subtitled compound.

$^1$H-NMR (400 MHz, acetone-d$_6$): δ 9.76 (br.s, 1H), 9.32 (br.s, 1H), 8.15 (m, 2H), 7.71 (m, 1H), 7.60 (m, 2H), 7.47 (d, 1H), 6.85 (m, 1H), 6.75 (m, 1H), 2.20 (s, 3H). APCI-MS: m/z 272 [MH$^+$].

Step IV:

4-(Acetylamino)-3-{[(2S)-2-methyloxiran-2-yl]methoxy}phenyl benzoate

This compound was prepared from 4-(acetylamino)-3-hydroxyphenyl benzoate (2.71 g, 10 mmol) and [(2S)-2-methyloxiran-2-yl]methyl 3-nitrobenzenesulfonate using the standard procedure and 1-methylpyrrolidin-2-one as a solvent. Flash chromatography on silica gel (ethyl acetate/n-heptane) afforded the subtitled compound as a colourless solid (1.31 g, 3.9 mmol, 39%).

$^1$H-NMR (400 MHz, CDCl$_3$): δ 8.41 (d, 1H), 8.18 (m, 2H), 7.91 (br.s, 1H), 7.63 (m, 1H), 7.50 (m, 2H), 6.83 (m, 1H), 4.15 (d, J=10.8 Hz, 1H), 4.03 (d, J=10.8 Hz, 1H), 3.99 (d, J=10.8 Hz, 1H), 2.92 (d, J=4.6 Hz, 1H), 2.78 (d, J=4.6 Hz, 1H), 2.22 (s, 3H), 1.48 (s, 3H). APCI-MS: m/z 342 [MH$^+$].

Step V:

N-(2-{[(2S)-3-(5-Chloro-1'H,3H-spiro[1-benzofuran-2,4'-piperidin]-1'-yl)-2-hydroxy-2-methylpropyl]oxy}-4-hydroxyphenyl)acetamide trifluoroacetate A solution of 5-chloro-3H-spiro[1-benzofuran-2,4'-piperidine] (20.0 mg, 0.09 mmol) and 4-(acetylamino)-3-{[(2S)-2-methyloxiran-2-yl]methoxy}phenyl benzoate (30.5 mg, 0.09 mmol) in methanol (2 mL) was refluxed for 3 h. The reaction mixture was cooled to room temperature, and 1 drop of 20% NaOH in ethanol was added. The mixture was stirred at room temperature for 3 h. The solvent was distilled off under reduced pressure. The residue was purified by HPLC ("Kromasil" column; eluant: [acetonitrile+0.1% trifluoroacetic acid (TFA)/water+0.1% TFA]) to afford a colourless solid (41 mg, 0.07 mmol, 79%).

$^1$H-NMR (400 MHz, acetone-d$_6$): δ 8.67 (br. s, 1H), 7.71 (d, J=7.0 Hz, 1H), 7.22 (s, 1H), 7.12 (dd, J=2.3, 8.5 Hz, 1H), 6.75 (d, J=8.5 Hz, 1H), 6.59 (d, J=2.6 Hz, 1H), 6.42 (dd, J=2.6, 8.6 Hz, 1H), 4.03 (d, 1H), 3.97 (d, J=9.7 Hz, 1H), 3.92 (br.s, 1H), 3.82 (br. s, 1H), 3.70 (d, J=13.6 Hz, 1H), 3.52 (m, 3H), 2.1-2.5 (m, 4H), 2.10 (s, 3H), 1.51 (s, 3H). APCI-MS: m/z 461 [MH$^+$].

Example 10

N-(5-Chloro-2-{[(2S)-3-(6-chloro-1'H,3H-spiro[2-benzofuran-1,4'-piperidin]-1'-yl)-2-hydroxypropyl]oxy}phenyl)acetamide Step I:

N-(5-Chloro-2-hydroxyphenyl)acetamide

To a suspension of 2-amino-4-chlorophenol (1.43 g, 10.0 mmol) in methanol was added acetic anhydride (0.945 mL, 10.0 mmol) and the reaction mixture was stirred at room temperature for 2 h. The volatiles were removed in vacuo to give the subtitled compound (1.5 g).

$^1$H-NMR (DMSO-d$_6$, 400 MHz): δ 10.20 (br.s, 1H); 9.21 (s, 1H); 8.00 (d, J=2.6 Hz, 1H); 6.94 (dd, J=2.6, 8.7 Hz, 1H); 6.84 (d, J=8.7 Hz, 1H); 2.02 (s, 3H).

Step II:

N-{5-Chloro-2-[(2S)-oxiran-2-ylmethoxy]phenyl}acetamide

A mixture of N-(5-chloro-2-hydroxyphenyl)acetamide (500 mg, 2.69 mmol), (2S)-oxiran-2-ylmethyl3-nitrobenzenesulfonate (697 mg, 2.69 mmol) and Cs$_2$CO$_3$ (1.04 g, 3.22 mmol) in DMF (10 mL) was stirred at room temperature overnight. The reaction mixture was partitioned between ethyl acetate and water. The organic layer was dried over Na$_2$SO$_4$, filtered and concentrated. The residue was purified by silica gel flash chromatography (0-50% ethyl acetate in petroleum ether) to give the subtitled compound (600 mg).

$^1$H-NMR (CDCl$_3$, 400 MHz): δ 8.47 (d, J=2.3 Hz, 1H); 7.93 (br.s, 1H); 6.98 (dd, J=2.3, 8.7 Hz, 1H); 6.83 (d, J=8.7 Hz, 1H); 4.36 (dd, J=2.4, 11.3 Hz, 1H); 3.94 (dd, J=6.1, 11.3 Hz, 1H); 3.39 (m, 1H); 2.98 (m, 1H); 2.81 (dd, J=2.7, 4.8 Hz, 1H); 2.22 (s, 3H). APCI-MS: m/z 242 (MH$^+$).

Step III:

N-(5-Chloro-2-{[(2S)-3-(6-chloro-1'H,3H-spiro[2-benzofuran-1,4'-piperidin]-1'-yl)-2-hydroxypropyl]oxy}phenyl)acetamide A mixture of 6-chloro-3H-spiro[2-benzofuran-1,4'-piperidine] (26 mg, 0.116 mmol) and N-{5-chloro-2-[(2S)-oxiran-2-ylmethoxy]phenyl}acetamide (28 mg, 0.116 mmol) in ethanol (3 mL) was stirred at 80° C. overnight. The volatiles were removed in vacuo and the residue was purified by silica gel flash chromatography (0-2% methanol in dichloromethane, 0.2% NH$_4$OH) to give the titled compound (28 mg).

$^1$H-NMR (CD$_3$OD, 400 MHz): δ 8.18 (d, J=2.4 Hz, 1H); 7.30-7.20 (m, 3H); 7.10-7.00 (m, 2H); 5.02 (s, 2H); 4.23 (m, 1H); 4.14 (dd, J=3.1, 9.9 Hz, 1H); 3.99 (dd, J=6.5, 9.9 Hz, 1H); 2.93 (m, 2H); 2.63 (d, J=6.3 Hz, 2H); 2.55 (m, 2H); 2.21 (s, 3H); 2.00 (m, 2H); 1.73 (m, 2H). APCI-MS: m/z 467 (MH$^+$).

Example 11

N-(2-{[(2S)-3-(6-Chloro-1'H,3H-spiro[2-benzofuran-1,4'-piperidin]-1'-yl)-2-hydroxypropyl]oxy}-4-fluorophenyl)acetamide A mixture of 6-chloro-3H-spiro[2-benzofuran-1,4'-piperidine] (30 mg, 0.134 mmol) and N-{4-fluoro-2-[(2S)-oxiran-2-ylmethoxy]phenyl}acetamide (30 mg, 0.134 mmol) in ethanol (3 mL) was stirred at 80° C. overnight. The volatiles were removed in vacuo and the residue was purified by silica gel flash chromatography (0-1% methanol in dichloromethane, 0.2% NH$_4$OH) to give the titled compound (40 mg).

$^1$H-NMR (CD$_3$OD, 400 MHz): δ 7.90 (dd, J=6.2, 8.9 Hz, 1H); 7.29-7.20 (m, 3H); 6.89 (dd, J=2.7, 10.5 Hz, 1H); 6.67 (m, 1H); 5.02 (s, 2H); 4.23 (m, 1H); 4.13 (dd, J=3.1, 9.9 Hz, 1H); 4.01 (dd, J=6.3, 9.9 Hz, 1H); 2.93 (m, 2H); 2.69-2.50 (m, 4H); 2.20 (s, 3H); 2.00 (m, 2H); 1.73 (br.d, J=13.5 Hz, 2H). APCI-MS: m/z 451(MH$^+$).

Example 12

N-(2-{[(2S)-3-(6-Chloro-1'H,3H-spiro[2-benzofuran-1,4'-piperidin]-1'-yl)-2-hydroxypropyl]oxy}phenyl)acetamide A mixture of 6-chloro-3H-spiro[2-benzofuran-1,4'-piperidine] (25 mg, 0.111 mmol) and N-{2-[(2S)-oxiran-2-ylmethoxy]phenyl}acetamide (23 mg, 0.111 mmol) in ethanol (2 mL) was stirred at 80° C. overnight. The volatiles were removed in vacuo and the residue was purified by silica gel flash chromatography (0-1% methanol in dichloromethane, 0.2% NH$_4$OH) to give the titled compound (20 mg).

$^1$H-NMR (CD$_3$OD, 400 MHz): δ 8.00 (dd, J=1.3, 8.0 Hz, 1H); 7.30-7.20 (m, 3H); 7.12-7.05 (m, 2H); 6.93 (m, 1H); 5.01 (s, 2H); 4.22 (m, 1H); 4.14 (dd, J=3.3, 9.9 Hz, 1H); 4.00 (dd, J=6.4, 9.9 Hz, 1H); 2.94 (m, 2H); 2.69-2.52 (m, 4H); 2.20 (s, 3H); 2.01 (m, 2H); 1.74 (br.d, J=13.5 Hz, 2H). APCI-MS: m/z 433(MH$^+$).

Example 13

N-(2-{[(2S)-3-(6-Chloro-1'H,3H-spiro[2-benzofuran-1,4'-piperidin]-1'-yl)-2-hydroxypropyl]oxy}-4-methoxyphenyl)acetamide A mixture of 6-chloro-3H-spiro[2-benzofuran-1,4'-piperidine] (46 mg, 0.205 mmol) and N-{4-methoxy-2[(2S)-oxiran-2-ylmethoxy]phenyl}acetamide (48.6 mg, 0.205 mmol) in ethanol (2 mL) was stirred at 80° C. overnight. The volatiles were removed in vacuo and the residue was purified by silica gel flash chromatography (0-1.5% methanol in dichloromethane, 0.2% NH$_4$OH) to give the titled compound (80 mg).

¹H-NMR (CD₃OD, 400 MHz): δ 7.75 (d, J=8.9 Hz, 1H); 7.29-7.20 (m, 3H); 6.64 (d, J=2.7 Hz, 1H); 6.51 (dd, J=2.7, 8.9 Hz, 1H); 5.02 (s, 2H); 4.44 (m, 1H); 4.12 (dd, J=3.3, 10.0 Hz, 1H); 3.98 (dd, J=6.2, 10.0 Hz, 1H); 3.80 (s, 3H); 2.96 (m, 2H); 2.68-2.50 (m, 4H); 2.18 (s, 3H); 2.00 (m, 2H); 1.74 (br.d, J=13.2 Hz, 2H). APCI-MS: m/z 461(MH⁺).

Example 14

2-{[(2S)-3-(6-Chloro-1'H,3H-spiro[2-benzofuran-1,4'-piperidin]-1'-yl)-2-hydroxypropyl]oxy}-N-cyclopropyl-4-fluorobenzamide A mixture of 6-chloro-3H-spiro[2-benzofuran-1,4'-piperidine] (25 mg, 0.111 mmol) and N-cyclopropyl-4-fluoro-2-(oxiran-2-ylmethoxy)benzamide (28 mg, 0.111 mmol) in ethanol was stirred at 80° C. overnight. The volatiles were removed in vacuo and the residue was purified by silica gel flash chromatography (0-1% methanol in dichloromethane, 0.2% NH₄OH) to give the titled compound (32 mg).

¹H-NMR (CD₃OD, 400 MHz): δ 7.98 (dd, J=6.9, 8.8 Hz, 1H); 7.29-7.20 (m, 3H); 6.98 (dd, J=2.4, 10.8 Hz, 1H); 6.82 (ddd, J=2.4, 8.0, 8.8 Hz, 1H); 5.01 (s, 2H); 4.25 (dd, J=3.1, 9.4 Hz, 1H); 4.19 (m, 1H); 4.11 (dd, J=5.5, 9.4 Hz, 1H); 2.92 (m, 3H); 2.59 (m, 4H); 2.01 (m, 2H); 1.73 (m, 2H); 0.80 (m, 2H); 0.69 (m, 2H). APCI-MS: m/z 477(MH⁺).

Example 15

N-(2-{[(2S)-3-(5-Fluoro-1'H,3H-spiro[2-benzofuran-1,4'-piperidin]-1'-yl)-2-hydroxypropyl]phenyl)acetamide A mixture of 5-fluoro-3H-spiro[2-benzofuran-1,4'-piperidine] (15 mg, 0.072 mmol) and is N-{2-[(2S)-oxiran-2-ylmethoxy]phenyl}acetamide (15 mg, 0.072 mmol) in ethanol (1.5 mL) was stirred at 80° C. overnight. The volatiles were removed in vacuo and the residue was purified by silica gel flash chromatography (0-2% methanol in dichloromethane, 0.2% NH₄OH) to give the titled compound (9 mg).

¹H-NMR (CD₃OD, 400 MHz): δ 7.99 (dd, J=1.2, 8.0 Hz, 1H); 7.18 (dd, J=4.9, 8.0 Hz, 1H); 7.11-6.90 (m, 5H); 5.00 (s, 2H); 4.27 (m, 1H); 4.13 (dd, J=3.2, 9.9 Hz, 1H); 3.99 (dd, J=6.4, 9.9 Hz, 1H); 2.99 (m, 2H); 2.72-2.52 (m, 4H); 2.20 (s, 3H); 2.02 (m, 2H); 1.73 (br.d, J=13.6 Hz, 2H). APCI-MS: m/z 415 (MH⁺).

Example 16

N-(4-Chloro-2-{[(2S)-2-hydroxy-3-(3-oxo-1'H,3H-spiro[2-benzofuran-1,4'-piperidin]-1'-yl)propyl]oxy)phenyl)acetamide Step I:

N-(4-Chloro-2-hydroxyphenyl)acetamide

To a suspension of 2-amino-5-chlorophenol (1.01 g, 7.0 mmol) in methanol (10 mL) was added acetic anhydride (1.08 g, 10.55 mmol) and the reaction mixture was stirred at room temperature for 30 min. The volatiles were removed in vacuo and the residue was purified by silica gel flash chromatography (hexane:ethyl acetate 5:2) to give the subtitled compound (1.19 g).

¹H-NMR (DMSO-d₆, 400 MHz): δ 10.29 (br.s, 1H); 9.26 (br.s, 1H); 7.77 (d, J=8.6 Hz, 1H); 6.86 (d, J=2.4 Hz, 1H); 6.80 (dd, J=2.4, 8.6 Hz, 1H); 2.12 (s, 3H). APCI-MS: m/z 186 (MH⁺).

Step II:

N-{4-Chloro-2-[(2S)-oxiran-2-ylmethoxy]phenyl}acetamide

To a mixture of (2S)-oxiran-2ylmethyl3-nitrobenzenesulfonate (3.37 g, 13.25 mmol), N-(4-chloro-2-hydroxyphenyl)acetamide (2.46 g, 17.23 mmol) and Cs₂CO₃ (6.48 g, 19.88 mmol) was added DMF (20 mL) at 0° C. and the reaction mixture was stirred at 0° C. for 3 h. The reaction mixture was partitioned between ethyl acetate and water. The organic layer was dried over Na₂SO₄, filtered and concentrated. The residue was purified by silica gel flash chromatography (hexane:ethyl acetate 3:2) to give the subtitled compound (2.36 g).

¹H-NMR (CD₃COCD₃, 400 MHz): δ 8.67 (br.s, 1H); 8.30 (d, J=8.7 Hz, 1H); 7.07 (d, J=2.3 Hz, 1H); 6.95 (dd, J=2.2, 8.7 Hz, 1H); 4.46 (dd, J=2.3, 11.5 Hz, 1H); 3.94 (dd, J=6.6, 11.5 Hz, 1H); 3.34 (m, 1H); 2.87 (dd, J=4.3, 5.0 Hz, 1H); 2.73 (dd, J=2.7, 5.0 Hz, 1H); 2.18 (s, 3H).

Step III

N-(4-Chloro-2-{[(2S)-2-hydroxy-3-(3-oxo-1'H,3H-spiro[2-benzofuran-1,4'-piperidin]-1'-yl)propyl]oxy}phenyl)acetamide A mixture of 3H-spiro[2-benzofuran-1,4'-piperidin]-3-one (Marxer, A; Rodriguez, H. R; McKenna, J. M; Tsai, H. M., *J. Org. Chem.*, 1975, 40, 1427-1433) (61 mg, 0.3 mmol) and N-{4-chloro-2-[(2S)-oxiran-2ylmethoxy]phenyl}acetamide (72.5 mg, 0.3 mmol) in ethanol (3 mL) was stirred at 80° C. overnight. The volatiles were removed in vacuo and the residue was purified by silica gel flash chromatography (0-1.5% methanol in dichloromethane, 0.2% NH₄OH) to give the titled compound (40 mg).

¹H-NMR (CD₃OD, 400 MHz): δ 7.93 (d, J=7.7 Hz, 1H); 7.84 (m, 2H); 7.71-7.61 (m, 2H); 7.13 (d, J=2.0 Hz, 1H); 7.00 (dd, J=2.0, 8.5 Hz, 1H); 4.58 (m, 1H); 4.13 (m, 2H); 3.86 (m, 2H); 3.65-3.45 (m, 4H); 2.64 (m, 2H); 2.20 (s, 3H); 2.06 (m, 2H). APCI-MS: m/z 445(MH⁺).

Example 17

N-Cyclopropyl-2-{[(2S)-2-hydroxy-3-(1'H,3H-spiro[2-benzofuran-1,4'-piperidin]-1'-yl)propyl]oxy)benzamide A mixture 3H-spiro[2-benzofuran-1,4'-piperidine] (Marxer, A; Rodriguez, H. R; McKenna, J. M; Tsai, H. M., *J. Org. Chem.*, 1975, 40, 1427-1433) (46.5 mg, 0.246 mmol) and N-cyclopropyl-2-[(2S)-oxiran-2-ylmethoxy]benzamide (57.4 mg, 0.246 mmol) in ethanol (3 mL) was kept on stirring at 80° C. overnight. The volatiles were removed in vacuo and the residue was purified by silica gel flash chromatography (0-2% methanol in dichloromethane, 0.2% NH₄OH) to give the titled compound (55 mg).

¹H-NMR (CDCl₃, 400 MHz): δ 8.43 (d, J=1.8 Hz, 1H); 8.20 (dd, J=1.8, 7.8 Hz, 1H); 7.40 (m, 1H); 7.30 (m, 2H); 7.23 (m, 1H); 7.18 (m, 1H); 7.08 (t, J=7.5 Hz, 1H); 6.93 (d, J=8.2 Hz, 1H); 5.10 (s, 2H); 4.20 (m, 2H); 4.00 (dd, J=5.0, 9.3 Hz, 1H); 3.02 (m, 2H); 2.85 (m, 2H); 2.69 (m, 1H); 2.58 (m, 2H); 2.02 (m, 2H); 1.82 (d, 2H); 0.85 (m, 2H); 0.63 (m, 2H). APCI-MS: m/z 423(MH⁺).

Example 18

N-(4-Chloro-2-{[(2S-2-hydroxy-3-(1'H,3H-spiro[2-benzofuran-1,4'-piperidin]-1'-yl)propyl]oxy)phenyl)acetamide A mixture 3H-spiro[2-benzofuran-1,4'-piperidine] (38 mg, 0.2 mmol) and N-{4-chloro-2-[(2S)-oxiran-2ylmethoxy]phenyl}acetamide (48.3 mmol) in ethanol (3 mL) was stirred at 80° C. overnight. The volatiles were removed in vacuo and the residue was purified by silica gel flash chromatography (0-1.5% methanol in dichloromethane, 0.2% NH$_4$OH) to give the titled compound (35 mg).

$^1$H-NMR (CDCl$_3$, 400 MHz): δ 8.05 (d, J=8.7 Hz, 1H); 7.29-7.18 (m, 4H); 7.10 (d, J=2.2 Hz, 1H); 6.94 (dd, J=2.2, 8.7 Hz, 1H); 5.08 (s, 2H); 4.26 (m, 1H); 4.16 (dd, J=3.0, 10.0 Hz, 1H); 4.01 (dd, J=6.4, 9.9 Hz, 1H); 2.97 (m, 2H); 2.69-2.52 (m, 4H); 2.19 (s, 3H); 2.07 (m, 2H); 1.73 (m, 2H). APCI-MS: m/z 433(MH$^+$).

Example 19

N-(5-Chloro-2{[(2S)-2-hydroxy-3-(1'H,3H-spiro[2-benzofuran-1,4'-piperidin]-1'-yl)propyl]oxy}phenyl)acetamide A mixture 3H-spiro[2-benzofuran-1,4'-piperidine] (63 mg, 0.33 mmol) and N-{5-chloro-2-[(2S)-oxiran-2-ylmethoxy]phenyl}acetamide (80 mg, 0.33 mmol) in ethanol (5 mL) was stirred at 77° C. for 4 h. The volatiles were removed in vacuo and the residue was purified by silica gel flash chromatography (0-3% methanol in chloroform) to give the titled compound (77 mg).

$^1$H-NMR (CDCl$_3$, 400 MHz): δ 8.50 (m, 1H); 7.31 (m, 3H); 7.18 (m, 1H); 6.98 (m, 1H); 6.83 (m, 1H); 5.10 (s, 2H); 4.10 (m, 1H); 4.03 (dd, 1H); 3.91 (dd, 1H); 2.97 (m, 1H); 2.76 (m, 2H); 2.60-2.43 (m, 3H); 2.20 (s, 3H); 2.05-1.89 (m, 2H); 1.60 (m, 2H). APCI-MS: m/z 431(MH$^+$).

Example 20

N-(2-{[(2S)-2-hydroxy-2-methyl-3-(1'H,3H-spiro[2-benzofuran-1,4'-piperidin]-1'-yl)propyl]oxy}-4-methoxyphenyl)acetamide Step I:

[(2S)-2-Methyloxiranyl]methyl3-nitrobenzenesulfonate

To an oven-dried 1000 mL three-necked flask was added powdered activated molecular sieves (8.0 g, 4 Å) and CH$_2$Cl$_2$ (440 mL), D-(−)-diisopropyl tartrate (4 mL, 14.2 mmol) and 2-methyl-2-propene-1-ol (20 mL, 240 mmol) was added and the mixture was cooled to −20° C. Titanium tetraisopropoxide (3.5 mL, 11.9 mmol) was added with a few mL of CH$_2$Cl$_2$ and the mixture was stirred at −20° C. for 30 min. Cumene hydroperoxide (75 mL, 430 mmol) was added dropwise over 1.5 hours maintaining the temperature at −20° C. The mixture was stirred at this temperature overnight. Trimethyl phosphite (40 mL, 340 mmol) was added dropwise over 5 hours maintaining the temperature at −20° C. Triethylamine (50 mL, 360 mmol) and 4-dimethylaminopyridine (DMAP) (3.48 g, 28.5 mmol) was added followed by a solution of 3-nitrobenzenesulphonyl chloride (47 g, 212 mmol) in CH$_2$Cl$_2$ (400 mL). The temperature was raised to −10° C. and the mixture was stirred at this temperature overnight. After removing the external cooling vessel, the reaction mixture was filtered through celite. The organic phase was washed with 10% tartaric acid (500 mL), saturated NaHCO$_3$ (300 mL) and brine (300 mL). The organic layer was dried over magnesium sulphate (MgSO$_4$) and concentrated in vacuo to give 150 g of a yellow oil. The crude material was purified by silica gel flash chromatography (0-50% ethyl acetate in heptane) to give the subtitled compound (48.8 g).

$^1$H-NMR (CDCl$_3$, 400 MHz): δ 8.79-8.75 (m, 1H); 8.52 (ddd, J=1.1, 2.3, 8.3 Hz, 1H); 8.25 (ddd, J=1.1, 1.8, 7.8 Hz, 1H); 7.81 (t, J=8.5 Hz, 1H); 4.28 (d, J=11.3 Hz, 1H); 4.05 (d, J=11.3 Hz, 1H); 2.73 (d, J=4.4 Hz, 1H); 2.67 (d, J=4.4 Hz, 1H); 1.56 (s, 3H).

Step II:

N-(4-Methoxy-2-{[(2S)-2-methyloxiran-2-yl]methoxy}phenyl)acetamide

A mixture of [(2S)-2-methyloxiran-2-yl]methyl3-nitrobenzenesulfonate (2.04 g, 7.46 mmol), N-(2-hydroxy-4-methoxyphenyl)acetamide ((1.04 g, 5.74 mmol) and Cs$_2$CO$_3$ (2.80 g, 8.61 mmol) in DMF (12 mL) was kept on stirring at room temperature overnight. The reaction mixture was partitioned between ethyl acetate and water. The organic layer was dried over Na$_2$SO$_4$, filtered and concentrated. The residue was purified by silica gel flash chromatography (ethyl acetate:hexane 1:1) to give the subtitled compound (1.19 g).

$^1$H-NMR (CDCl$_3$, 400 MHz): δ 8.20 (d, J=8.8 Hz, 1H); 7.72 (br.s, 1H); 6.52 (m, 2H); 4.12 (d, J=11.0 Hz, 1H); 3.98 (d, J=11.0 Hz, 1H); 3.77 (s, 3H); 2.91 (d, J=4.7 Hz, 1H); 2.77 (d, J=4.7 Hz, 1H); 2.20 (s, 3H); 1.48 (s, 3H).

Step III:

N-(2-{1[(2S)-2-Hydroxy-2-methyl-3-(1'H,3H-spiro[2-benzofuran-1,4'-piperidin]-1'-yl)propyl]oxy}-4-methoxyphenyl)acetamide A mixture of 3H-spiro[2-benzofuran-1,4'-piperidine] (57 mg, 0.3 mmol) and N-(4-methoxy-2-{[(2S)-2-methyloxiran-2-yl]methoxy}phenyl)acetamide (75.4 mg, 0.3 mmol) in ethanol (3 mL) was stirred at 80° C. overnight. The volatiles were removed in vacuo and the residue was purified by silica gel flash chromatography (0-1.5% methanol in dichloromethane, 0.2% NH$_4$OH) to give the titled compound (70 mg).

$^1$H-NMR (CD$_3$OD, 400 MHz): δ 7.65 (d, J=8.8 Hz, 1H); 7.28-7.15 (m, 4H); 6.61 (d, J=2.7 Hz, 1H); 6.50 (dd, J=2.7, 8.8 Hz, 1H); 5.10 (s, 2H); 3.99 (d, J=9.2 Hz, 1H); 3.90 (d, J=9.2 Hz, 1H); 3.79 (s, 3H); 2.88 (m, 2H); 2.73-2.53 (m, 4H); 2.16 (s, 3H); 2.00 (m, 2H); 1.63 (m, 2H); 1.31 (s, 3H). APCI-MS: m/z 441(MH$^+$).

Example 21

N-[2-{[(2S)-2-Hydroxy-3-(1'H,3H-spiro[2-benzofuran-1,4'-piperidin]-1'-yl)propyl]oxy)-5-(trifluoromethyl)phenyl]acetamide Step I:

N-[2-[(2S)-Oxiran-2-ylmethoxy]-5-(trifluoromethyl)phenyl]acetamide

A mixture of N-[2-hydroxy-5-(trifluoromethyl)phenyl]acetamide (282 mg, 1.28 mmol), (2S)-oxiran-2-ylmethyl-3-nitrobenzenesulfonate (331.5 mg, 1.28 mmol) and Cs$_2$CO$_3$ (487.5 mg, 1.28 mmol) in DMF (5 mL) was stirred at room temperature overnight. The reaction mixture was partitioned between ethyl acetate and water. The organic layer was dried over Na$_2$SO$_4$, filtered and concentrated. The residue was purified by silica gel flash chromatography (0-40% ethyl acetate in petroleum ether) to give the subtitled compound (150 mg).

$^1$H-NMR (CDCl$_3$, 400 MHz): δ 8.72 (br.s, 1H); 7.90 (br.s, 1H); 7.31 (m, 1H); 6.97 (d, 1H); 4.46 (dd, J=2.4, 11.3 Hz, 1H); 4.00 (dd, J=6.3, 11.3 Hz, 1H); 3.44 (m, 1H); 3.00 (d, J=4.5 Hz, 1H); 2.80 (dd, J=2.7, 4.8 Hz, 1H); 2.25 (s, 3H).

Step II:

N-[2-{[(2S)-2-Hydroxy-3-(1'H,3H-spiro[2-benzofuran-1,4'-piperidin]-1'-yl)propyl]oxy)-5-(trifluoromethyl)phenyl]acetamide A mixture of 3H-spiro[2-benzofuran-1,4'-piperidine] (47.3 mg, 0.25 mmol) and N-[2-[(2S)-oxiran-2-ylmethoxy]-5-(trifluoromethyl)phenyl]acetamide (69 mg, 0.25 mmol) in ethanol (3 mL) was stirred at 80° C. overnight. The volatiles were removed in vacuo and the residue was purified by silica gel flash chromatography (0-1.5% methanol in dichloromethane, 0.2% NH$_4$OH) to give the titled compound (38 mg).

$^1$H-NMR (CD$_3$OD, 400 MHz): δ 8.49 (d, 1H); 7.39 (dd, 1H); 7.30-7.17 (m, 5H); 5.08 (s, 2H); 4.28 (m, 2H); 4.10 (dd, J=6.5, 9.8 Hz, 1H); 2.98 (m, 2H); 2.68-2.53 (m, 4H); 2.22 (s, 3H); 2.02 (m, 2H); 1.73 (m, 2H). APCI-MS: m/z 465(MH$^+$).

Example 22

N-(2-{[(2S)-2-Hydroxy-3-(2-methyl-1'H-spiro[indene-1,4'-piperidin]-1'-yl)propyl]oxy}phenyl)acetamide A mixture of 2-methylspiro[indene-1,4'-piperidine] (Efange, S. M. N; Khare, A. B; Foulon, C; Akella, S. K; Parsons, S. M., J. Med. Chem., 1994, 37, 2574-2582) (82.5 mg, 0.35 mmol) and N-{2-[(2S)-oxiran-2-ylmethoxy]phenyl}acetamide (72.5 mg, 0.35 mmol) in ethanol (3 mL) was stirred at 80° C. overnight. The volatiles were removed in vacuo and the residue was purified by silica gel flash chromatography (0-2% methanol in dichloromethane, 0.2% NH$_4$OH) to give the titled compound (80 mg).

$^1$H-NMR (CD$_3$OD, 400 MHz): δ 7.84 (m, 2H); 7.28 (m, 2H); 7.16 (m, 2H); 7.07 (m, 1H); 6.98 (m, 1H); 6.53 (br.s, 1H); 4.58 (m, 1H); 4.14 (m, 2H); 3.90-3.49 (m, 6H); 2.45 (m, 2H); 2.19 (s, 3H); 1.99 (s, 3H); 1.40 (br.t, J=14.0 Hz, 2H). APCI-MS: m/z 407(MH$^+$).

Example 23

N-(2-{[(2S)-3-(2,3-Dihydro-1'H-spiro[indene-1,4'-piperidin]-1'-yl)-2-hydroxypropyl]oxy}phenyl)acetamide A mixture of 2,3-dihydrospiro[indene-1,4'-piperidine] (Efange, S. M. N; Khare, A. B; Foulon, C; Akella, S. K; Parsons, S. M., J. Med. Chem., 1994, 37, 2574-2582; Chambers, M. S; Baker, R; Billington, D. C.; Knight, A. K; Middlemiss, D. N; Wong, E. H. F., J. Med. Chem., 1992, 35, 2033-2039). (78.3 mg, 0.35 mmol) and N-{2-[(2S)-oxiran-2-ylmethoxy]phenyl}acetamide (72.5 mg, 0.35 mmol) in ethanol (3 mL) was stirred at 80° C. overnight. The volatiles were removed in vacuo and the residue was purified by silica gel flash chromatography (0-2% methanol in dichloromethane, 0.2% NH$_4$OH) to give the titled compound (65 mg).

$^1$H-NMR (CD$_3$OD, 400 MHz): δ 7.82 (m, 1H); 7.26-7.12 (m, 5H); 7.06 (m, 1H); 6.98 (m, 1H); 4.50 (m, 1H); 4.10 (d, 2H); 3.72 (m, 2H); 3.45-3.22 (m, 5H); 2.99 (t, J=7.3 Hz, 2H); 2.33-2.13 (m, 6H); 1.82 (m, 2H). APCI-MS: m/z 395(MH$^+$).

Example 24

N-(2-{[(2S)-2-Hydroxy-3-(2-oxo-1'H-spiro[1-benzofuran-3,4'-piperidin]-1'-yl)propyl]oxy}phenyl)acetamide A mixture of spiro[1-benzofuran-3,4'-piperidin]-2-one (80 mg, 0.28 mmol) and N-{2-[(2S)-oxiran-2-ylmethoxy]phenyl}acetamide (60 mg, 0.28 mmol) in ethanol (2 mL) was kept on stirring at 80° C. overnight. The volatiles were removed in vacuo and the residue was purified by high pressure liquid chromatography (HPLC) to give the titled compound (65 mg).

$^1$H-NMR (DMSO-d$_6$, 400 MHz): δ 9.03 (br.s, 1H); 7.95-7.90 (m, 1H); 7.44-7.39 (m, 1H); 7.32-7.24 (m, 3H); 7.05 (m, 2H); 6.94 (m, 1H); 6.09 (br.s, 1H); 4.41 (m, 1H); 4.07-3.91 (m, 2H); 3.74-3.36 (m, 8H); 2.31-2.22 (m, 2H); 2.11 (s, 3H). APCI-MS: m/z 411(MH$^+$).

Example 25

2-{[(2S)-3-(5-Chloro-1'H,3H-spiro[1-benzofuran-2,4'-piperidin]-1'-yl)-2-hydroxypropyl]oxy}-N-cyclopropyl-4-hydroxybenzamide Step I:

Methyl 2-hydroxy-4-(trityloxy)benzoate

To a solution of methyl 2,4-dihydroxybenzoate (388 mg, 2.0 mmol) in dimethylformamide (5 mL) was added triethylamine, Et$_3$N, (0.556 mL, 4.0 mmol) followed by trityl chloride (557.5 mg, 2.0 mmol) and 4-dimethylaminopyridine (DMAP) (20 mg). The reaction mixture was kept on stirring at room temperature overnight, poured into a mixture of ice-water, the white precipitate was collected by filtration. This precipitate was subjected to silica gel flash chromatography (0-5% ethyl acetate in petroleum ether) to give the subtitled compound (350 mg).

$^1$H-NMR (CDCl$_3$, 400 MHz): δ 10.65 (s, 1H); 7.58-7.22 (m, 16H); 6.38 (m, 2H); 3.89 (s, 3H).

Step II:

N-Cyclopropyl-2-hydroxy-4-(trityloxy)benzamide

Methyl 2-hydroxy-4-(trityloxy)benzoate (340 mg, 0.83 mmol) was dissolved in cyclopropylamine (3 mL) and left at room temperature for a week. The volatiles were removed in vacuo and the residue was purified by silica gel flash chromatography (0-20% ethyl acetate in petroleum ether) to give the subtitled compound (210 mg).

$^1$H-NMR (CDCl$_3$, 400 MHz): δ 12.30 (s, 1H); 7.48 (m, 6H); 7.35-7.22 (m, 9H); 6.92 (d, J=9.0 Hz, 1H); 6.31 (d, J=2.4 Hz, 1H); 6.24 (dd, J=2.4, 8.8 Hz, 1H); 6.08 (br. S, 1H); 2.80 (m, 1H); 0.85 (m, 2H); 0.60 (m, 2H).

Step III:

N-Cyclopropyl-2-[(2S)-oxiran-2-ylmethoxy]4-(trityloxy)benzamide

A mixture of (2S)-oxiran-2-ylmethyl-3-nitrobenzenesulfonate (119 mg, 0.459 mmol), N-cyclopropyl-2-hydroxy-4-(trityloxy)benzamide (200 mg, 0.459 mmol) and cesium carbonate, Cs$_2$CO$_3$, (186.2 mg, 0.573 mmol) in dimethylformamide (3 mL) was kept on stirring at room temperature overnight. The reaction mixture was partitioned between ethyl acetate and water. The organic layer was dried over sodium sulphate, Na$_2$SO$_4$, filtered, concentrated and the residue was purified by silica gel flash chromatography (0-40% ethyl acetate in petroleum ether) to give the subtitled compound (160 mg).

¹H-NMR (CDCl₃, 400 MHz): δ 8.04 (s, 1H); 7.86 (d, J=8.8 Hz, 1H); 7.73 (br.d, J=3.0 Hz, 1H); 7.46-7.39 (m, 5H); 7.34-7.23 (m, 9H); 6.44 (dd, J=2.2, 8.8 Hz, 1H); 6.23 (d, J=2.2 Hz, 1H); 4.03 (dd, J=2.7, 10.8 Hz, 1H); 3.68 (dd, J=5.0, 10.8 Hz, 1H); 3.23 (m, 1H); 2.88 (m, 2H); 2.70 (dd, J=2.7, 4.9 Hz, 1H); 0.80 (m, 2H); 0.58 (m, 2H).

Step IV:

2-{[(2S)-3-(5-Chloro-1'H,3H-spiro[1-benzofuran-2,4'-piperidin]-1'-yl)-2-hydroxypropyl]oxy}-N-cyclopropyl-4-hydroxybenzamide A mixture of N-cyclopropyl-2-[(2S)-oxiran-2-ylmethoxy]-4-(trityloxy)benzamide (152 mg, 0.307 mmol) and 5-chloro-3H-spiro[1-benzofuran-2,4'-piperidine] (69 mg, 0.307 mmol) in ethanol (3 mL) was kept on stirring at 80° C. overnight. The volatiles were removed in vacuo and the residue was treated with 80% aqueous acetic acid (10 mL) at reflux for 90 min. The volatiles were removed in vacuo and the residue was purified by silica gel flash chromatography (0-3% methanol in dichloromethane, 0.2% NH₄OH) to give the titled compound (75 mg).

¹H-NMR (CD₃OD, 400 MHz): δ 7.83 (d, J=8.4 Hz, 1H); 7.13 (m, 1H); 6.94 (dd, J=2.3, 8.4 Hz, 1H); 6.65 (d, J=8.4 Hz, 1H); 6.51-6.45 (m, 2H); 4.21-4.13 (m, 2H); 4.08-4.02 (m, 1H); 3.01 (s, 2H); 2.90 (m, 1H); 2.75 (br.s, 4H); 2.58 (d, J=6.2 Hz, 2H); 1.98 (m, 2H); 1.88 (m, 2H); 0.80 (m, 2H); 0.65 (m, 2H). APCI-MS: m/z 473(MH⁺).

Example 26

2-{[(2S)-3-(5-Chloro-1'H,3H-spiro[1-benzofuran-2,4'-piperidin]-1'-yl)-2-hydroxy-2-methylpropyl]oxy}-N-cyclopropyl-4-hydroxybenzamide Step I:

N-Cyclopropyl-2-hydroxy-4-[(4-methoxybenzyl)oxy]benzamide

Methyl 2-hydroxy-4-[(4-methoxybenzyl)oxy]benzoate (Percec, V; Tomazos, D. *J. Mater. Chem.* 1993, 3, 643-650) (530 mg, 1.83 mmol) was dissolved in cyclopropyl amine (3 mL) and left at room temperature for a week. The volatiles were removed in vacuo and the residue was purified by silica gel flash chromatography (040% ethyl acetate in petroleum ether) to give the subtitled compound (407 mg).

¹H-NMR (DMSO-d₆, 400 MHz): δ 13.20 (br.s, 1H); 8.56 (d, J=2.7 Hz, 1H); 7.72 (d, J=8.7 Hz, 1H); 7.38-7.33 (m, 2H); 6.96-6.92 (m, 2H); 6.49-6.45 (m, 2H); 5.00 (s, 2H); 3.79 (s, 3H); 2.80 (m, 1H); 0.78 (m, 2H); 0.58 (m, 2H).

Step II:

[(2S)-2-Methyloxiranyl]methyl3-nitrobenzenesulfonate

To an oven-dried 1000 mL three-necked flask was added powdered activated molecular sieves (8.0 g, 4 Å) and dichloromethane, CH₂Cl₂, (440 mL), D-(−)-diisopropyl tartrate (4 mL, 14.2 mmol) and 2-methyl-2-propene-1-ol (20 mL, 240 mmol) was added and the mixture was cooled to −20° C. Titanium tetraisopropoxide (3.5 mL, 11.9 mmol) was added with a few mL of dichloromethane and the mixture was stirred at −20° C. for 30 min. Cumene hydroperoxide (75 mL, 430 mmol) was added dropwise over 1.5 hours maintaining the temperature at −20° C. The mixture was stirred at this temperature overnight. Trimethyl phosphite (40 mL, 340 mmol) was added dropwise over 5 hours maintaining the temperature at −20° C. Triethyl amine (50 mL, 360 mmol) and 4-dimethylaminopyridine (DMAP) (3.48 g, 28.5 mmol) was added followed by a solution of 3-nitrobenzenesulphonyl chloride (47 g, 212 mmol) in dichloromethane (400 mL). The temperature was raised to −10° C. and the mixture was stirred at this temperature overnight. After removing the external cooling vessel, the reaction mixture was filtered through celite. The organic phase was washed with 10% tartaric acid (500 mL), saturated sodium hydrogencarbonate, NaHCO₃, (300 mL) and brine (300 mL). The organic layer was dried over magnesium sulphate, MgSO₄, and concentrated in vacuo to give 150 g of a yellow oil. The crude material was purified by silica gel flash chromatography (0-50% ethyl acetate in heptane) to give the subtitled compound (48.8 g).

¹H-NMR (CDCl₃, 400 MHz): δ 8.79-8.75 (m, 1H); 8.52 (ddd, J=1.1, 2.3, 8.3 Hz, 1H); 8.25 (ddd, J=1.1, 1.8, 7.8 Hz, 1H); 7.81 (t, J=8.5 Hz, 1H); 4.28 (d, J=11.3 Hz, 1H); 4.05 (d, J=11.3 Hz, 1H); 2.73 (d, J=4.4 Hz, 1H); 2.67 (d, J=4.4 Hz, 1H); 1.56 (s, 3H).

Step III:

N-Cyclopropyl-4-[(4-methoxybenzyl)oxy]-2-{[(2S)-2-methloxiran-2-yl]methoxy}benzamide A mixture of [(2S)-2-methyloxiran-2-yl]methyl3-nitrobenzenesulfonate (218 mg, 0.797 mmol), N-cyclopropyl-2-hydroxy-4-[(4-methoxybenzyl)oxy]benzamide (250 mg, 0.797 mmol) and cesium carbonate, Cs₂CO₃, (311 mg, 0.956 mmol) in dimethylformamide (5 mL) was kept on stirring at room temperature overnight. The reaction mixture was partitioned between ethyl acetate and water. The organic layer was dried over sodium sulphate, Na₂SO₄, filtered, concentrated and the residue was purified by silica gel flash chromatography (0-40% ethyl acetate in petroleum ether) to give the subtitled compound (260 mg).

¹H-NMR (CDCl₃, 400 MHz): δ 8.19 (d, J=8.8 Hz, 1H); 7.90 (d, J=3.0 Hz, 1H); 7.38-7.33 (m, 2H); 6.96-6.92 (m, 2H); 6.70 (dd, J=2.3, 8.8 Hz, 1H); 6.48 (d, J=2.3 Hz, 1H); 5.02 (s, 2H); 4.14 (d, J=10.3 Hz, 1H); 4.06 (d, J=10.3 Hz, 1H); 3.80 (s, 3H); 3.04-2.98 (m, 1H); 2.94 (d, J=4.7 Hz, 1H); 2.87 (d, J=4.7 Hz, 1H); 1.50 (s, 3H); 0.86 (m, 2H); 0.65 (m, 2H). APCI-MS: m/z 384(MH⁺).

Step IV:

2-{[(2S)-3-(5-Chloro-1'H,3H-spiro[1-benzofuran-2,4'-piperidin]-1'-yl)-2-hydroxy-2-methylpropyl]oxy}-N-cyclopropyl-4-[(4-methoxybenzyl)oxy]benzamide A mixture of 5-chloro-3H-spiro(1-benzofuran-2,4'-piperidine] (70 mg, 0.313 mmol) and N-cyclopropyl-4-[(4-methoxybenzyl)oxy]-2-{[(2S)-2-methloxiran-2-yl]methoxy}benzamide (120 mg, 0.313 mmol) in ethanol (3 mL) was kept on stirring at 80° C. for 6 h. The volatiles were removed in vacuo and the residue was purified by silica gel flash chromatography (0-1% methanol in dichloromethane, 0.2% ammonium hydroxide, NH₄OH) to give the subtitled compound (100 mg).

¹H-NMR (CDCl₃, 400 MHz): δ 8.22-8.15 (m, 2H); 7.39-7.34 (m, 2H); 7.13-7.06 (m, 2H); 6.97-6.92 (m, 2H); 6.72-6.66 (m, 2H); 6.50 (d, J=2.3 Hz, 1H); 5.08 (s, 2H); 3.88 (s, 3H); 3.05 (m, 1H); 2.99 (s, 2H); 2.90 (m, 2H); 2.75 (m, 1H); 2.66 (d, J=13.8 Hz, 1H); 2.64 (m, 1H); 2.49 (d, J=13.8 Hz, 1H); 1.99 (m, 2H); 1.82 (m, 2H); 1.60 (br.s, 2H); 1.33 (s, 3H); 0.86 (m, 2H); 0.65 (m, 2H). APCI-MS: m/z 607(MH⁺).

Step V:

2-{[(2S)-3-(5-Chloro-1'H,3H-spiro[1-benzofuran-2,4'-piperidin]-1'-yl)-2-hydroxy-2-methylpropyl]oxy}-N-cyclopropyl-4-hydroxybenzamide 2-{[(2S)-3-(5-Chloro-1'H,3H-spiro[1-benzofuran-2,4'-piperidin]-1'-yl)-2-hydroxy-2-methylpropyl]oxy}-N-cyclopropyl-4-[(4-methoxybenzyl)oxy]benzamide (80 mg, 0.131 mmol) was treated with 10% trifluoroacetic acid in dichloromethane (10 mL) at room temperature for 15 min. The volatiles were removed in vacuo and the residue was purified by silica gel flash chromatography (0-2% methanol in dichloromethane, 0.2% ammonium hydroxide, NH$_4$OH) to give the titled compound (40 mg).

$^1$H-NMR (CD$_3$OD, 400 MHz): δ 7.83 (m, 1H); 7.12 (m, 1H); 7.03 (dd, J=2.3, 8.5 Hz, 1H); 6.64 (d, J=8.5 Hz, 1H); 6.49-6.45 (m, 2H); 4.09 (d, J=9.2 Hz, 1H); 3.90 (d, J=9.2 Hz, 1H); 2.99 (s, 2H); 2.92 (m, 1H); 2.79 (m, 2H); 2.66 (m, 2H); 2.58 (d, J=13.9 Hz, 1H); 2.50 (d, J=13.9 Hz, 1H); 1.93-1.75 (m, 4H); 1.31 (s, 3H); 0.80 (m, 2H); 0.68 (m, 2H). APCI-MS: m/z 487(MH$^+$).

Example 27

N-(4-hydroxy-2-{[(2S)-2-hydroxy-3-(1'H,4H-spiro[chromene-3,4'-piperidin]-1'-yl)propyl]oxy}phenyl)acetamide Step I (1Z)-1-(2,4-dihydroxyphenyl)ethanone oxime 1-(2,4-dihydroxyphenyl)ethanone (4.5 g, 29.6 mmol) was dissolved in pyridin (17 mL). Hydroxylamine hydrochloride (2.1 g, 29.6 mmol) was added in small portions over 10 minutes. After stirring at room temperature over night the green-yellowish solution was partitioned between water and ethyl acetate. The organic phase was washed twice with water and once with 0.2 M hydrochloric acid, and was finally concentrated. The oily residue was treated with water, evaporated to yield a white semi solid residue, which was treated with toluene and evaporated to give the titled compound (4.8 g, 98%) as a white solid.

Step II 2-methyl-1,3-benzoxazol-6-ol

To a cooled (5° C.) solution of (1Z)-1-(2,4-dihydroxyphenyl)ethanone oxime (9.7 g, 57.7 mmol) in acetonitrile (65 mL) and dimethylacetamide (11 mL) was added phosphorus oxychloride (5.6 mL, 60.3 mmol) drop wise. The temperature was not allowed to exceed 10° C. during the addition. After 1 hrs stirring at room temperature the yellow slurry was poured on a mixture of sodium hydrogen carbonate and ice. The resulting precipitate was filtered off and dried yielding 6.3 g (73%) the titled compound.

Step III 2-methyl-1,3-benzoxazol-6-yl acetate

A slurry of 2-methyl-1,3-benzoxazol-6-ol (7.1 g, 47.8 mmol) in tetrahydrofuran was cooled to 10° C. and triethylamine (5.8 mL, 81.3 mmol) was added in one portion, followed by the addition of acetyl chloride (11.3 mL, 81.6 mmol) in small portions. After stirring at room temperature over night the reaction mixture was partitioned between water and ethyl acetate. The organic phase was washed twice with water and concentrated to give the titled compound (8.2 g, 90%) as a beige solid.

Step IV 4-(acetylamino)-3-hydroxyphenyl acetate 2-methyl-1,3-benzoxazol-6-yl acetate (8.1 g, 42.3 mmol) was dissolved in tetrahydrofuran (60 mL), and trifluoroacetic acid (4 mL, 53.2 mmol) was added. The light brown solution was stirred over night at room temperature. Sodium hydrogen carbonate (aq, sat) was added, and the solution was extracted twice with ethyl acetate. The combined organic layers were concentrated to the titled compound (8.0 g, 91%) as a beige solid.

Step V 4-(acetylamino)-3-[(2S)-oxiran-2-ylmethoxy]phenyl acetate

A solution of 4-(acetylamino)-3-hydroxyphenyl acetate (669 mg, 3.2 mmol), (2S)-oxiran-2-ylmethyl 3-nitrobenzenesulfonate (748 mg, 2.9 mol) and caesium carbonate (1.05 g, 3.2 mmol) in 1-methyl-pyrrolidinone (10 mL) was stirred over night at room temperature, and then partitioned between water and ethyl acetate. The organic phase was washed twice with water and concentrated to an yellow oil, which was suspended in methanol/diethyl ether, ½. The precipitated beige solid was filtered off and dried to give the titled compound (296 mg, 38%).

Step VI

N-(4-hydroxy-2-{[(2S)-2-hydroxy-3-(1'H,4H-spiro[chromene-3,4'-piperidin]-1'-yl)propyl]oxy}phenyl)acetamide A solution of 4-(acetylamino)-3-[(2S)-oxiran-2-ylmethoxy]phenyl acetate (56 mg, 0.21 mmol) and 4H-spiro[chromene-3,4'-piperidine] (43 mg, 0.21 mmol) in methanol (1 mL) was stirred over night at 60° C., and then concentrated. The dark grey residue was purified by HPLC on C 18 ("Kromasil" column, 5 um, acetonitrile/water 10/90 to 60/40 over 20 min with 0.1% trifluoroacetic acid) to give the title compound (39 mg, 33%) trifluoroacetate salt.

$^1$H-NMR (acetone-d$_6$, 400 MHz), δ: 11.27 (1H, bs); 8.52 (1H, bs); 7.95 (1H, d); 7.10 (2H, t); 6.86 (1H, t); 6.78 (1H, d); 6.53 (1H, d); 6.40 (1H, dd); 4.55-4.48 (1H, m); 4.21 (1H, s); 4.09-4.01 (2H, m); 3.91 (1H, s); 3.83-3.65 (2H, m); 3.65-3.49 (2H, m); 3.49-3.35 (2H, m); 3.00 (1H, s); 2.70 (1H, s); 2.08 (3H, s); 2.02-1.74 (4H, m) APCI-MS: m/z 427 [MH+]

Example 28

2-{[(2S)-3-(5-Chloro-1'H,3H-spiro[1-benzofuran-2,4'-piperidin]-1'-yl)-2-hydroxy-2-methylpropyl]oxy}-4-hydroxy-N-methylbenzamide(trifluoroacetate)

Step I:

2-Hydroxy-4[(4-methoxybenzyl)oxy]-N-methylbenzamide

To a suspension of methyl 2-hydroxy-4-[(4-methoxybenzyl)oxy]benzoate (500 mg, 1.73 mmol) in methanol (15 mL) was slowly added aqueous 40% methylamine (3 mL) at 0° C. After addition was complete the reaction mixture was kept on stirring at room temperature for 2 days. The volatiles were removed in vacuo to give the subtitled compound (500 mg).

$^1$H-NMR (DMSO-d$_6$, 400 MHz): δ 13.20 (br.s, 1H); 8.60 (m, 1H); 7.70 (d, J=8.8 Hz, 1H); 7.35 (m, 2H); 6.96-6.92 (m, 2H); 6.50 (dd, J=2.6, 8.8 Hz, 1H); 6.42 (d, J=2.6 Hz, 1H) 5.04 (s, 2H); 3.76 (s, 3H); 2.79 d, J=4.6 Hz, 3H). APCI-MS: m/z 288(MH$^+$).

Step II:

4-[(4-Methoxybenzyl)oxy]-N-methyl-2-{[(2S)-2-methyloxiran-2-yl]methoxy}benzamide A mixture of [(2S)-2-methyloxiran-2-yl]methyl 3-nitrobenzenesulfonate (133 mg, 0.487 mmol), 2-hydroxy-4-[(4-methoxybenzyl)oxy]-N-methylbenzamide (140 mg, 0.487 mmol) and cesium carbonate, Cs$_2$CO$_3$, (198 mg, 0.608 mmol) in dimethylformamide (5 mL) was kept on stirring at room temperature overnight. The reaction mixture was partitioned between ethyl acetate and water. The organic layer was dried over sodium sulphate, Na$_2$SO$_4$, filtered and concentrated. The residue was purified by silica gel flash chromatography (0-60% ethyl acetate in petroleum ether) to give the subtitled compound (130 mg).

$^1$H-NMR (CDCl$_3$, 400 MHz): δ 8.18 (d, J=8.8 Hz, 1H); 7.82 (m, 1H); 7.37 (m, 2H); 6.97-6.92 (m, 2H); 6.71 (dd J=2.3, 8.8 Hz, 1H); 6.53 (d, J=2.3 Hz, 1H); 5.01 (s, 2H); 4.18 (d, J=10.5 Hz, 1H); 4.10 (d, J=10.5 Hz, 1H); 3.85 (s, 3H); 3.02 (d, J=4.9 Hz, 3H); 2.97 (d, J=4.6 Hz, 1H); 2.80 (d, J=4.6 Hz, 1H); 1.50 (s, 3H). APCI-MS: m/z 358(MH$^+$).

Step III:

2-{[(2S)-3-(5-Chloro-1'H,3H-spiro[1-benzofuran-2,4'-piperidin]-1'-yl)-2-hydroxy-2-methylpropyl]oxy}-4-[(4-methoxybenzyl)oxy]-N-methylbenzamide A mixture of 5-chloro-3H-spiro[1-benzofuran-2,4'-piperidine] (70 mg, 0.313 mmol) and 4-[(4-methoxybenzyl)oxy]-N-methyl-2-{[(2S)-2-methyloxiran-2-yl]methoxy}benzamide (112 mg, 0.313 mmol) in ethanol (2 mL) was kept on stirring at 80° C. for 4.5 h. The volatiles were removed in vacuo and the residue was purified by silica gel flash chromatography (0-1.5% methanol in dichloromethane, 0.2% ammonium hydroxide, NH$_4$OH) to give the subtitled compound (135 mg).

$^1$H-NMR (CDCl$_3$, 400 MHz): δ 8.18 (d, J=8.7 Hz, 1H); 8.12 (m, 1H); 7.39-7.35 (m, 2H); 7.12 (m, 2H); 7.08 (dd, J=2.3, 8.5 Hz, 1H); 6.97-6.92 (m, 2H); 6.72-6.66 (m, 2H); 6.52 (d, J=2.3 Hz, 1H); 5.05 (s, 2H); 3.90 (m, 2H); 3.82 (s, 3H); 3.0 (d, J=4.9 Hz, 3H); 2.98 (s, 2H); 2.94-2.84 (m, 2H); 2.73 (m, 1H); 2.69 (d, J=13.9 Hz, 1H); 2.63 (m, 1H); 2.49 (d, J=13.9 Hz, 1H); 1.99 (m, 2H); 1.82 (m, 2H). APCI-MS: m/z 581(MH$^+$).

Step IV:

2-{[(2S)-3-(5-Chloro-1'H,3H-spiro[1-benzofuran-2,4'-piperidin]-1'-yl)-2-hydroxy-2-methylpropyl]oxy}-4-hydroxy-N-methylbenzamide(trifluoroacetate)

2-{[(2S)-3-(5-Chloro-1'H,3H-spiro[1-benzofuran-2,4'-piperidin]-1'-yl)-2-hydroxy-2-methylpropyl]oxy}-4-[(4-methoxybenzyl)oxy]-N-methylbenzamide (125 mg, 0.215 mmol) was treated with 10% trifluoroacetic acid in dichloromethane (10 mL) at room temperature for 20 min. The volatiles were removed in vacuo and the residue was purified by HPLC (acetonitrile/water (CH$_3$CN/H$_2$O), 0.1% trifluoroacetic acid) to give the titled compound (50 mg).

$^1$H-NMR (CD$_3$OD, 400 MHz): δ 7.52-7.47 (m, 1H); 7.20 (br.s, 1H); 7.10 (dd, J=2.3, 8.5 Hz, 1H); 6.75 (d, J=8.5 Hz, 1H); 6.52 (br.s, 1H); 6.49 (dd, J=2.1, 8.5 Hz, 1H); 4.20 (m, 2H); 4.00 (m, 1H); 3.62-3.35 (m, 4H); 3.18 (2xs, 2H); 3.90 (2xs, 3H); 2.60 (m, 2H); 2.32-2.05 (m, 3H); 1.39 (s, 3H). APCI-MS: m/z 461(MH$^+$).

Example 29

2-{[(2S)-3-(5-Chloro-1'H,3H-spiro[1-benzofuran-2,4'-piperidin]-1'-yl)-2-hydroxy]oxy}-4-hydroxy-N-methylbenzamide Step I:

4-[4-Methoxybenzyl)oxy]-N-methyl-2-[(2S)-oxiran-2-ylmethoxy]benzamide

A mixture of (2S)-oxiran-2-ylmethyl3-nitrobenzenesulfonate (151 mg, 0.584 mmol), methyl 2-hydroxy-4-[(4-methoxybenzyl)oxy]benzoate (168 mg, 0.584 mmol) and cesium carbonate, Cs$_2$CO$_3$, (228 mg, 0.70 mmol) in dimethylformamide (4 mL) was kept on stirring at room temperature overnight. The reaction mixture was partitioned between ethyl acetate and water. The organic layer was dried over sodium sulphate, Na$_2$SO$_4$, filtered and concentrated. The residue was purified by silica gel flash chromatography (0-90% ethyl acetate in petroleum ether) to give the subtitled compound (150 mg).

$^1$H-NMR (DMSO-d$_6$, 400 MHz): δ 7.90 (m, 1H); 7.75 (d, J=8.7 Hz, 1H); 7.37 (d, J=8.6 Hz, 2H); 6.96-6.91 (m, 2H); 6.74 (d, J=2.3 Hz, 1H); 6.68 (dd, J=2.3, 8.7 Hz, 1H); 5.08 (s, 2H); 4.48 (dd, J=2.5, 11.5 Hz, 1H); 4.04 (dd, J=6.0, 11.5 Hz, 1H); 3.78 (s, 3H); 3.45 (m, 1H); 2.86 (t, J=4.9 Hz, 1H); 2.79 (d, J=4.7 Hz, 3H); 2.73 (dd, J=2.7, 5.0 Hz, 1H). APCI-MS: m/z 344(MH$^+$).

Step II:

2-{[(2S)-3-(5-Chloro-1'H,3H-spiro[1-benzofuran-2,4'-piperidin]-1'-yl)-2-hydroxypropyl]oxy}-4-[(4-methoxybenzyl)oxy]-N-methylbenzamide A mixture of 5-chloro-3H-spiro[1-benzofuran-2,4'-piperidine] (70 mg, 0.313 mmol) and 4-[4-methoxybenzyl)oxy]-N-methyl-2-[(2S)-oxiran-2-ylmethoxy]benzamide (107.5 mg, 0.313 mmol) in ethanol (3 mL) was kept on stirring at 80° C. for 6 h. The volatiles were removed in vacuo and the residue was purified by silica gel flash chromatography (0-1% methanol in dichloromethane, 0.2% ammonium hydroxide, NH$_4$OH) to give the subtitled compound (122 mg).

$^1$H-NMR (CDCl$_3$, 400 MHz): δ 8.18 (d, J=8.8 Hz, 1H); 8.10 (m, 1H); 7.34 (d, J=8.7 Hz, 2H); 7.14 (br.s, 1H); 7.08 (m, 1H); 6.95 (d, J=8.7 Hz, 2H); 6.70 (m, 2H); 6.55 (d, J=2.1 Hz, 1H); 5.08 (s, 2H); 4.22-4.12 (m, 2H); 3.98 (dd, J=5.3, 9.3 Hz, 1H); 3.85 (s, 3H); 3.01 (s, 2H); 3.00 (d, J=4.8 Hz, 3H); 2.95-2.87 (m, 1H); 2.80 (m, 1H); 2.65-2.50 (m, 4H); 2.01 (m, 2H); 1.82 (m, 2H). APCI-MS: m/z 567(MH$^+$).

Step III:

2-{[(2S)-3-(5-Chloro-1'H,3H-spiro[1-benzofuran-2,4'-piperidin]-1'-yl)-2-hydroxy]oxy}-4-hydroxy-N-methylbenzamide 2-{[(2S)-3-(5-Chloro-1'H,3H-spiro[1-benzofuran-2,4'-piperidin]-1'-yl)-2-hydroxypropyl]oxy}-4-[(4-methoxybenzyl)oxy]-N-methylbenzamide (110 mg, 0.194 mmol) was treated with 10% trifluoroacetic acid in dichloromethane (10 mL) at room temperature for 20 min. The volatiles were removed in vacuo and the residue was purified by silica gel flash chromatography (0-3% methanol in dichloromethane, 0.2% ammonium hydroxide, NH$_4$OH) to give the titled compound (45 mg).

$^1$H-NMR (CD$_3$OD, 400 MHz): δ 7.81 (d, J=8.7 Hz, 1H); 7.13 (m, 1H); 7.04 (dd, J=2.3, 8.5 Hz, 1H); 6.66 (d, J=8.5 Hz, 1H); 6.52 (d, J=2.2 Hz, 1H); 6.48 (dd, J=2.2, 8.6 Hz, 1H); 4.25-4.17 (m, 2H); 4.05 (m, 1H); 3.02 (s, 2H); 2.92 (s, 3H); 2.70 (br.s, 4H); 2.60 (d, J=6.2 Hz, 2H); 1.94 (m, 2H); 1.84 (m, 2H). APCI-MS: m/z 447(MH$^+$).

Example 30

N-(2-{[(2S)-3-(5-Chloro-1'H-spiro[1,3-benzodioxole-2,4'-piperidin]-1'-yl)-2-hydroxypropyl]oxy}-4-hydroxyphenyl)acetamide trifluoroacetate Step I:

Ethyl 5-chloro-1'H-spiro[1,3-benzodioxole-2,4'-piperidine]-1'-carboxylate

A mixture of ethyl 4-oxopiperidine-1-carboxylate (1.71 g, 10 mmol), 4-chlorobenzene-1,2-diol (1.73 g, 12 mmol), and a catalytic amount of 4-methylbenzenesulfonic acid hydrate in dry toluene (30 ml) were refluxed with water separator for 7 h. After cooling, the reaction mixture was washed with 2N sodium hydroxide (2×25 ml), and the solvent was removed in vacuo. Flash chromatography on silica gel (heptane/ethyl acetate, 2:1) of the residual semi-solid product afforded ethyl 5-chloro-1'H-spiro[1,3-benzodioxole-2,4'-piperidine]-1'-carboxylate as colourless crystals (0.43 g, 15%).

APCI-MS: m/z 298 [MH$^+$]. $^1$H-NMR (400 MHz, CDCl$_3$): δ 6.77 (m, 2H), 6.67 (m, 1H), 4.16 (q, 2H, J=7.1 Hz), 3.67 (t, 4H, J=5.7 Hz), 1.98 (t, 4H, J=5.7 Hz), 1.28 (t, 3H, J=7.1 Hz).

Step II:

5-Chlorospiro[1,3-benzodioxole-2,4'-piperidine]

Ethyl 5-chloro-1'H-spiro[1,3-benzodioxole-2,4'-piperidine]-1'-carboxylate (0.43 g, 1.45 mmol) was dissolved in ethanol (5 ml) and water (0.4 ml). Sodium hydroxide (0.2 g) was added followed by reflux for 2 days. After cooling, the solution was concentrated in vacuo, and acidified with 10% HCl to pH <1. After the gas evolution had ceased, the solution was made alkaline by addition of saturated aqueous sodium hydrogencarbonate, NaHCO$_3$, and extracted with dichloromethane. Drying with sodium sulphate, Na$_2$SO$_4$, and evaporation of the solvent afforded a colourless solid (0.28 g, 1.2 mol, 86%).

APCI-MS: m/z 226 [MH$^+$]. $^1$H-NMR (400 MHz, CDCl$_3$): δ 6.6-6.9 (m, 3H), 3.06 (t, 4H, J=5.0 Hz), 1.99 (t, 4H, J=5.2 Hz).

Step III:

N-2-{[(2S)-3-(5-Chloro-1'H-spiro[1,3-benzodioxole-2,4'-piperidin]-1'-yl)-2-hydroxypropyl]oxy}-4-hydroxyphenyl) acetamide trifluoroacetate A solution of 5-chlorospiro[1,3-benzodioxole-2,4'-piperidine] (45 mg, 0.2 mmol) and 4-(acetylamino)-3-[(2S)-oxiran-2-ylmethoxy]phenyl acetate (53 mg, 0.2 mmol) in methanol (5 ml) was refluxed for 15 h. The solvent was distilled off under reduced pressure. The residue was purified by preparative HPLC ("Kromasil" column; eluent: [acetonitrile+0.1% trifluoroacetic acid (TFA)/water+0.1% TFA]) to afford the titled compound as a colourless solid (37 mg, 0.07 mmol, 33%).

APCI-MS: m/z 449 [MH$^+$]. $^1$H-NMR (400 MHz, acetone-d$_6$): δ 8.47 (br. s, 1H), 7.93 (d, 1H, J=8.7 Hz), 6.8-7.0 (m, 3H), 6.53 (d, 1H, J=2.6 Hz), 6.41 (dd, 1H, J=2.6 Hz, J=8.7 Hz), 4.54 (m, 1H), 4.08 (m, 2H), 3.66 (m, 2H), 2.51 (m, 4H), 2.08 (s, 3H), 2.06 (m, 4H).

Example 31

N-(2-{[(2S)-3-(5-Chloro-1'H-spiro[1,3-benzodioxole-2,4'-piperidin]-1'-yl)-2-hydroxy-2-methylpropyl]oxy}-4-hydroxyphenyl)acetamide trifluoroacetate The title compound was prepared as described in Example 9 from 5-chlorospiro[1,3-benzodioxole-2,4'-piperidine] (45 mg, 0.2 mmol) and 4-(acetylamino)-3-{[(2S)-2-methyloxiran-2-yl]methoxy}phenyl benzoate (68 mg, 0.2 mmol) as a colourless solid (30 mg, 0.05 mmol, 26%).

APCI-MS: m/z 463 [MH$^+$]. $^1$H-NMR (400 MHz, acetone-d$_6$): δ 8.59 (br. s, 1H), 7.73 (d, 1H, J=8.7 Hz), 6.8-7.0 (m, 3H), 6.58 (d, 1H, J=2.6 Hz), 6.42 (dd, 1H, J=2.6 Hz, J=8.7 Hz), 4.42 (d, 1H, J=9.7 Hz), 3.97 (d, 1H, J=9.7 Hz), 3.71 (d, 1H, J=14 Hz), 3.54 (d, 1H, J=14 Hz), 2.52 (m, 4H), 2.09 (s, 3H), 2.06 (m, 4H), 1.51 (s, 3H).

Example 32

N-4-Hydroxy-2-{[(2S)-2-hydroxy-3-(1'H-spiro[1,3-benzodioxole-2,4'-piperidin]-1'-yl)propyl] oxy}phenyl)acetamide trifluoroacetate The title compound was prepared from spiro[1,3-benzodioxole-2,4'-piperidine] (E. K. Moltzen, J. Perrengaard, E. Meier, *J. Med. Chem.* 1995, 38 (11), 2009-2007) (38 mg, 0.2 mmol) as described Example 30. Yield 78 mg, 0.15 mmol, 74%.

APCI-MS: m/z 415 [MH$^+$]. $^1$H-NMR (400 MHz, acetone-d$_6$): δ 7.90 (d, 1H, J=8.7 Hz), 6.87 (s, 4H), 6.53 (d, 1H, J=2.6 Hz), 6.75 (dd, 1H, J=2.6 Hz, J=8.7 Hz), 4.56 (m, 1H), 4.08 (m, 2H), 3.69 (m, 2H), 2.46 (m, 4H), 2.09 (s, 3H), 2.07 (m, 4H).

Example 33

N-(4-Hydroxy-2-{[(2S)-2-hydroxy-2-methyl-3-(1'H-spiro[1,3-benzodioxole-2,4'-piperidin]-1'-yl)propyl] oxy)phenyl)acetamide trifluoroacetate The title compound was prepared from spiro[1,3-benzodioxole-2,4'-piperidine] (38 mg, 0.2 mmol) as described in Example 9. Yield 88 mg, 0.16 mmol, 81%.

APCI-MS: m/z 429 [MH$^+$]. $^1$H-NMR (400 MHz, acetone-d$_6$): δ 7.68 (d, 1H, J=8.7 Hz), 6.86 (s, 4H), 6.60 (d, 1H, J=2.5 Hz), 6.43 (dd, 1H, J=2.6 Hz, J=8.7 Hz), 4.06 (d, 1H, J=9.7 Hz), 3.98 (d, 1H, J=9.7 Hz), 4.03 (d, 1H, J=9.7 Hz), 3.77 (d, 1H, J=13.6 Hz), 3.60 (d, 1H, J=13.6 Hz), 2.51 (m, 4H), 2.10 (s, 3H), 2.08 (m, 4H), 1.52 (s, 3H).

Intermediate Compound: 5-Chloro-3H-spiro[2-benzofuran-1,4'-piperidine]

Step I:

1'-Benzyl-5-chloro-3H-spiro[2-benzofuran-1,4'-piperidin]-3-one

To a solution of 2-bromo-5-chlorobenzoic acid (2.35 g, 10.0 mmol) in tetrahydrofuran (THF) (15 mL) was added, a 1.6 M solution in hexane, n-butyllithium (20 mL, 32.0 mmol) slowly at −78° C. under nitrogen. After addition was complete the reaction mixture was kept on stirring at −78° C. for 3 h. Then a solution of 1-benzylpiperidin-4-one (3.78 g, 20.0 mmol) in THF (10 mL) was added slowly to the reaction mixture at −78° C. After addition was complete the reaction temperature was raised to room temperature and the reaction mixture was kept on stirring at room temperature overnight. The reaction mixture was poured into a mixture of water (60 mL) and diethyl ether (60 mL), layers were separated. The aqueous layer was extracted with diethyl ether (2×20 mL). The aqueous layer was acidified with aqueous 6M hydrochloric acid (HCl) to pH 2 and boiled for 1 h, cooled to 0° C., pH was adjusted to 10.0 by addition of aqueous sodium hydroxide (NaOH) (6M) and rapidly extracted with trichloromethane (CHCl$_3$). The organic layer was washed with water, dried over sodium sulphate (Na$_2$SO$_4$), filtered and concentrated in vacuo to give the subtitled compound (1.22 g) and it was pure enough for the next step.

$^1$H-NMR (CDCl$_3$, 400 MHz): δ 7.85 (m, 1H); 7.65 (dd, J=1.9, 8.2 Hz, 1H); 7.41-7.26-1.69 (m, 2H). APCI-MS: m/z 328(MH$^+$).

Step II:

1'-Benzyl-5-chloro-3H-spiro[2-benzofuran-1,4'-piperidine]

To a solution of 1'-benzyl-5-chloro-3H-spiro[2-benzofuran-1,4'-piperidin]-3-one (1.1 g, 3.35 mmol) in THF (12 mL) was added 1 M solution of borane complex in THF (7 mL, 7.0 mmol) slowly at 0° C. After addition was complete reaction mixture was kept at room temperature for 30 min, then kept at reflux overnight, cooled to 0° C. and 6M aqueous HCl (3.5 mL) was added slowly. The reaction mixture was kept at reflux for 5 h, cooled to 0° C., pH of the reaction mixture was adjusted to 10 by addition of aqueous NaOH (6M) and the whole was extracted with ethyl acetate. The organic layer was washed with water, dried over sodium sulphate ($Na_2SO_4$), filtered, and concentrated in vacuo. The residue was purified by silica gel flash chromatography (0-30% ethyl acetate in petroleum ether) to give the subtitled compound (1.0 g).

$^1$H-NMR ($CDCl_3$, 400 MHz): δ 7.40-7.06 (m, 8H); 5.03 (s, 2H); 3.60 (s, 2H); 2.87 (m, 2H); 2.45 (m, 2H); 1.95 (m, 2H); 1.80 (m, 2H). APCI-MS: m/z 314(MH$^+$).

Step III:

5-Chloro-3H-spiro[2-benzofuran-1,4'-piperidine]

To a solution of 1'-benzyl-5-chloro-3H-spiro[2-benzofuran-1,4'-piperidine] (950 mg, 3.02 mmol) in dichloromethane ($CH_2Cl_2$) (6 mL) was added chloroethyl chloroformate (560.6 mg, 3.92 mmol) slowly at 0° C. After addition was complete the reaction mixture was kept on stirring at 0° C. for 25 min. The volatiles were removed in vacuo, the residue was dissolved in methanol (6 mL) and kept at reflux for 40 min. The volatiles were removed in vacuo and the residue was purified by silica gel flash chromatography (0-5% methanol in dichloromethane, 0.2% ammonium hydroxide, $NH_4OH$) to give the titled compound (300 mg) and 1'-benzyl-5-chloro-3H-spiro[2-benzofuran-1,4'-piperidin] was recovered (320 mg).

$^1$H-NMR($CD_3OD$, 400 MHz): δ 1.28-7.24 (m, 2H); 7.18-7.13 (m, 1H); 5.00 (s, 2H); 2.95 (m, 4H); 1.90-1.77 (m, 2H); 1.72-1.63 (m, 2H). APCI-MS: m/z 224(MH$^+$).

Intermediate Compound: 5-Fluoro-3H-spiro[1-benzofuran-2,4'-piperidine]

Step I:

1'-Benzyl-5-fluoro-3H-spiro[1-benzofuran-2,4'-piperidine]

To a stirring suspension of magnesium strip (763 mg) in diethyl ether (7 mL) was added a crystal of iodine followed by 0.4 mL of 2-(bromomethyl)-1,4-difluorobenzene under nitrogen. The reaction was initiated with a high intensity heat gun, then 2-(bromomethyl)-1,4-difluorobenzene (5.0 g, 24.25 mmol) in diethyl ether (7 mL) was added at such a rate that a gentle reflux was maintained. After addition was complete the reaction mixture was kept on stirring at reflux for 100 min, cooled to room temperature. To this reaction mixture a solution of 1-benzylpiperidin-4-one (4.57 g, 24.25 mmol) in diethyl ether (12 mL) was added dropwise with vigorous stirring. After addition was complete a white cake was formed which was left overnight at room temperature. The cake was hydrolized by treatment with aqueous ammonium chloride ($NH_4Cl$) solution, extracted with diethyl ether. The organic layer was washed with water, dried over sodium sulphate ($Na_2SO_4$), filtered, concentrated and the residue was purified by silica gel flash chromatography (0-1% methanol in dichloromethane, 0.1% ammonium hydroxide, $NH_4OH$) to give intermediate compound 1-benzyl-4-(2,5-difluorobenzyl)piperidin-4-ol (2.74 g) containing large amount of impurities. To a suspension of sodium hydride (NaH) (55%, 1.12 g, 26.0 mmol) in toluene (10 mL) was slowly added a solution of 1-benzyl-4-(2,5-difluorobenzyl)piperidin-4-ol in toluene (15 mL). After addition was complete, the reaction mixture was kept on stirring at 110° C. (in a preheated oil bath), after 5 minutes dimethylformamide (9 mL) was added and stirring was continued at reflux for 2 h. The reaction mixture was cooled to room temperature, water (20 mL) was added and extracted with ethyl acetate. The organic layer was dried over sodium sulphate ($Na_2SO_4$), filtered, concentrated and the residue was purified by silica gel flash chromatography (0-1.5% methanol in dichloromethane, 0.1% ammonium hydroxide, $NH_4OH$) to give the subtitled compound (190 mg).

$^1$H-NMR ($CDCl_3$, 400 MHz): δ 7.39-7.26 (m, 5H); 6.88-6.76 (m, 2H); 6.67 (dd, J=4.2, 8.7 Hz, 1H); 3.59 (s, 2H); 2.99 (s, 2H); 2.68-2.47 (m, 4H); 2.03-1.94 8M, 2H); 1.86-1.76 (m, 2H). APCI-MS: m/z 298(MH$^+$).

Step II:

5-Fluoro-3H-spiro[1-benzofuran-2,4'-piperidine]

Ethyl chloroformate (65.6 mg, 0.604 mmol) was added to a solution of 1'-benzyl-5-fluoro-3H-spiro[1-benzofuran-2,4'-piperidine] (150 mg, 0.504 mmol) in toluene (2 mL) and the reaction mixture was refluxed overnight. The reaction mixture was cooled to room temperature, diluted by addition of toluene, washed successively with aqueous sodium hydrogencarbonate ($NaHCO_3$) and water. The organic layer was dried over sodium sulphate ($Na_2SO_4$) filtered and concentrated in vacuo. The residue was dissolved in ethanol (3.5 mL), aqueous potassium hydroxide (KOH) (800 mg KOH in 0.8 mL water) was added and the reaction mixture was kept on stirring at reflux overnight, cooled to room temperature, extracted with ethyl acetate. The organic layer was well washed with water, dried over sodium sulphate ($Na_2SO_4$), filtered and concentrated. The residue was purified by HPLC (10% acetonitrile ($CH_3CN$)-55% $CH_3CN$ in water containing 0.1% ammonium hydroxide, $NH_4OH$) to give the titled compound (49 mg).

$^1$H-NMR ($CD_3OD$, 400 MHz): δ 6.92-6.87 (m, 1H); 6.81-6.75 (m, 1H); 6.64 (dd, J=4.2, 8.7 Hz, 1H); 3.08-2.98 (m, 4H); 2.89-2.81 (m, 2H); 1.92-1.83 (m, 2H); 1.78-1.71 (m, 2H). APCI-MS: m/z 208(MH$^+$).

Intermediate Compound: 5-Chloro-3H-spiro[1-benzofuran-2,3'-pyrrolidine]

Step I:

1-Benzyl-3-(5-chloro-2-fluorobenzyl)pyrrolidin-3-ol

To a stirring suspension of magnesium strip (1.39 g, 57.06 mmol) in diethyl ether (10 mL) was added a crystal iodine followed by 0.5 mL of 2-(bromomethyl)-4-chloro-1-fluorobenzene under nitrogen. The reaction was initiated with a high intensity heat gun, then a solution of 2-(bromomethyl)-4-chloro-1-fluorobenzene (12.75 g, 57.06 mmol) in diethyl ether was added at such a speed that gentle reflux was maintained. After addition was complete the reaction mixture was kept on stirring at reflux for 3.5 h, cooled to room temperature and a solution of 1-benzylpyrrolidin-3-one (10.0 g, 57.06 mmol) in diethyl ether (20 mL) was added dropwise with vigorous stirring. After addition was complete the reaction mixture was left overnight at room temperature. This reaction mixture was treated with aqueous ammonium chloride ($NH_4Cl$) solution and extracted with ethyl acetate. The organic layer was washed with water, dried over sodium sulphate ($Na_2SO_4$), filtered, concentrated and the residue was purified by silica gel flash chromatography (0-2% methanol in dichloromethane, 0.2% ammonium hydroxide, NH$_4$OH) to give the subtitled compound (650 mg).

$^1$H-NMR (CDCl$_3$, 400 MHz): δ 7.39-7.23 (m, 6H); 7.21-7.15 (m, 1H); 6.98 (t, J=9.0 Hz, 1H); 3.68 (d, J=13.0 Hz, 1H); 3.63 (d, J=13.0 Hz, 1H); 3.01-2.89 (m, 3H); 2.65 (d, J=9.5 Hz, 1H); 2.42-2.34 (m, 2H); 2.07-1.98 (m, 1H); 1.88-1.75 (m, 1H); 1.64 (br.s, 1H). APCI-MS: m/z 320 (MH$^+$).

Step II:

1'-Benzyl-5-chloro-3H-spiro[1-benzofuran-2,3'-pyrrolidine]

To a suspension of sodium hydride (NaH) (55%, 612 mg, 14.0 mmol) in toluene (10 mL) was added a solution of 1-benzyl-3-(5-chloro-2-fluorobenzyl)pyrrolidin-3-ol (1.3 g, 4.06 mmol) in toluene (20 mL) and the reaction mixture was kept on stirring at reflux, after 5 minutes dimethylformamide (10 mL) was added and the reaction mixture was refluxed for 90 minutes, cooled to room temperature, water (20 mL) was added and extracted with ethyl acetate. The organic layer was dried over sodium sulphate (Na$_2$SO$_4$), filtered, concentrated and the residue was purified by silica gel flash chromatography (0-1.5% methanol in dichloromethane, 0.2% ammonium hydroxide, NH$_4$OH) to give the subtitled compound (560 mg).

$^1$H-NMR (CD$_3$OD, 400 MHz): δ 7.39-7.24 (m, 5H); 7.10 (s, 1H); 7.06 (dd, J=2.3, 8.5 Hz, 1H); 6.68 (d, J=8.4 Hz, 1H); 3.73 (d, J=13.0 Hz, 1H); 3.70 (d, J=13.0 Hz, 1H); 3.24 (d, J=16.0 Hz, 1H); 3.20 (d, J=16.0 Hz, 1H); 2.99 (d, J=10.4 Hz, 1H); 2.95-2.88 (m, 1H); 2.74-2.64 (m, 2H); 2.43-2.34 (m, 1H); 2.11-2,02 (m, 1H). APCI-MS: m/z 300(MH$^+$).

Step III:

5-Chloro-3H-spiro[1-benzofuran-2,3'-pyrrolidine]

The experimental procedure is the same as described above for the corresponding piperidine derivative using 1'-benzyl-5-chloro-3H-spiro[1-benzofuran-2,3'-pyrrolidine] (555 mg, 1.85 mmol), ethyl chloroformate (261 mg, 2.4 mmol), toluene (5 mL), potassium hydroxide (KOH) (3.0 g), water (3 mL) and ethanol (6 mL) to give the titled compound (240 mg) after silica gel flash chromatography (0-2% methanol in dichloromethane, 0.2% ammonium hydroxide, NH$_4$OH).

$^1$H-NMR (CDCl$_3$, 400 MHz): δ 7.13 (s, 1H); 7.08 (dd, J=2.3, 8.5 Hz, 1H); 6.65 (d, J=8.5 Hz, 1H); 3.32-3.16 (m, 4H); 3.07 (ddd, J=4.8, 9.1, 11.2 Hz, 1H); 2.80 (d, J=12.3 Hz, 1H); 2.33-2.24 (m, 1H); 1.93 (ddd, J=7.3, 9.1, 13.7 Hz, 1H). APCI-MS: m/z 210(MH$^+$).

Example 34

N-(2-{[(2S)-3-(5-Chloro-1'H,3H-spiro[2-benzofuran-1,4'-piperidin]-1'-yl)-2-hydroxypropyl]oxy}-4-hydroxyphenyl)acetamide A mixture of 5-chloro-3H-spiro[2-benzofuran-1,4'-piperidin] (29.3 mg, 0.131 mmol) and 4-(acetylamino)-3-[(2S)-oxiran-2-ylmethoxy]phenyl acetate (35 mg, 0.131 mmol) in ethanol (1.5 mL) was kept on stirring at 80° C. overnight. The volatiles were removed in vacuo and the residue was purified by HPLC (acetonitrile (CH$_3$CN) 10-55% in water, 0.1% trifluoroacetic acid, CF$_3$COOH) to give the titled compound (35 mg).

$^1$H-NMR (CD$_3$OD, 400 MHz): δ 7.36 (m, 3H); 7.21 (d, J=8.7 Hz, 1H); 6.50 (d, J=2.4 Hz, 1H); 6.40 (dd, J=2.4, 8.7 Hz, 1H); 5.10 (s, 2H); 4.48 (m, 1H); 4.05 (d, J=4.6 Hz, 2H); 3.78-3.63 (m, 2H); 3.56-3.35 (m, 4H); 2.40-2.21 (m, 2H); 2.13 (s, 3H); 2.08-1.95 (m, 2H). APCI-MS: m/z 447(MH$^+$).

Example 35

N-(2-{[(2S)-3-(5-Chloro-1'H,3H-spiro[2-benzofuran-1,4'-piperidin]-1'-yl)-2-hydroxypropyl]oxy}phenyl)acetamide A mixture of 5-chloro-3H-spiro[2-benzofuran-1,4'-piperidin] (35 mg, 0.156 mmol) and N-{2-[(2S)-oxiran-2-ylmethoxy]phenyl}acetamide (32.3 mg, 0.156 mmol) in ethanol (1.5 mL) was kept on stirring at 80° C. overnight. The volatiles were removed in vacuo and the residue was purified by silica gel flash chromatography (0-1% methanol in dichloromethane, 0.1% ammonium hydroxide, NH$_4$OH) to give the titled compound (45 mg).

$^1$H-NMR (CD$_3$OD, 400 MHz): δ 7.99 (dd, J=1.3, 7.9 Hz, 1H); 7.29-7.25 (m, 2H); 7.18 (d, J=7.8 Hz, 1H); 7.12-7.01 (m, 2H); 6.96-6.91 (m, 1H); 5.00 (s, 2H); 4.25 (m, 1H); 4.13 (dd, J=3.2, 9.9 Hz, 1H); 3.99 (dd, J=6.4, 9.9 Hz, 1H); 3.00-2.89 (m, 2H); 2.67-2.50 (m, 4H); 2.20 (s, 3H); 2.08-1.96 (m, 2H); 1.73 (m, 2H). APCI-MS: m/z 431 (MH$^+$).

Example 36

2-{[(2S)-3-(5-Chloro-1'H,3H-spiro[2-benzofuran-1,4'-piperidin]-1'-yl)-2-hydroxypropyl]oxy}-4-hydroxy-N-methylbenzamide Step I:

2-{[(2S)-3-(5-Chloro-1'H,3H-spiro[2-benzofuran-1,4'-piperidin]-1'-yl)-2-hydroxypropyl]oxy}-4-[(4-methoxybenzyl)oxy]-N-methylbenzamide A mixture of 5-chloro-3H-spiro[2-benzofuran-1,4'-piperidine] (26 mg, 0.116 mmol) and 4-[(4-methoxybenzyl)oxy]-N-methyl-2-[(2S)-oxiran-2-ylmethoxy]benzamide (40 mg, 0.116 mmol) in ethanol (2 mL) was stirred at 80° C. overnight. The volatiles were removed in vacuo and the residue was purified by silica gel flash chromatography (0-1% methanol in dichloromethane, 0.1% ammonium hydroxide, NH$_4$OH) to give the subtitled compound (50 mg).

$^1$H-NMR (CDCl$_3$, 400 MHz): δ 78.18 (d, J=8.8 Hz, 1H); 8.14 (m, 1H); 7.37 (d, J=8.7 Hz, 2H); 7.28 (m, 2H); 7.22 (s, 1H); 7.09 (d, J=8.0 Hz, 1H); 6.97-6.92 (m, 2H); 6.71 (dd, J=2.3, 8.8 Hz, 1H); 6.52 (d, J=2.3 Hz, 1H); 5.08 (s, 2H); 5.05 (s, 2H); 4.25-4.15 (m, 2H); 3.85 (s, 3H); 3.00 (m, 4H); 2.88-2.75 (m, 2H); 2.66-2.46 (m, 3H); 2.06-1.90 (m, 2H); 1.82 (d, J=12.9 Hz, 2H). APCI-MS: m/z 567(MH$^+$).

Step II:

2-{[(2S)-3-(5-Chloro-1'H,3H-spiro[2-benzofuran-1,4'-piperidin]-1'-yl)-2-hydroxypropyl]oxy}-4-hydroxy-N-methylbenzamide 2-{[(2S)-3-(5-Chloro-1'H,3H-spiro[2-benzofuran-1,4'-piperidin]-1'-yl)-2-hydroxypropyl]oxy}-4-[(4-methoxybenzyl)oxy]-N-methylbenzamide (45 mg, 0.079 mmol) was treated with 10% trifluoroacetic acid (CF$_3$COOH) in dichloromethane (CH$_2$Cl$_2$) (3 mL) for 25 min at room temperature. The volatiles were removed in vacuo and the residue was purified by HPLC (10-45% acetonitrile (CH$_3$CN) in water, 0.1% ammonium hydroxide, NH$_4$OH) to give the titled compound (17 mg).

$^1$H-NMR (CD$_3$OD, 400 MHz): δ 7.82 (d, J=8.7 Hz, 1H); 7.30-7.25 (m, 2H); 7.18 (d, J=7.9 Hz, 1H); 6.55 (d, J=2.2 Hz, 1H); 6.48 (dd, J=2.2, 8.7 Hz, 1H); 5.05 (s, 2H); 4.26-4.19 (m, 2H); 4.09-4.04 (m, 1H); 2.98-2.87 (m, 5H); 2.64-2.50 (m, 4H); 2.09-1.97 (m, 2H); 1.73 (d, J=13.2 Hz, 2H). APCI-MS: m/z 447(MH$^+$).

Example 37

2-{[(2S)-3-(5-Chloro-1'H,3H-spiro[2-benzofuran-1,4'-piperidin]-1'-yl)-2-hydroxy-2-methoxypropyl]oxy}-N-cyclopropyl-4-hydroxybenzamide Step I:

2-{[(2S)-3-(5-Chloro-1'H,3H-spiro[2-benzofuran-1,4'-piperidin]-1'-yl)-2-hydroxy-2-methylpropyl]oxy}-N-cyclopropyl-4[(4-methoxybenzyl)oxy]benzamide A mixture of 5-chloro-3H-spiro[2-benzofuran-1,4'-piperidine] (40 mg, 0.178 mmol) and N-cyclopropyl-4-[(4-methoxybenzyl)oxy]-2-{[(2S)-2-methyloxiran-2-yl]methoxy}benzamide (68 mg, 0.178 mmol) in ethanol (2 mL) was stirred at 80° C. for 6 h. The volatiles were removed in vacuo and the residue was purified by silica gel flash chromatography (0-0.9% methanol in dichloromethane, 0.1% ammonium hydroxide, NH$_4$OH) to give the subtitled compound (45 mg).

$^1$H-NMR (CDCl$_3$), 400 MHz): δ 8.21 (br.s, 1H); 7.99 (d, J=8.7 Hz, 1H); 7.36 (d, J=8.7 Hz, 2H) 7.27 (m, 1H); 7.20 (s, 1H); 7.03 (d, J=8.0 Hz, 1H); 6.92 (m, 2H); 6.70 (dd, J=2.3, 8.8 Hz, 1H); 6.50 (d, J=2.3 Hz, 1H); 5.03 (s, 2H); 5.01 (s, 2H); 3.86 (s, 2H); 2.85 (s, 3H); 3.05 (m, 1H); 2.91-2.80 (m, 3H); 2.75 (m, 1H); 2.67 (d, J=13.9 Hz, 1H); 2.50 (d, J=13.9 Hz, 1H); 1.95 (m, 2H); 1.75 (m, 2H); 1.30 (s, 3H); 0.83 (m, 2H); 0.62 (m, 2H). APCI-MS: m/z 607(MH$^+$).

Step II:

2-{[(2S)-3-(5-Chloro-1'H,3H-spiro[2-benzofuran-1,4'-piperidin]-1'-yl)-2-hydroxy-2-methoxypropyl]oxy}-N-cyclopropyl-4-hydroxybenzamide 2-{[(2S)-3-(5-chloro-1'H,3H-spiro[2-benzofuran-1,4'-piperidin]-1'-yl)-2-hydroxy-2-methylpropyl]oxy}-N-cyclopropyl-4-[(4-methoxybenzyl)oxy]benzamide (40 mg, 0.065 mmol) was treated with 10% trifluoroacetic acid (CF$_3$COOH) (3 mL) for 25 min at room temperature. The volatiles were removed in vacuo and the residue was purified by HPLC (10-55% acetonitrile (CH$_3$CN) in water, 0.1% ammonium hydroxide, NH$_4$OH) to give the titled compound (30 mg).

$^1$H-NMR (CD$_3$OD), 400 MHz): δ 7.84 (d, J=8.4 Hz, 1H); 7.25 (m, 2H); 7.16 (d, J=7.6 Hz, 1H); 6.45 (m, 2H); 5.00 (s, 2H); 4.11 (d, J=9.0 Hz, 1H); 3.93 (d, J=9.0 Hz, 1H); 2.93 (m, 1H); 2.88 (m, 2H); 2.74-2.49 (m, 4H); 1.99 (m, 2H); 1.62 (m, 2H); 1.31 (s, 3H); 0.79 (m, 2H); 0.65 (m, 2H). APCI-MS: m/z 487(MH$^+$).

Example 38

2-{[(2S)-3-(5-Chloro-1'H,3H-spiro[1-benzofuran-2,4'-piperidin]-1'-yl)-2-hydroxypropyl]oxy}-4-hydroxy-N-(2-hydroxyethyl)benzamide Step I:

Methyl-4-[(4-methoxybenzyl)oxy]-2-[(2S)-oxiran-2-ylmethoxy]benzoate

A mixture of 2(S)-oxiran-2-ylmethyl3-nitrobenzenesulfonate (518 mg, 2.0 mmol), methyl 2-hydroxy-4-[(4-methoxybenzyl)oxy]benzoate (576.6 mg, 2.0 mmol) and cesium carbonate (Cs$_2$CO$_3$) (812.5 mg, 2.5 mmol) in dimethylformamide (10 mL) was stirred at room temperature overnight. The reaction mixture was partitioned between ethyl acetate and water. The organic layer was dried over sodium sulphate, Na$_2$SO$_4$, filtered, concentrated in vacuo and the residue was purified by silica gel flash chromatography (0-30% ethyl acetate in petroleum ether) to give the subtitled compound (600 mg).

$^1$H-NMR (CDCl$_3$), 400 MHz): δ 7.87 (d, J=8.7 Hz, 1H); 7.39-7.34 (m, 2H); 6.97-6.92 (m, 2H); 6.61 (dd, J=2.4, 8.7 Hz, 1H); 6.59 (d, J=2.2 Hz, 1H); 5.04 (s, 2H); 4.31 (dd, J=2.9, 11.1 Hz, 1H); 4.07 (dd, J=4.8, 11.1 Hz, 1H); 3.88 (s, 3H); 3.85 (s, 3H); 3.40 (m, 1H); 2.92 (m, 2H). APCI-MS: m/z 345 (MH$^+$).

Step II:

Methyl 2-{[(2S-3-(5-chloro-1'H,3H-spiro[1-benzofuran-2,4'-piperidin]-1'-yl)-2-hydroxypropyl]oxy}-[(4-methoxybenzyl)oxy]benzoate A mixture of 5-chloro-3H-spiro[1-benzofuran-2,4'-piperidine] (150 mg, 0.67 mmol) and methyl-4-[(4-methoxybenzyl)oxy]-2-[(2S)-oxiran-2-ylmethoxy]benzoate (230.5 mg, 0.67 mmol) in ethanol (3 mL) was stirred at 80° C. overnight. The volatiles were removed in vacuo and the residue was purified by silica gel flash chromatography (0-3% methanol in dichloromethane) to give the subtitled compound (370 mg).

$^1$H-NMR (CDCl$_3$), 400 MHz): δ 7.87 (d, J=8.8 Hz, 1H); 7.40-7.35 (m, 2H); 7.12 (m, 1H); 7.07 (dd, J=2.2, 8.4 Hz, 1H); 6.98-6.93 (m, 2H); 6.69 (d, J=8.4 Hz, 1H); 6.63 (d, J=2.2 Hz, 1H); 6.60 (s, 1H); 5.06 (s, 2H); 4.19 (m, 2H); 4.03 (m, 1H); 3.89 (s, 3H); 3.85 (s, 3H); 3.00 (s, 2H); 2.80 (m, 1H); 2.73-2.58 (m, 5H); 2.00 (m, 2H); 1.82 (m, 2H). APCI-MS: m/z 568(MH$^+$).

Step III:

2-{[(2S)-3-(5-Chloro-1'H,3H-spiro[1-benzofuran-2,4'-piperidin]-1'-yl)-2-hydroxypropyl]oxy}-N-(2-hydroxyethyl)4-[(4-methoxybenzyl)oxy]benzamide A mixture of methyl2-{[(2S)-3-(5-chloro-1'H,3H-spiro[1-benzofuran-2,4'-piperidin]-1'-yl)-2-hydroxypropyl]oxy}-4-[(4-methoxybenzyl)oxy]benzoate (60 mg, 0.105 mmol) and 2-aminoethanol (0.256 mL, 4.2 mmol) in methanol (2 mL) was refluxed for 72 h. The volatiles were removed in vacuo and the residue was purified by silica gel flash chromatography (0-3% methanol in dichloromethane, 0.2% ammonium hydroxide, NH$_4$OH) to give the subtitled compound (30 mg).

$^1$H-NMR (CDCl$_3$), 400 MHz): δ 8.49 (t, J=5.4 Hz, 1H); 8.17 (d, J=8.8 Hz, 1H); 7.40-7.35 (m, 2H); 7.12 (s, 1H); 7.09 (dd, J=2.2, 8.4 Hz, 1H); 6.98-6.93 (m, 2H); 6.72 (dd, J=2.2, 8.8 Hz, 1H); 6.69 (d, J=8.5 Hz, 1H); 6.55 (d, J=2.2 Hz, 1H); 5.06 (s, 2H); 4.21 (m, 2H); 3.94 (dd, J=7.2, 10.1 Hz, 1H); 3.85 (s, 3H); 3.83 (d, J=4.8 Hz, 2H); 3.70 (m, 1H); 3.60 (m, 1H); 3.00 (s, 2H); 2.91-2.76 (m, 2H); 2.68-2.53 (m, 4H); 2.00 (m, 2H); 1.80 (m, 2H). APCI-MS: m/z 597(MH$^+$).

Step IV:

2-{[(2S)-3-(5-Chloro-1'H,3H-spiro[1-benzofuran-2,4'-piperidin]-1'-yl)-2-hydroxypropyl]oxy}-4-hydroxy-N-(2-hydroxyethyl)benzamide 2-{[(2S)-3-(5-Chloro-1'H,3H-spiro[1-benzofuran-2,4'-piperidin]-1'-yl)-2-hydroxypropyl]oxy}-N-(2-hydroxyethyl)-4-[(4-methoxybenzyl)oxy]benzamide (27 mg, 0.045 mmol) was treated with 10% trifluoroacetic acid (CF$_3$COOH) in dichloromethane (CH$_2$Cl$_2$) (3 mL) for 30 min at room temperature. The volatiles were removed in vacuo and the residue was purified by silica gel flash chromatography (0-4% methanol in dichloromethane, 0.2% ammonium hydroxide, NH$_4$OH) to give the titled compound (16 mg).

$^1$H-NMR (CD$_3$OD), 400 MHz): δ 7.85 (d, J=8.6 Hz, 1H); 7.13 (m, 1H); 7.19 (dd, J=2.4, 8.5 Hz, 1H); 6.65 (d, J=8.5 Hz, 1H); 6.52 (d, J=2.2 Hz, 1H); 6.49 (dd, J=2.2, 8.6 Hz, 1H); 4.27-4.17 (m, 2H); 4.06 (dd, J=5.9, 9.4 Hz, 1H); 3.73 (t, J=5.6 Hz, 2H); 3.53 (m, 2H); 3.00 (s, 2H); 2.70 (m, 4H); 2.62 (d, J=6.4 Hz, 2H); 1.95 (m, 2H); 1.84 (m, 2H). APCI-MS: m/z 477(MH$^+$).

Example 39

N-(2-Aminoethyl)-2-{[(2S)-3-(5-chloro-1'H,3H-spiro[1-benzofuran-2,4'-piperidin]-1'-yl)-2-hydroxypropyl]oxy}-4-hydroxybenzamide Step I:

N-(2-Aminoethyl)-2-{[(2S)-3-(5-chloro-1'H,3H-spiro[1-benzofuran-2,4'-piperidin]-1'-yl)-2-hydroxypropyl]oxy}-4-[(4-methoxybenzyl)oxy]benzamide A mixture of 2-{[(2S)-3-(5-chloro-1'H,3H-spiro[1-benzofuran-2,4'-piperidin]-1'-yl)-2-hydroxypropyl]oxy}-4-hydroxybenzoic acid (50 mg, 0.084 mmol) and N,N-carbonyldiimidazole (14 mg, 0.084 mmol) in dimethylformamide (3 mL) was kept on stirring at room temperature for 1 h. Then ethylenediamine (11 mg, 0.168 mmol) was added and the reaction mixture was stirred at room temperature overnight. The reaction mixture was partitioned between ethyl acetate and water, the organic layer was dried over sodium sulphate, Na$_2$SO$_4$, filtered, concentrated in vacuo and the residue was purified by silica gel flash chromatography (0-3% methanol in dichloromethane, 0.2% ammonium hydroxide, NH$_4$OH) to give the subtitled compound (22 mg).
$^1$H-NMR (CD$_3$OD), 400 MHz): δ 7.93 (d, J=8.9 Hz, 1H); 7.45 (m, 2H); 7.12 (s, 1H); 7.04 (dd, J=2.3, 8.6 Hz, 1H); 6.95-6.90 (m, 2H); 6.73 (s, 1H); 6.70 (d, J=2.2 Hz, 1H); 6.64 (d, J=8.5 Hz, 1H); 5.08 (s, 2H); 4.27 (dd, J=2.7, 9.7 Hz, 1H); 4.23-4.15 (m, 1H); 4.05 (dd, J=6.6, 9.8 Hz, 1H); 3.80 (s, 3H); 3.48 (t, J=5.9 Hz, 2H); 2.96 (s, 2H); 2.86 (t, J=6.1 Hz, 2H); 2.68 (m, 4H); 2.56 (d, J=6.4 Hz, 2H); 1.90 (m, 2H); 1.80 (m, 2H). APCI-MS: m/z 596(MH$^+$).

Step II:

N-(2-Aminoethyl)-2-{[(2S)-3-(5-chloro-1'H,3H-spiro[1-benzofuran-2,4'-piperidin]-1'-yl)-2-hydroxypropyl]oxy}-4-hydroxybenzamide N-(2-Aminoethyl)-2-{[(2S)-3-(5-chloro-1'H,3H-spiro[1-benzofuran-2,4'-piperidin]-1'-yl)-2-hydroxypropyl]oxy}-4-[(4-methoxybenzyl)oxy]benzamide ((22 mg, 0.037 mmol) was treated with 10% trifluoroacetic acid (CF$_3$COOH) in dichloromethane (2 mL) for 20 min at room temperature. The volatiles were removed in vacuo and the residue was purified by HPLC (10-60% acetonitrile (CH$_3$CN) in water, 0.1% ammonium hydroxide, NH$_4$OH) to give the titled compound (8 mg).
$^1$H-NMR (CD$_3$OD), 400 MHz): δ 7.83 (d, J=8.6 Hz, 1H); 7.14 (m, 1H); 7.04 (dd, J=2.2, 8.4 Hz, 1H); 6.65 (d, J=8.4 Hz, 1H); 6.50 (d, J=2.1 Hz, 1H); 6.47 (dd, J=2.2, 8.6 Hz, 1H); 4.27-4.19 (m, 2H); 4.04 (m, 1H); 3.50 (t, J=6.0 Hz, 2H); 3.02 (s, 2H); 2.90 (t, J=6.0 Hz, 2H); 2.69 (m, 4H); 2.60 (d, J=6.2 Hz, 2H); 1.94 (m, 2H); 1.84 (m, 2H). APCI-MS: m/z 476 (MH$^+$).

Example 40

2-{[(2S)-3-(5-Fluoro-1'H,3H-spiro[1-benzofuran-2,4'-piperidin]-1'-yl)-2-hydroxypropyl]oxy)}hydroxy-N-methylbenzamide Step I:

2-{[(2S)-3-(5-Fluoro-1'H,3H-spiro[1-benzofuran-2,4'-piperidin]-1'-yl)-2-hydroxypropyl]oxy}-4-[(4-methoxybenzyl)oxy]-N-methylbenzamide A mixture of 5-fluoro-3H-spiro[1-benzofuran-2,4'-piperidine] (20 mg, 0.096 mmol) and 4-[(4-methoxybenzyl)oxy]-N-methyl-2-[(2S)-oxiran-2-ylmethoxy]benzamide (34.3 mg, 0.099 mmol) in ethanol (2 mL) was stirred at 80° C. overnight. The volatiles were removed in vacuo and the residue was purified by silica gel flash chromatography (0-0.8% methanol in dichloromethane, 0.1% ammonium hydroxide, NH$_4$OH) to give the subtitled compound (36 mg).
$^1$H-NMR (CDCl$_3$), 400 MHz): δ 8.16 (d, J=8.7 Hz, 1H); 8.10 (m, 1H); 7.36 (m, 2H); 6.96-6.91 (m, 2H); 6.89-6.77 (m, 2H); 7.72-6.64 (m, 2H); 6.54 (d, J=2.3 Hz, 1H); 5.00 (s, 2H); 4.20-4.10 (m, 2H); 3.96 (dd, J=5.4, 9.4 Hz, 1H); 3.83 (s, 3H); 3.01 (s, 3H); 3.00 (s, 2H); 2.90 (m, 1H); 2.80 (m, 1H); 2.64-2.50 (m, 4H); 2.00 (m, 2H); 1.83 (m, 2H). APCI-MS: m/z 551 (MH$^+$).

Step II:

2-{[(2S)-3-(5-fluoro-1'H,3H-spiro[1-benzofuran-2,4'-piperidin]-1'-yl)-2-hydroxypropyl]oxy}-4-hydroxy-N-methylbenzamide 2-{[(2S)-3-(5-Fluoro-1'H,3H-spiro[1-benzofuran-2,4'-piperidin]-1'-yl)-2-hydroxypropyl]oxy}-4-[(4-methoxybenzyl)oxy]-N-methylbenzamide (32 mg, 0.058 mmol) was treated with 10% trifluoroacetic acid (CF$_3$COOH) in dichloromethane (2.5 mL) for 20 min at room temperature. The volatiles were removed in vacuo and the residue was purified by HPLC (10-50% acetonitrile (CH$_3$CN) in water, 0.1% ammonium hydroxide, NH$_4$OH) to give the titled compound (11 mg).
$^1$H-NMR (CDCl$_3$), 400 MHz): δ 7.82 (d, J=8.6 Hz, 1H); 6.50 (dd, J=2.7, 8.1 Hz, 1H); 6.81-6.74 (m, 1H); 6.62 (dd, J=4.2, 8.7 Hz, 1H); 6.52 (d, J=2.2 Hz, 1H); 6.48 (dd, J=2.2, 8.6 Hz, 1H); 4.24-4.17 (m, 2H); 4.08-4.02 (m, 1H); 3.01 (s, 2H); 2.92 (s, 3H); 2.77-2.63 (m, 4H); 2.60 (d, J=6.2 Hz, 2H); 1.94 (m, 2H); 1.84 (m, 2H). APCI-MS: m/z 431 (MH$^+$).

Example 41

N-(2-{[(2S)-3-(5-Fluoro-1'H,3H-spiro[1-benzofuran-2,4'-piperidin]-1'-yl)-2-hydroxypropyl]oxy}-4-hydroxyphenyl)acetamide A mixture of 5-fluoro-3H-spiro[1-benzofuran-2,4'-piperidine] (20 mg, 0.096 mmol) and 4-(acetylamino)-3-[(2S)-oxiran-2-ylmethoxy]phenyl acetate (25.5 mg, 0.096 mmol) in ethanol (2 mL) was kept on stirring at 80° C. over the weekend. The volatiles were removed in vacuo and the residue was purified by HPLC (10-35% acetonitrile (CH$_3$CN) in water, 0.1% ammonium hydroxide, NH$_4$OH) to give the titled compound (14 mg).
$^1$H-NMR (CD$_3$OD), 400 MHz): δ 7.57 (d, J=8.7 Hz, 1H); 6.90 (m, 1H); 6.81-6.74 (m, 1H); 6.63 (dd, J=4.2, 8.7 Hz, 1H); 6.48 (d, J=2.5 Hz, 1H); 6.36 (dd, J=2.6, 8.7 Hz, 1H); 4.18 (m, 1H); 4.05 (dd, J=3.4, 9.8 Hz, 1H); 3.93 (dd, J=6.2, 9.8 Hz, 1H); 3.01 (s, 2H); 2.70 (m, 4H); 2.61 (t, J=7.0 Hz, 2H); 2.14 (s, 3H); 1.96 (m, 2H); 1.85 (m, 2H). APCI-MS: m/z 431 (MH$^+$).

Example 42

N-(2-{[(2S)-3-(5-Fluoro-1'H,3H-spiro[1-benzofuran-2,4'-piperidin]-1'-yl)-2-hydroxypropyl]oxy)phenyl)acetamide A mixture of 5-fluoro-3H-spiro[1-benzofuran-2,4'-piperidine] (8 mg, 0.038 mmol) and N-{2-[(2S)-oxiran-2-ylmethoxy]phenyl}acetamide (8 mg, 0.038 mmol) in ethanol (1.5 mL) was stirred at 80° C. overnight. The volatiles were removed in vacuo and the residue was purified by HPLC (10-70% acetonitrile (CH$_3$CN) in water, 0.1% ammonium hydroxide, NH$_4$OH) to give the titled compound (11 mg).

¹H-NMR (CD₃OD), 400 MHz): δ 7.99 (dd, J=1.5, 8.1 Hz, 1H); 7.08 (m, 1H); 7.03 (m, 1H); 6.94 (m, 1H); 6.90 (m, 1H); 6.77 (m, 1H); 6.63 (dd, J=4.2, 8.8 Hz, 1H); 4.19 (m, 1H); 4.12 (dd, J=3.2, 9.9 Hz, 1H); 3.98 (dd, J=6.4, 9.9 Hz, 1H); 3.05 (s, 2H); 2.70 (m, 4H); 2.62 (m, 2H); 2.19 (s, 3H); 1.94 (m, 2H); 1.85 (m, 2H). APCI-MS: m/z 415 (MH⁺).

Example 43

N-[2-({(2S)-3 [(2S)-5-Chloro-1'H,3H-spiro[1-benzo-furan-2,3'-pyrrolidin]-1'-yl]-2-hydroxypropyl}oxy)phenyl]acetamide A mixture of 5-chloro-3H-spiro[1-benzofuran-2,3'-pyrrolidine] (34.5 mg, 0.167 mmol) and N-{2-[(2S)-oxiran-2-ylmethoxy]phenylacetamide (35 mg, 0.167 mmol) in ethanol (1.5 mL) was stirred at 80° C. overnight. The volatiles were removed in vacuo and the residue was purified by silica gel flash chromatography (0-1% methanol (CH₃OH) in dichloromethane (CH₂Cl₂), 0.2% ammonium hydroxide, NH₄OH) to give a mixture of two isomers (55 mg). This mixture was subjected to chiral HPLC to give the titled compound (17 mg) and other isomer (14 mg).

¹H-NMR (CD₃OD), 400 MHz): δ 7.99 (dd, J=1.4, 8.0 Hz, 1H); 7.15 (m, 1H); 7.11-7.01 (m, 3H); 6.93 (m, 1H); 6.66 (d, J=8.5 Hz, 1H); 4.18-4.11 (m, 2H); 3.99 (dd, J=7.0, 10.6 Hz, 1H); 3.25 (m, 2H); 3.11 (d, J=10.8 Hz, 1H); 3.00 (m, 1H); 2.86-2.69 (m, 4H); 2.33-2.25 (m, 1H); 2.18 (s, 3H); 2.13-2.05 (m, 1H). APCI-MS: m/z 417 (MH⁺).

Example 44

N-[2-({(2S)-3[(2R)-5-Chloro-1'H,3H-spiro[1-benzo-furan-2,3'-pyrrolidin]-1'-yl]-2-hydroxypropyl}oxy)phenyl]acetamide ¹H-NMR (CD₃OD), 400 MHz): δ 7.99 (dd, J=1.4, 8.0 Hz, 1H); 7.15 (m, 1H); 7.11-7.01 (m, 3H); 6.93 (m, 1H); 6.66 (d, J=8.5 Hz, 1H); 4.18-4.11 (m, 2H); 3.99 (dd, J=7.0, 10.6 Hz, 1H); 3.25 (m, 2H); 3.11 (d, J=10.8 Hz, 1H); 3.00 (m, 1H); 2.86-2.69 (m, 4H); 2.33-2.25 (m, 1H); 2.18 (s, 3H); 2.13-2.05 (m, 1H). APCI-MS: m/z 417 (MH⁺).

Example 45

N-[2-({(2S)-3-[(2S)-5-Chloro-1'H,3H-spiro[1-benzofuran-2,3'-pyrrolidin]-1'-yl]-2-hydroxypropyl)oxy}-4-methoxyphenyl]acetamide A mixture of 5-chloro-3H-spiro[1-benzofuran-2,3'-pyrrolidine] (60 mg, 0.286 mmol) and N-{4-methoxy-2-[(2S)-oxiran-2-ylmethoxy]phenyl}acetamide (68 mg, 0.286 mmol) in ethanol (2 mL) was stirred at 80° C. overnight. The volatiles were removed in vacuo and the residue was purified by silica gel flash chromatography (0-1% methanol (CH₃OH) in dichloromethane (CH₂Cl₂), 0.2% ammonium hydroxide, NH₄OH) to give a mixture of two isomers and this was subjected to chiral HPLC to give the titled compound (35 mg) and the other isomer (35 mg).

¹H-NMR (CD₃OD), 400 MHz): δ 7.73 (d, J=8.8 Hz, 1H); 7.14 (m, 1H); 7.04 (dd, J=2.2, 8.4 Hz, 1H); 6.65 (d, J=8.5 Hz, 1H); 6.60 (d, J=2.5 Hz, 1H); 6.49 (dd, J=2.6, 8.8 Hz, 1H); 4.15-4.06 (m, 2H); 3.96 (dd, J=6.2, 9.8 Hz, 1H); 3.79 (s, 3H); 3.25 (m, 2H); 3.11 (dd, J=10.7, 15.9 Hz, 1H); 2.99 (m, 1H); 2.85-2.64 (m, 4H); 2.25 (m, 1H); 2.13 (s, 3H); 2.08 (m, 1H). APCI-MS: m/z 447 (MH⁺).

Example 46

N-[2-({(2S)-3-[(2R)-5-Chloro-1'H,3H-spiro[1-benzofuran-2,3'-pyrrolidin]-1'-yl]-2-hydroxypropyl)oxy)-4-methoxyphenyl]acetamide ¹H-NMR (CD₃OD), 400 MHz): δ 7.73 (d, J=8.8 Hz, 1H); 7.14 (m, 1H); 7.04 (dd, J=2.2, 8.4 Hz, 1H); 6.65 (d, J=8.5 Hz, 1H); 6.60 (d, J=2.5 Hz, 1H); 6.49 (dd, J=2.6, 8.8 Hz, 1H); 4.15-4.06 (m, 2H); 3.96 (dd, J=6.2, 9.8 Hz, 1H); 3.79 (s, 3H); 3.25 (m, 2H); 3.11 (dd, J=10.7, 15.9 Hz, 1H); 2.99 (m, 1H); 2.85-2.64 (m, 4H); 2.25 (m, 1H); 2.13 (s, 3H); 2.08 (m, 1H). APCI-MS: m/z 447 (MH⁺).

Example 47

2-{[(2S)-3-(5-Chloro-1'H,3H-spiro[1-benzofuran-2,3'-pyrrolidin]-1'-yl)-2-hydroxypropyl]oxy}-4-hydroxy-N-methylbenzamide Step I:

2-{[(2S)-3-(5-Chloro-1'H,3H-spiro[1-benzofuran-2,3'-pyrrolidin]-1'-yl)-2-hydroxypropyl]oxy}-4-[(4-methoxybenzyl)oxy]-N-methylbenzamide A mixture of 5-chloro-3H-spiro[1-benzofuran-2,3'-pyrrolidine] (80 mg, 0.381 mmol) and 4-[(4-methoxybenzyl)oxy]-N-methyl-2-[(2S)-oxiran-2-ylmethoxy]benzamide (130.8 mg, 0.381 mmol) in ethanol (3 mL) was stirred at 80° C. overnight. The volatiles were removed in vacuo and the residue was purified by silica gel flash chromatography (0-1% methanol in dichloromethane, 0.2% ammonium hydroxide, NH₄OH) to give the subtitled compound (165 mg).

¹H-NMR (CDCl₃), 400 MHz): δ 8.15 (d, J=8.8 Hz, 1H); 8.04 (m, 1H); 7.36 (m, 2H); 7.13 (br,s, 1H); 7.09 (m, 1H); 6.93 (m, 2H); 6.72-6.66 (m, 2H); 6.54 (d, J=2.2 Hz, 1H); 5.05 (s, 2H); 4.17 (dd, J=3.2, 9.5 Hz, 1H); 4.09 (m, 1H); 3.98 (dd, J=5.7, 9.5 Hz, 1H); 3.83 (s, 3H); 3.30-2.83 (m, 9H); 2.72 (m, 1H); 2.60 (dd, J=3.4, 12.1 Hz, 1H); 2.34 (m, 2H); 2.08 (m, 2H). APCI-MS: m/z 553 (MH⁺).

Step II:

2-{[(2S)-3-(5-Chloro-1'H,3H-spiro[1-benzofuran-2,3'-pyrrolidin]-1'-yl)-2-hydroxypropyl]oxy}-4-hydroxy-N-methylbenzamide 2-{[(2S)-3-(5-Chloro-1'H,3H-spiro[1-benzofuran-2,3'-pyrrolidin]-1'-yl)-2-hydroxypropyl]oxy}4-[(4-methoxybenzyl)oxy]-N-methylbenzamide (160 mg, 0.289 mmol) was treated with 10% trifluoroacetic acid (CF₃COOH) in dichloromethane (CH₂Cl₂) for 25 min at room temperature. The volatiles were removed in vacuo and the residue was purified by silica gel flash chromatography (0-3% methanol (CH₃OH) in dichloromethane (CH₂Cl₂), 0.2% ammonium hydroxide, NH₄OH) to give the titled compound (80 mg).

APCI-MS: m/z 433 (MH⁺).

Example 48

2-{[(2S)-3-(5-Chloro-1'H,3H-spiro[1-benzofuran-2,4'-piperidin]-1'-yl)-2-hydroxypropyl]oxy}-4-hydroxybenzoic acid (trifluoroacetate)

Step I:

2-{[(2S)-3-(5-Chloro-1'H,3H-spiro[1-benzofuran-2,4'-piperidin]-1'-yl)-2-hydroxypropyl]oxy}-4-[(4-methoxybenzyl] benzoic acid To a solution of methyl 2-{[(2S)-3-(5-chloro-1'H,3H-spiro[1-benzofuran-2,4'-piperidin]-1'-yl)-2-hydroxypropyl]oxy}-

4-[(4-methoxybenzyl)oxy]benzoate (150 mg, 0.264 mmol) in ethanol (2 mL) was added aqueous solution of potassium hydroxide (KOH) (770 mg, KOH in 0.77 mL water) and the reaction mixture was stirred at reflux overnight, cooled to 0° C. and the pH was adjusted to 2.0 by addition of aqueous hydrochloric acid (HCl). The whole was extracted with ethyl acetate. The organic layer was dried over sodium sulphate, $Na_2SO_4$, filtered and concentrated to give the subtitled compound (145 mg).

$^1$H-NMR (CD$_3$OD), 400 MHz): δ 7.78 (d, J=8.4 Hz, 1H); 7.35 (m, 2H); 7.19 (m, 1H); 7.09 (dd, J=2.2, 8.4 Hz, 1H); 6.93 (m, 2H); 6.75-6.65 (m, 3H); 5.09 (s, 2H); 4.40 (m, 1H); 4.24 (dd, J=4.0, 9.3 Hz, 1H); 4.06 (dd, J=5.5, 9.3 Hz, 1H); 3.80 (s, 3H); 3.70-3.53 (m, 2H); 3.51-3.35 (m, 4H); 3.14 (s, 2H); 2.33 (m, 2H); 2.12 (d, J=14.8 Hz, 2H). APCI-MS: m/z 554 (MH$^+$).

Step II:

2-{[(2S)-3-(5-Chloro-1'H,3H-spiro[1-benzofuran-2,4'-piperidin]-1'-yl)-2-hydroxypropyl]oxy}-4-hydroxybenzoic acid (trifluoroacetate)

2-{[(2S)-3-(5-Chloro-1'H,3H-spiro[1-benzofuran-2,4'-piperidin]-1'-yl)-2-hydroxypropyl]oxy}-4-[(4-methoxybenzyl]benzoic acid (31 mg, 0.052 mmol) was treated with 10% trifluoroacetic acid (CF$_3$COOH) in dichloromethane (CH$_2$Cl$_2$) (2 mL) at room temperature for 20 min. The volatiles were removed in vacuo and the residue was purified by HPLC (10-55% acetonitrile (CH$_3$CN) in water, 0.1% trifluoroacetic acid (CF$_3$COOH)) to give the titled compound (15 mg).

APCI-MS: m/z 434 (MH$^+$).

Example 49

3(S)-1-(2-{[(2S)-3-(5-Chloro-1'H,3H-spiro[1-benzofuran-2,4'-piperidin]-1'-yl)-2-hydroxypropyl]oxy})hydroxybenzoyl)pyrrolidin-3-ol Step I:

(3S)-1-{2-{[(2S)-3-(5-Chloro-1'H,3H-spiro[1-benzofuran-2,4'-piperidin]-1'-yl)-2-hydroxypropyl]oxy)-4-[(4-methoxybenzyl)oxy]benzoyl)pyrrolidin-3-ol A mixture of 2-{[(2S)-3-(5-chloro-1'H,3H-spiro[1-benzofuran-2,4'-piperidin]-1'-yl)-2-hydroxypropyl]oxy}-4-hydroxybenzoic acid (100 mg, 0.169 mmol) and N,N-carbonyldiimidazole (30 mg, 0.186 mmol) in dimethylformamide (3 mL) was stirred at room temperature for 1 h. Then (3S)-pyrrolidin-3-ol (76.3 mg, 0.845 mmol) was added and the reaction mixture was stirred at room temperature overnight. The reaction mixture was partitioned between ethyl acetate and water, the organic layer was dried over sodium sulphate, Na$_2$SO$_4$, filtered, concentrated in vacuo and the residue was purified by silica gel flash chromatography (0-2.5% methanol in dichloromethane, 0.2% ammonium hydroxide, NH$_4$OH) to give the subtitled compound (55 mg).

APCI-MS: m/z 623 (MH$^+$).

Step II:

3(S)-1-(2-{[(2S)-3-(5-Chloro-1'H,3H-spiro[1-benzofuran-2,4'-piperidin]-1'-yl)-2-hydroxypropyl]oxy}-4-hydroxybenzoyl)pyrrolidin-3-ol (3S)-1-{2-{[(2S)-3-(5-Chloro-1'H,3H-spiro[1-benzofuran-2,4'-piperidin]-1'-yl)-2-hydroxypropyl]oxy}-4-[(4-methoxybenzyl)oxy]benzoyl)pyrrolidin-3-ol (50 mg, 0.08 mmol) was treated with 10% trifluoroacetic acid (CF$_3$COOH) in dichloromethane (CH$_2$Cl$_2$) (3 mL) at room temperature for 20 min. The volatiles were removed in vacuo and the residue was purified by silica gel flash chromatography (0-4.5% methanol (CH$_3$OH) in dichloromethane (CH$_2$Cl$_2$), 0.2% ammonium hydroxide, NH$_4$OH) to give the titled compound (25 mg).

$^1$H-NMR (CD$_3$OD), 400 MHz): δ 7.13 (m, 1H); 7.08 (dd, J=2.5, 8.2 Hz, 1H); 7.03 (dd, J=2.3, 8.5 Hz, 1H); 6.65 (d, J=8.4 Hz, 1H); 6.49 (m, 1H); 6.44 (m, 1H); 4.48 (m, 0.5H); 4.35 (m, 0.5H); 4.10 (m, 1H); 4.03 (m, 1H); 3.96 (dd, J=5.6, 9.7 Hz, 1H); 3.67 (m, 1H); 3.62-3.50 (m, 2H); 3.30 (m, 1H); 3.00 (s, 2H); 2.78-2.52 (m, 6H); 2.12-1.77 (m, 6H). APCI-MS: m/z 503 (MH$^+$).

Example 50

3(R)-1-(2-{[(2S)3-(5-Chloro-1'H,3H-spiro[1-benzofuran-2,4'-piperidin]-1'-yl)-2-hydroxypropyl]oxy}-4-hydroxybenzoyl)pyrrolidin-3-ol Step I:

(3R)-1-{2-{[(2S)-3-(5-Chloro-1'H,3H-spiro[1-benzofuran-2,4'-piperidin]-1'-yl)-2-hydroxypropyl]oxy}-4-[(4-methoxybenzyl)oxy]benzoyl)pyrrolidin-3-ol A mixture of 2-{[(2S)-3-(5-chloro-1'H,3H-spiro[1-benzofuran-2,4'-piperidin]-1'-yl)-2-hydroxypropyl]oxy}-4-hydroxybenzoic acid (60 mg, 0.101 mmol) and N,N-carbonyldiimidazole (17.5 mg, 0.108 mmol) in dimethylformamide (3 mL) was stirred at room temperature for 1 h. Then (3R)-pyrrolidin-3-ol (47 mg, 0.540 mmol) was added and the reaction mixture was stirred at room temperature overnight. The reaction mixture was partitioned between ethyl acetate and water, the organic layer was dried over sodium sulphate, Na$_2$SO$_4$, filtered, concentrated in vacuo and the residue was purified by silica gel flash chromatography (0-3% methanol in dichloromethane, 0.2% ammonium hydroxide, NH$_4$OH) to give the subtitled compound (64 mg).

APCI-MS: m/z 623 (MH$^+$).

Step II:

3(R)-1-(2-{[(2S)-3-(5-Chloro-1'H,3H-spiro[1-benzofuran-2,4'-piperidin]-1'-yl)-2-hydroxypropyl]oxy}-4-hydroxybenzoyl)pyrrolidin-3-ol (3R)-1-{2-{[(2S)-3-(5-Chloro-1'H,3H-spiro[1-benzofuran-2,4'-piperidin]-1'-yl)-2-hydroxypropyl]oxy}-4-[(4-methoxybenzyl)oxy]benzoyl}pyrrolidin-3-ol (60 mg, 0.096 mmol) was treated with 10% trifluoroacetic acid (CF$_3$COOH) in dichloromethane (CH$_2$Cl$_2$) (3 mL) at room temperature for 20 min. The volatiles were removed in vacuo and the residue was purified by silica gel flash chromatography (0-5% methanol (CH$_3$OH) in dichloromethane (CH$_2$Cl$_2$), 0.2% ammonium hydroxide, NH$_4$OH) to give the titled compound (8 mg).

$^1$H-NMR (CD$_3$OD), 400 MHz): δ 7.13 (m, 1H); 7.08 (dd, J=2.5, 8.2 Hz, 1H); 7.03 (dd, J=2.3, 8.5 Hz, 1H); 6.65 (d, J=8.4 Hz, 1H); 6.49 (m, 1H); 6.44 (m, 1H); 4.48 (m, 0.5H); 4.35 (m, 0.5H); 4.10 (m, 1H); 4.03 (m, 1H); 3.96 (dd, J=5.6, 9.7 Hz, 1H); 3.67 (m, 1H); 3.62-3.50 (m, 2H); 3.30 (m, 1H); 3.00 (s, 2H); 2.78-2.52 (m, 6H); 2.12-1.77 (m, 6H). APCI-MS: m/z 503 (MH$^+$).

Example 51

3-{[(2S)-3-(5-Chloro-1'H,3H-spiro[1-benzofuran-2,4'-piperidin]-1'-yl)-2-hydroxypropyl]oxy}-4-(morpholin-4-ylcarbonyl)phenol Step I:

(2S)-1-(5-Chloro-1'H,3H-spiro[1-benzofuran-2,4'-piperidin]-1'-yl)-3-[5-[(4-methoxybenzyl)oxy]-2-(morpholin-4-ylcarbonyl)phenoxy]propan-2-ol A mixture of 2-{[(2S)-3-(5-chloro-1'H,3H-spiro[1-benzofuran-2,4'-piperidin]-1'-yl)-2-hydroxypropyl]oxy}-4-hydroxybenzoic acid (100 mg, 0.169 mmol) and N,N-carbonyldiimidazole (35 mg, 0.215 mmol) in dimethylformamide (3 mL) was stirred at room temperature for 1 h. Then morpholine (250 mg, 2.86 mmol) was added and the reaction mixture was stiffed at room temperature overnight. The reaction mixture was partitioned between ethyl acetate and water, the organic layer was dried over sodium sulphate, $Na_2SO_4$, filtered, concentrated in vacuo and the residue was purified by silica gel flash chromatography (0-1.5% methanol in dichloromethane, 0.2% ammonium hydroxide, $NH_4OH$) to give the subtitled compound (58 mg).

APCI-MS: m/z 623 ($MH^+$).

Step II:

3-{[(2S)-3-(5-Chloro-1'H,3H-spiro[1-benzofuran-2,4'-piperidin]-1'-yl)-2-hydroxypropyl]oxy}-4-(morpholin-4-ylcarbonyl)phenol (2S)-1-(5-Chloro-1'H,3H-spiro[1-benzofuran-2,4'-piperidin]-1'-yl)-3-[5-[(4-methoxybenzyl)oxy]-2-(morpholin-4-ylcarbonyl)phenoxy]propan-2-ol (55 mg, 0.088 mmol) was treated with 10% trifluoroacetic acid ($CF_3COOH$) in dichloromethane ($CH_2Cl_2$) (3 mL) for 25 min at room temperature. The volatiles were removed in vacuo and the residue was purified by silica gel flash chromatography (0-3% methanol ($CH_3OH$) in dichloromethane ($CH_2Cl_2$), 0.2% ammonium hydroxide, $NH_4OH$) to give the titled compound (24 mg).

$^1$H-NMR ($CD_3OD$), 400 MHz): δ 7.13 (m, 1H); 7.07-7.01 (m, 2H); 6.65 (d, J=8.5 Hz, 1H); 6.50 (d, J=2.1 Hz, 1H); 6.45 (dd, J=2.1, 8.2 Hz, 1H); 4.15-3.92 (m, 3H); 3.87-3.37 (m, 8H); 3.00 (s, 2H); 2.78-2.49 (m, 6H); 1.94 (m, 2H); 1.83 (m, 2H). APCI-MS: m/z 503 ($MH^+$).

Example 52

2-{[(2S)-3-(5-chloro-1'H-spiro[1,3-benzodioxole-2,4'-piperidin]-1'-yl)-2-hydroxypropyl]oxy}-N-methylbenzamide trifluoroacetate (salt)

Step I:

2-Hydroxy-N-methylbenzamide

A solution of methyl salicylate (5.16 mL, 40 mmol) in methanol (10 mL) was added dropwise to aqueous 40% methylamine (18.1 mL, 210 mmol) at 0° C. After addition was complete the reaction mixture was kept on stirring at room temperature overnight. The volatiles were removed in vacuo to give the subtitled compound (5.48 g).

$^1$H-NMR ($CD_3OD$, 400 MHz): δ 7.70 (dd, J=1.5, 7.9 Hz, 1H); 7.38-7.32 (, 2H); 6.90-6.83 (m, 2H); 2.85 (s, 3H).

Step II:

N-Methyl-2-[(2S)-oxiran-2-ylmethoxy]benzamide

A mixture of (2S)-oxiran-2-ylmethyl-3-nitrobenzenesulfonate (388.5 mg, 1.50 mmol), 2-hydroxy-N-methylbenzamide (226.5 mg, 1.50 mmol) and cesium carbonate (586 mg, 1.80 mmol) in dimethylformamide (6 mL) was kept on stirring at room temperature overnight. The reaction mixture was partitioned between ethyl acetate and water. The organic phase was dried over sodium sulphate, $Na_2SO_4$, filtered and concentrated. The residue was purified by silica gel flash chromatography (0-50% ethyl acetate in petroleum ether) to give the subtitled compound (284 mg).

$^1$H-NMR ($CDCl_3$, 400 MHz): δ 8.39 (m, 1H); 7.90 (br.s, 1H); 7.06-6.98 (m, 2H); 6.95-6.89 (m, 1H); 4.38 (dd, J=2.5, 11.4 Hz, 1H); 3.98 (dd, J=6.0, 11.4 Hz, 1H); 3.40 (m, 1H); 2.97 (t, J=5.0 Hz, 1H); 2.81 (dd, J=2.7, 4.8 Hz, 1H); 2.21 (s, 3H). APCI-MS: m/z 208 ($MH^+$).

Step III:

2-{[(2S)-3-(5-chloro-1'H-spiro[1,3-benzodioxole-2,4'-piperidin]-1'-yl)-2-hydroxypropyl]oxy}-N-methylbenzamide trifluoroacetate (salt)

A mixture of 5-chlorospiro[1,3-benzodioxole-2,4'-piperidine] (22.5 mg, 0.1 mmol) and N-methyl-2-[(2S)-oxiran-2-ylmethoxy]benzamide (20.7 mg, 0.1 mmol) in ethanol (2 mL) was is kept on stirring at 80° C. overnight. The volatiles were removed in vacuo and the residue was purified by preparative HPLC (eluent: [acetonitrile/water+0.1% TFA]) to afford the titled compound as a colourless solid (28 mg, 51%)

$^1$H-NMR (acetone-$d_6$, 400 MHz): δ 7.94 (dd, J=7.7, 1.7 Hz, 1H), 7.46 (td, J=7.8, 1.8 Hz, 1H), 7.15 (d, J=8.3 Hz, 1H), 7.07 (t, J=7.5 Hz, 1H), 6.93-6.86 (m, 3H), 4.73 (m, 1H), 4.27 (m, 2H), 3.71 (dd, J=13.4, 2.9 Hz, 2H), 3.58 (dd, J=13.4, 9.5 Hz, 2H), 2.92 (s, 3H), 2.55 (br. s, 4H), 2.08 (m, 2H, covered by the signal of solvent). APCI-MS: m/z 433 ($MH^+$).

Example 53

N-(2-{[(2S)-3-(6-chloro-3,4-dihydro-1'H-spiro[chromene-2,4'-piperidin]-1'-yl)-2-hydroxypropyl]oxy)phenyl)acetamide trifluoroacetate (salt)

A mixture of 6-chloro-3,4-dihydrospiro[chromene-2,4'-piperidine] (23.8 mg, 0.1 mmol) and N-(2-[(2S)-Oxiran-2-ylmethoxy]phenyl}acetamide (20.7 mg, 0.1 mmol) in ethanol (3 mL) was kept on stirring at 80° C. overnight. The volatiles were removed in vacuo and the residue was purified by preparative HPLC (eluent: [acetonitrile/water+0.1% TFA]) to afford the titled compound as a colourless solid (40 mg, 71%).

$^1$H-NMR (acetone-$d_6$, 400 MHz): δ 8.74 (br. s, 1H), 8.29 (d, J=7.5 Hz, 1H), 7.15 (s, 1H), 7.11 (d, J=8.8 Hz, 1H), 6.99 (d, J=3.8 Hz, 2H), 6.97-6.85 (m, 2H), 4.54 (m, 1H), 4.11 (m, 2H), 3.81-3.43 (m, 6H), 2.88 (t, J=6.8 Hz, 2H), 2.24-2.09 (m, 2H), 2.13 (s, 3H), 2.08 (m, 2H, covered by the signal of solvent), 1.95 (t, J=6.8 Hz, 2H) APCI-MS: m/z 445 ($MH^+$).

Example 54

N-(2-{[(2S)-3-(6-chloro-3,4-dihydro-1'H-spiro[chromene-2,4'-piperidin]-1'-yl)-2-hydroxypropyl]oxy}-4-fluorophenyl)acetamide trifluoroacetate (salt)

Prepared as described in Example 53 using N-{4-fluoro-2-[(2S)-oxiran-2-ylmetoxy]phenyl}acetamide.

$^1$H-NMR (acetone-$d_6$, 400 MHz): δ 8.69 (br. s, 1H), 8.24 (m, 1H), 7.15 (s, 1H), 7.11 (dd, J=8.7, 2.6 Hz, 1H), 6.85 (m, 2H), 6.69 (td, J=8.7, 2.8 Hz, 1H), 4.55 (m, 1H), 4.13 (m, 2H), 3.80-3.44 (m, 6H), 2.88 (t, J=6.8 Hz, 2H), 2.29-2.05 (m, 4H, covered by the signal of solvent), 2.12 (s, 3H), 1.95 (t, J=6.6 Hz, 2H) APCI-MS: m/z 463 ($MH^+$).

Example 55

2-{[(2S)-3-(6-chloro-3,4-dihydro-1'H-spiro[chromene-2,4'-piperidin]-1'-yl)-2-hydroxypropyl]oxy}-N-methylbenzamide trifluoroacetate (salt)

Prepared as described in Example 53 using N-methyl-2-[(2S)-oxiran-2-ylmethoxy]benzamide.

$^1$H-NMR (acetone-$d_6$, 400 MHz): δ 8.08 (br. s, 1H), 7.96 (dd, J=7.7, 1.5 Hz, 1H), 7.44 (ddd, J=8.3, 7.3, 1.8 Hz, 1H), 7.15-7.05 (m, 4H), 6.86 (d, J=8.7 Hz, 1H), 4.70 (m, 1H), 4.24 (m, 2H), 3.77 (m, 2H), 3.60-3.45 (m, 4H), 2.91 (d, J=4.4 Hz, 3H), 2.87 (t, J=6.9 Hz, 2H), 2.24 (td, J=14.5, 4.3 Hz, 2H), 2.11-2.05 (m, 2H, covered by the signal of solvent), 1.92 (m, 2H) APCI-MS: m/z 445 (MH⁺).

Example 56

N-(2-{[(2S)-3-(6-chloro-3,4-dihydro-1'H-spiro [chromene-2,4'-piperidin]-1'-yl)-2-hydroxypropyl] oxy}-4-hydroxyphenyl)acetamide trifluoroacetate (salt)

Prepared from 6-chloro-3,4-dihydrospiro[chromene-2,4'-piperidine] as described in Example 27.

$^1$H-NMR (acetone-$d_6$, 400 MHz): δ 7.92 (d, J=8.7 Hz, 1H), 7.14 (s, 1H), 7.11 (dd, J=8.7, 2.5 Hz, 1H), 6.86 (d, J=8.6 Hz, 1H), 6.52 (d, J=2.4 Hz, 1H), 6.40 (dd, J=8.7, 2.5 Hz, 1H), 4.52 (m, 1H), 4.06 (m, 2H), 3.83-3.41 (m, 6H), 2.87 (t, J=6.8 Hz, 2H), 2.27-2.08 (m, 4H, covered by the signal of solvent), 2.08 (s, 3H), 1.93 (t, J=6.7 Hz, 2H) APCI-MS: m/z 461 (MH⁺).

Example 57

N-(2-{[(2S)-3-(6-chloro-3,4-dihydro-1'H-spiro [chromene-2,4'-piperidin]-1'-yl)-2-hydroxy-2-methylpropyl]oxy}-4-hydroxyphenyl)acetamide trifluoroacetate Prepared from 6-chloro-3,4-dihydrospiro[chromene-2,4'-piperidine] as described in Example 9.

$^1$H-NMR (acetone-$d_6$, 400 MHz): δ 7.72 (d, J=7.3 Hz, 1H), 7.11 (m, 2H), 6.86 (d, J=8.5 Hz, 2H), 6.58 (s, 1H), 6.42 (d, J=8.7 Hz, 1H), 3.99 (dd, J=22.2, 9.3 Hz, 2H), 3.91-3.46 (m, 6H), 2.85 (t, J=6.7 Hz, 2H), 2.29 (t, J=12.6 Hz, 2H), 2.08 (s, 3H, covered by the signal of solvent), 2.07 (m, 2H, covered by the signal of solvent), 1.90 (s, 28H), 1.50 (s, 3H) APCI-MS: m/z 475 (MH⁺).

Example 58

N-[2-({(2S)-3-[(2R)-5-chloro-1'H,3H-spiro[1-benzofuran-2,3'-pyrrolidin]-1'-yl-2-hydroxypropyl}oxy}-4-hydroxyphenyl]acetamide To a cold solution (ice-water bath) of N-[2-({(2S)-3-[(2R)-5-chloro-1'H,3H-spiro[1-benzofuran-2,3'-pyrrolidin]-1'-yl]-2-hydroxypropyl}oxy)-4-methoxyphenyl]acetamide (30 mg, 0.067 mmol) in $CH_2Cl_2$ (1.5 mL) was slowly added 1 M solution of $BBr_3$ in $CH_2Cl_2$ (0.2 mL). After addition was completed the reaction mixture was stirred at 0° C. for 3 h. After addition of methanol (0.2 mL) the stirring was continued for another 10 min. The volatiles were removed in vacuo and the residue was dissolved in ethyl acetate, washed successively with aqueous $NaHCO_3$ solution and $H_2O$. The organic layer was dried over $Na_2SO_4$, filtered and concentrated in vacuo. The residue was purified by HPLC (10-60% $CH_3CN$ in $H_2O$ in the presence of 0.1% $NH_4OH$) to give the titled compound (14 mg).

$^1$H-NMR ($CD_3OD$, 400 MHz): δ 7.57 (d, J=8.7 Hz, 1H); 7.15 (br.s, 1H); 7.05 (dd, J=2.3, 8.6 Hz, 1H); 6.66 (d, J=8.5 Hz, 1H); 6.47 (d, J=2.5 Hz, 1H); 6.36 (dd, J=2.5, 8.7 Hz, 1H); 4.14-4.08 (m, 1H); 4.05 (dd, J=3.5, 9.7 Hz, 1H); 3.92 (dd, J=6.2, 9.7 Hz, 1H); 3.25 (m, 2H); 3.09 (d, J=10.6 Hz, 1H); 3.02-2.92 (m, 1H); 2.86-2.75 (m, 3H); 2.69 (dd, J=7.3, 12.2 Hz, 1H); 2.32-2.24 (m, 1H); 2.13-2.05 (m, 4H). APCI-MS: m/z 433 (MH⁺).

Example 59

N-[2-({(2S)-3-[(2S)-5-chloro-1"H,3H-spiro[1-benzofuran-2,3'-pyrrolidin]-1'-yl]-2-hydroxypropyl) oxy}-4-hydroxyphenyl]acetamide To a cold solution (ice-water bath) of N-[2-({(2S)-3-[(2S)-5-chloro-1'H,3H-spiro[1-benzofuran-2,3'-pyrrolidin]-1'-yl]-2-hydroxypropyl}oxy)-4-methoxyphenyl]acetamide (30 mg, 0.067 mmol) in $CH_2Cl_2$ (1.5 mL) was slowly added 1 M solution of $BBr_3$ in $CH_2Cl_2$ (0.2 mL). After addition was completed the reaction mixture was stirred at 0° C. for 3 h. After addition of methanol (0.2 mL) the stirring was continued for another 10 min. The volatiles were removed in vacuo and the residue was dissolved in ethyl acetate, washed successively with aqueous $NaHCO_3$ solution and $H_2O$. The organic layer was dried over $Na_2SO_4$, filtered and concentrated in vacuo. The residue was purified by HPLC (10-60% $CH_3CN$ in $H_2O$ in the presence of 0.1% $NH_4OH$) to give the titled compound (15 mg).

$^1$H-NMR ($CD_3OD$, 400 MHz): δ 7.57 (d, J=8.7 Hz, 1H); 7.15 (m, 1H); 7.05 (dd, J=2.3, 8.5 Hz, 1H); 6.65 (d, J=8.5 Hz, 1H); 6.47 (d, J=2.5 Hz, 1H); 6.36 (dd, J=2.5, 8.5 Hz, 1H); 4.14-4.07 (m, 1H); 4.04 (dd, J=3.7, 9.9 Hz, 1H); 3.93 (dd, J=6.1, 9.9 Hz, 1H); 3.25 (m, 2H); 3.13 (d, J=10.7 Hz, 1H); 3.03-2.96 (m, 1H); 2.82-2.73 (m, 3H); 3.93 (dd, J=6.1, 9.9 Hz, 1H); 2.32-2.24 (m, 1H); 2.14-2.05 (m, 4H). APCI-MS: m/z 433 (MH⁺).

Example 60

3-{[(2S)-3-(5-Chloro-1'H,3H-spiro[1-benzofuran-2, 4'-piperidin]-1'-yl)-2-hydroxypropyl]oxy}-4-(pyrrolidin-1-ylcarbonyl)phenol Step I (2S)-1-(5-Chloro-1'H,3H-spiro[1-benzofuran-2,4'-piperidin]-1'-yl)-3-[5-[(4-methoxybenzyl)oxy]-2-(pyrrolidin-1-ylcarbonyl)phenoxy]propan-2-ol A mixture of 2-{[(2S)-3-(5-chloro-1'H,3H-spiro[1-benzofuran-2,4'-piperidin]-1'-yl)-2-hydroxypropyl]oxy}-4-[(4-methoxybenzyl]benzoic acid (hydrochloride) (100 mg, 0.169 mmol) and N,N-carbonyldiimidazole (27.5 mg, 0.169 mmol) in DMF (3 mL) was stirred at room temperature for 1 h. Then, pyrrolidine (120 mg, 1.69 mmol) in DMF (1 mL) was added and the reaction mixture was stirred at room temperature overnight. The reaction mixture was partitioned between ethyl acetate and water. The organic layer was dried over $Na_2SO_4$, filtered and concentrated. The residue was purified by silica gel flash chromatography (0-1% methanol in dichloromethane, 0.2% $NH_4OH$) to give the subtitled compound (38 mg.).

$^1$H-NMR ($CDCl_3$, 400 MHz): δ 7.39-7.34 (m, 2H); 7.27-7.20 (m, 1H); 7.13 (m, 1H); 7.05 (dd, J=2.3, 8.5 Hz, 1H); 6.95 (m, 1H); 6.69 (d, J=8.4 Hz, 1H); 6.64-6.59 (m, 2H); 4.13-3.98 (m, 3H); 3.87 (s, 3H); 3.64 (t, J=6.9 Hz, 2H); 3.38 (m, 2H); 3.00 (s, 2H); 2.80 (m, 1H); 2.73-2.49 (m, 5H); 2.03-1.76 (m, 8H). APCI-MS: m/z 607 (MH⁺).

Step II

3-{[(2S)-3-(5-Chloro-1'H,3H-spiro[1-benzofuran-2,4'-piperidin]-1'-yl)-2-hydroxypropyl]oxy}-4-(pyrrolidin-1-ylcarbonyl)phenol (2S)-1-(5-Chloro-1'H,3H-spiro[1-benzofuran-2,4'-piperidin]-1'-yl)-3-[5-[(4-methoxybenzyl)oxy]-2-(pyrrolidin-1-ylcarbonyl)phenoxy]propan-2-ol (35 mg, 0.057 mmol) was treated with 10% CF$_3$CO$_2$H in CH$_2$Cl$_2$ (3 mL) at room temperature for 25 min. The volatiles were removed in vacuo and the residue was purified by silica gel flash chromatography (0-3% methanol in dichloromethane, 0.2% NH$_4$OH) to give the titled compound (20 mg).

$^1$H-NMR (CD$_3$OD, 400 MHz): δ 7.09 (m, 1H); 7.04-6.97 (m, 2H); 6.61 (d, J=8.5 Hz, 1H); 6.45 (d, J=2.2 Hz, 1H); 6.39 (dd, J=2.0, 8.3 Hz, 1H); 4.09-4.02 (m, 1H); 3.97 (dd, J=4.3, 9.7 Hz, 1H); 3.91 (dd, J=5.7, 9.7 Hz, 1H); 3.51 (t, J=6.8 Hz, 2H); 3.30 (m, 2H); 2.99 (s, 2H); 2.74-2.46 (m, 6H); 1.98-1.74 (m, 8H). APCI-MS: m/z 487 (MH$^+$).

Example 61

1-(2-{[(2S)-3-(5-Chloro-1'H,3H-spiro[1-benzofuran-2,4'-piperidin]-1'-yl)-2-hydroxypropyl]oxy}-4-hydroxybenzoyl)piperidin-4-ol Step I 1-(2-{[(2S)-3-(5-Chloro-1'H,3H-spiro[1-benzofuran-2,4'-piperidin]-1'-yl)-2-hydroxypropyl]oxy}-4-[(4-methoxybenzyl)oxy]benzoyl}piperidin-4-ol A mixture of 2-{[(2S)-3-(5-chloro-1'H,3H-spiro[1-benzofuran-2,4'-piperidin]-1'-yl)-2-hydroxypropyl]oxy}-4-[(4-methoxybenzyl)benzoic acid (hydrochloride) (100 mg, 0.169 mmol) and N,N-carbonyldiimidazole (27.5 mg, 0.169 mmol) in DMF (3 mL) was stirred at room temperature for 1 h. Then piperidin-4-ol (20.5 mg, 0.202 mmol) in DMF was added and the reaction mixture was stirred at room temperature overnight. The reaction mixture was partitioned between ethyl acetate and water. The organic layer was dried over Na$_2$SO$_4$, filtered and concentrated. The residue was purified by silica gel flash chromatography (0-2% methanol in dichloromethane, 0.2% NH$_4$OH) to give the subtitled compound (50 mg).

APCI-MS: m/z 637 (MH$^+$).

Step II 1-(2-{[(2S)-3-(5-Chloro-1'H,3H-spiro[1-benzofuran-2,4'-piperidin-1'-yl)-2-hydroxypropyl]oxy}-4-hydroxybenzoyl)piperidin-4-ol 1-{2-{[(2S)-3-(5-Chloro-1'H,3H-spiro[1-benzofuran-2,4'-piperidin]-1'-yl)-2-hydroxypropyl]oxy}-4-[(4-methoxybenzyl)oxy]benzoyl}piperidin-4-ol (45 mg, 0.07 mmol) was treated with 10% CF$_3$CO$_2$H in CH$_2$Cl$_2$ (3 mL) for 25 min at room temperature.

The volatiles were removed in vacuo and the residue was purified by silica gel flash chromatography (0-4.5% methanol in dichloromethane, 0.2% NH$_4$OH) to give the titled compound (20 mg).

$^1$H-NMR (CD$_3$OD, 400 MHz): δ 7.09 (m, 1H); 7.02-6.92 (m, 2H); 6.60 (d, J=8.5 Hz, 1H); 6.47-6.37 (m, 2H); 4.21-3.78 (m, 4H); 3.58-3.03 (m, 4H); 3.00 (s, 2H); 2.76-2.44 (m, 6H); 1.96-1.22 (m, 8H). APCI-MS: m/z 637 (MH$^+$).

Example 62

(3S)-1-(2-{[(2S)-3-(5-Chloro-1'H,3H-spiro[1-benzofuran-2,4'-piperidin]-1'-yl)-2-hydroxypropyl]oxy)benzoyl)pyrrolidin-3-ol A mixture of 2-{[(2S)-3-(5-chloro-1'H,3H-spiro[1-benzofuran-2,4'-piperidin]-1'-yl)-2-hydroxypropyl]oxy}-4-[(4-methoxybenzyl]benzoic acid (hydrochloride) (60 mg, 0.132 mmol) and N,N-carbonyldiimidazole (30 mg, 0.184 mmol) in DMF (1.5 mL) was stirred at room temperature for 1 h. Then 3(S)-pyrrolidin-3-ol (57.5 mg, 0.66 mmol) in DMF (1 mL) was added and the reaction mixture was stirred at room temperature overnight. The reaction mixture was partitioned between ethyl acetate and water. The organic layer was dried over Na$_2$SO$_4$, filtered and concentrated. The residue was purified by silica gel flash chromatography (0-2.5% methanol in dichloromethane, 0.2% NH$_4$OH) to give the titled compound (13 mg).

$^1$H-NMR (CD$_3$OD, 400 MHz): δ 7.45-7.39 (m, 1H); 7.26 (br. d, J=7.2 Hz, 1H); 7.15-7.09 (m, 2H); 7.08-7.01 (m, 2H); 6.65 (d, J=8.5 Hz, 1H); 4.50 (m, 0.5H); 4.38 (m, 0.5H); 4.17-3.98 (m, 3H); 3.77-3.42 (m, 3H); 3.25 (m, 1H); 3.02 (s, 2H); 2.77-2.52 (m, 6H); 2.14-1.77 (m, 6H). APCI-MS: m/z 487 (MH$^+$).

Example 63

3-{[(2S)-3-(5-Chloro-1'H,3H-spiro[1-benzofuran-2,4'-piperidin]-1'-yl)-2-hydroxypropyl]oxy}-4-(piperidin-1-ylcarbonyl)phenol Step I (2S)-1-(5-Chloro-1'H,3H-spiro[1-benzofuran-2,4'-piperidin]-1'-yl)-3-[5-[(4-methoxybenzyl)oxy]-2-(piperidin-1-ylcarbonyl)phenoxy]propan-2-ol A mixture of 2-{[(2S)-3-(5-chloro-1'H,3H-spiro[1-benzofuran-2,4'-piperidin]-1'-yl)-2-hydroxypropyl]oxy}-4-[(4-methoxybenzyl]benzoic acid (hydrochloride) (100 mg, 0.169 mmol) and N,N-carbonyldiimidazole (41 mg, 0.253 mmol) in DMF (1.5 mL) was stirred at room temperature for 1 h. Then piperidin (144 mg, 1.79 mmol) in DMF was added and the reaction mixture was stirred at room temperature overnight. The reaction mixture was partitioned between ethyl acetate and water. The organic layer was dried over Na$_2$SO$_4$, filtered and concentrated. The residue was purified by silica gel flash chromatography (0-1% methanol in dichloromethane, 0.2% NH$_4$OH) to give the subtitled compound (24 mg).

APCI-MS: m/z 621 (MH$^+$).

Step II

3-{[(2S)-3-(5-Chloro-1'H,3H-spiro[1-benzofuran-2,4'-piperidin]-1'-yl)-2-hydroxypropyl]oxy}-4-(piperidin-1-ylcarbonyl)phenol 2S)-1-(5-Chloro-1'H,3H-spiro[1-benzofuran-2,4'-piperidin]-1'-yl)-3-[5-[(4-methoxybenzyl)oxy]-2-(piperidin-1-ylcarbonyl)phenoxy]propan-2-ol (23 mg, 0.037 mmol) was treated with 10% CF$_3$CO$_2$H in CH$_2$Cl$_2$ (3 mL) at room temperature for 30 min. The volatilles were removed in vacuo and the residue was purified by silica gel flash chromatography (0-2.5% methanol in dichloromethane, 0.2% NH$_4$OH) to give the titled compound (10 mg).

$^1$H-NMR (CD$_3$OD, 400 MHz): δ 7.13 (m, 1H); 7.03 (dd, J=2.2, 8.5 Hz, 1H); 7.00 (d, J=8.2 Hz, 1H); 6.65 (d, J=8.5 Hz, 1H); 6.50 (d, J=2.1 Hz, 1H); 6.44 (dd, J=2.1, 8.2 Hz, 1H); 4.10 (m, 1H); 4.07-3.93 (m, 2H); 3.80 (m, 1H); 3.58 (m, 1H); 3.30 (m, 2H, inside the methanol peak); 3.00 (s, 2H); 2.78-2.51 (m, 6H); 1.98-1.80 (m, 4H); 1.75-1.40 (m, 6H). APCI-MS: m/z 503 (MH$^+$).

Example 64

(3S)-1-(2-{[(2S)-3-(5-Chloro-1'H,3H-spiro[2-benzofuran-1,4'-piperidin]-1'-yl)-2-hydroxypropyl]oxy)-4-hydroxybenzoyl)pyrrolidin-3-ol Step I Methyl 2-{[(2S)-3-(5-chloro-1'H,3H-spiro[2-benzofuran-1,4'-piperidin]-1'-yl)-2-hydroxypropyl]oxy)-4-[(4-methoxybenzyl)oxy]benzoate A mixture of 5-chloro-3H-spiro[2-benzofuran-1,4'-piperidin] (195 mg, 0.87 mmol) and methyl 4-[(4-methoxybenzyl)oxy]-2-[(2S)-oxiran-2-ylmethoxy]benzoate (300 mg, 0.87 mmol) in ethanol (4 mL) was stirred at 80° C. overnight. The volatiles were removed in vacuo and the residue was purified by silica gel flash chromatography (0-2% methanol in dichloromethane, 0.2% $NH_4OH$) to give the subtitled compound (450 mg).

$^1$H-NMR ($CDCl_3$, 400 MHz): δ 7.89-7.85 M, 1H); 7.39-7.35 (m, 2H); 7.26 (dd, J=1.8, 8.1 Hz, 1H); 7.20 (br,s, 1H); 7.08 (d, J=8.0 Hz, 1H); 6.97-6.93 (m, 2H); 6.64-6.59 (m, 2H); 5.08 (s, 4H); 4.24-4.15 (m, 2H); 4.03 (dd, J=5.8, 9.0 Hz, 1H); 3.88 (s, 3H); 3.84 (s, 3H); 2.98-2.85 (m, 2H); 2.75-2.46 (m, 4H); 2.03-1.90 (m, 2H); 1.77 (br, d, J=13.5 Hz, 2H). APCI-MS: m/z 570).

Step II

2-{[(2S)-3-(5-Chloro-1'H,3H-spiro[2-benzofuran-1,4'-piperidin]-1'-yl)-2-hydroxypropyl]oxy}-4-[(4-methoxybenzyl)oxy]benzoic acid (hydrochloride)

Methyl 2-{[(2S)-3-(5-chloro-1'H,3H-spiro[2-benzofuran-1,4'-piperidin]-1'-yl)-2-hydroxypropyl]oxy}-4-[(4-methoxybenzyl)oxy]benzoate (450 mg, 0.792 mmol) was taken in ethanol (6 mL). Aqueous KOH (2.31 gm KOH in 2.3 mL of $H_2O$) was added and the reaction mixture was refluxed for overnight, cooled to 0° C. and the pH was made to 2.0 by addition of aqueous HCl, extracted with ethyl acetate. The organic layer was washed with $H_2O$, dried over $Na_2SO_4$, filtered and concentrated to give the subtitled compound (370 mg).

$^1$H-NMR ($CD_3OD$, 400 MHz): δ 7.97-7.93 (m, 1H); 7.39-7.32 (m, 5H); 6.96-6.91 (m, 2H); 6.75-6.70 (m, 2H); 5.10 (s, 4H); 4.48-4.42 (m, 1H); 4.30 (dd, J=4.0, 9.5 Hz, 1H); 4.11 (dd, J=5.3, 9.5 Hz, 1H); 3.81 (s, 3H); 3.80-3.42 (m, 6H); 2.55-2.41 (m, 2H); 1.98-1.88 (m, 2H). APCI-MS: m/z 554 (MH$^+$).

Step III (3S)-1-{2-{[(2S)-3-(5-Chloro-1'H,3H-spiro[2-benzofuran-1,4'-pipwridin]-1'-yl)-2hydroxypropyl]oxy}-4-[(4-methoxybenzyl)oxy]benzoyl}pyrrolidin-3-ol A mixture of 2-{[(2S)-3-(5-chloro-1'H,3H-spiro[2-benzofuran-1,4'-piperidin]-1'-yl)-2-hydroxypropyl]oxy}-4-[(4-methoxybenzyl)oxy]benzoic acid (hydrochloride) (150 mg, 0.254 mmol) and N,N-carbonyldiimidazole (54 mg, 0.33 mmol) in DMF (4 mL) was stirred at room temperature for 1 h, 3(S)-pyrrolidin-3-ol (111 mg, 1.27 mmol) in DMF (1.5 mL) was added and the reaction mixture was stirred at room temperature overnight, partitioned between ethyl acetate and water. The organic layer was dried over $Na_2SO_4$, filtered and concentrated. The residue was purified by silica gel flash chromatography (0-2% methanol in dichloromethane, 0.2% $NH_4OH$) to give the subtitled compound (100 mg).

APCI-MS: m/z 623 (MH$^+$).

Step IV (3S)-1-(2-{[(2S)-3-(5-Chloro-1'H,3H-spiro[2-benzofuran-1,4'-piperidin]-1'-yl)-2-hydroxypropyl]oxy}-4-hydroxybenzoyl)pyrrolidin-3-ol (3S)-1-{2-{[(2S)-3-(5-Chloro-1'H,3H-spiro[2-benzofuran-1,4'-piperidin]-1'-yl)-2-hydroxypropyl]oxy}-4-[(4-methoxybenzyl)oxy]benzoyl}pyrrolidin-3-ol (95 mg, 0.152 mmol) was treated with 10% $CF_3CO_2H$ in $CH_2Cl_2$ (4 mL) at room temperature for 25 min. The volatiles were removed in vacuo and the residue was purified by silica gel flash chromatography (0-5% methanol in dichloromethane, 0.2% $NH_4OH$) to give the titled compound (34 mg).

$^1$H-NMR ($CD_3OD$, 400 MHz): δ 7.31-7.27 (m, 2H); 7.20 (d, J=8.3 Hz, 1H); 7.10 (d, J=8.3 Hz, 1H); 6.52 (t, J=2.5 Hz, 1H); 6.46 (dt, J=2.0 Hz, 1H); 5.02 (s, 2H); 4.49 (m, 0.5H); 4.38 (m, 0.5H); 4.20 (m, 1H); 4.08-3.98 (m, 2H); 3.73-3.49 (m, 3H); 3.30 (m, 1H); 3.12 (br.s, 2H); 2.95-2.70 (m, 4H); 2.18-1.75 (m, 6H). APCI-MS: m/z 503 (MH$^+$).

Example 65

1-(2-{[(2S)-3-(5-Chloro-1'H,3H-spiro[2-benzofuran-1,4'-piperidin]-1'-yl)-2-hydroxypropyl]oxy}-4-hydroxybenzoyl)piperidin-4-ol Step I 1-{[(2S)-3-(5-Chloro-1'H,3H-spiro[2-benzofuran-1,4'-piperidin]-1'-yl)-2-hydroxypropyl]oxy}-4-[(4-methoxybenzyl)oxy]benzoyl}piperidin-4-ol A mixture of 2-{[(2S)-3-(5-chloro-1'H,3H-spiro[2-benzofuran-1,4'-piperidin]-1'-yl)-2-hydroxypropyl]oxy}-4-[(4-methoxybenzyl)oxy]benzoic acid (hydrochloride) (150 mg, 0.254 mmol) and N,N-carbonyldiimidazole (54 mg, 0.33 mmol) in DMF (4 mL) was stirred at room temperature for 1 h, piperidin-4-ol (77 mg, 0.762 mmol) was added and the reaction mixture was stirred at room temperature overnight, partitioned between ethyl acetate and water. The organic layer was dried over $Na_2SO_4$, filtered and concentrated. The residue was purified by silica gel flash chromatography (0-2.5% methanol in dichloromethane, 0.2% $NH_4OH$) to give the subtitled compound (70 mg).

APCI-MS: m/z 637 (MH$^+$).

Step II 1-(2-{[(2S)-3-(5-Chloro-1'H,3H-spiro[2-benzofuran-1,4'-piperidin]-1'-yl)-2-hydroxypropyl]oxy}-4-hydroxybenzoyl)piperidin-4-ol 1-{[(2S)-3-(5-Chloro-1'H,3H-spiro[2-benzofuran-1,4'-piperidin]-1'-yl)-2-hydroxypropyl]oxy}-4-[(4-methoxybenzyl)oxy]benzoyl}piperidin-4-ol (65 mg, 0.102 mmol) was treated with 10% $CF_3CO_2H$ in dichloromethane (3 mL) for 25 min at room temperature. The volatiles were removed in vacuo and the residue was purified by silica gel flash chromatography (0-5% methanol in dichloromethane, 0.2% $NH_4OH$) to give the titled compound (26 mg).

$^1$H-NMR ($CD_3OD$, 400 MHz): δ 7.30-7.25 (m, 2H); 7.19 (d, J=8.1 Hz, 1H); 7.07-6.98 (m, 1H); 6.53 (br.s, 1H); 6.45 (d, J=8.2 Hz, 1H); 5.01 (s, 2H); 4.30-3.70 (m, 5H); 3.62-3.10 (m, 3H); 3.00 (br.s, 2H); 2.73-2.50 (m, 4H); 2.10-1.32 (m, 8H). APCI-MS: m/z 517 (MH$^+$).

Example 66

N-[4-Hydroxy-2-({(2S)-2-hydroxy-3-[5-(trifluoromethyl)-1'H,3H-spiro[1-benzofuran-2,4'-piperidin]-1'-yl]propyl}oxy)phenyl]acetamide A mixture of 4-(acetylamino)-3-[(2S)-oxiran-2-ylmethoxy]phenyl acetate (41 mg, 0.155 mmol) and 5-(trifluoromethyl)-3H-spiro[1-benzofuran-2,4'-piperidine] (40 mg, 0.155 mmol) in ethanol (2 mL) was stirred at 80° C. overnight. The volatiles were removed in vacuo and the residue was purified by silica gel flash chromatography (0-2.5% methanol in dichloromethane, 0.2% NH$_4$OH) to give the titled compound (54 mg).

$^1$H-NMR (CD$_3$OD, 400 MHz): δ 7.57 (d, J=8.7 Hz, 1H); 7.45 (s, 1H); 7.39 (d, J=8.5 Hz, 1H); 6.82 (d, J=8.4 Hz, 1H); 6.48 (d, J=2.5 Hz, 1H); 6.46 (dd, J=2.6, 8.7 Hz, 1H); 4.20-4.14 (m, 1H); 4.05 (dd, J=3.5, 9.9 Hz, 1H); 3.93 (dd, J=6.2, 9.9 Hz, 1H); 3.08 (s, 2H); 2.80-2.55 (m, 6H); 2.13 (s, 3H); 2.02-1.83 (m, 4H). APCI-MS: m/z 481 (MH$^+$).

Example 67

(3S)-1-{[2-{[(2S)-3-(5-Chloro-1'H,3H-spiro[1-benzofuran-2,4'-piperidin]-1'-yl)-2-hydroxypropyl]oxy}-4-hydroxybenzoyl)pyrrolidin-3-ylbenzoate

Step I tert-Butyl(3S)-3-(benzoyloxy)pyrrolidine-1-carboxylate

To a solution of (3S)-pyrrolidin-3-ol (0.87 g, 10.0 mmol) in THF (20 mL) was slowly added a solution of di-tert-butyl dicarbonate (2.18 g, 10.0 mmol) in THF (10 mL) at room temperature. After addition was completed, the reaction mixture was stirred at room temperature overnight. The volatiles were removed in vacuo and the residue was purified by silica gel flash chromatography (0-2.5% methanol in dichloromethane) to give intermediate tert-Butyl(3S)-3-hydroxypyrrolidine-1-carboxylate. To a solution of tert-butyl (3S)-3-hydroxypyrrolidine-1-carboxylate (900 mg, 4.8 mmol) in CH$_2$Cl$_2$ (6 mL) was added Et$_3$N (699 mg, 6.91 mmol) followed by benzoyl chloride (809 mg, 5.76 mmol) at 0° C. After addition was completed, the reaction mixture was stirred at room temperature overnight. The reaction mixture was partitioned between CH$_2$Cl$_2$ and H$_2$O. The organic layer was successively washed with aqueous NaHCO$_3$ and water, dried over Na$_2$SO$_4$, filtered and concentrated. The residue was purified by silica gel flash chromatography (0-1% methanol in dichloromethane) to give the subtitled compound (642 mg).

$^1$H-NMR (CDCl$_3$, 400 MHz): δ 8.03 (d, J=7.3 Hz, 2H); 7.59 (t, J=7.3 Hz, 1H); 7.46 (t, J=7.7 Hz, 2H); 5.58 (m, 1H); 3.75-3.45 (m, 4H); 2.20 (s, 2H); 1.50 (s, 9H). APCI-MS: m/z 192 (MH$^+$-Boc).

Step II (3S)-Pyrrolidin-3-yl-benzoate (trifluoroacetate)

tert-Butyl(3S)-3-(benzoyloxy)pyrrolidine-1-carboxylate (635 mg, 2.18 mmol) was treated with 20% CF$_3$CO$_2$H in CH$_2$Cl$_2$ (20 mL) overnight at room temperature. The volatiles were removed in vacuo to give the subtitled compound (800 mg).

$^1$H-NMR (CDCl$_3$, 400 MHz): δ 9.29 (brd, 2H); 8.06 (m, 2H); 7.64-7.59 (m, 1H); 7.47 (t, J=7.9 Hz, 2H); 5.70 (m, 1H); 3.72-3.50 (m, 4H); 2.40 (m, 2H). APCI-MS: m/z 192 (MH$^+$).

Step III (3S)-1-{2-{[(2S)-3-(5-Chloro-1'H,3H-spiro[1-benzofuran-2,4'-piperidin]-1'-yl)-2-hydroxypropyl]oxy}-4-[(4-methoxybenzyl)oxy]benzoyl}pyrrolidin-3-yl-benzoate A mixture of 2-{[(2S)-3-(5-chloro-1'H,3H-spiro[1-benzofuran-2,4'-piperidin]-1'-yl)-2-hydroxypropyl]oxy}-4-[(4-methoxybenzyl]benzoic acid (hydrochloride) (218 mg, 0.369 mmol) and N,N-carbonyldiimidazole (77.5 mg, 0.478 mmol) in DMF (3 mL) was stirred at room temperature for 50 min. Then (3S)-pyrrolidin-3-yl-benzoate (trifluoroacetate) (225 mg, 0.738 mmol) in DMF (1 mL) was added followeed by Et$_3$N (0.102 mL, 0.738 mmol) and the reaction mixture was stirred at room temperature overnight. The reaction mixture was partitioned between ethyl acetate and water. The organic layer was dried over Na$_2$SO$_4$, filtered and concentrated. The residue was purified by silica gel flash chromatography (0-2.5% methanol in dichloromethane) to give the subtitled compound (140 mg).

APCI-MS: m/z 727 (MH$^+$).

Step IV (3S)-1-(2-{[(2S)-3-(5-Chloro-1'H,3H-spiro[1-benzofuran-2,4'-piperidin]-1'-yl)-2-hydroxypropyl]oxy}-4-hydroxybenzoyl)pyrrolidin-3-ylbenzoate (3S)-1-{2-{[(2S)-3-(5-Chloro-1'H,3H-spiro[1-benzofuran-2,4'-piperidin]-1'-yl)-2-hydroxypropyl]oxy}-4-[(4-methoxybenzyl)oxy]benzoyl}pyrrolidin-3-yl-benzoate (135 mg, 0.185 mmol) was treated with 10% CF$_3$CO$_2$H in CH$_2$Cl$_2$ (3 mL) for 35 min. at room temperature. The volatiles were removed in vacuo and the residue was purified by silica gel flash chromatography (0-3.5% methanol in dichloromethane) to give the titled compound (73 mg).

$^1$H-NMR (CDCl$_3$, 400 MHz): δ 8.06 (d, J=7.4 Hz, 1H); 8.00 (d, J=7.4 Hz, 1H); 7.61-7.56 (m, 1H); 7.52-7.43 (m, 2H); 7.17-7.04 (m, 3H); 6.71 (dd, J=2.4, 8.5 hz, 1H); 6.56-6.45 (m, 2H); 5.16 (m, 0.5H); 5.50 (m, 0.5H); 4.45 (m, 1H); 4.05-3.48 (m, 7H); 3.33-2.92 (m, 8H); 2.40-1.95 (m, 5H). APCI-MS: m/z 607 (MH$^+$).

Example 68

(3S)-1-(2-{[(2S)-3-(5-Chloro-1'H,3H-spiro[1-benzofuran-2,4'-piperidin]-1'-yl)-2-hydroxypropyl]oxy}-4-fluorobenzoyl)pyrrolidin-3-ol

Step I

Methyl 4-fluoro-2-[(2S)-oxiran-2-ylmethoxy]benzoate

A mixture of methyl 4-fluoro-2-hydroxybenzoate (456.3 mg, 1.76 mmol), (2S)-oxiran-2-ylmethyl 3-nitrobenzenesulfonate (300 mg, 1.76 mmol) and Cs$_2$CO$_3$ (687.4 mg, 2.11 mmol) in DMF (4.5 mL) was stirred at room temperature overnight. The reaction mixture was partitioned between ethyl acetate and H$_2$O, organic layer was dried over Na$_2$SO$_4$, filtered and concentrated in vacuo. The residue was opurified by silica gel flash chromatography (0-30% ethyl acetate in petroleum spirit) to give the subtitled compound (385 mg).

$^1$H-NMR (CDCl$_3$, 400 MHz): δ 7.93-7.85 (m, 1H); 6.77-6.69 (m, 2H); 4.36 (dd, J=2.6, 11.2 Hz, 1H); 4.08 (dd, J=4.9, 11.2 Hz, 1H); 3.90 (s, 3H); 3.44 (m, 1H); 2.95 (m, 2H). APCI-MS: m/z 227 (MH$^+$).

Step II

Methyl 2-{[(2S)-3-(5-chloro-1'H,3H-spiro[1-benzofuran-2,4'-piperidin]-1'-yl)-2-hydroxypropyl]oxy}-4-fluorobenzoate A mixture of 5-chloro-3H-spiro[1-benzofuran-2,4'-piperidine] (224 mg, 1.0 mmol), methyl 4-fluoro-2-[(2S)-oxiran-2-ylmethoxy]benzoate (226 mg, 1.0 mmol) in ethanol (2 mL)

was stirred at 80° C. overnight. The volatiles were removed in vacuo and the residue was purified by silica gel flash chromatography (0-2.5% methanol in dichloromethane) to give the subtitled compound (290 mg).

$^1$H-NMR (CDCl$_3$, 400 MHz): δ 7.90 (m, 1H); 7.12 (s, 1H); 7.07 (dd, J=2.2, 8.4 Hz, 1H); 6.77-6.67 (m, 3H); 4.25-4.14 (m, 2H); 4.06 (dd, J=5.6, 9.0 Hz, 1H); 3.90 (s, 3H); 3.00 (s, 2H); 2.90-2.60 (m, 6H); 2.00 (m, 2H); 1.86 (m, 2H). APCI-MS: m/z 452 (MH$^+$).

Step II

2-{[(2S)-3-(5-Chloro-1'H,3H-spiro[1-benzofuran-2,4'-piperidin]-1'-yl)-2-hydroxypropyl]oxy}4-fluorobenzoic acid (hydrochloride)

Methyl 2-{[(2S)-3-(5-chloro-1'H,3H-spiro[1-benzofuran-2,4'-piperidin]-1'-yl)-2-hydroxypropyl]oxy}-4-fluorobenzoate (286 mg, 0.635 mmol) in THF (3 mL) was treated with aqueous KOH (106 mg KOH in 1 mL H$_2$O) at room temperature for 7 h. The reaction mixture was cooled to 0° C. and pH was made to 2 by addition of aqueous HCl, extracted with ethyl acetate. The organic layer was washed with H$_2$O, dried over Na$_2$SO$_4$, filtered and concentrated to give the subtitled compound (250 mg).

$^1$H-NMR (CD$_3$OD, 400 MHz): δ 7.98 (dd, J=6.9, 8.8 Hz, 1H); 7.20 (s, 1H); 7.11 (dd, J=2.0, 8.6 Hz, 1H); 6.97 (dd, J=2.3, 10.9 Hz, 1H); 6.86-6.79 (m, 1H); 6.74 (d, J=8.5 Hz, 1H); 4.50-4.43 (m, 1H); 4.27 (dd, J=4.0, 9.6 Hz, 1H); 4.13 (dd, J=5.3, 9.6 Hz, 1H); 3.80-3.43 (m, 6H); 3.15 (s, 2H); 2.10 (m, 2H); 2.18 (m, 2H). APCI-MS: m/z 436 (MH$^+$).

Step IV (3S)-1-(2-{[(2S)-3-(5-Chloro-1'H,3H-spiro[1-benzofuran-2,4'-piperidin]-1'-yl)-2-hydroxypropyl]oxy}-4-fluorobenzoyl)pyrrolidin-3-ol A mixture of 2-{[(2S)-3-(5-chloro-1'H,3H-spiro[1-benzofuran-2,4'-piperidin]-1'-yl)-2-hydroxypropyl]oxy}-4-fluorobenzoic acid (hydrochloride) (200 mg, 0.423 mmol) and N,N-carbonyldiimidazole (89.2 mg, 0.55 mmol) in DMF (3 mL) was stirred at room temperature for 50 min. Then (3S)-pyrrolidin-3-ol (184 mg, 2.11 mmol) in DMF (1 mL) was added and the reaction mixture was stirred at room temperature overnight, partitioned between ethyl acetate and H$_2$O. The organic layer was dried over Na$_2$SO$_4$, filtered and concentrated. The residue was purified by silica gel flash chromatography (0-2.5% methanol in dichloromethane, 0.2% NH$_4$OH) to give the titled compound (60 mg).

$^1$H-NMR (CD$_3$OD, 400 MHz): δ 7.28 (m, 1H); 7.13 (s, 1H); 7.07-7.02 (m, 1H); 6.97-6.91 (m, 1H); 6.81-6.75 (m, 1H); 6.65 (d, J=8.5 Hz, 1H); 4.49 (m, 0.5H); 4.38 (m, 0.5H); 4.16-3.99 (m, 3H); 3.70 (dd, J=5.2, 9.3 Hz, 1H); 3.64-3.46 (m, 2H); 3.37-3.19 (m, 1H); 3.00 (s, 2H); 2.75-2.52 (m, 6H); 2.14-1.78 (m, 6H). APCI-MS: m/z 506 (MH$^+$).

Example 69

(3S)-1-[4-Hydroxy-2-({(2S)-2-hydroxy-3-[5-(trifluoromethyl)-1'H,3H-spiro[1-benzofuran-2,4'-piperidin]-1'-yl]propyl)oxy)benzoyl]pyrrolidin-3-ol Step I Methyl-2-({(2S)-2-hydroxy-3-[5-(trifluoromethyl)-1'H,3H-spiro[1-benzofuran-2,4'-piperidin]-1'-yl]propyl)oxy)-4-[(4-methoxybenzyl)oxy]benzoate A mixture of 5-(trifluoromethyl)-3H-spiro[1-benzofuran-2,4'-piperidine] (107 mg, 0.416 mmol) and methyl 4-[(4-methoxybenzyl)oxy]-2-[(2S)-oxiran-2-ylmethoxy]benzoate (143.25 mg, 0.416 mmol) in ethanol (2 mL) was stirred at 75° C. over the weekend. The volatiles were removed in vacuo and the residue was purified by silica gel flash chromatography (0-2.5% methanol in dichloromethane) to give the subtitled compound (200 mg).

APCI-MS: m/z 602 (MH$^+$).

Step II 2-({(2S)-2-Hydroxy-3-[5-(trifluoromethyl)-1'H,3H-spiro 1-benzofuran-2,4'-piperidin]-1'-yl]propyl)oxy)-4-[(4-methoxybenzyl)oxy]benzoicacid (hydrochloride)

Methyl-2-({(2S)-2-hydroxy-3-[5-(trifluoromethyl)-1'H,3H-spiro[1-benzofuran-2,4'-piperidin]-1'-yl]propyl}oxy)-4-[(4-methoxybenzyl)oxy]benzoate (190 mg, 0.315 mmol) was taken in ethanol (4 mL), aqueous KOH (918 mg KOH in 1 mL H$_2$O) was added and thereaction mixture was stirred at reflux temperature overnight, cooled to 0° C. and pH was made to 2 by addition of aqueous HCl, extracted with ethyl acetate. The organic layer was washed with H$_2$O, dried over Na$_2$SO$_4$, filtered and concentrated to give the subtitled compound (170 mg).

$^1$H-NMR (CD$_3$OD, 400 MHz): δ 7.93 (d, J=9.0 Hz, 1H); 7.52 (s, 1H); 7.45 (d, J=8.6 Hz, 1H); 7.36 (d, J=8.6 Hz, 2H); 6.96-6.88 (m, 3H); 6.75-6.69 (m, 2H); 5.10 (s, 2H); 4.44 (m, 1H); 4.28 (dd, J=4.0, 9.5 Hz, 1H); 4.11 (dd, J=5.3, 9.5 Hz, 1H); 3.80 (s, 3H); 3.77-3.43 (m, 6H); 3.22 (s, 2H); 2.38 (m, 2H); 2.20 (m, 2H). APCI-MS: m/z 588 (MH$^+$).

Step III (3S)-1-{2-({(2S)-2-Hydroxy-3-[5-(trifluoromethyl)-1'H,3H-spiro[1-benzofuran-2,4'-piperidin]-1'-yl]propyl}oxy}-4-[(4-methoxybenzyl)oxy]benzoyl}pyrrolidin-3-01

A mixture of 2-({(2S)-2-hydroxy-3-[5-(trifluoromethyl)-1'H,3H-spiro(1-benzofuran-2,4'-piperidin]-1'-yl] propyl}oxy)-4-[(4-methoxybenzyl)oxy]benzoicacid(hydrochloride) (150 mg, 0.24 mmol) and N,N-carbonyldiimidazole (47 mg, 0.288 mmol) in DMF (3 mL) was stirred at room temperature for 50 min. Then (3S)-pyrrolidin-3-ol (104.5 mg, 1.2 mmol) in DMF (1 mL) was added and the reaction mixture was stirred at room temperature overnight. The reaction mixture was partitioned between ethyl acetate and H$_2$O. The organic layer was dried over Na$_2$SO$_4$, filtered and concentrated. The residue was purified by silica gel flash chromatography (0-2.5% methanol in dichloromethane, 0.2% NH$_4$OH) to give the subtitled compound (80 mg).

APCI-MS: m/z 657 (MH$^+$).

Step IV

3S)-1-[4-Hydroxy-2-({(2S)-2-hydroxy-3-[5-(trifluoromethyl)-1'H,3H-spiro[1-benzofuran-2,4'-piperidin]-1'-yl]propyl}oxy)benzoyl]pyrrolidin-3-ol (3S)-1-{2-({(2S)-2-Hydroxy-3-[5-(trifluoromethyl)-1'H,3H-spiro[1-benzofuran-2,4'-piperidin]-1'-yl]propyl}oxy)-4-[(4-methoxybenzyl)oxy]benzoyl}pyrrolidin-3-ol (75 mg, 0.114 mmol) was treated with 10% CF$_3$CO$_2$H in CH$_2$Cl$_2$ (3 mL) for 20 min at room temperature. The volatiles were removed in vacuo and the residue was purified by silica gel flash chromatography (0-3% methanol in dichloromethane, 0.2% NH$_4$OH) to give the titled compound (26 mg).

$^1$H-NMR (CD$_3$OD, 400 MHz): δ 7.45 (s, 1H); 7.39 (d, J=8.5 Hz, 1H); 7.09 (dd, J=2.4, 8.2 Hz, 1H); 6.82 (d, J=8.4 Hz, 1H); 6.50 (m, 1H); 6.45 (m, 1H); 4.48 (m, 0.5H); 4.36 (m, 0.5H); 4.1-54.01 (m, 2H); 3.97 (dd, J=5.6, 9.7 Hz, 1H); 3.72-3.50 (m, 3H); 3.38-3.23 (m, 1H); 3.06 (s, 2H); 2.79-2.52 (m, 6H); 2.12-1.80 (m, 6H). APCI-MS: m/z 537 (MH$^+$).

Example 70

(3S)-1-(4-Fluoro-2-{[(2S)-2-hydroxy-3-(1'H,3H-spiro[1-benzofuran-2,4'-piperidin]-1'-yl)propyl]oxy)benzoyl)pyrrolidin-3-ol Step I Methyl-4-fluoro-2-{[(2S)-2-hydroxy-3-(1'H,3H-spiro[1-benzofuran-2,4'-piperidin]-1'-yl)propyl]oxy}benzoate A mixture of 3H-spiro[1-benzofuran-2,4'-piperidine] (55 mg, 0.29 mmol) and methyl 4-fluoro-2[(2S)-oxiran-2-ylmethoxy]benzoate (66 mg, 0.29 mmol) in ethanol (1.5 mL) was stirred at 78° C. overnight. The volatiles were removed in vacuo and the residue was purified by silica gel flash chromatography (0-1% methanol in dichloromethane) to give the subtitled compound (50 mg).

APCI-MS: m/z 416 (MH$^+$).

Step II

4-Fluoro-2-{[(2S)-2-hydroxy-3-(1'H,3H-spiro[1-benzofuran-2,4'-piperidin]-1'-yl)propyl]oxy}benzoic acid (hydrochloride)

Methyl4-fluoro-2-{[(2S)-2-hydroxy-3-(1'H,3H-spiro[1-benzofuran-2,4'-piperidin]-1'-yl)propyl]oxy}benzoate (50 mg, 0.12 mmol) was dissolved in THF (1.5 mL). Aqueous KOH (20 mg KOH in 0.5 mL H$_2$O) was added and the reaction mixture was stirred at room temperature for 24 h, cooled to 0° C. and pH was adjusted to 2 by addition of aqueous HCl, extracted with ethyl acetate. The organic layer was washed with H$_2$O, dried over Na$_2$SO$_4$, filtered and concentrated to give the subtitled compound (37 mg).

$^1$H-NMR (CD$_3$OD, 400 MHz): δ 7.96 (dd, J=6.9, 8.8 Hz, 1H); 7.20 (d, J=7.2 Hz, 1H); 7.12 (t, J=7.5 Hz, 1H); 6.97 (dd, J=2.4, 11.0 Hz, 1H); 6.88-6.78 (m, 2H); 6.76 (d, J=8.0 Hz, 1H); 4.43 (m, 1H); 4.27 (dd, J=4.1, 9.5 Hz, 1H); 4.13 (dd, J=5.3, 9.5 Hz, 1H); 3.79-3.42 (m, 6H); 3.14 (s, 2H); 2.30 (m, 2H); 2.16 (m, 2H). APCI-MS: m/z 402 (MH$^+$).

Step III (3S)-1-(4-Fluoro-2-{[(2S)-2-hydroxy-3-(1'H,3H-spiro[1-benzofuran-2,4'-piperidin]-1'-yl)propyl]oxy}benzoyl)pyrrolidin-3-ol A mixture of 4-fluoro-2-{[(2S)-2-hydroxy-3-(1'H,3H-spiro[1-benzofuran-2,4'-piperidin]-1'-yl)propyl]oxy}benzoic acid (hydrochloride) (35 mg, 0.079 mmol) and N,N-carbonyldiimidazole (15.4 mg, 0.095 mmol) in DMF (1.5 mL) was stirred at room temperature for 45 min, (3S)-pyrrolidin-3-ol (34.4 mg, 0.395 mmol) in DMF (0.5 mL) was added and the reaction mixture was stirred at room temperature overnight. The reaction mixture was partitioned between ethyl acetate and H$_2$O. The organic layer was dried over Na$_2$SO$_4$, filtered and concentrated. The residue was purified by silica gel flash chromatography (0-2.5% methanol in dichloromethane, 0.2% NH$_4$OH) to give the titled compound (15 mg).

$^1$H-NMR (CD$_3$OD, 400 MHz): δ 7.32-7.26 (m, 1H); 7.13 (d, J=7.3 Hz, 1H); 7.05 (t, J=7.6 Hz, 1H); 6.94 (dt, J=2.2 Hz, 1H); 6.82-6.75 (m, 2H); 6.67 (d, J=7.9 Hz, 1H); 4.48 (m, 0.5H); 4.38 (m, 0.5H); 4.18-3.98 (m, 3H); 3.70 (dd, J=5.3, 9.3 Hz, 1H); 3.66-3.46 (m, 2H); 3.37-3.18 (m, 1H); 3.00 (s, 2H); 2.78-2.51 (m, 6H); 2.15-1.78 (m, 6H). APCI-MS: m/z 471 (MH$^+$).

Example 71

4-Fluoro-2-{[(2S)-3-(5-fluoro-1'H,3H-spiro[1-benzofuran-2,4'-piperidin]-1'-yl)-2-hydroxypropyl]oxy)benzoic acid (hydrochloride)

Step I

Methyl-4-fluoro-2-{[(2S)-3-(5-fluoro-1'H,3H-spiro[1-benzofuran-2,4'-piperidin]-1'-yl)-2-hydroxypropyl]oxy}benzoate A mixture of 5-fluoro-3H-spiro[1-benzofuran-2,4'-piperidine](50 mg, 0.241 mmol) and methyl 4-fluoro-2-[(2S)-oxiran-2-ylmethoxy]benzoate (54.5 mg, 0.241 mmol) in ethanol (1.5 mL) was stirred at 77° C. overnight. The volatiles were removed in vacuo and the residue was purified by silica gel flash chromatography (0-2.5% methanol in dichloromethane) to give the subtitled compound (80 mg).

APCI-MS: m/z 434 (MH$^+$).

Step II

4-Fluoro-2-{[(2S)-3-(5-fluoro-1'H,3H-spiro[1-benzofuran-2,4'-piperidin]-1'-yl)-2-hydroxypropyl]oxy}benzoic acid (hydrochloride)

To a solution of methyl-4-fluoro-2-{[(2S)-3-(5-fluoro-1'H,3H-spiro[1-benzofuran-2,4'-piperidin]-1'-yl)-2-hydroxypropyl]oxy}benzoate (80 mg, 0.184 mmol) in THF (1.5 mL) was added aqueous KOH solution (31 mg KOH in 0.5 mL of H$_2$O) and the reaction mixture was stirred at room temperature for 24 h, cooled to 0° C. and pH was adjusted to 2 by addition of aqueous HCl, extracted with ethyl acetate. The organic layer was washed with H$_2$O, dried over Na$_2$SO$_4$, filtered and concentrated to give the titled compound (60 mg).

$^1$H-NMR (CD$_3$OD, 400 MHz): δ 7.97 (dd, J=6.9, 8.7 Hz, 1H); 6.97 (m, 2H); 6.88-6.79 (m, 2H); 6.72 (dd, J=4.2, 8.8 Hz, 1H); 4.45 (m, 1H); 4.27 (dd, J=4.1, 9.6 Hz, 1H); 4.13 (dd, J=5.3, 9.6 Hz, 1H); 3.78-3.42 (m, 6H); 3.14 (s, 2H); 2.30 (m, 2H); 2.16 (m, 2H). APCI-MS: m/z 420 (MH$^+$).

Example 72

(3S)-1-(4-Fluoro-2-{[(2S)-3-(5-fluoro-1'H,3H-spiro[1-benzofuran-2,4'-piperidin]-1'-yl)-2-hydroxypropyl]oxy}benzoyl)pyrrolidin-3-ol A mixture of 4-fluoro-2-{[(2S)-3-(5-fluoro-1'H,3H-spiro[1-benzofuran-2,4'-piperidin]-1'-yl)-2-hydroxypropyl]oxy}benzoic acid (hydrochloride) (50 mg, 0.109 mmol) and N,N-carbonyldiimidazole (21.2 mg, 0.131 mmol) in DMF (1.5 mL) was stirred at room temperature for 1 h, (3S)-pyrrolidin-3-ol (47.5 mg, 0.545 mmol) in DMF (0.5 mL) was added and the reaction mixture was stirred at room temperature overnight. The reaction mixture was partitioned between ethyl acetate and H$_2$O. The organic layer was dried over Na$_2$SO$_4$, filtered and concentrated. The residue was purified by silica gel flash chromatography (0-2.5% methanol in dichloromethane, 0.2% NH$_4$OH) to give the titled compound (21 mg).

$^1$H-NMR (CD$_3$OD, 400 MHz): δ 7.29 (m, 1H); 6.97-6.87 (m, 2H); 6.82-6.74 (m, 2H); 6.93 (dd, J=4.1, 8.7 Hz, 1H); 4.48 (m, 0.5H); 4.37 (m, 0.5H); 4.16-3.98 (m, 3H); 3.70 (dd, J=5.3, 9.4 Hz, 1H); 3.67-3.47 (m, 2H); 3.36-3.18 (m, 1H); 3.05 (s, 2H); 2.78-2.52 (m, 6H); 2.16-1.78 (m, 6H). APCI-MS: m/z 489 (MH$^+$).

Example 73

N-[(3S)-1-(2-{[(2S)-3-(5-Chloro-1'H,3H-spiro[1-benzofuran-2,4'-piperidin]-1'-yl)-2-hydroxypropyl]oxy}-4-hydroxybenzoyl)pyrrolidin-3-yl]acetamide Step I N-((3S)-1-{1[(2S)-3-(5-chloro-1'H,3H-spiro[1-benzofuran-2,4'-piperidin]-1'-yl)-2-hydroxypropyl]oxy}-4-[(4-methoxybenzyl)oxy]benzoyl}pyrrolidin-3-yl)acetamide A mixture of 2-{[(2S)-3-(5-chloro-1'H,3H-spiro[1-benzofuran-2,4'-piperidin]-1'-yl)-2-hydroxypropyl]oxy}-4-[(4-methoxybenzyl]benzoic acid (hydrochloride) (150 mg, 0.254 mmol) and N,N-carbonyldiimidazole (50 mg, 0.308 mmol) in DMF (2 mL) was stirred at room temperature for 50 min. Then, N-[(3S)-pyrrolidin-3-yl]acetamide (110 mg, 1.26 mmol) in DMF (0.5 mL) was added and the reaction mixture was stirred at room temperature overnight. The reaction mixture was partitioned between ethyl acetate and water. The organic layer was dried over $Na_2SO_4$, filtered and concentrated. The residue was purified by silica gel flash chromatography (0-2% methanol in dichloromethane) to give the subtitled compound (100 mg).
APCI-MS: m/z 664 ($MH^+$).

Step II

N-[(3S)-1-(2-{[(2S)-3-(5-Chloro-1'H,3H-spiro[1-benzofuran-2,4'-piperidin]-1'-yl)-2-hydroxypropyl]oxy}-4-hydroxybenzoyl)pyrrolidin-3-yl]acetamide N-((3S)-1-{[(2S)-3-(5-Chloro-1'H,3H-spiro[1-benzofuran-2,4'-piperidin]-1'-yl)-2-hydroxypropyl]oxy}-4-[(4-methoxybenzyl)oxy]benzoyl}pyrrolidin-3-yl)acetamide (100 mg, 0.15 mmol) was treated with 10% $CF_3CO_2H$ in $CH_2Cl_2$ (3 mL) for 25 min at room temperature. The volatiles were removed in vacuo and the residue was purified by silica gel flash chromatography (0-4% methanol in dichloromethane, 0.2% $NH_4OH$) to give the titled compound (22 mg).
$^1$H-NMR ($CD_3OD$, 400 MHz): δ 7.13 (m, 1H); 7.09 (dd, J=3.7, 8.2 Hz, 1H); 7.04 (dd, J=1.7, 8.5 Hz, 1H); 6.65 (d, J=8.5 Hz, 1H); 6.50 (t, J=2.0 Hz, 1H); 6.45 (dt, J=2.2 Hz, 1H); 4.44 (m, 0.5H); 4.26 (m, 0.5H); 4.16-3.77 (m, 3H); 3.74-3.58 (m, 2H); 3.52-3.14 (m, 2H); 3.00 (s, 2H); 2.77-2.52 (m, 6H); 2.28-2.10 (m, 1H); 1.98-1.78 (m, 8H). APCI-MS: m/z 545 ($MH^+$).

Example 74

2-{[(2S)-3-(5-Chloro-1'H,3H-spiro[1-benzofuran-2,4'-piperidin]-1'-yl)-2-hydroxypropyl]oxy}-4-methylbenzoic acid (hydrochloride)

Step I

Methyl 4-methyl-2-[(2S)-oxiran-2-ylmethoxy]benzoate

A mixture of (2S)-oxiran-2-ylmethyl 3-nitrobenzenesulfonate (777.7 mg, 3.0 mmol), methyl 2-hydroxy-4-methylbenzoate ((498.5 mg, 3.0 mmol) and $Cs_2CO_3$ (1.17 g, 3.6 mmol) in DMF (10 mL) was stirred at room temperature overnight. The reaction mixture was partitioned between ethyl acetate and $H_2O$. The organic layer was dried over $Na_2SO_4$, filtered and concentrated. The residue was purified by silica gel flash chromatography (0-20% ethyl acetate in petroleum spirit) to give the subtitled compound (500 mg).
$^1$H-NMR ($CDCl_3$, 400 MHz): δ 7.75 (d, J=7.9 Hz, 1H); 6.84 (d, J=7.9 Hz, 1H); 6.81 (s, 1H); 4.33 (dd, J=3.0, 11.2 Hz, 1H); 4.12 (dd, J=4.8, 11.2 Hz, 1H); 3.89 (s, 3H); 3.42 (m, 1H); 2.94 (m, 2H); 2.38 (s, 3H). APCI-MS: m/z 223 ($MH^+$).

Step II

Methyl 2-{[(2S)-3-(5-chloro-1'H,3H-spiro[1-benzofuran-2,4'-piperidin]-1'-yl)-2-hydroxypropyl]oxy}-4-methylbenzoate A mixture of 5-chloro-3H-spiro[1-benzofuran-2,4'-piperidin] (223.7 mg, 1.0 mmol) and methyl 4-methyl-2-[(2S)-oxiran-2-ylmethoxy]benzoate (222.24 mg, 1.0 mmol) in ethanol (2 mL) was stirred at 80° C. for 5 h. The volatiles were removed in vacuo and the residue was purified by silica gel flash chromatography (0-2% methanol in dichloromethane) to give the subtitled compound (410 mg).
$^1$H-NMR ($CDCl_3$, 400 MHz): δ 7.76 (d, J=8.4 Hz, 1H); 7.13 (s, 1H); 7.08 (dd, J=2.2, 8.5 Hz, 1H); 6.85 (m, 2H); 6.68 (d, J=8.4 Hz, 1H); 4.24 (m, 1H); 4.19 (dd, J=4.3, 9.2 Hz, 1H); 4.08 (dd, J=6.0, 9.1 Hz, 1H); 3.90 (s, 3H); 3.02 (s, 2H); 2.94-2.67 (m, 6H); 2.40 (s, 3H); 2.06-1.86 (m, 4H). APCI-MS: m/z 448 ($MH^+$).

Step III

2-{[(2S)-3-(5-Chloro-1'H,3H-spiro[1-benzofuran-2,4'-piperidin]-1'-yl)-2-hydroxypropyl]oxy}-4-methylbenzoic acid (hydrochloride)

Methyl 2-{[(2S)-3-(5-chloro-1'H,3H-spiro[1-benzofuran-2,4'-piperidin]-1'-yl)-2-hydroxypropyl]oxy}-4-methylbenzoate (400 mg, 0.89 mmol) was taken in ethanol, aqueous KOH (2.6 g KOH in 2.6 mL $H_2O$) solution was added and the reaction mixture was stirred at reflux temperature for 5 h, cooled to 0° C. and the pH was made to 2 by addition of aqueous HCl, extracted with ethyl acetate. The organic layer was washed with $H_2O$, dried over $Na_2SO_4$, filtered and concentrated to give the titled compound (330 mg).
$^1$H-NMR ($CD_3OD$, 400 MHz): δ 7.82 (d, J=7.9 Hz, 1H); 7.20 (s, 1H); 7.10 (dd, J=2.2, 8.5 Hz, 1H); 6.98 (s, 1H); 6.90 (d, J=8.1 Hz, 1H); 6.74 (d, J=8.5 Hz, 1H); 4.44 (m, 1H); 4.29 (dd, J=4.0, 9.5 Hz, 1H); 4.12 (dd, J=5.4, 9.6 Hz, 1H); 3.78-3.42 (m, 6H); 3.14 (s, 2H); 2.40 (s, 3H); 2.30 (m, 2H); 2.16 (m, 2H). APCI-MS: m/z 432 ($MH^+$).

Example 75

(3S)-1-(2-{[(2S)-3-(5-Chloro-1'H,3H-spiro[1-benzofuran-2,4'-piperidin]-1'-yl)-2-hydroxypropyl]oxy]}-4-methylbenzoyl)pyrrolidin-3-ol A mixture of 2-{[(2S)-3-(5-chloro-1'H,3H-spiro[1-benzofuran-2,4'-piperidin]-1'-yl)-2-hydroxypropyl]oxy}-4-methylbenzoic acid (hydrochloride) (150 mg, 0.32 mmol) and N,N-carbonyldiimidazole (65 mg, 0.4 mmol) in DMF (2.5 mL) was stirred at room temperature for 45 min. Then (3S)-pyrrolidin-3-ol (139.4 mg, 1.6 mmol in DMF (0.5 mL) was added and the reaction mixture was stirred at room temperature overnight. The reaction mixture was partitioned between ethyl acetate and $H_2O$. The organic layer was dried over $Na_2SO_4$, filtered and concentrated. The residue was purified by silica gel flash chromatography (0-2.5% methanol in dichloromethane, 0.2% $NH_4OH$) to give the titled compound (90 mg).
$^1$H-NMR ($CD_3OD$, 400 MHz): δ 7.13 (m, 2H); 7.04 (dd, J=2.1, 8.5 Hz, 1H); 6.92 (s, 1H); 6.85 (d, J=7.6 Hz, 1H); 6.60 (d, J=8.5 Hz, 1H); 4.47 (m, 0.5H); 4.35 (m, 0.5H); 4.17-3.96 (m, 3H); 3.74-3.44 (m, 3H); 3.37-3.18 (m, 1H); 3.00 (s, 2H); 2.77-2.50 (m, 6H); 2.36 (s, 3H); 2.14-1.78 (m, 6H). APCI-MS: m/z 501 ($MH^+$).

Example 76

2-{[(2S)-3-(5-Fluoro-1'H,3H-spiro[1-benzofuran-2,4'-piperidin]-1'-yl)-2-hydroxypropyl]oxy}-4-methylbenzoic acid (hydrochloride)

Step I

Methyl2-{[(2S)-3-(5-fluoro-1'H,3H-spiro 1-benzofuran-2,4'-piperidin]-1'-yl)-2-hydroxypropyl]oxy}-4-methylbenzoate A mixture of 5-fluoro-3H-spiro[1-benzofuran-2,4'-piperidin] (85 mg, 0.41 mmol) and methyl-4-methyl-2-[(2S)-oxiran-2-ylmethoxy]benzoate-(91 mg, 0.41 mmol) in ethanol (2 mL) was stirred at 85° C. for 4.5 h. The volatiles were removed in vacuo and the residue was purified by silica gel flash chromatography (0-2.5% methanol in dichloromethane) to give the subtitled compound (136 mg).
APCI-MS: m/z 430 (MH$^+$).

Step II

2-{[(2S)-3-(5-Fluoro-1'H,3H-spiro[1-benzofuran-2,4'-piperidin]-1'-yl)-2-hydroxypropyl]oxy}-4-methylbenzoic acid (hydrochloride)

Methyl2-{[(2S)-3-(5-fluoro-1'H,3H-spiro[1-benzofuran-2,4'-piperidin]-1'-yl)-2-hydroxypropyl]oxy}-4-methylbenzoate (133 mg, 0.309 mmol) was taken in ethanol (2.5 mL), aqueous KOH (902 mg KOH in 1 mL $H_2O$) was added. The reaction mixture was srirred at reflux temperature for 5 h, cooled to 0° C. and the pH was adjusted to 2 by addition of aqueous HCl, extracted with ethyl acetate. The organic layer was washed with $H_2O$, dried over $Na_2SO_4$, filtered and concentrated to give the titled compound (50 mg).
$^1$H-NMR (CD$_3$OD, 400 MHz): δ 7.74 (d, J=7.9 Hz, 1H); 6.96 (m, 2H); 6.89 (d, J=8.0 Hz, 1H); 6.84 (m, 1H); 6.71 (dd, J=4.1, 8.7 Hz, 1H); 4.43 (m, 1H); 4.28 (dd, J=4.0, 9.4 Hz, 1H); 4.11 (dd, J=5.6, 9.5 Hz, 1H); 3.75-3.40 (m, 6H); 3.14 (s, 2H); 2.39 (s, 3H); 2.32 (m, 2H); 2.14 (m, 2H). APCI-MS: m/z 416 (MH$^+$).

Example 77

(2S)-1-(5-Chloro-1'H,3H-spiro[1-benzofuran-2,4'-piperidin]-1'-yl)-3-(2-{[2-(hydroxymethyl)morpholin-4-yl]carbonyl}-5-methylphenoxy)propan-2-ol Step I 4-(tert-Butyl)-2-methyl 2,4-morpholinedicarboxylate Methyl iodide (9.38 mL, 150 mmol) was added to a suspension of 4(tert-butoxycarbonyl)-2-morpholinecarboxylic acid (14.5 g, 62.6 mmol) and dry K$_2$CO$_3$ (17.3 g, 125 mmol) in dry DMF (360 mL). The mixture was stirred overnight at room temperature, filtered through celite and concentrated. The residue was partitioned between CH$_2$Cl$_2$ and H$_2$O. The organic layer was dried over Na$_2$SO$_4$ filtered and concentrated to give the subtitled compound (22 g).
$^1$H-NMR (CDCl$_3$, 400 MHz): δ 4.07 (dd, 2H); 3.99 (m, 1H); 3.77 (s, 3H); 3.73 (m, 1H); 3.55 (m, 1H); 3.07 (m, 2H); 1.45 (s, 9H).

Step II

Tert-Butyl 2-(hydroxymethyl)-4-morpholinecarboxylate
4-(tert-Butyl)-2-methyl 2,4-morpholinedicarboxylate (62.6 mmol) was dissolved in dry THF (100 mL) and added drop wise at 0° C. to a suspension of lithium borohydride (2.5 g, 115 mmol) in dry THF (100 mL). After addition was completed the reaction mixture was stirred at room temperature overnight. Water (10 mL) was added and stirred at room temperature for 1 h. The volatiles were removed in vacuo and the residue was partitioned between ethyl acetate and H$_2$O. The organic layer was washed successively with 0.5M aqueous HCl, saturated aqueous NaHCO$_3$ and H$_2$O. The organic layer was dried over Na$_2$SO$_4$, filtered and concentrated to give the subtitled compound (13.3 g).
$^1$H-NMR (CDCl$_3$, 400 MHz): δ 3.88 (m, 3H); 3.46-3.42 (m, 4H); 2.93 (m, 1H); 2.75 (m, 1H); 2.09 (m, 1H); 1.46 (s, 9H).

Step III

Morpholin-2-ylmethyl trifluoroacetate (trifluoroacetic acid salt)

Tert-Butyl 2-(hydroxymethyl)-4-morpholinecarboxylate (5.13 g, 23.61 mmol) was treated with CF$_3$CO$_2$H (20 mL) in CH$_2$Cl$_2$ (50 mL) at room temperature for 3 h. The volatiles were removed in vacuo to give the subtitled compound (7.6 g).
$^1$H-NMR (DMSO-d$_6$, 400 MHz): δ 9.25 (br.s, 2H); 3.86 (dd, J=3.3, 12.6 Hz, 1H); 3.62 (m, 2H); 3.39 (m, 2H); 3.19 (m, 2H); 2.96 (t, J=11.2 Hz, 1H); 2.76 (t, J=11.2 Hz, 1H).

Step IV

2S)-1-(5-Chloro-1'H,3H-spiro[1-benzofuran-2,4'-piperidin]-1'-yl)-3-(2-{[2-(hydroxymethyl)morpholin-4-yl]carbonyl)-5-methylphenoxy)propan-2-ol A mixture of 2-{[(2S)-3-(5-chloro-1'H,3H-spiro[1-benzofuran-2,4'-piperidin]-1'yl)-2-hydroxypropyl]oxy}-4-methylbenzoic acid(hydrochloride) (100 mg, 0.213 mmol) and N,N-carbonyldiimidazole (41.5 mg, 0.255 mmol) in DMF (2.5 mL) was stirred at room temperature for 50 min, morpholin-2-ylmethyl trifluoroacetate(trifluoroacetic acid salt) (347 mg, 1.06 mmol) in DMF (1 mL) was added followed by Et$_3$N (0.3 mL) and the reaction mixture was stirred at room temperature for 5 h. The reaction mixture was partitioned between ethyl acetate and H$_2$O. The organic layer was dried over Na$_2$SO$_4$, filtered and concentrated. The residue was purified by silica gel flash chromatography (0-2.5% methanol in dichloromethane, 0.2% NH$_4$OH) to give the titled compound (58 mg).
APCI-MS: m/z 531 (MH$^+$).

Example 78

(3S)-1-(2-{[(2S)-3-(5-Fluoro-1'H,3H-spiro[1-benzofuran-2,4'-piperidin]-1'-yl)-2-hydroxypropyl]oxy}-4-methylbenzoyl)pyrrolidin-3-ol A mixture of 2-{[(2S)-3-(5-fluoro-1'H,3H-spiro[1-benzofuran-2,4'-piperidin]-1'-yl)-2-hydroxypropyl]oxy}-4-methylbenzoic acid (hydrochloride) (45 mg, 0.099 mmol) and N,N-carbonyldiimidazole (20 mg, 0.123 mmol) in DMF (2 mL) was stirred at room temperature for 50 min, (3S)-pyrrolidin-3-ol (43 mg, 0.495 mmol) in DMF (1 mL) was added and the reaction mixture was stirred at room temperature overnight. The reaction mixture was partitioned between ethyl acetate and H$_2$O. The organic layer was dried over Na$_2$SO$_4$, filtered and concentrated. The residue was purified by silica gel flash chromatography (0-2.5% methanol in dichloromethane, 0.2% NH$_4$OH) to give the titled compound (35 mg).
$^1$H-NMR (CD$_3$OD, 400 MHz): δ 7.14 (dd, J=1.0, 7.6 Hz, 1H); 6.94-6.84 (m, 3H); 6.77 (m, 1H); 6.62 (dd, J=4.2, 8.8 Hz, 1H); 4.48 (m, 0.5H); 4.35 (m, 0.5H); 4.16-3.96 (m, 3H);

3.73-3.43 (m, 3H); 3.38-3.18 (m, 1H); 3.00 (s, 2H); 2.76-2.52 (m, 6H); 2.35 (s, 3H); 2.12-1.77 (m, 6H). APCI-MS: m/z 485 (MH$^+$).

Example 79

2-{[(2S)-3-(5-Chloro-1'H,3H-spiro[1-benzofuran-2,4'-piperidin]-1'-yl)-2-hydroxypropyl]oxy}-N-{[(4R)-2,5-dioxoimidazolidin-4-yl]methyl}-4-hydroxybenzamide Step I 2-{[(2S)-3-(5-Chloro-1'H,3H-spiro[1-benzofuran-2,4'-piperidin]-1'-yl)-2-hydroxypropyl]oxy}-N-{[(4R)-2,5-dioxoimidazolidin-4-yl]methyl}4-[(4-methoxybenzyl)oxy]benzamide A mixture of 2-{[(2S)-3-(5-chloro-1'H,3H-spiro[1-benzofuran-2,4'-piperidin]-1'-yl)-2-hydroxypropyl]oxy}-4-[(4-methoxybenzyl]benzoic acid (hydrochloride) (125 mg, 0.211 mmol) and N,N-carbonyldiimidazole (43 mg, 0.264 mmol) in DMF (3 mL) was stirred at room temperature for 40 min. Then, (5R)-5-(aminomethyl)imidazolidine-2,4-dione (hydrochloride) (150 mg, 0.906 mmol) was added followed by Et$_3$N (0.54 mL (3.62 mmol) and the reaction mixture was stirred at room temperature overnight. The reaction mixture was partitioned between ethyl acetate and water. The organic layer was dried over Na$_2$SO$_4$, filtered and concentrated. The residue was purified by silica gel flash chromatography (0-2.5% methanol in dichloromethane, 0.2% NH$_4$OH) to give the subtitled compound (30 mg).
APCI-MS: m/z 665 (MH$^+$).

Step II

2-{[(2S)-3-(5-Chloro-1'H,3H-spiro[1-benzofuran-2,4'-piperidin]-1'-yl)-2-hydroxypropyl]oxy}-N-{[(4R)-2,5-dioxoimidazolidin-4-yl]methyl}-4-hydroxybenzamide 2-{[(2S)-3-(5-Chloro-1'H,3H-spiro[1-benzofuran-2,4'-piperidin]-1'-yl)-2-hydroxypropyl]oxy}-N-{[(4R)-2,5-dioxoimidazolidin-4-yl]methyl}-4-[(4-methoxybenzyl)oxy]benzamide (28 mg, 0.042 mmol) was treated with 10% CF$_3$CO$_2$H in CH$_2$Cl$_2$ (3 mL) at room temperature for 25 min. The volatiles were removed in vacuo and the residue was purified by silica gel flash chromatography (0-5% methanol in dichloromethane, 0.2% NH$_4$OH) to give the titled compound (9 mg).
$^1$H-NMR (CD$_3$OD, 400 MHz): δ 7.83 (d, J=8.6 Hz, 1H); 7.14 (s, 1H); 7.04 (dd, J=1.9, 8.3 Hz, 1H); 6.65 (d, J=8.5 Hz, 1H); 6.53 (s, 1H); 6.48 (m, 1H); 4.37-4.17 (m, 3H); 4.07 (m, 1H); 3.90-3.64 (m, 2H); 3.03 (s, 2H); 2.85-2.59 (m, 6H); 2.02-1.82 (m, 4H). APCI-MS: m/z 545 (MH$^+$).

Example 80

1-(2-{[(2S)-3-(5-Chloro-1'H,3H-spiro[1-benzofuran-2,4'-piperidin]-1'-yl)-2-hydroxypropyl]oxy}-4-hydroxybenzoyl)-3-(trifluoromethyl)pyrrolidin-3-ol Step I tert-Butyl 3-hydroxy-3-(trifluoromethyl)pyrrolidine-1-carboxylate tert-Butyl 3-oxopyrrolidine-1-carboxylate (926 mg, 5.0 mmol) was dissolved in THF (10 mL) and the solution was cooled to 0° C., trimethyl(trifluoromethyl)silane (0.872 mL) and tetrabutylammonium fluoride (TBAF) (176 mg, 0.557 mmol) were added. The ice-bath was removed and the reaction mixture was stirred at room temperature overnight. Saturated aqueous NH$_4$Cl solution (8 mL) was added and stirring was continued. After 15 min TBAF (2.36 g TBAF in 7.5 mL THF) was added and the reaction mixture was stirred at room temperature for 1 h. The reaction mixture was extracted with ethyl acetate, washed with H$_2$O, dried over Na$_2$SO$_4$, filtered and concentrated. The residue was purified by silica gel flash chromatography (0-40% ethyl acetate in petroleum spirit) to give the subtitled compound (800 mg).
$^1$H-NMR (CDCl$_3$, 400 MHz): δ 3.78-3.38 (m, 4H); 2.25 (m, 1H); 2.00 (m, 1H); 1.40 (s, 9H).

Step II 3-(Trifluoromethyl)pyrrolidin-3-ol (trifluoroacetate)

tert-Butyl 3-hydroxy-3-(trifluoromethyl)pyrrolidine-1-carboxylate (310 mg, 1.21 mmol) was treated with 20% CF$_3$CO$_2$H in CH$_2$Cl$_2$ for 4 h at room temperature. The volatiles were removed in vacuo to give the subtitled compound (330 mg).
$^1$H-NMR (CD$_3$OD, 400 MHz): δ 3.72-3.59 (m, 4H); 2.38 (m, 1H); 2.22 (m, 1H). APCI-MS: m/Z 156 (MH$^+$).

Step III

1-{2-{[(2S)-3-(5-Chloro-1'H,3H-spiro[1-benzofuran-2,4'-piperidin]-1'-yl)-2-hydroxypropyl]oxy}-4-[(4-methoxybenzyl)oxy]benzoyl}-3-(trifluoromethyl)pyrrolidin-3-ol A mixture of 2-{[(2S)-3-(5-chloro-1'H,3H-spiro[1-benzofuran-2,4'-piperidin]-1'-yl)-2-hydroxypropyl]oxy}-4-[(4-methoxybenzyl]benzoic acid (hydrochloride) (150 mg, 0.254 mmol) and N,N-carbonyldiimidazole (51.5 mg, 0.317 mmol) in DMF (3 mL) was stirred at room temperature for 40 min. Then (3-(trifluoromethyl)pyrrolidin-3-ol (trifluoroacetate) (326 mg, 1.21 mmol) was added followed by Et$_3$N (0.337 mL 2.42 mmol) and the reaction mixture was stirred at room temperature for 20 h. The reaction mixture was partitioned between ethyl acetate and water. The organic layer was dried over Na$_2$SO$_4$, filtered and concentrated. The residue was purified by silica gel flash chromatography (0-2.0% methanol in dichloromethane, 0.2% NH$_4$OH) to give the subtitled compound (83 mg).
APCI-MS: m/z 691 (MH$^+$).

Step IV 1-(2-{[(2S)-3-(5-Chloro-1'H,3H-spiro[1-benzofuran-2,4'-piperidin]-1'-yl)-2-hydroxypropyl]oxy}-4-hydroxybenzoyl)-3-(trifluoromethyl)pyrrolidin-3-ol 1-(2-{[(2S)-3-(5-Chloro-1'H,3H-spiro[1-benzofuran-2,4'-piperidin]-1'-yl)-2-hydroxypropyl]oxy}-4-[(4-methoxybenzyl)oxy]benzoyl}-3-(trifluoromethyl)pyrrolidin-3-ol (83 mg, 0.12 mmol) was treated with 10% CF$_3$CO$_2$H in CH$_2$Cl$_2$ (3 mL) for 25 min at room temperature. The volatiles were removed in vacuo and the residue was purified by silica gel flash chromatography (0-3% methanol in dichloromethane, 0.2% NH$_4$OH) to give the titled compound (15 mg).
$^1$H-NMR (CD$_3$OD, 400 MHz): δ 7.16-7.09 (m, 2H); 7.05 (m, 1H); 6.66 (d, J=8.5 Hz, 1H); 6.50 (s, 1H); 6.46 (d, J=8.3 Hz, 1H); 4.12 (m, 1H); 4.00 (m, 2H); 3.89-3.40 (m, 4H); 3.02 (s, 2H); 2.87-2.60 (m, 6H); 2.35-1.80 (m, 6H). APCI-MS: m/z 571 (MH$^+$).

Example 81

3-{[(2S)-3-(5-Chloro-1'H,3H-spiro[1-benzofuran-2, 4'-piperidin]-1'-yl)-2-hydroxypropyl]oxy}-4-{[3-(trifluoromethyl)pyrrolidin-1-yl]carbonyl}phenol Step I tert-Butyl 3-(trifluoromethyl)pyrrolidine-1-carboxylate To a solution of tert-butyl3-hydroxy-3-(trifluoromethyl) pyrrolidine-1-carboxylate (468 mg, 1.83 mmol) in pyridine (10 mL) was added $SOCl_2$ (1.71 mL) and the reaction mixture was stirred at reflux temperature under nitrogen for 25 min, cooled to room temperature, $H_2O$ (20 mL) was added, extracted with ethyl acetate. The combined organic layer was washed with dilute aqueous HCl, saturated aqueous $NaHCO_3$ and $H_2O$ successively. The organic layer was dried over $Na_2SO_4$, filtered and concentrated. The residue was dissolved in ethanol (10 mL), Pd/C (10%) (300 mg) was added and it was hydrogenated at room temperature over the weekend. The catalyst was removed by filtration. The filtrate was concentrated in vacuo to give the subtitled compound (100 mg).

APCI-MS: m/z 140 ($MH^+$-Boc).

Step II 3-(Trifluoromethyl)pyrrolidine (trifluoroacetate)

tert-Butyl 3-(trifluoromethyl)pyrrolidine-1-carboxylate (100 mg, 0.42 mmol) was treated with 20% $CF_3CO_2H$ in $CH_2Cl_2$ at room temperature overnight. The volatiles were removed in vacuo to give the subtitled compound (106 mg).

APCI-MS: m/z 140 ($MH^+$).

Step III (2S)-1-(5-Chloro-1'H,3H-spiro[1-benzofuran-2,4'-piperidin]-1'-yl)-3-(5-[(4-methoxybenzyl)oxy]-2-([3-(trifluoromethyl)pyrrolidin-1-yl]carbonyl}phenoxy)propan-2-ol A mixture of 2-{[(2S)-3-(5-chloro-1'H,3H-spiro[1-benzofuran-2,4'-piperidin]-1'-yl)-2-hydroxypropyl]oxy}-4-[(4-methoxybenzyl]benzoic acid (hydrochloride) (177 mg, 0.3 mmol) and N,N-carbonyldiimidazole (61 mg, 0.375 mmol) in DMF (3 mL) was stirred at room temperature for 45 min, 3-(trifluoromethyl)pyrrolidine (trifluoroacetate) (106 mg, 0.42 mmol) in DMF (1 mL) was added followed by $Et_3N$ (0.17 mL, 1.2 mmol) and the reaction mixture was stirred at room temperature overnight. The reaction mixture was partitioned between ethyl acetate and $H_2O$. The organic layer was dried over $Na_2SO_4$, filtered and concentrated. The residue was purified by silica gel flash chromatography (0-1% methanol in dichloromethane, 0.2% $NH_4OH$) to give the subtitled compound (89 mg).

APCI-MS: m/z 675 ($MH^+$).

Step IV

3-{[(2S)-3-(5-Chloro-1'H,3H-spiro[1-benzofuran-2,4'-piperidin]-1'-yl)-2-hydroxypropyl]oxy}-4-{[3-(trifluoromethyl)pyrrolidin-1-yl]carbonyl)phenol (2S)-1-(5-Chloro-1'H,3H-spiro[1-benzofuran-2,4'-piperidin]-1'-yl)-3-(5-[(4-methoxybenzyl)oxy]-2-{[3-(trifluoromethyl)pyrrolidin-1-yl]carbonyl}phenoxy)propan-2-ol (88 mg, 0.13 mmol) was treated with 10% $CF_3CO_2H$ in $CH_2Cl_2$ (3 mL) for 25 min at room temperature. The volatiles were removed in vacuo and the residue was purified by silica gel flash chromatography (0-3% methanol in dichloromethane, 0.2% $NH_4OH$) to give the titled compound (22 mg).

$^1$H-NMR ($CD_3OD$, 400 MHz): δ 7.14 (s, 1H); 7.08 (dd, J=4.3, 8.3 Hz, 1H); 7.05 (m, 1H); 6.66 (d, J=8.5 Hz, 1H); 6.51 (m, 1H); 6.46 (m, 1H); 4.15-3.42 (m, 7H); 3.18 (m, 1H); 3.02 (s, 2H); 2.78-2.52 (m, 6H); 2.34-1.80 (m, 6H). APCI-MS: m/z 555 ($MH^+$).

Example 82

N-[2-(Acetylamino)ethyl]-2-{[(2S)-3-(5-chloro-1'H, 3H-spiro[1-benzofuran-2,4'-piperidin]-1'-yl)-2-hydroxypropyl]oxy}-4-hydroxybenzamide Step I N-[2-(Acetylamino)ethyl]-2-{[(2S)-3-(5-chloro-1'H,3H-spiro[1-benzofuran-2,4'-piperidin]-1'-yl)-2-hydroxypropyl]oxy}-4-[(4-methoxybenzyl)oxy]benzamide A mixture of 2-{[(2S)-3-(5-chloro-1'H,3H-spiro[1-benzofuran-2,4'-piperidin]-1'-yl)-2-hydroxypropyl]oxy}-4-[(4-methoxybenzyl]benzoic acid (hydrochloride) (100 mg, 0.169 mmol) and N,N-carbonyldiimidazole 834 mg, 0.211 mmol) in DMF (3 mL) was stirred at room temperature for 45 min, N-(2-aminoethyl)acetamide (86 mg, 0.845 mmol) was added and the reaction mixture was stirred at room temperature overnight. The reaction mixture was partitioned between ethyl acetate and $H_2O$. The organic layer was dried over $Na_2SO_4$, filtered and concentrated. The residue was purified by silica gel flash chromatography (0-2% methanol in dichloromethane, 0.2% $NH_4OH$) to give the subtitled compound (77 mg).

$^1$H-NMR ($CDCl_3$, 400 MHz): δ 8.38 (t, J=5.6 Hz, 1H); 8.10 (d, J=8.8 Hz, 1H); 7.36 (d, J=8.6 Hz, 2H); 7.13 (m, 2H); 7.07 (dd, J=2.1, 8.4 Hz, 1H); 6.94 (d, J=8.6 Hz, 2H); 6.73-6.65 (m, 3H); 6.57 (d, J=2.2 Hz, 1H); 5.02 (s, 2H); 4.34 (m, 1H); 4.22 (dd, J=3.0, 9.7 Hz, 1H); 4.00 (dd, J=6.3, 9.7 Hz, 1H); 3.83 (s, 3H); 3.65 (m, 2H); 3.48 (m, 2H); 3.06-2.67 (m, 8H); 2.08 (m, 4H); 1.97 (s, 3H). APCI-MS: m/z 638 ($MH^+$).

Step II

N-[2-(Acetylamino)ethyl]-2-{[(2S)-3-(5-chloro-1'H,3H-spiro[1-benzofuran-2,4'-piperidin]-1'-yl)-2-hydroxypropyl]oxy}-4-hydroxybenzamide N-[2-(Acetylamino)ethyl]-2-{[(2S)-3-(5-chloro-1'H,3H-spiro[1-benzofuran-2,4'-piperidin]-1'-yl)-2-hydroxypropyl]oxy}-4-[(4-methoxybenzyl)oxy]benzamide (72 mg, 0.112 mmol) was treated with 10% $CF_3CO_2H$ in $CH_2Cl_2$ (3 mL) for 25 min at room temperature. The volatiles were removed in vacuo and the residue was purified by silica gel flash chromatography (0-3.5% methanol in dichloromethane, 0.2% $NH_4OH$) to give the titled compound (32 mg).

$^1$H-NMR ($CD_3OD$, 400 MHz): δ 8.5 Hz, 1H); 6.66 (d, J=8.5 Hz, 1H); 6.53 (d, J=2.1 Hz, 1H); 6.49 (dd, J=2.1, 8.7 Hz, 1H); 4.23 (m, 2H); 4.07 (dd, J=7.0, 10.7 Hz, 1H); 3.51 (t, J=6.1 Hz, 2H); 3.39 (t, J=6.1 Hz, 2H); 3.02 (s, 2H); 2.74 (br. s, 4H); 2.64 (d, J=6.0 Hz, 2H); 1.99-1.82 (m, 7H). APCI-MS: m/z 518 ($MH^+$).

Example 83

N-(5-chloro-2-{[(2S)-3-(5-chloro-1'H,3H-spiro[1-benzofuran-2,4'-piperidin]-1'-yl)-2-hydroxypropyl]oxy}-4-methoxyphenyl)acetamide Step I:

N-(5-chloro-2-hydroxy-4-methoxyphenyl)acetamide

This compound was prepared as described by Kun Hoe Chung; Kyong Mahn Kim; Jae Nyoung Kim and Eung Kul Ryu, *Synth. Comm.*, 1991, 21 (18&19), 1917-1922, using N-(2-hydroxy-4-methoxyphenyl)acetamide as starting material.

APCI-MS: m/z 216 [MH$^+$]

Step II:

N-{5-chloro-4-methoxy-2-[(2S)-oxiran-2-ylmethoxy] phenyl}acetamide To a slurry of N-(5-chloro-2-hydroxy-4-methoxyphenyl)acetamide (227 mg, 1.05 mmol) and caesium carbonate (376 mg, 1.25 mmol) in 1-methyl-2-pyrrolidinone (2 mL) was added (2S)-oxirane-2-ylmethyl 3-nitrobenzenesulfonate (301 mg, 1.16 mmol) dissolved 2-methyl-2-pyrrolidine (2 mL) drop wise. The resulting brown slurry was stirred over night, at room temperature. The mixture was partitioned between water and ethyl acetate. The organic phase was dried over magnesium sulphate, filtered and concentrated to yield crude 280 mg (98%) of the titled compound.

APCI-MS: m/z 272 [MH$^+$]

Step III:

N-(5-chloro-2-{[(2S)-3-(5-chloro-1'H,3H-spiro[1-benzofuran-2,4'-piperidin]-1'-yl)-2-hydroxypropyl]oxy}-4-methoxyphenyl)acetamide A solution of N-(5-chloro-4-methoxy-2-[(2S)-oxiran-2-ylmethoxy]phenyl}acetamide (101 mg, 0.37 mmol) and 5-chloro-3H-spiro[1-benzofuran-2,4'-piperidine] (83.5 mg, 0.37 mmol) in ethanol (10 mL) was refluxed over night, and then concentrated. The crude material was purified on C18 ("Kromasil" column, 10 um, acetonitrile/water 25/75 to 50/50 over 30 min with 0.1% trifluoroacetic acid). Pure fractions were pooled and freeze-dried to give 116 mg (51%) of the title compound as the trifluoroacetate salt.

$^1$H-NMR (400 MHz, (CD$_3$)$_2$CO) δ: 8.36 (1H, s); 7.24 (1H, bs); 7.14 (1H, dd); 6.87 (1H, s); 6.76 (1H, d); 4.59-4.52 (1H, m); 4.25-4.15 (2H, m); 3.89-3.40 (6H, m); 3.88 (3H, s); 3.20 (2H, bs); 2.45-2.19 (4H, m); 2.12 (3H, s) APCI-MS: m/z 495 [MH$^+$]

Example 84

(3S)-N-(5-chloro-2-{[(2S)-3-(5-chloro-1'H,3H-spiro [1-benzofuran-2,4'-piperidin]-1'-yl)-2-hydroxypropyl]oxy}phenyl)-3-hydroxypyrrolidine-1-carboxamide Step I:

(3S)-N-(5-chloro-2-hydroxyphenyl)-3-hydroxypyrrolidine-1-carboxamide 5-chloro-1,3-benzoxazole-2(3H)-one (577 mg, 0.34 mmol) and (3S)-pyrrolidin-3-ol (0.6 mL, 0.74 mmol) was heated to 90° C. for 2 hrs. The resulting red solidified oil was purified on silica (dichloromethane/methanol) to give the titled compound (768 mg, 88%).

APCI-MS: m/z 257 [MH$^+$]

Step II:

(3S)-N-(5-chloro-2-[(2S)-oxiran-2-ylmethoxy]phenyl}-3-hydroxypyrrolidine-1-carboxamide A solution of (3S)-N-(5-chloro-2-hydroxyphenyl)-3-hydroxypyrrolidine-1-carboxamide (232 mg, 0.90 mmol), (2S)-oxiran-2-ylmethyl 3-nitrobenzenesulfonate (234 mg, 0.90 mmol) and caesium carbonate (369 mg, 1.13 mmol) in dimethylformamide (9 mL) was stirred at room temperature, over night. The mixture was partitioned between water and ethyl acetate, and the organic phase was washed twice with water and once with brine, and finally concentrated. The crude material was purified by HPLC on C18 ("Kromasil" column, 10 um, acetonitrile/water 35/65 to 85/15 over 30 min), yielding the titled compound (82 mg, 29%).

APCI-MS: m/z 313 [MH$^+$]

(3S)-N-(5-chloro-2-{[(2S)-3-(5-chloro-1'H,3H-spiro [1-benzofuran-2,4'-piperidin]-1'-yl)-2-hydroxypropyl]oxy}phenyl)-3-hydroxypyrrolidine-1-carboxamide A solution of (3S)-N-{5-chloro-2-[(2S)-oxiran-2-ylmethoxy]phenyl}-3-hydroxypyrrolidine-1-carboxamide (63.2 mg, 0.20 mmol) and 5-chloro-3H-spiro[1-benzofuran-2,4'-piperidine] (45.4 mg, 0.20 mmol) in isopropanol (8 mL) was stirred at 80° C. over night. The concentrated crude material was purified by HPLC on C18 ("Kromasil" column, 10 um, acetonitrile/water 50/50 to 85/15 over 45 min, with 0.1% trifluoroacetic acid). Pure fractions were pooled and freeze-dried to give the title compound (83 mg, 65%) as the trifluoroacetate salt.

$^1$H-NMR (400 MHz, DMSO-d$_6$) δ: 9.69 (1H, bs); 9.60 (1H, bs); 8.00 (1H, d); 7.39 (1H, bs); 7.29 (1H, bs); 7.16 (1H, d); 7.06 (1H, d); 7.00 (1H, dd); 6.78 (1H, d); 4.41-4.34 (1H, m); 4.32 (1H, bs); 4.09-3.97 (2H, m); 3.62-3.40 (7H, m); 3.36-3.16 (4H, m); 3.10 (2H, s); 2.22-2.03 (3H, m); 2.03-1.90 (1H, m); 1.88-1.79 (1H, m) APCI-MS: m/z 536 [MH$^+$]

Example 85

(3S)-N-(2-{[(2S)-3-(5-chloro-1'H,3H-spiro[1-benzofuran-2,4'-piperidin]-1'-yl)-2-hydroxypropyl] oxy}phenyl)-3-hydroxypyrrolidine-1-carboxamide The title compound was prepared using 1,3-benzoxazole-2(3H)-one by methods analogous to the methods described in Example 84.

$^1$H-NMR (400 MHz, DMSO-d$_6$) δ: 9.70 (1H, bs); 9.62 (1H, bs); 7.82 (1H, d); 7.36 (1H, s); 7.29 (1H, bs); 7.00 (2H, dt); 6.91 (1H, t); 6.80 (1H, d); 4.41-4.34 (1H, m); 4.32 (1H, bs); 4.09-3.97 (2H, m); 3.62-3.41 (7H, m); 3.35-3.15 (4H, m); 3.10 (2H, s); 2.22-2.03 (3H, m); 2.03-1.90 (1H, m); 1.88-1.79 (1H, m) APCI-MS: m/z 502 [MH$^+$]

Example 86

N-(2-{[(2S)-3-(5-chloro-1'H,3H-spiro[1-benzofuran-2,4'-piperidin]-1'-yl)-2-hydroxypropyl]oxy}phenyl)-4-hydroxypiperidine-1-carboxamide The title compound was prepared using 1,3-benzoxazole-2(3H)-one and 4-hydroxypiperidine by methods analogous to the methods described in Example 84.

$^1$H-NMR (400 MHz, DMSO-d$_6$) δ: 9.67 (1H, bs); 9.60 (1H, bs); 7.81 (1H, s); 7.63 (1H, d); 7.30 (1H, d); 7.15 (1H, d); 7.06-6.98 (2H, m); 6.91 (1H, dt); 6.80 (1H, d); 4.41-4.28 (2H, m); 4.08-3.95 (2H, m); 3.84-3.75 (2H, m); 3.69 (1H, sept); 3.63-3.41 (3H, m); 3.32-3.04 (4H, m); 3.10 (2H, s); 2.22-1.98 (4H, m); 1.80-1.71 (2H, m); 1.41-1.29 (2H, m) APCI-MS: m/z 516 [MH$^+$]

Example 87

N-(2-{[(2S)-3-(5-Chloro-1'H,3H-spiro[1-benzofuran-2,4'-piperidin]-1'-yl)-2-hydroxypropyl]oxy}phenyl)urea trifluoroacetate (salt)

Step I:

(2S)-3-(2-Aminophenoxy)-1-(5-chloro-1'H,3H-spiro[1-benzofuran-2,4'-piperidin]-1'-yl)propan-2-ol bis(hydrochloride) (salt)

N-(2-{[(2S)-3-(5-Chloro-1'H,3H-spiro[1-benzofuran-2,4'-piperidin]-1'-yl)-2-hydroxypropyl]oxy}phenyl)acetamide (117 mg, 0.27 mmol) was stirred in 1M hydrochloric acid (2 mL) at 100° C. for 2 h. The solution was diluted with water and freeze dried to give the subtitled compound as a white amorphous solid (112 mg).

$^1$H-NMR (MeOH-d$_4$, 400 MHz): δ 7.49-7.44 (m, 1H); 7.40 (d, J=8.0 Hz, 1H); 7.25 (d, J=8.4 Hz, 1H); 7.21 (bs, 1H); 7.15-7.09 (m, 2H); 6.75 (d, J=8.4 Hz, 1H); 4.64-4.52 (m, 1H); 4.21 (d, J=4.8 Hz, 2H); 3.84-3.65 (m, 2H); 3.49 (dd, J=10.3, 13.1 Hz, 2H); 3.62-3.38 (m, 2H); 3.16 (bs, 2H); 2.33-2.15 (m, 4H) APCI-MS: m/z 389 (MH$^+$)

Step II:

N-(2-{[(2S)-3-(5-Chloro-1'H,3H-spiro[1-benzofuran-2,4'-piperidin]-1'-yl)-2-hydroxypropyl]oxy}phenyl)urea trifluoroacetate (salt)

To (2S)-3-(2-aminophenoxy)-1-(5-chloro-1'H,3H-spiro[1-benzofuran-2,4'-piperidin]-1'-yl)propan-2-ol bis(hydrochloride) (46.2 mg, 0.1 mmol) dissolved in acetic acid/water (1/1 mL) potassium cyanate (16.2 mg, 0.2 mmol) dissolved in water (0.5 mL) was added. The mixture was stirred at ambient temperature overnight. After purification by preparative HPLC using acetonitrile/water containing 0.1% TFA as mobile phase and freeze drying the titled compound was obtained as a white amorphous solid (43 mg, 78%).

$^1$H-NMR (400 MHz, acetone-d$_6$): δ 8.38-8.34 (m, 1H); 7.83 (bs, 1H); 7.25 & 7.21 (s, 1H); 7.14 (d, J=8.4 Hz, 1H); 6.93-6.81 (m, 3H); 6.77 (d, J=8.4 Hz, 1H); 5.95 (bs, 2H); 4.60-4.52 (m, 1H); 4.18 (d, J=9.6 Hz, 1H); 4.07-4.00 (m, 1H); 3.92-3.71 (m, 3H); 3.70-3.40 (m, 3H); 3.30 & 3.22 (s, 2H); 2.44-2.19 (m, 4H) APCI-MS: m/z 432 (MH$^+$)

Example 88

N-(2-{[(2S)-3-(5-chloro-1'H,3H-spiro[1-benzofuran-2,4'-piperidin]-1'-yl)-2-hydroxypropyl]oxy}-4-hydroxyphenyl)urea trifluoroacetate (salt)

Step I:

4-Amino-3-{[(2S)-3-(5-chloro-1'H,3H-spiro[1-benzofuran-2,4'-piperidin]-1'-yl)-2-hydroxypropyl]oxy)phenol bis(trifluoroacetate) (salt)

The compound was prepared analogous to the compound Example 87 Step I from N-(2-{[(2S)-3-(5-Chloro-1'H,3H-spiro[1-benzofuran-2,4'-piperidin]-1'-yl)-2-hydroxypropyl]oxy}-4-hydroxyphenyl)acetamide (135 mg, 0.3 mmol) and 1M hydrochloric acid (3 mL). After purification by preparative HPLC using acetonitrile/water containing 0.1% TFA as mobile phase and freeze drying the subtitled compound was obtained as a white amorphous solid (150 mg).

$^1$H-NMR (MeOH-d$_4$, 400 MHz): δ 7.21 (bs, 1H); 7.18 (d, J=8.8 Hz, 1H); 7.11 (dd, J=2.0, 8.4 Hz, 1H); 6.74 (d, J=8.4 Hz, 1H); 6.62 (d, J=2.4 Hz, 1H); 6.49 (dd, J=2.4, 8.8 Hz, 2H); 4.58-4.49 (m, 1H); 4.13 (d, J=4.8 Hz, 2H); 3.8-3.6 (m, 2H); 3.6-3.4 (m, 2H); 3.48 (d, J=13.2 Hz, 1H); 3.45 (d, J=13.2 Hz, 1H); 3.16 (s, 2H); 2.31-2.17 (m, 4H) APCI-MS: m/z 405 (MH$^+$)

Step II:

N-(2-{[(2S)-3-(5-chloro-1'H,3H-spiro[1-benzofuran-2,4'-piperidin]-1'-yl)-2-hydroxypropyl]oxy}-4-hydroxyphenyl)urea trifluoroacetate (salt)

The compound was prepared analogous to the compound Example 87 Step II from 4-amino-3-{[(2S)-3-(5-chloro-1'H,3H-spiro[1-benzofuran-2,4'-piperidin]-1'-yl)-2-hydroxypropyl]oxy}phenol bis(hydrochloride) (63.3 mg, 0.1 mmol) and potassium cyanate (16.2 mg, 0.2 mmol). After purification and freeze drying the titled compound was obtained as a white amorphous solid (51 mg, 90%).

$^1$H-NMR (400 MHz, acetone-d$_6$): δ 8.01 (d, J=8.8 Hz, 1H); 7.60 (s, 1H); 7.25 & 7.21 (s, 1H); 7.14 (dd, J=2.2, 8.4 Hz, 1H); 6.77 (d, J=8.4 Hz, 1H); 6.45 (d, J=2.5 Hz, 1H); 6.37 (dd, J=2.5, 8.8 Hz, 1H); 4.57-4.49 (m, 1H); 4.12 (dd, J=9.7, 2.6 Hz, 1H); 4.01 (dd, J=9.7, 5.1 Hz, 1H); 3.95-3.65 (m, 3H); 3.62-3.40 (m, 3H); 3.33 & 3.21 (s, 3H); 2.44-2.20 (m, 4H) APCI-MS: m/z 448 (MH$^+$)

Example 89

N-(2-{[(2S)-3-(5-Chloro-1'H,3H-spiro[1-benzofuran-2,4'-piperidin]-1'-yl)-2-hydroxypropyl]oxy}-4-fluorophenyl)urea trifluoroacetate (salt)

Step I:

(2S)-1-(2-Amino-5-fluorophenoxy)-3-(5-chloro-1'H,3H-spiro[1-benzofuran-2,4'-piperidin]-1'-yl)propan-2-ol bis(hydrochloride) (salt)

The subtitled compound was preparad analogous to the compound Example 87 Step I from N-(2-{[(2S)-3-(5-chloro-1'H,3H-spiro[1-benzofuran-2,4'-piperidin]-1'-yl)-2-hydroxypropyl]oxy}-4-fluorophenyl)acetamide (150 mg, 0.27 mmol) and 1M hydrochloric acid (2 mL).

APCI-MS: m/z 407 (MH$^+$)

Step II:

N-(2-{[(2S)-3-(5-Chloro-1'H,3H-spiro[1-benzofuran-2,4'-piperidin]-1'-yl)-2-hydroxypropyl]oxy}-4-fluorophenyl)urea trifluoroacetate (salt)

The reaction solution obtained from Step I was buffered with ammonia acetate (200 mg) dissolved in acetic acid (1 mL). Potassium cyanate (44 mg, 0.54 mmol) dissolved in water (0.5 mL) was added and the mixture was stirred at ambient temperature over night. After purification of the reaction mixture by preparative HPLC using acetonitrile/water containing 0.1% TFA as mobile phase and freeze drying the titled compound was obtained as a white amorphous solid (105 mg).

$^1$H-NMR (MeOH-d$_4$, 300 MHz): δ 7.70 (dd, J=8.7, 6.3 Hz, 1H); 7.22-7.19 (m, 1H); 7.11 (dd, J=8.4, 2.4 Hz, 1H); 6.86 (dd, J=10.2, 2.7 Hz, 1H); 6.74 (d, J=8.4 Hz, 1H); 6.69 (ddd, J=8.4, 8.4, 2.7 Hz, 1H); 4.53-4.43 (m, 1H); 4.09 (d, J=5.1 Hz, 2H); 3.76-3.62 (m, 2H); 3.56-3.34 (m, 4H); 3.21 & 3.14 (s, 2H); 2.30-2.05 (m, 4H) APCI-MS: m/z 450 (MH$^+$)

Example 90

N-{[(2-{[(2S)-3-(5-Chloro-1'H,3H-spiro[1-benzofuran-2,4'-piperidin]-1'-yl)-2-hydroxypropyl]oxy}-4-hydroxyphenyl)amino]carbonyl}methanesulfonamide trifluoroacetate (salt)

To a solution of 4-nitrophenyl chloroformate (50 mg, 0.25 mmol) in DCM (3 mL) DMAP (30 mg, 0.25 mmol) was added. After stirring the mixture for 5 min methanesulfonamide (24 mg, 0.25 mmol) and TEA (25 µL, 0.25 mmol) was added and the stirring continued for 1 h. 4-Amino-3-{[(2S)-3-(5-chloro-1'H,3H-spiro[1-benzofuran-2,4'-piperidin]-1'-yl)-2-hydroxypropyl]oxy}phenol (78 mg, 0.12 mmol) dissolved in DCM (2 mL) and TEA (75 µL, 0.75 mmol) was added and the stirring continued at ambient temperature. The reaction was complete after 2 h as monitored by LCMS. After evaporation of the solvent the crude product was purified by preparative HPLC using acetonitrile/water containing 0.1% TFA as mobile phase. The titled compound was obtained as a white amorphous solid (7 mg) after freeze drying.

$^1$H-NMR (Acetone-$d_6$, 300 MHz): δ 8.32 (bs, 1H); 7.91 (d, J=8.7 Hz, 1H); 7.24 (bs, 1H); 7.14 (dd, J=8.4, 2.2 Hz, 1H); 6.78 (d, J=8.6 Hz, 1H); 6.51 (d, J=2.4 Hz, 1H); 6.43 (dd, J=8.6, 2.6 Hz, 1H); 4.61-4.52 (m, 1H); 4.11 (dd, J=9.5, 3.8 Hz, 1H); 3.98 (dd, J=9.5, 6.4 Hz, 1H); 4.01-3.78 (m, 2H); 3.65 (d, J=9.4 Hz, 1H); 3.74-3.42 (m, 4H); 3.27 (s, 3H); 3.30-3.15 (m, 2H); 2.43-2.20 (m, 4H) APCI-MS: m/z 526 (MH$^+$)

Example 91

(4S)-2-(2-{[(2S)-3-(5-Chloro-1'H,3H-spiro[1-benzofuran-2,4'-piperidin]-1-yl)-2-hydroxypropyl]oxy}-4-hydroxybenzoyl)isoxazolidin-4-ol trifluoroacetate (salt)

Step I:

(S)-Methyl 2-[4-hydroxyisoxazolidin-2-yl]carbonylbenzoate

Triethylamine (0.28 ml) was added to a solution of N-hydroxyphthalimide (5.00 g, 30 mmol) and (R)-(−)-epichlorohydrin (2.40 ml, 30.6 mmol) in anhydrous dioxane (10 ml) under nitrogen. The mixture was stirred at 50° C. for 48 h, further (2R)-2-(chloromethyl)oxirane (0.24 ml) and triethylamine (0.28 ml) were added and stirring continued at 50° C. for 24 h. Methanol (10 ml) and further triethylamine (4.27 ml) were added and stirring continued at 50° C. for 2 h. The mixture was evaporated under reduced pressure, the residue dissolved in saturated aqueous sodium bicarbonate solution (100 ml) and extracted with ethyl acetate (6×100 ml). Combined organic extracts were dried over anhydrous magnesium sulfate, filtered and evaporated under reduced pressure. The residue was recrystallised from ethyl acetate to give the sub-title compound (3.4 g).

$^1$H-NMR (CDCl$_3$; 400 MHz): δ 3.66 (1H, d, br), 3.79 (1H, d, br), 3.89-3.99 (1H, m), 3.99-4.10 (1H, m), 4.74-4.81 (1H, m), 7.46 (1H, d), 7.49 (1H, t), 7.62 (1H, t), 7.99 (1H, d) MS(ESI): m/z 252 [M+H]$^+$

Step II:

(S)-4-Isoxazolidinol hydrochloride

Hydrochloric acid (4M, 15 ml) was added to (s)-Methyl 2-[4-hydroxyisoxazolidin-2-yl]carbonylbenzoate (1.87 g, 7.4 mmol) and the solution heated under reflux for 3 h. The mixture was cooled to room temperature, filtered and evaporated under reduced pressure. The residue was recrystallised from propan-2-ol to give the sub-title compound as white needles (0.78 g).

$^1$H-NMR (DMSO-$d_6$; 400 MHz): δ 3.35 (1H, d), 3.47 (1H, dd), 4.03 (1H, dd), 4.07 (1H, d), 4.78-4.81 (1H, m).

Step III:

(4S)-2-(2-{[(2S)-3-(5-Chloro-1'H,3H-spiro[1-benzofuran-2,4'-piperidin]-1'-yl)-2-hydroxypropyl]oxy}-4-[(4-methoxybenzyl)oxy]benzoyl}isoxazolidin-4-ol After stirring PS-carbodiimide (1.28 mmol/g) (312 mg, 0.4 mmol) in DCM (5 mL) for 15 min 2-{[(2S)-3-(5-chloro-1'H,3H-spiro[1-benzofuran-2,4'-piperidin]-1'-yl)-2-hydroxypropyl]oxy}-4-[(4-methoxybenzyl)oxy]benzoic acid (118 mg, 0.2 mmol) dissolved in DCM (2 mL) was added and stirring continued for 30 min. A solution of (s)-4-isoxazolidinol hydrochloride (25 mg, 0.2 mmol) and TEA (70 uL, 0.5 mmol) in DCM (1 mL) was added and stirring continued at ambient temperature over night. The reaction was complete as monitored by LCMS. All solids were filtered off and the filtrate evaporated in vacuo. The residue was partitioned between ethylacetate and water, the organic phase washed with water, dried and evaporated in vacuo leaving an oil (93 mg).

APCI-MS: m/z 625 (MH$^+$)

Step IV:

(4S)-2-(2-{[(2S)-3-(5-Chloro-1'H,3H-spiro[1-benzofuran-2,4'-piperidin]-1'-yl)-2-hydroxypropyl]oxy}-4-hydroxybenzoyl)isoxazolidin-4-ol trifluoroacetate (salt)

(4S)-2-{2-{[(2S)-3-(5-Chloro-1'H,3H-spiro[1-benzofuran-2,4'-piperidin]-1'-yl)-2-hydroxypropyl]oxy}-4-[(4-methoxybenzyl)oxy]benzoyl}isoxazolidin-4-ol (93 mg, 0.15 mmol) was dissolved in a mixture of TFA/DCM 1/9 (10 mL) and the solution stirred at ambient temperature for 30 min. After evaporation of the solvent in vacuo the residue was purified by preparative HPLC using acetonitrile/water containing 0.1% TFA as mobile phase. The titled compound was obtained as a white amorphous solid (18 mg) after freeze drying.

$^1$H-NMR (Acetone-$d_6$, 300 MHz): δ 7.23 (bs, 1H); 7.22 (d, J=8.2 Hz, 1H); 7.14 (dd, J=8.5, 2.4 Hz, 1H); 6.78 (d, J=8.5 Hz, 1H); 6.61 (d, J=2.0 Hz, 1H); 6.50 (dd, J=8.3, 2.0 Hz, 1H); 4.88-4.81 (m, 1H); 4.60-4.48 (m, 1H); 4.15 (dd, J=9.5, 4.5 Hz, 1H); 4.02 (dd, J=9.5, 6.3 Hz, 1H); 3.97 (dd, J=11.7, 5.9 Hz, 1H); 3.94-3.87 (m, 2H); 3.86-3.72 (bs, 2H); 3.70 (d, J=11.7 Hz, 2H); 3.56-3.40 (bs, 2H); 3.41 (dd, J=13.5, 9.2 Hz, 1H); 3.17 (bs, 2H); 2.48-2.14 (m, 4H) APCI-MS: m/z 505 (MH$^+$)

Example 92

(4R)-2-(2-{[(2S)-3-(5-Chloro-1'H,3H-spiro[1-benzofuran-2,4'-piperidin-1'-yl)-2-hydroxypropyl]oxy}-4-hydroxybenzoyl)isoxazolidin-4-ol trifluoroacetate (salt)

Step I:

(R)-Methyl 2-[4-hydroxyisoxazolidin-2-yl]carbonylbenzoate

Prepared from (2S)-2-(chloromethyl)oxirane by the method of described in Example 91 Step I.

$^1$H-NMR (CDCl$_3$; 400 MHz): δ 3.66 (1H, d, br), 3.79 (1H, d, br), 3.89-3.99 (1H, m), 3.99-4.10 (1H, m), 4.74-4.81 (1H, m), 7.46 (1H, d), 7.49 (1H, t), 7.62 (1H, t), 7.99 (1H, d). MS(ESI): m/z 252 [M+H]$^+$.

Step II:

(R)-4-Isoxazolidinol hydrochloride

Prepared from (R)-Methyl 2-[4-hydroxyisoxazolidin-2-yl]carbonylbenzoate following the procedure of Example 91 Step II.

$^1$H-NMR (CDCl$_3$; 400 MHz): δ 3.35 (1H, d), 3.47 (1H, dd), 4.03 (1H, dd), 4.07 (1H, d), 4.78-4.81 (1H, m).

Step III:

(4R)-2-{2-{[(2S)-3-(5-Chloro-1'H,3H-spiro[1-benzofuran-2,4'-piperidin]-1'-yl)-2-hydroxypropyl]oxy}-4-[(4-methoxybenzyl)oxy]benzoyl}isoxazolidin-4-ol The subtitled compound was prepared analogous to the compound Example 91 Step III from 2-{[(2S)-3-(5-chloro-1'H,3H-spiro[1-benzofuran-2,4'-piperidin]-1'-yl)-2-hydroxypropyl]oxy}-4-[(4-methoxybenzyl)oxy]benzoic acid (118 mg, 0.2 mmol) and (R)-4-isoxazolidinol hydrochloride (25 mg, 0.2 mmol).

APCI-MS: m/z 625 (MH$^+$)

Step IV:

(4R)-2-(2-{[(2S)-3-(5-Chloro-1'H,3H-spiro[1-benzofuran-2,4'-piperidin]-1'-yl)-2-hydroxypropyl]oxy}-4-hydroxybenzoyl)isoxazolidin-4-ol trifluoroacetate (salt)

The titled compound was prepared analogous to the compound Example 91 Step IV from (4R)-2-{2-{[(2S)-3-(5-Chloro-1'H,3H-spiro[1-benzofuran-2,4'-piperidin]-1'-yl)-2-hydroxypropyl]oxy}-4-[(4-methoxybenzyl)oxy]benzoyl}isoxazolidin-4-ol and TFA/DCM 1/9. After purification and freeze drying the titled compound was obtained as a white amorphous solid (26 mg).

$^1$H-NMR (Acetone-d$_6$, 300 MHz): δ 7.23 (bs, 1H); 7.22 (d, J=8.2 Hz, 1H); 7.14 (dd, J=8.5, 2.4 Hz, 1H); 6.78 (d, J=8.5 Hz, 1H); 6.61 (d, J=2.0 Hz, 1H); 6.50 (dd, J=8.3, 2.0 Hz, 1H); 4.88-4.81 (m, 1H); 4.60-4.48 (m, 1H); 4.15 (dd, J=9.5, 4.5 Hz, 1H); 4.02 (dd, J=9.5, 6.3 Hz, 1H); 3.97 (dd, J=11.7, 5.9 Hz, 1H); 3.94-3.87 (m, 2H); 3.86-3.72 (bs, 2H); 3.70 (d, J=11.7 Hz, 2H); 3.56-3.40 (bs, 2H); 3.41 (dd, J=13.5, 9.2 Hz, 1H); 3.17 (bs, 2H); 2.48-2.14 (m, 4H) APCI-MS: m/z 505 (MH$^+$)

Example 93

(4S)-2-(2-{[(2S)-3-(5-Chloro-1'H,3H-spiro[1-benzofuran-2,4'-piperidin]-1'-yl)-2-hydroxypropyl]oxy}-4-hydroxybenzoyl)-4-methylisoxazolidin-4-ol trifluoroacetate (salt)

Step I:

2-[[(2S)-2-Methyloxiranyl]methoxy]-1H-isoindole-1,3(2H)-dione

A mixture of N-hydroxypthalimide (5.3 g, 32.5 mmol), [(2S)-2-methyloxiran-2-yl]methyl 3-nitrobenzenesulfonate (5.9 g, 21.6 mmol) and triethylamine (10.6 ml) in dichloromethane (15 ml) was stirred under nitrogen at ambient temperature for 24 h. The reaction mixture was poured onto a silica column and eluted with dichloromethane to give the sub-title compound as a colourless solid (3.1 g).

$^1$H-NMR (CDCl$_3$; 400 MHz): δ 1.63 (3H, s), 2.69 (1H, d), 2.76 (1H, d), 4.17 (1H, d), 4.21 (1H, d), 7.73-7.78 (2H, m), 7.82-7.87 (2H, m) MS (APCI) 234 [M+H]$^+$

Step II:

2-[[(2R)-3-Chloro-2-hydroxy-2-methylpropyl]oxy]-1H-isoindole-1,3(2H)-dione

2-[[(2S)-2-Methyloxiranyl]methoxy]-1H-isoindole-1,3 (2H)-dione (3.0 g, 12.9 mmol) was treated with concentrated hydrochloric acid (12 ml) and stirred at ambient temperature for 2 h. The mixture was partitioned between water and dichloromethane, the organics were dried and purified by chromatography (EtOAc) to give the sub-title compound as a colourless solid (3.3 g).

$^1$H-NMR (CDCl$_3$; 400 MHz): δ 1.29 (3H, S), 3.67 (1H, d), 3.76 (1H, d), 4.09 (1H, d), 4.15 (1H, d), 7.86 (4H, s), 5.24 (1H, s)

Step III:

2-[[(4S)-4-Hydroxy-4-methyl-2-isoxazolidinyl]carbonyl]-benzoic acid methyl ester A solution of 2-[[(2R)-3-Chloro-2-hydroxy-2-methylpropyl]oxy]-1H-isoindole-1,3 (2H)-dione (3.3 g, 12.2 mmol) in methanol (25 ml) was treated with triethylamine (3.4 ml) and heated under nitrogen at reflux for 1 h. The mixture was concentrated to dryness and purified by chromatography eluting with a gradient from dichloromethane to 5% methanol in dichloromethane. The chiral purity of the product was enhanced by recrystallising twice from acetonitrile to give the sub-title compound as a colourless solid (1.92 g).

$^1$H-NMR (CDCl$_3$; 400 MHz): δ 1.52 (3H, s), 3.59 (1H, d), 3.81 (1H, d), 3.88 (1H, d), 4.04 (1H, s), 4.34 (1H, d), 3.92 (3H, s), 7.45 (1H, d), 7.49 (1H, t), 7.62 (1H, t), 8.00 (1H, d). HPLC: (9010THIP.M) 50 mm chiracel AD column, ee >99%

Step IV:

(4S)-4-Methyl-4-isoxazolidinol hydrochloride

A solution of 2-[[(4S)-4-Hydroxy-4-methyl-2-isoxazolidinyl]carbonyl]-benzoic acid methyl ester (4.9 g, 19.5 mmol) in 2N hydrochloric acid (30 ml) was heated under nitrogen at reflux for 4 h. After cooling the precipitate was removed by filtration and the liquors concentrated to dryness under vacuo. The residue was triturated with acetonitrile to give the sub-title compound as a white solid (1.79 g).

$^1$H-NMR (CDCl$_3$; 400 MHz): δ 1.42 (3H, s), 3.29 (1H, d), 3.41 (1H, dD), 3.87 (1H, d), 4.05 (1H, dd)

Step V:

(4S)-2-{2-{[(2S)-3-(5-chloro-1'H,3H-spiro[1-benzofuran-2,4'-piperidin]-1'-yl)-2-hydroxypropyl]oxy}-4-[(4-methoxybenzyl)oxy]benzoyl}-4-methylisoxazolidin-4-ol The subtitled compound was prepared analogous to the compound Example 91 Step III from 2-{[(2S)-3-(5-chloro-1'H,3H-spiro[1-benzofuran-2,4'-piperidin]-1'-yl)-2-hydroxypropyl]oxy}-4-[(4-methoxybenzyl)oxy]benzoic acid (118 mg, 0.2 mmol) and (4S)-4-methyl-4-isoxazolidinol hydrochloride (28 mg, 0.2 mmol).

APCI-MS: m/z 639 (MH$^+$)

Step VI:

(4S)-2-(2-{[(2S)-3-(5-Chloro-1'H,3H-spiro[1-benzofuran-2,4'-piperidin]-1'-yl)-2-hydroxypropyl]oxy}-4-hydroxybenzoyl)-4-methylisoxazolidin-4-ol trifluoroacetate (salt)

The titled compound was prepared analogous to the compound Example 91 Step IV from (4S)-2-{2-{[(2S)-3-(5-chloro-1'H,3H-spiro[1-benzofuran-2,4'-piperidin]-1'-yl)-2-hydroxypropyl]oxy}-4-[(4-methoxybenzyl)oxy]benzoyl}-4-methylisoxazolidin-4-ol (crude product from (4S)-2-{2-{[(2S)-3-(5-chloro-1'H,3H-spiro[1-benzo furan-2,4'-piperidin]-1'-yl)-2-hydroxypropyl]oxy}-4-[(4- methoxybenzyl)oxy]benzoyl)}-4-methylisoxazolidin-4-ol and TFA/DCM 1/9. After purification and freeze drying the titled compound was obtained as a white amorphous solid (33 mg).

$^1$H-NMR (Acetone-d$_6$, 300 MHz): δ 7.23 (bs, 1H); 7.22 (d, J=8.2 Hz, 1H); 7.14 (dd, J=8.5, 2.4 Hz, 1H); 6.78 (d, J=8.5 Hz, 1H); 6.61 (d, J=2.0 Hz, 1H); 6.50 (dd, J=8.3, 2.0 Hz, 1H); 4.59-4.47 (m, 1H); 4.15 (dd, J=9.8, 5.1 Hz, 1H); 4.06 (dd, J=9.8, 5.6 Hz, 1H); 3.92 (d, J=8.3 Hz, 1H); 3.86-3.74 (bs, 2H); 3.85 (d, J=11.2 Hz, 1H); 3.77 (d, J=8.3 Hz, 1H); 3.66 (d, J=11.2 Hz, 1H); 3.65-3.56 (m, 2H); 3.50 (d, J=9.0 Hz, 1H); 3.55-3.40 (m, 2H); 3.46 (d, J=9.0 Hz, 1H); 3.16 (bs, 2H); 2.48-2.14 (m, 4H); 1.48 (s, 3H) APCI-MS: m/z 519 (MH$^+$)

Example 94

(4R)-2-(2-{[(2S)-3-(5-Chloro-1'H,3H-spiro[1-benzofuran-2,4'-piperidin]-1'-yl)-2-hydroxypropyl]oxy}-4-hydroxybenzoyl)-4-methylisoxazolidin-4-ol trifluoroacetate (salt)

Step I:

2-[[(2R)-2-Methyloxiranyl]methoxy]-1H-isoindole-1,3(2H)-dione

Prepared from N-hydroxyphthalimide and [(2R)-2-methyloxiran-2-yl]methyl 3-nitrobenzenesulfonate (Chen, J.; Shum, W., *Tetrahedron Letters*, 1993, 34(48), 7663-6) by the method of Example 93 Step I.

$^1$H-NMR (CDCl$_3$; 400 MHz): δ 1.63 (3H, s), 2.69 (1H, d), 2.76 (1H, d), 4.17 (1H, d), 4.21 (1H, d), 7.73-7.78 (2H, m), 7.82-7.87 (2H, m) MS (APCI) 234 [M+H]$^+$

Step II:

2-[[(2R)-3-Chloro-2-hydroxy-2-methylpropyl]oxy]-1H-isoindole-1,3(2H)-dione

Prepared from 2-[[(2R)-2-Methyloxiranyl]methoxy]-1H-isoindole-1,3(2H)-dione by the method of Example 93 Step II.

$^1$H-NMR (CDCl$_3$; 400 MHz): δ 1.29 (3H, S), 3.67 (1H, d), 3.76 (1H, d), 4.09 (1H, d), 4.15 (1H, d), 7.86 (4H, s), 5.24 (1H,s)

Step III:

2-[[(4R)-4-Hydroxy-4-methyl-2-isoxazolidinyl]carbonyl]-benzoic acid methyl ester Prepared from 2-[[(2R)-3-Chloro-2-hydroxy-2-methylpropyl]oxy]-1H-isoindole-1,3(2H)-dione by the method of Example 93 Step III.

$^1$H-NMR (CDCl$_3$; 400 MHz): δ 1.52 (3H, s), 3.59 (1H, d), 3.81 (1H, d), 3.88 (1H, d), 4.04 (1H, s), 4.34 (1H, d), 3.92 (3H, s), 7.45 (1H, d), 7.49 (1H, t), 7.62 (1H, t), 8.00 (1H, d)

Step IV:

(4R)-4-Methyl-4-isoxazolidinol hydrochloride

Prepared from 2-[[(4R)-4-Hydroxy-4-methyl-2-isoxazolidinyl]carbonyl]-benzoic acid methyl ester by the method of Example 93 Step IV.

$^1$H-NMR (CDCl$_3$; 400 MHz): δ 1.42 (3H, s), 3.29 (1H, d), 3.41 (1H, dD), 3.87 (1H, d), 4.05 (1H, dd)

Step V:

(4R)-2-2-{[(2S)-3-(5-chloro-1'H,3H-spiro[1-benzofuran-2,4'-piperidin]-1'-yl)-2-hydroxypropyl]oxy}-4-[(4-methoxybenzyl)oxy]benzoyl}-4-methylisoxazolidin-4-ol The subtitled compound was prepared analogous to the compound Example 91 Step III from 2-{[(2S)-3-(5-chloro-1'H,3H-spiro[1-benzofuran-2,4'-piperidin]-1'-yl)-2-hydroxypropyl]oxy}-4-[(4-methoxybenzyl)oxy]benzoic acid (118 mg, 0.2 mmol) and (4R)-4-methyl-4-isoxazolidinol hydrochloride (28 mg, 0.2 mmol).

APCI-MS: m/z 639 (MH$^+$)

Step VI:

(4R)-2-(2-{[(2S)-3-(5-Chloro-1'H,3H-spiro[1-benzofuran-2,4'-piperidin]-1'-yl)-2-hydroxypropyl]oxy}-4-hydroxybenzoyl)-4-methylisoxazolidin-4-ol trifluoroacetate (salt)

The titled compound was prepared analogous to the compound Example 91 Step IV from (4R)-2-{2-{[(2S)-3-(5-chloro-1'H,3H-spiro[1-benzofuran-2,4'-piperidin]-1'-yl)-2-hydroxypropyl]oxy}-4-[(4-methoxybenzyl)oxy]benzoyl}-4-methylisoxazolidin-4-ol and TFA/DCM 1/9. After purification and freeze drying the titled compound was obtained as a white amorphous solid (30 mg).

$^1$H-NMR (Acetone-d$_6$, 300 MHz): δ 7.23 (bs, 1H); 7.22 (d, J=8.2 Hz, 1H); 7.14 (dd, J=8.5, 2.4 Hz, 1H); 6.78 (d, J=8.5 Hz, 1H); 6.61 (d, J=2.0 Hz, 1H); 6.50 (dd, J=8.3, 2.0 Hz, 1H); 4.60-4.48 (m, 1H); 4.15 (dd, J=9.5, 4.5 Hz, 1H); 4.03 (dd, J=9.5, 6.3 Hz, 1H); 3.92 (d, J=8.4 Hz, 1H); 3.87-3.72 (bs, 2H); 3.82 (d, J=10.9 Hz, 1H); 3.75 (d, J=8.4 Hz, 1H); 3.69 (d, J=10.9 Hz, 1H); 3.66 (bs, 1H); 3.56-3.38 (m, 2H); 3.42 (dd, J=8.8, 13.5 Hz, 1H); 3.17 (bs, 2H); 2.48-2.14 (m, 4H); 1.48 (s, 3H) APCI-MS: m/z 519 (MH$^+$)

Example 95

2-{[(2S)-3-(5-chloro-1'H,3H-spiro[1-benzofuran-2,4'-piperidin]-1'-yl)-2-hydroxypropyl]oxy}-N-(methylsulfonyl)benzamide trifluoroacetate Step I:

tert-butyl 2-[(2S)-oxiran-2-ylmethoxy]benzoate

A mixture of tert-butyl salicylate (2.01 g, 10.3 mmol), (2S)-oxiran-2-ylmethyl 3-nitrobenzenesulfonate (2.69 g, 10.4 mmol) and cesium carbonate (4.05 g, 12.4 mmol) in dimethylformamide (20 mL) was stirred at room temperture overnight. The reaction mixture was partitioned between ethyl acetetate and water. The organic layer was dried over sodium sulphate, Na$_2$SO$_4$, filtered, concentrated in vacuo. The residue was purified by silica gel flash chromatography (ethyl acetate 40%, heptane 60%) and gave the subtitle compound (2.3 g, 89%).

$^1$H-NMR (CDCl$_3$, 400 MHz): δ 7.71 (dd, J=1.8, 7.7 Hz, 1H); 7.41 (dd, J=1.8, 7.8 Hz, 1H); (dd, J=0.8, 7.5 Hz, 1H); 6.98 (d, J=8.4 Hz, 1H); 4.29 (dd, J=3.2, 11.0 Hz, 1H); 4.06 (dd, J=5.2, 11.0 Hz, 1H); 3.42-3.37 (m, 1H); 2.93-2.89 (m, 1H); 2.86-2.83 (m, 1H) APCI-MS: m/z 251 (MH$^+$)

Step II:

tert-butyl 2-{[(2S)-3-(5-chloro-1'H,3H-spiro[1-benzofuran-2,4'-piperidin]-1'-yl)-2-hydroxypropyl]oxy)benzoate A mixture of 5-chloro-3H-spiro[1-benzofuran-2,4'-piperidine] (390 mg, 1.6 mmol) and tert-butyl 2-[(2S)-oxiran-2-ylmethoxy]benzoate (350 mg, 1.6 mmol) in ethanol was heated at reflux overnight. The volatiles were removed in vacuo, the residue was used without further purification.

APCI-MS: m/z 474 (MH$^+$)

Step III:

2-({(2S)-3-(5-chloro-1'H,3H-spiro[1-benzofuran-2,4'-piperidin]-1'-yl)-2-[(4-methoxybenzyl)oxy]propyl}oxy)benzoic acid To a suspension of sodium hydride (170 mg, 4.2 mmol) in THF (10 mL) under argon at 0° C., was added tert-butyl 2-{[(2S)-3-(5-chloro-1'H, 3H-spiro[1-benzofuran-2,4'-piperidin]-1'-yl)-2-hydroxypropyl]oxy}benzoate (750 mg, 1.6 mmol) in THF (10 mL) and 1-(chloromethyl)-4-methoxybenzene (250 mg, 1.6 mmol) in THF (10 mL). The mixture was stirred at room temperture overnight, poured over ice and pH adjusted to 1 with HCl (aq). It was then extracted with ethyl acetate, the organic layer was dried over sodium sulphate (Na$_2$SO$_4$), the volatiles were removed in vacuo. The residue was purified by HPLC (acetonitrile/water, 0.025% ammonium hydroxid) and gave the subtitle compound (91 mg)

APCI-MS: m/z 538 (MH$^+$)

Step IV:

2-({(2S)-3-(5-chloro-1'H,3H-spiro[1-benzofuran-2,4'-piperidin]-1'-yl)-2-[(4-methoxybenzyl)oxy]propyl}oxy}-N-(methylsulfonyl)benzamide A mixture of 2-({(2S)-3-(5-chloro-1'H,3H-spiro[1-benzofuran-2,4'-piperidin]-1'-yl)-2-[(4-methoxybenzyl)oxy]propyl}oxy)benzoic acid (90 mg, 0.17 mmol), N,N-dimethylpyridin-4-amine (22 mg, 0.18 mmol), methanesulfonamide (18 mg, 0.19 mmol) and N-[3-(dimethylamino)propyl]-N'-ethylcarbodiimide hydrochloride (35 mg, 0.18 mmol) in dichloromethane (5 mL) was stirred under argon at room temperture overnight. The mixture was poured in 1M HCl (aq), the two layers were separated, the aqueous layer was extracted with dichloromethane. The combined organic layers were dried over sodium sulphate, the volatiles were removed in vacuo, the residue (117 mg) was used without further purification.

APCI-MS: m/z 615 (MH$^+$)

Step V:

2-{[(2S)-3-(5-chloro-1'H,3H-spiro[1-benzofuran-2,4'-piperidin]-1'-yl)-2-hydroxypropyl]oxy}-N-(methylsulfonyl)benzamide 2-({(2S)-3-(5-chloro-1'H,3H-spiro[1-benzofuran-2,4'-piperidin]-1'-yl)-2-[(4-methoxybenzyl)oxy]propyl}oxy)-N-(methylsulfonyl)benzamide (104 mg, 0.17 mmol) was stirred in a mixture of trifluoroacetic acid (500 μL) and dichloromethane (3 mL), at room temperature for 1 hour. The volatiles were removed in vacuo, the residue was purified by HPLC (acetonitrile/water, 0.025% ammonium hydroxid) and gave the subtitle compound (31 mg, overall yield Steps II-V 3.9%).

$^1$H-NMR (acetone-d$_6$, 400 MHz): δ 7.92 (dd, J=1.8, 7.8 Hz, 1H); 7.62 (dd, J=1.8, 8.3 Hz, 1H); 7.28-7.22 (m, 2H); 7.19-7.11 (m, 2H); 6.77 (d, J=8.5 Hz, 1H); 4.76-4.69 (m, 1H); 4.42-4.32 (m, 2H); 3.98-3.44 (m, 6H); 3.42 (s, 3H); 3.19 (br.s, 2H); 2.41-2.19 (m, 4H) APCI-MS: m/z 495 (MH$^+$)

Step VI:

2-{[(2S)-3-(5-chloro-1'H,3H-spiro[1-benzofuran-2,4'-piperidin]-1'-yl)-2-hydroxypropyl]oxy}-N-(methylsulfonyl)benzamide trifluoroacetate 2-{[(2S)-3-(5-chloro-1'H,3H-spiro[1-benzofuran-2,4'-piperidin]-1'-yl)-2-hydroxypropyl]oxy}-N-(methylsulfonyl)benzamide (31 mg, 0.06 mmol was dissolved in dichloromethane, trifluoroacetic acid (100 μL) was added. Volatiles were removed in vacuo and the subtitle compound (35 mg) was obtained.

APCI-MS: m/z 495 (MH$^+$)

Example 96

2-{[(2S)-3-(5-chloro-1'H,3H-spiro[1-benzofuran-2,4'-piperidin]-1'-yl)-2-hydroxypropyl]oxy}-N-1H-tetrazol-5-ylbenzamide bis(trifluoroacetate)

Step I:

2-{[(2S)-3-(5-chloro-1'H,3H-spiro[1-benzofuran-2,4'-piperidin]-1'-yl)-2-hydroxypropyl]oxy}benzoic acid hydrochloride A mixture of tert-butyl 2-{[(2S)-3-(5-chloro-1'H,3H-spiro[1-benzofuran-2,4'-piperidin]-1'-yl)-2-hydroxypropyl]oxy}benzoate (200 mg, 0.42 mmol) and conc. aqueous HCl (3 mL) in dichloromethane (25 mL) was stirred at room temperture for 48 hours. Volatiles were removed in vacuo, the brown residue was used without further purification APCI-MS: m/z 418 (MH$^+$)

Step II:

2-{[(2S)-3-(5-chloro-1'H,3H-spiro[1-benzofuran-2,4'-piperidin]-1'-yl)-2-hydroxypropyl]oxy}-N-1H-tetrazol-5-ylbenzamide bis(trifluoro acetate)

A mixture of 2-{[(2S)-3-(5-chloro-1'H,3H-spiro[1-benzofuran-2,4'-piperidin]-1'-yl)-2-hydroxypropyl]oxy}benzoic acid hydrochloride (110 mg, 0.24 mmol), 1H-tetrazol-5-amine (27 mg, 0.26 mmol) and PS-Carbodiimid (850 mg, 1 mmol) was stirred in dichloromethane (10 ml) at room temperature overnight. Volatiles were removed in vacuo, the residue was purified by HPLC (acetonitrile/water, 0.1% trifluoroacetic acid), and gave the subtitle compound (23 mg, overall yield Steps I-II 11%).

$^1$H-NMR (acetone-d$_6$, 400 MHz): δ 11.43 (br. s, 1H); 8.03 (dd, J=1.7, 7.8 Hz, 1H); 7.65 (dd, J=1.9, 7.1 Hz, 1H); 7.32 (d, J=8.3 Hz, 1H); 7.25-7.17 (m, 2H); 7.14 (dd, J=2.4, 8.5 Hz, 1H); 6.79 (d, J=8.5 Hz, 1H); 4.85-4.78 (m, 1H); 4.52-4.39 (m, 2H); 3.98-3.76 (m, 2H); 3.75-3.67 (m, 2H); 3.66-3.50 (m, 2H); 3.22 (br. s, 2H); 2.47-2.32 (m, 2H); 2.31-2.20 (m, 2H) APCI-MS: m/z 485 (MH$^+$)

Example 97

3-{{[(2S)-3-(5-chloro-1'H,3H-spiro[1-benzofuran-2,4'-piperidin]-1'-yl)-2-hydroxypropyl]oxy}-4{[(3R)-3-(dimethylamino)pyrrolidin-1-yl]carbonyl}phenol bis(trifluoroacetate) (salt)

Step I:

(2S)-1-(5-chloro-1'H,3H-spiro[1-benzofuran-2,4'-piperidin]-1'-yl)-3-{2-{[(3R)-3-(dimethylamino)pyrrolidin-1-yl]carbonyl)-5-[(4-methoxybenzyl)oxy]phenoxy}propan-2-ol A mixture of PS-carbodiimide (530 mg, 0.68 mmol) and dichloromethane (6 mL) was stirred at room temperature for 15 minutes, a solution of 2-{[(2S)-3-(5-chloro-1'H,3H-spiro[1-benzofuran-2,4'-piperidin]-1'-yl)-2-hydroxypropyl]oxy}-4-[(4-methoxybenzyl)oxy]benzoic acid hydrochloride (200 mg, 0.32 mmol) in NMP (1 mL) and dichloromethane (2 mL) was added, the mixture was stirred for 30 minutes, a solution of (3R)-N,N-dimethylpyrrolidin-3-amine (48 mg, 0.42 mmol) in dichloromethane (2 mL) was added. The mixture was stirred at room temperture overnight, filtrated, the filtrate was washed with brine, dried with sodium sulphate. Volatiles were removed in vacuo, the residue was used without further purification APCI-MS: m/z 650 (MH+)

Step II:

3-{{[(2S)-3-(5-chloro-1'H,3H-spiro[1-benzofuran-2,4'-piperidin]-1'-yl)-2-hydroxypropyl]oxy}-4-{[(3R)-3-isopropylpyrrolidin-1-yl]carbonyl}phenol bis(trifluoroacetate)

To a solution of (2S)-1-(5-chloro-1'H,3H-spiro[1-benzofuran-2,4'-piperidin]-1-yl)-3-{2-{[(3R)-3-isopropylpyrrolidin-1-yl]carbonyl}-5-[(4-methoxybenzyl)oxy]phenoxy}propan-2-ol (crude product from the previous step) and dichloromethane (3 mL) was added trifluoroacetic acid (600 µL). The mixture was stirred at room temperature for 1 h, volatiles were removed in vacuo, the residue was purified by HPLC (acetonitrile/water, 0.1% trifluoroacetic acid) and gave (60 mg, overall yield Steps I-II 25%) of the subtitle compound.

$^1$H-NMR (acetone-d$_6$, 400 MHz): δ 7.22 (s, 1H); 7.15-7.11 (m, 2H); 6.77 (d, J=8.5 Hz, 1H); 6.64-6.60 (m, 1H); 6.53-6.49 (m, 1H); 4.63-4.49 (m, 2H); 4.17-3.96 (m, 4H); 3.96-3.72 (m, 4H); 3.71-3.38 (m, 6H); 3.17 (br. s, 2H); 3.00 (br. s, 3H); 2.94 (br. s, 3H); 2.60-2.18 (m, 6H). APCI-MS: m/z 530 (MH+)

Example 98

3-{[(2S)-3-(5-chloro-1'H,3H-spiro[1-benzofuran-2,4'-piperidin]-1'-yl)-2-hydroxypropyl]oxy}-4-{[(3S)-3-(dimethylamino)pyrrolidin-1-yl]carbonyl}phenol bis(trifluoroacetate)

The title compound was prepared using (3S)-N,N-dimethylpyrrolidin-3-amine as described in Example 97.

$^1$H-NMR (Acetone-d$_6$, 300 MHz): δ 7.25-7.20 (m, 1H); 7.16-7.11 (m, 2H); 6.77 (d, J=8.5 Hz, 1H); 6.63-6.58 (m, 1H); 6.54-6.48 (m, 1H); 4.70-4.52 (m, 1H); 4.20-3.98 (m, 3H); 3.96-3.72 (m, 4H); 3.70-3.36 (m, 6H); 3.17 (bs, 2H); 3.00 (s, 3H); 2.95 (s, 3H); 2.62-2.16 (m, 6H) APCI-MS: m/z 530 (MH+)

Example 99

(3S)-1-(5-chloro-2-{[(2S)-3-(5-chloro-1 $^9$H,3H-spiro [1-benzofuran-2,4'-piperidin]-1'-yl)-2-hydroxypropyl]oxy}-4-hydroxybenzoyl)pyrrolidin-3-ol trifluoroacetate Step I:

Methyl 5-chloro-2,4-dihydroxybenzoate

Prepared from methyl 2,4-dihydroxybenzoate using the procedure described by Anderson, W. K., et al., *J. Med. Chem.* 1996, 39, 46-55.

$^1$H-NMR (CDCl$_3$, 400 MHz): δ 10.85 (s, 1H), 7.84 (s, 1H), 6.63 (s, 1H), 5.99 (s, 1H), 3.95 (s, 3H)

Step II:

Methyl 5-chloro-2-hydroxy-4-[(4-methoxybenzyl)oxy]benzoate

To a solution of methyl 5-chloro-2,4-dihydroxybenzoate (0.41 g, 2 mmol) in acetone were added 1-(chloromethyl)-4-methoxybenzene (0.32 g, 2 mmol) and K$_2$CO$_3$ (0.28 g, 2 mmol). The reaction mixture was heated with reflux for 3 days, than cooled to room temperature. The inorganic material was removed by filtration. The solvent was distilled in vacuo, and the residue was recrystallized from methanol to afford white solid (0.37 g, 60%).

$^1$H-NMR (CDCl$_3$, 400 MHz): δ 10.89 (s, 1H), 7.82 (s, 1H), 7.37 (d, J=8.7 Hz, 2H), 6.92 (d, J=8.7 Hz, 2H), 6.56 (s, 1H), 5.09 (s, 2H), 3.92 (s, 3H), 3.82 (s, 3H)

Step III:

Methyl 5-chloro-4-[(4-methoxybenzyl)oxy]-2-[(2S)-oxiran-2-ylmethoxy]benzoate

A solution of methyl 5-chloro-2-hydroxy-4-[(4-methoxybenzyl)oxy]benzoate (0.37 g, 1.16 mmol), (2S)-oxiran-2-ylmethyl 3-nitrobenzenesulfonate (0.30 g, 1.16 mmol) and caesium carbonate (0.45 g, 1.4 mmol) in dimethylformamide (15 mL) was stirred at room temperature overnight. The mixture was partitioned between water and ethyl acetate, and the organic phase was washed twice with water and once with brine, and finally concentrated. The crude material was purified by flash chromatoghrphy on silica gel (eluent:ethyl acetate/n-heptane), yielding the titled compound (0.33, 74%).

$^1$H-NMR (CDCl$_3$, 400 MHz): δ 7.91 (s, 1H), 7.37 (d, J=8.7 Hz, 2H), 6.92 (dd, J=6.7, 2.0 Hz, 2H), 6.66 (s, 1H), 5.14 (m, 2H), 4.33 (dd, J=11.4, 2.6 Hz, 1H), 3.98 (dd, J=11.5, 5.1 Hz, 1H), 3.86 (s, 3H), 3.82 (s, 3H), 3.36 (m, 1H), 2.93-2.87 (m, 2H) APCI-MS: m/z 379 (MH+)

Step IV

Methyl 5-chloro-2-{[(2S)-3-(5-chloro-1'H,3H-spiro[1-benzofuran-2,4'-piperidin]-1'-yl)-2-hydroxypropyl]oxy}-4-[(4-methoxybenzyl)oxy]benzoate trifluoroacetate (salt)

A solution of 5-chloro-3H-spiro[1-benzofuran-2,4'-piperidine) (100 mg, 0.45 mmol) and methyl 5-chloro-4-[(4-methoxybenzyl)oxy]-2-[(2S)-oxiran-2-ylmethoxy]benzoate (170 mg, 0.45 mmol) in ethanol (5 mL) was refluxed for 6 h. The solvent was distilled off under reduced pressure. The residue was purified by HPLC (eluent: [acetonitrile/water +0.1% TFA]) to afford a colourless solid (218 mg, 67%).

APCI-MS: m/z 602 (MH+)

Step V:

5-chloro-2-{[(2S)-3-(5-chloro-1'H,3H-spiro[1-benzofuran-2,4'-piperidin]-1'-yl)-2-hydroxypropyl]oxy}-4-[(4-methoxybenzyl)oxy]benzoic acid hydrochloride To a mixture of methyl 5-chloro-2-{[(2S)-3-(5-chloro-1'H,3H-spiro[1-benzofuran-2,4'-piperidin]-1'-yl)-2-hydroxypropyl]oxy}-4-[(4-methoxybenzyl)oxy]benzoate trifluoroacetate (220 mg, 0.3 mmol) in ethanol (10 mL) was added a solution of potassium hydroxide (4 g) and water (4 mL). The mixture was stirred at room temperture for 3 hours, pH was adjusted to 1 with aqueous HCl (37%), extracted with ethyl acetate, dried with sodium sulphate. Volatiles was removed in vacuo, the subtitle compound (180 mg) required no further purification.

APCI-MS: m/z 588 (MH+)

Step VI:

(3S)-1-{5-chloro-2-{[(2S)-3-(5-chloro-1'H,3H-spiro[1-benzofuran-2,4'-piperidin]-1'-yl)-2-hydroxypropyl]oxy}-4-[(4-methoxybenzyl)oxy]benzoyl}pyrrolidin-3-ol trifluoroacetate A mixture of PS-carbodiimide (250 mg, 0.32 mmol) and dichloromethane (3 mL) was stirred at room temperature for 15 minutes, a solution of 5-chloro-2-{[(2S)-3-(5-chloro-1'H,3H-spiro[1-benzofuran-2,4'-piperidin]-1'-yl)-2-hydroxypropyl]oxy}-4-[(4-methoxybenzyl)oxy]benzoic acid hydrochloride (100 mg, 0.16 mmol) in NMP (0.5 mL) and dichloromethane (1 mL) was added, the mixture was stirred for 30 minutes, a solution of (3S)-pyrrolidin-3-ol (18 mg, 0.21 mmol) in dichloromethane (1 mL) was added. The mixture was stirred at room temperature overnight, filtrated, the filtrate was washed with brine, dried with sodium sulphate. Volatiles were removed in vacuo, the residue was purified by HPLC (acetonitrile/water, 0.1% trifluoroacetic acid), and gave (45 mg) of the subtitle compound.

APCI-MS: m/z 657 (MH$^+$)

Step VII:

(3S)-1-(5-chloro-2-{[(2S)-3-(5-chloro-1'H,3H-spiro 1-benzofuran-2,4'-piperidin]-1'-yl)-2-hydroxypropyl]oxy}-4-hydroxybenzoyl)pyrrolidin-3-ol trifluoroacetate To a solution of (3S)-1-{5-chloro-2-{[(2S)-3-(5-chloro-1'H,3H-spiro[1-benzofuran-2,4'-piperidin]-1'-yl)-2-hydroxypropyl]oxy}-4-[(4-methoxybenzyl)oxy]benzoyl}pyrrolidin-3-ol trifluoroacetate (45 mg, 0.05 mmol) in dichloromethane (3 mL) was added trifluoroacetic acid (0.3 mL). The mixture was stirred at room temperature for 20 minutes, volatiles was removed in vacuo. The residue was purified by HPLC (acetonitrile/water, 0.1% trifluoroacetic acid), and gave (22 mg, overall yield Steps V-VII 11%) of the subtitle compound.

$^1$H-NMR (acetone-d$_6$, 400 MHz): δ 7.24-7.22 (m, 2H); 7.13 (d, J=8.4 Hz, 1H); 6.87 (d, J=13.7 Hz, 1H); 6.77 (d, J=8.5 Hz, 1H); 4.56-4.46 (m, 2H); 4.44-4.39 (m, 1H); 4.17-4.02 (m, 2H); 3.87-3.72 (m, 2H); 3.70-3.60 (m, 2H); 3.60-3.26 (m, 7H); 3.16 (br. s, 2H); 2.45-2.16 (m, 4H); 2.03-1.80 (m, 2H). APCI-MS: m/z 537 (MH$^+$)

Example 100

3-{1[(2S)-3-(5-chloro-1'H,3H-spiro[1-benzofuran-2,4'-piperidin]-1'-yl)-2-hydroxypropyl]oxy}-4-{[(3S)-3-methoxypyrrolidin-1-yl]carbonyl)phenol trifluoroacetate Step I:

(2S)-1-(5-chloro-1'H,3H-spiro[1-benzofuran-2,4'-piperidin]-1'-yl)-3-(5-[(4-methoxybenzyl)oxy]-2-{[(3S)-3-methoxypyrrolidin-1-yl]carbonyl)phenoxy)propan-2-ol A mixture of PS-carbodiimide (277 mg, 0.35 mmol) and dichloromethane (3 mL) was stirred at room temperature for 15 minutes, a solution of 2-{[(2S)-3-(5-chloro-1'H,3H-spiro[1-benzofuran-2,4'-piperidin]-1'-yl)-2-hydroxypropyl]oxy}-4-[(4-methoxybenzyl)oxy]benzoic acid hydrochloride (100 mg, 0.16 mmol) in NMP (0.5 mL) and dichloromethane (1 mL) was added, the mixture was stirred for 30 minutes, a solution of (3S)-3-methoxypyrrolidine (27 mg, 0.27 mmol) in dichloromethane (1 mL) was added. The mixture was stirred at room temperature overnight, filtrated, the filtrate was washed with brine, dried with sodium sulphate. Volatiles were removed in vacuo, the residue was purified by HPLC (acetonitrile/water, 0.025% ammonium hydroxid) and gave (35 mg) of the subtitle compound.

APCI-MS: m/z 637 (MH$^+$)

Step II:

3-{[(2S)-3-(5-chloro-1'H,3H-spiro[1-benzofuran-2,4'-piperidin]-1'-yl)-2-hydroxypropyl]oxy}-4-{[(3S)-3-methoxypyrrolidin-1-yl]carbonyl}phenol trifluoroacetate To a solution of (2S)-1-(5-chloro-1'H,3H-spiro[1-benzofuran-2,4'-piperidin]-1'-yl)-3-(5-[(4-methoxybenzyl)oxy]-2-{[(3S)-3-methoxypyrrolidin-1-yl]carbonyl}phenoxy)propan-2-ol (35 mg, 0.05 mmol) in dichloromethane (3 mL) was added trifluoroacetic acid (0.3 mL). The mixture was stirred at room temperature for 2 hours, volatiles were removed and the residue was purified by HPLC (acetonitrile/water, 0.1% trifluoroacetic acid) and gave 25 mg (overall yield Steps I-II 25%) of the title compound.

$^1$H-NMR (acetone-d$_6$, 400 MHz): δ 7.23 (s, 1H); 7.16-7.10 (m, 2H); 6.77 (d, J=8.7 Hz, 1H); 6.64-6.61 (m, 1H); 6.52 (dd, J=2.1, 8.2 Hz, 1H); 4.54-4.45 (m, 1H); 4.17-3.95 (m, 3H); 3.88-3.70 (m, 2H); 3.69-3.60 (m, 2H); 3.60-3.42 (m, 4H); 3.40-3.31 (m, 3H); 3.26 (s, 2H); 3.17 (br. s, 2H); 2.46-2.17 (m, 4H); 2.10-1.92 (m, 2H). APCI-MS: m/z 517 (MH$^+$)

Example 101

3-{[(2S)-3-(5-chloro-1'H,3H-spiro[1-benzofuran-2,4'-piperidin]-1'-yl)-2-hydroxypropyl]oxy}-4-{[(2R)-2-(hydroxymethyl)pyrrolidin-1-yl]carbonyl)phenol trifluoroacetate Step I:

(2S)-1-(5-chloro-1'H,3H-spiro[1-benzofuran-2,4'-piperidin]-1'-yl)-3-{2-{{[(2R)-2-(hydroxymethyl)pyrrolidin-1-yl]carbonyl}-5-[(4-methoxybenzyl)oxy]phenoxy}propan-2-ol A mixture of PS-carbodiimide (280 mg, 0.36 mmol) and dichloromethane (2.5 mL) was stirred at room temperature for 15 minutes, a solution of 2-{[(2S)-3-(5-chloro-1'H,3H-spiro[1-benzofuran-2,4'-piperidin]-1'-yl)-2-hydroxypropyl]oxy}-4-[(4-methoxybenzyl)oxy]benzoic acid hydrochloride (100 mg, 0.16 mmol) in NMP (0.6 mL) and dichloromethane (1 mL) was added, the mixture was stirred for 30 minutes, a solution of (2R)-pyrrolidin-2-ylmethanol (30 mg, 0.30 mmol) in dichloromethane (1 mL) was added. The mixture was stirred at room temperature overnight and filtered. Volatiles were removed in vacuo, the residue was purified by HPLC (acetonitrile/water, 0.025% ammonium hydroxid) and gave (51 mg) of the subtitle compound.

APCI-MS: m/z 637 (MH$^+$)

Step II:

3-{[(2S)-3-(5-chloro-1'H,3H-spiro[1-benzofuran-2,4'-piperidin]-1'-yl)-2-hydroxypropyl]oxy}-4-{[(2R)-2-(hydroxymethyl)pyrrolidin-1-yl]carbonyl}phenol trifluoroacetate To a solution of (2S)-1-(5-chloro-1'H,3H-spiro[1-benzofuran-2,4'-piperidin]-1'-yl)-3-{2-{[(2R)-2-(hydroxymethyl)pyrrolidin-1-yl]carbonyl}-5-[(4-methoxybenzyl)oxy]phenoxy}propan-2-ol (51 mg, 0.08 mmol) in dichloromethane (3 mL) was added trifluoroacetic acid (0.3 mL). The mixture was stirred at room temperature for 30 minutes, volatiles were removed, the residue was purified by HPLC (acetonitrile/water, 0.1% trifluoroacetic acid) and gave 20 mg (overall yield Steps I-II 20%) of the title compound.

$^1$H-NMR (acetone-d$_6$, 400 MHz): δ 7.23 (s, 1H); 7.15-7.10 (m, 2H); 6.77 (d, J=8.6 Hz, 1H); 6.60-6.57 (m, 1H); 6.50 (dd, J=2.1, 8.2 Hz, 1H); 4.58-4.48 (m, 1H), 4.32-4.24 (m, 1H); 4.14-4.06 (m, 2H); 3.90-3.60 (m, 4H); 3.60-3.40 (m, 4H); 3.32-3.20 (m, 2H); 3.16 (br. s, 2H); 2.46-2.16 (m, 4H); 1.95-1.66 (m, 2H); 1.35-1.29 (m, 2H). APCI-MS: m/z 517 (MH$^+$)

Example 102

3-{[(2S)-3-(5-chloro-1'H,3H-spiro[1-benzofuran-2,4'-piperidin]-1'-yl)-2-hydroxypropyl]oxy}-4-{[(2S)-2-(hydroxymethyl)pyrrolidin-1-yl]carbonyl}phenol trifluoroacetate The title compound was prapared as described in Example 101 using (2R)-pyrrolidin-2-ylmethanol.

$^1$H-NMR (acetone-d$_6$, 400 MHz): δ 7.23 (s, 1H); 7.16-7.05 (m, 2H); 6.77 (d, J=8.5 Hz, 1H); 6.64-6.57 (m, 1H); 6.50 (dd, J=2.2, 8.4 Hz, 1H); 4.60-4.51 (m, 1H), 4.30-4.22 (m, 1H); 4.14-4.10 (m, 2H); 3.90-3.72 (m, 2H); 3.70-3.24 (m, 8H); 3.17 (br. s, 2H); 2.44-2.14 (m, 4H); 1.92-1.68 (m, 4H). APCI-MS: m/z 517 (MH$^+$)

Example 103

3-{[(2S)-3-(5-chloro-1'H,3H-spiro[1-benzofuran-2,4'-piperidin]-1'-yl)-2-hydroxypropyl]oxy}-4-{[3-(hydroxymethyl)pyrrolidin-1-yl]carbonyl}phenol trifluoroacetate The title compound was prapared as described in Example 101 pyrrolidin-3-ylmethanol hydrochloride.
$^1$H-NMR (acetone-$d_6$, 400 MHz): δ 7.23 (s, 1H); 7.16-7.08 (m, 2H); 6.80-6.75 (m, 1H); 6.67-6.62 (m, 1H); 6.53-6.48 (m, 1H); 4.52-4.44 (m, 1H), 4.17-4.02 (m, 2H); 3.90-3.10 (m, 15H); 2.50-2.16 (m, 4H); 2.02-1.68 (m, 2H). APCI-MS: m/z 517 (MH$^+$)

Example 104

1-(2-{[(2S)-3-(5-chloro-1'H,3H-spiro[1-benzofuran-2,4l-piperidin]-1'-yl)-2-hydroxypropyl]oxy}-4-hydroxybenzoyl)-D-prolinamide trifluoroacetate Step I:

1-{2-{[(2S)-3-(chloro-1'H,3H-spiro[1-benzofuran-2,4'-piperidin]-1'-yl)-2-hydroxypropyl]oxy}-4-[(4-methoxybenzyl)oxy]benzoyl}-D-prolinamide
A mixture of PS-carbodiimide (280 mg, 0.36 mmol) and dichloromethane (2.5 mL) was stirred at room temperature for 15 minutes, a solution of 2-{[(2S)-3-(5-chloro-1'H,3H-spiro[1-benzofuran-2,4'-piperidin]-1'-yl)-2-hydroxypropyl]oxy}-4-[(4-methoxybenzyl)oxy]benzoic acid hydrochloride (100 mg, 0.16 mmol) in NMP (0.6 mL) and dichloromethane (1 mL) was added, the mixture was stirred for 30 minutes, a solution of D-prolinamide (29 mg, 0.25 mmol) in dichloromethane (1 mL) was added. The mixture was stirred at room temperture overnight and filtrated. Volatiles were removed in vacuo, the residue was purified by HPLC (acetonitrile/water, 0.025% ammonium hydroxid) and gave (68 mg) of the subtitle compound.
APCI-MS: m/z 650 (MH$^+$)

Step II:

1-(2-{[(2S)-3-(5-chloro-1'H,3H-spiro[1-benzofuran-2,4'-piperidin]-1'-yl)-2-hydroxypropyl]oxy}-4-hydroxybenzoyl)-D-prolinamide trifluoroacetate
To a solution of 1-{2-{[(2S)-3-(5-chloro-1'H,3H-spiro[1-benzofuran-2,4'-piperidin]-1'-yl)-2-hydroxypropyl]oxy}-4-[(4-methoxybenzyl)oxy]benzoyl}-D-prolinamide (68 mg, 0.10 mmol) in dichloromethane was added trifluoroacetic acid (0.3 mL). The mixture was stirred at room temperature for 30 minutes, volatiles were removed, the residue was purified by HPLC (acetonitrile/water, 0.1% trifluoroacetic acid) and gave 28 mg (overall yield Steps I-II 27%) of the title compound.
$^1$H-NMR (acetone-$d_6$, 400 MHz, 2 rotamers): δ 7.23 (s, 1H); 7.22-7.16 and 6.64-6.54 (m, 3H); 7.15-7.10 and 7.06-7.02 (m, 2H); 6.77 (d, J=8.4 Hz, 1H); 6.53-6.48 and 6.46-6.41 (m, 1H); 4.62-4.47 (m, 2H); 4.16-4.02 (m, 2H); 3.92-3.42 (m, 8H); 3.34-3.22 (m, 2H); 3.16 (br. s, 2H); 2.46-2.14 (m, 4H); 2.12-1.76 (m, 2H). APCI-MS: m/z 530 (MH$^+$)

Example 105

N-(4-hydroxy-2-{[(2S)-2-hydroxy-3-(1'H,3H-spiro[1-benzofuran-2,4'-piperidin]-1'-yl)propyl]oxy)phenyl)acetamide trifluoroacetate (salt)

The title compound was prepared from 3H-spiro[1-benzofuran-2,4'-piperidine] as described in Example 27.
$^1$H-NMR (acetone-$d_6$, 400 MHz): δ 8.52 (s, 1H), 7.93 (d, J=8.7 Hz, 1H), 7.21 (d, J=7.2 Hz, 1H), 7.12 (t, J=7.7 Hz, 1H), 6.86 (t, J=7.3 Hz, 1H), 6.75 (d, J=7.9 Hz, 1H), 6.53 (d, J=2.4 Hz, 1H), 6.40 (dd, J=8.8, 2.4 Hz, 1H), 4.53 (m, 1H), 4.08 (m, 2H), 3.94-3.39 (m, 6H), 3.15 (s, 2H), 2.45-2.15 (m, 4H), 2.09 (s, 3H) APCI-MS: m/z 413 (MH$^+$).

Example 106

N-(4-hydroxy-2-{[(2S)-2-hydroxy-3-(5-methyl-1'H,3H-spiro[1-benzofuran-2,4'-piperidin]-1'-yl)propyl]oxy phenyl)acetamide trifluoroacetate (salt)

The title compound was prepared from 5-Methyl-3H-spiro[1-benzofuran-2,4'-piperidine] as described in Example 27.
$^1$H-NMR (acetone-$d_6$, 400 MHz): δ 8.56 (s, 1H), 7.90 (d, J=8.7 Hz, 1H), 7.01 (s, 1H), 6.92 (d, J=8.1 Hz, 1H), 6.63 (d, J=8.1 Hz, 1H), 6.53 (d, J=2.4 Hz, 1H), 6.41 (dd, J=8.7, 2.4 Hz, 1H), 4.52 (s, 1H), 4.07 (d, J=3.8 Hz, 2H), 3.92-3.38 (m, 6H), 3.09 (s, 2H), 2.42-2.13 (m, 4H), 2.24 (s, 3H), 2.10 (s, 3H) APCI-MS: m/z 427 (MH$^+$).

Example 107

N-(5-chloro-2-{[(2S)-2-hydroxy-3-(1'H,3H-spiro[1-benzofuran-2,4'-piperidin]-1'-yl)propyl]oxy}-4-methoxyphenyl)acetamide trifluoroacetate (salt)

The title compound was prepared from 3H-spiro[1-benzofuran-2,4'-piperidine] as described in Example 83.
$^1$H-NMR (DMSO-$d_6$, 400 MHz): δ 9.61 (br. s, 1H), 9.02 (m, 1H), 7.91 (s, 1H), 7.21 (d, J=7.3 Hz, 1H), 7.11 (m, 1H), 6.85 (m, 2H), 6.77 (d, J=7.9 Hz, 1H), 4.38 (m, 1H), 4.06 (m, 2H), 3.85 (s, 3H), 3.66-3.12 (m, 6H), 3.08 (s, 2H), 2.23-1.94 (m, 7H) APCI-MS: m/z 461 (MH$^+$).

Example 108

N-(5-chloro-4-hydroxy-2-{[(2S)-2-hydroxy-3-(1'H,3H-spiro[1-benzofuran-2,4'-piperidin]-1'-yl)propyl]oxy}phenyl)acetamide trifluoroacetate (salt)

To a stirred solution of N-(5-chloro-2-{[(2S)-2-hydroxy-3-(1'H,3H-spiro[1-benzofuran-2,4'-piperidin]-1'-yl)propyl]oxy}-4-methoxyphenyl)acetamide trifluoroacetate (116 mg, 0.2 mmol) in dichloromethane (50 ml) at 0° C. was added a solution of BBr$_3$ (1 M in dichloromethane, 2 ml, 2 mmol) under argon. The stirring was continued at 0° C. for 6 h, then the reaction mixture was quenched with methanol. The solvent was removed in vacuo, the resudue purified by HPLC (eluent: [acetonitrile/water+0.1% TFA]) to afford colourless solid (12 mg, 10%).
$^1$H-NMR (acetone-$d_6$, 400 MHz): δ 8.62 (s, 1H), 8.26 (s 1H), 7.21 (d, J=7.3 Hz, 1H), 7.12 (t, J=7.7 Hz, 1H), 6.86 (t, J=7.4 Hz, 1H), 6.75 (m, 2H), 4.55 (m, 1H), 4.10 (m, 2H), 3.93-3.19 (m, 8H), 3.16 (s, 2H), 2.43-2.15 (m, 4H), 2.11 (s, 3H) APCI-MS: m/z 447 (MH$^+$).

Example 109

(3S)-N-(2-{[(2S)-3-(5-chloro-1'H,3H-spiro[1-benzofuran-2,4'-piperidin]-1'-yl)-2-hydroxypropyl]oxy}-4-methoxyphenyl)-3-hydroxypyrrolidine-1-carboxamide trifluoroacetate (salt)

The title compound was prepared using 6-methoxy-1,3-benzoxazol-2(3H)-one as described in Example 84.
$^1$H-NMR (acetone-$d_6$, 400 MHz): δ 7.74 (m, 1H), 7.23 (s, 1H), 7.13 (dd, J=8.5, 2.2 Hz, 1H), 7.03 (s, 1H), 6.77 (d, J=8.5

Hz, 1H), 6.61 (d, J=2.7 Hz, 1H), 6.49 (dd, J=8.8, 2.7 Hz, 1H), 4.59 (m, 1H), 4.47 (m, 1H), 4.14 (m, 2H), 3.80 (m, 2H), 3.75 (s, 3H), 3.64-3.40 (m, 8H), 3.16 (s, 2H), 2.44-2.16 (m, 4H), 2.09-1.89 (m, 2H) APCI-MS: m/z 532 (MH$^+$).

Example 110

(3S)-N-(2-{[(2S)-3-(5-chloro-1'H,3H-spiro[1-benzofuran-2,4'-piperidin]-1'-yl)-2-hydroxypropyl]oxy}-4-hydroxyphenyl)-3-hydroxypyrrolidine-1-carboxamide trifluoroacetate (salt)

To a stirred solution of (3S)-N-(2-{[(2S)-3-(5-chloro-1'H,3H-spiro[1-benzofuran-2,4'-piperidin]-1'-yl)-2-hydroxypropyl]oxy}-4-methoxyphenyl)-3-hydroxypyrrolidine-1-carboxamide trifluoroacetate (59 mg, 0.09 mmol) in dichloromethane (50 ml) at 0° C. was added a solution of BBr$_3$ (1 M in dichloromethane, 1.8 ml, 1.8 mmol) under argon. The stirring was continued at 0° C. for 4 h, then the reaction mixture was quenched with methanol. The solvent was removed in vacuo, the resudue purified by HPLC (eluent: [acetonitrile/water+0.1% TFA]) to afford colourless solid (30 mg, 53%).

$^1$H-NMR (acetone-d$_6$, 400 MHz): δ 7.52 (m, 1H), 7.23 (s, 1H), 7.13 (dd, J=8.5, 2.3 Hz, 1H), 6.99 (s, 1H), 6.77 (d, J=8.5 Hz, 1H), 6.57 (d, J=2.5 Hz, 1H), 6.39 (dd, J=8.6, 2.6 Hz, 1H), 4.56 (m, 1H), 4.46 (m, 1H), 4.07 (m, 2H), 3.90-3.21 (m, 10H), 3.16 (s, 2H), 2.42-2.16 (m, 4H), 2.09-1.90 (m, 2H) APCI-MS: m/z 518 (MH$^+$).

Example 111

(3S)-1-(4-hydroxy-2-{[(2S)-2-hydroxy-3-(1'H,3H-spiro[1-benzofuran-2,4'-piperidin]-1'-yl)propyl]oxy}benzoyl)pyrrolidin-3-ol trifluoroacetate (salt)

Step I:

Methyl 2-{[(2S)-2-hydroxy-3-(1'H,3H-spiro[1-benzofuran-2,4'-piperidin]-1'-yl)propyl]oxy}-4-[(4-methoxybenzyl)oxy]benzoate trifluoroacetate (salt)

A solution of 3H-spiro[1-benzofuran-2,4'-piperidine] (50 mg, 0.26 mmol) and methyl methyl 4-[(4-methoxybenzyl)oxy]-2-[(2S)-oxiran-2-ylmethoxy]benzoate (91 mg, 0.26 mmol) in ethanol (3 mL) was refluxed for 6 h. The solvent was distilled off under reduced pressure. The residue was purified by HPLC (eluent: [acetonitrile/water+0.1% TFA]) to afford a colourless solid (103 mg, 61%).

APCI-MS: m/z 534 (MH$^+$)

Step II:

2-{[(2S)-2-hydroxy-3-(1'H,3H-spiro[1-benzofuran-2,4'-piperidin]-1'-yl)propyl]oxy}-4-[(4-methoxybenzyl)oxy]benzoic acid hydrochloride To a mixture of methyl 2-{[(2S)-2-hydroxy-3-(1'H,3H-spiro[1-benzofuran-2,4'-piperidin]-1'-yl)propyl]oxy}-4-[(4-methoxybenzyl)oxy]benzoate trifluoroacetate (103 mg, 0.16 mmol) in ethanol (5 mL) was added 10 N aq. NaOH solution (1 ml) and water (1 ml). The mixture was stirred at room temperture overnight, pH was adjusted to 1 with aqueous HCl (2 M), extracted with ethyl acetate, dried with sodium sulphate. Volatiles was removed in vacuo to afford the subtitle compound, which was used without purification.

APCI-MS: m/z 520 (MH$^+$)

Step III:

(3S)-1-(4-hydroxy-2-{[(2S)-2-hydroxy-3-(1'H,3H-spiro[1-benzofuran-2,4'-piperidin]-1'-yl)propyl]oxy}benzoyl)pyrrolidin-3-ol trifluoroacetate (salt)

A mixture of PS-carbodiimide (250 mg, 0.32 mmol) and dichloromethane (5 mL) was stirred at room temperature for 15 minutes, then 2-{[(2S)-2-hydroxy-3-(1'H,3H-spiro[1-benzofuran-2,4'-piperidin]-1'-yl)propyl]oxy}-4-[(4-methoxybenzyl)oxy]benzoic acid hydrochloride (89 mg, 0.16 mmol) was added, and the mixture was stirred for 30 minutes. A solution of (3S)-pyrrolidin-3-ol (14 mg, 0.16 mmol) in dichloromethane (1 mL) was added. The mixture was stirred at room temperture for 24 h, and filtered. Trifluoroacetic acid (10% in dichloromethane, 5 ml) was added, and the stirring was continued for 1 h at room temperature. Volatiles were removed in vacuo, the residue was purified by HPLC (acetonitrile/water, 0.1% trifluoroacetic acid) and gave (14 mg, overall yield Steps II-III 15%) of the title compound.

$^1$H-NMR (acetone-d$_6$, 400 MHz): δ 7.20 (d, J=7.2 Hz, 1H), 7.12 (m, 2H), 6.85 (t, J=7.4 Hz, 1H), 6.76 (d, J=7.9 Hz, 1H), 6.60 (dd, J=7.4, 2.0 Hz, 1H), 6.51 (dt, J=8.2, 2.4 Hz, 1H), 4.49 (s, 2H), 4.40 (m, 1H), 4.17-4.00 (m, 3H), 3.87-3.25 (m, 8H), 3.12 (s, 2H), 2.45-2.12 (m, 4H), 2.10-1.85 (m, 2H) APCI-MS: m/z 469 (MH$^+$).

Example 112

2-{[(2S)-3-(5-chloro-1'H,3H-spiro[1-benzofuran-2,4'-piperidin]-1'-yl)-2-hydroxypropyl]oxy)-5-methylbenzoic acid hydrochloride Step I:

Methyl 5-methyl-2-[(2S)-oxiran-2-ylmethoxy]benzoate

A solution of methyl 2-hydroxy-5-methylbenzoate (0.166 g, 1 mmol), (2S)-oxiran-2-ylmethyl 3-nitrobenzenesulfonate (0.26 g, 1 mmol) and caesium carbonate (0.39 g, 1.2 mmol) in dimethylformamide (5 mL) was stirred at room temperature overnight. The mixture was partitioned between water and ethyl acetate, and the organic phase was washed twice with water and once with brine, and finally concentrated. The crude material was purified by flash chromatoghrphy on silica gel (eluent:ethyl acetate/n-heptane), yielding the titled compound (0.16 g, 72%) as colourless oil.

$^1$H-NMR (CDCl$_3$, 400 MHz): δ 7.61 (d, J=2.0 Hz, 1H), 7.25 (d, J=9.9 Hz, 1H), 6.89 (d, J=8.4 Hz, 1H), 4.28 (dd, J=11.2, 3.0 Hz, 1H), 4.07 (dd, J=11.2, 4.9 Hz, 1H), 3.89 (s, 3H), 3.38 (m, 1H), 2.89 (m, 2H), 2.30 (s, 3H)

Step II:

Methyl 2-{[(2S)-3-(5-chloro-1'H,3H-spiro[1-benzofuran-2,4'-piperidin]-1'-yl)-2-hydroxypropyl]oxy}-5-methylbenzoate trifluoroacetate (salt)

A solution of 5-chloro-3H-spiro[1-benzofuran-2,4'-piperidine] (112 mg, 0.5 mmol) and methyl 5-methyl-2-[(2S)-oxiran-2-ylmethoxy]benzoate (111 mg, 0.5 mmol) in ethanol (5 mL) was refluxed for 6 h. The solvent was distilled off under reduced pressure. The residue was purified by HPLC (eluent: [acetonitrile/water+0.1% TFA]) to afford a colourless solid (153 mg, 54%).

APCI-MS: m/z 446 (MH$^+$)

Step III:

2-{[(2S)-3-(5-chloro-1'H,3H-spiro[1-benzofuran-2,4'-piperidin]-1'-yl)-2-hydroxypropyl]oxy)-5-methylbenzoic acid hydrochloride To a mixture of methyl 2-{[(2S)-3-(5-chloro-1'H,3H-spiro[1-benzofuran-2,4'-piperidin]-1'-yl)-2-hydroxypropyl]oxy}-

5-methylbenzoate trifluoroacetate (153 mg, 0.27 mmol) in ethanol (5 mL) was added 10 N aq. NaOH solution (1 ml) and water (1 ml). The mixture was stirred at room temperture for 3 hours, pH was adjusted to 1 with aqueous HCl (2 M), extracted with ethyl acetate, dried with sodium sulphate. Volatiles was removed in vacuo to afford the subtitle compound (123 mg, 96%).

$^1$H-NMR (acetone-$d_6$, 400 MHz): δ 7.68 (d, J=2.1 Hz, 1H), 7.36 (dd, J=8.6, 2.1 Hz, 1H), 7.22 (s, 1H), 7.11 (m, 2H), 6.76 (d, J=8.5 Hz, 1H), 4.68 (m, 1H), 4.27 (m, 1H), 4.17 (m, 1H), 3.72 (br. s, 2H), 3.67 (d, J=13.7 Hz, 1H), 3.51 (br. s, 2H), 3.43 (dd, J=13.5, 8.8 Hz, 1H), 3.19 (s, 2H), 2.47 (br. s, 2H), 2.30 (s, 3H), 2.22 (br. s, 2H) APCI-MS: m/z 423 (MH$^+$)

Example 113

2-{[(2S)-3-(5-chloro-1'H,3H-spiro[1-benzofuran-2,4'-piperidin]-1'-yl)-2-hydroxypropyl]oxy}-4-methoxybenzoic acid hydrochloride The title compounds was prepared using methyl 2-hydroxy-4-methoxybenzoate as described in Example 112.

$^1$H-NMR (acetone-$d_6$, 400 MHz): δ 7.89 (d, J=8.8 Hz, 1H), 7.23 (m, 1H), 7.12 (dd, J=8.5, 2.3 Hz, 1H), 6.76 (d, J=8.6 Hz, 2H), 6.74 (d, J=2.3 Hz, 2H), 6.65 (dd, J=8.8, 2.3 Hz, 1H), 4.70 (m, 1H), 4.31 (m, 1H), 4.22 (m, 1H), 3.89 (s, 3H), 3.73 (br. s, 2H), 3.67 (dd, J=13.4, 1.9 Hz, 1H), 3.58-3.45 (m, 2H), 3.41 (dd, J=13.5, 8.7 Hz, 1H), 3.19 (s, 2H), 2.49 (m, 2H), 2.24 (br. d, J=14.0 Hz, 2H) APCI-MS: m/z 448 (MH$^+$)

Example 114

(3S)-1-(2-{[(2S)-3-(5-chloro-1'H,3H-spiro[1-benzofuran-2,4'-piperidin]-1'-yl)-2-hydroxypropyl]oxy)-5-methylbenzoyl)pyrrolidin-3-ol trifluoroacetate (salt)

A mixture of PS-carbodiimide (78 mg, 0.1 mmol) and dichloromethane (5 mL) was stirred at room temperature for 15 minutes, then 2-{[(2S)-3-(5-chloro-1'H,3H-spiro[1-benzofuran-2,4'-piperidin]-1'-yl)-2-hydroxypropyl]oxy}-5-methylbenzoic acid hydrochloride (23 mg, 0.05 mmol) was added, and the mixture was stirred for 30 minutes. A solution of (3S)-pyrrolidin-3-ol (5 mg, 0.05 mmol) in dichloromethane (1 mL) was added. The mixture was stirred at room temperture for 24 h, and filtered. Volatiles were removed in vacuo, the residue was purified by HPLC (acetonitrile/water, 0.1% trifluoroacetic acid) and gave (6 mg, 21%) of the title compound.

$^1$H-NMR (acetone-$d_6$, 400 MHz): δ 7.17 (s, 2H), 7.08 (d, J=8.5 Hz, 2H), 7.04 (d, J=1.6 Hz, 2H), 6.99 (dd, J=8.3, 5.3 Hz, 2H), 6.70 (d, J=8.4 Hz, 1H), 4.49 (m, 1H), 4.39 (m, 1H), 4.15 (m, 2H), 3.98 (m, 3H), 3.63 (dd, J=9.1, 5.4 Hz, 2H), 3.59-3.40 (m, 3H), 3.28 (m, 2H), 3.04 (s, 3H), 2.75-2.49 (m, 4H), 2.27 (d, J=2.2 Hz, 4H) APCI-MS: m/z 501 (MH$^+$)

Example 115

(3S)-1-(2-{[(2S)-3-(5-chloro-1'H,3H-spiro[1-benzofuran-2,4'-piperidin]-1'-yl)-2-hydroxypropyl]oxy}-4-methoxybenzoyl)pyrrolidin-3-ol trifluoroacetate (salt)

The title compound prepared from 2-{[(2S)-3-(5-chloro-1'H,3H-spiro[1-benzofuran-2,4'-piperidin]-1'-yl)-2-hydroxypropyl]oxy}-4-methoxybenzoic acid hydrochloride as described in Example 114.

$^1$H-NMR (acetone-$d_6$, 400 MHz): δ 7.23 (s, 1H), 7.19 (dd, J=8.4, 3.1 Hz, 1H), 7.13 (d, J=8.6 Hz, 1H), 6.77 (d, J=8.5 Hz, 1H), 6.67 (t, J=2.4 Hz, 1H), 6.60 (dt, J=8.4, 2.2 Hz, 1H), 4.51 (m, 2H), 4.39 (m, 1H), 4.22-4.12 (m, 2H), 4.08 (m, 1H), 3.83 (s, 3H), 3.85-3.25 (m, 8H), 3.16 (s, 2H), 2.35 (br. s, 2H), 2.21 (br. s, 2H) APCI-MS: m/z 517 (MH$^+$)

Example 116

5-chloro-2-{[(2S)-3-(5-chloro-1'H,3H-spiro[1-benzofuran-2,4'-piperidin]-1'-yl)-2-hydroxypropyl]oxy) benzoic acid hydrochloride The title compounds was prepared using methyl 5-chloro-2-hydroxybenzoate as described in Example 112.

$^1$H-NMR (acetone-$d_6$, 400 MHz): δ 7.81 (d, J=2.8 Hz, 1H), 7.57 (dd, J=9.0, 2.8 Hz, 1H), 7.26 (d, J=9.0 Hz, 1H), 7.23 (s, 1H), 7.13 (dd, J=8.5, 2.2 Hz, 1H), 6.77 (d, J=8.5 Hz, 1H), 4.66 (m, 2H), 4.32 (m, 1H), 4.19 (m, 1H), 3.73 (br. s, 2H), 3.69 (d, J=13.3 Hz, 1H), 3.54 (br. s, 2H), 3.45 (dd, J=13.5, 8.9 Hz, 1H), 3.20 (s, 2H), 2.46 (br. s, 2H), 2.24 (br. d, J=12.3 Hz, 2H) APCI-MS: m/z 452 (MH$^+$)

Example 117

(3S)-1-(5-chloro-2-{[(2S)-3-(5-chloro-1'H,3H-spiro[1-benzofuran-2,4'-piperidin]-1'-yl)-2-hydroxypropyl]oxy}benzoyl)pyrrolidin-3-ol trifluoroacetate (salt)

The title compound prepared from 5-chloro-2-{[(2S)-3-(5-chloro-1'H,3H-spiro[1-benzofuran-2,4'-piperidin]-1'-yl)-2-hydroxypropyl]oxy}benzoic acid hydrochloride as described in Example 114.

$^1$H-NMR (acetone-$d_6$, 400 MHz): δ 7.39 (dt, J=8.8, 2.4 Hz, 1H), 7.25 (dd, J=4.1, 2.8 Hz, 1H), 7.23 (s, 1H), 7.15 (d, J=8.7 Hz, 1H), 7.12 (s, 1H), 6.77 (d, J=8.5 Hz, 1H), 4.53 (m, 2H), 4.42 (m, 1H), 4.23-4.06 (m, 3H), 3.76-3.14 (m, 12H), 2.33 (br. s, 2H), 2.23 (br. s, 2H) APCI-MS: m/z 521 (MH$^+$)

Example 118

2-{[(2S)-3-(5-chloro-1'H,3H-spiro[1-benzofuran-2,4'-piperidin]-1'-yl)-2-hydroxypropyl]oxy)-5-fluorobenzoic acid hydrochloride The title compounds was prepared using methyl 5-fluoro-2-hydroxybenzoate as described in Example 112.

$^1$H-NMR (acetone-$d_6$, 400 MHz): δ 7.56 (dd, J=8.9, 3.2 Hz, 1H), 7.35 (m, 1H), 7.27 (dd, J=9.2, 4.4 Hz, 1H), 7.13 (dd, J=8.4, 2.1 Hz, 1H), 6.76 (d, J=8.5 Hz, 1H), 4.68 (m, 1H), 4.29 (m, 1H), 4.18 (m, 1H), 3.72 (br. s, 2H), 3.68 (br. d, J=13.1 Hz, 3H), 3.51 (br. s, 1H), 3.41 (dd, J=13.4, 9.0 Hz, 3H), 3.19 (s, 2H), 2.53 (br. s, 2H), 2.22 (br. s, 2H) APCI-MS: m/z 436 (MH$^+$)

Example 119

(3S)-1-(2-{[(2S)-3-(5-chloro-1'H,3H-spiro[1-benzofuran-2,4'-piperidin]-1'-yl)-2-hydroxypropyl]oxy)-5-fluorobenzoyl)pyrrolidin-3-ol trifluoroacetate (salt)

The title compound prepared from 5-fluoro-2-{[(2S)-3-(5-chloro-1'H,3H-spiro[1-benzofuran-2,4'-piperidin]-1'-yl)-2-hydroxypropyl]oxy}benzoic acid hydrochloride as described in Example 114.

¹H-NMR (acetone-d₆, 400 MHz): δ 7.23 (s, 1H), 7.16 (m, 2H), 7.12 (s, 1H), 7.04 (m, 1H), 6.77 (d, J=8.5 Hz, 1H), 4.51 (m, 2H), 4.41 (m, 1H), 4.19-4.04 (m, 3H), 3.70-3.13 (m, 12H), 2.32 (br. s, 2H), 2.23 (br. s, 2H) APCI-MS: m/z 505 (MH⁺)

Example 120

N-(2-{[(2S)-3-(5-chloro-1'H,3H-spiro[1-benzofuran-2,4'-piperidin]-1'-yl)-2-hydroxypropyl]oxy}phenyl) pyrrolidine-1-carboxamide trifluoroacetate (salt)

The title compound was prepared using 1,3-benzoxazol-2 (3H)-one and pyrrolidine as described in Example 84.
¹H-NMR (acetone-d₆, 400 MHz): δ 8.14 (m, 1H), 7.23 (s, 2H), 7.13 (dd, J=8.5, 2.2 Hz, 1H), 6.99 (m, 1H), 6.90 (m, 2H), 6.76 (d, J=8.6 Hz, 1H), 4.64 (m, 1H), 4.13 (m, 1H), 3.82 (br. s, 2H), 3.61 (br. d, J=13.1 Hz, 2H), 3.55-3.42 (m, 8H), 3.18 (s, 2H), 2.35 (br. s, 2H), 2.25 (br. s, 2H), 1.93 (m, 4H) APCI-MS: m/z 486 (MH⁺).

Example 121

Methyl 4-(acetylamino)-3-{[(2S)-3-(5-chloro-1'H, 3H-spiro[1-benzofuran-2,4'-piperidin]-1'-yl)-2-hydroxypropyl]oxy)benzoate trifluoroacetate (salt)

Step I:
Methyl 4-(acetylamino)-3-hydroxybenzoate
A solution of methyl 3-hydroxy-4-nitrobenzoate (0.78 g, 3.96 mmol) in THF (40 ml) with Pd on charcoal (10%, 0.15 g) was stirred in the atmosphere of hydrogen at atmospheric pressure overnight. The mixture was filtered through celite. The solvent was removed in vacuo. The residue was taken into water (20 ml), and acetic anhydride (0.5 ml, 5.29 mmol) was added. The mixture was vigorously stirred at 65° C. for 30 min. After cooling to room temperature, the precipitate was collected by filtration, washed with water, and dried. White powder (0.64 g, 77%).

Step II:
Methyl 4-(acetylamino)-3-[(2S)-oxiran-2-ylmethoxy]benzoate
A solution of methyl 4-(acetylamino)-3-hydroxybenzoate (0.209 g, 1 mmol), (2S)-oxiran-2-ylmethyl 3-nitrobenzenesulfonate (0.26 g, 1 mmol) and caesium carbonate (0.39 g, 1.2 mmol) in dimethylformamide (5 mL) was stirred at room temperature overnight. The mixture was partitioned between water and ethyl acetate, and the organic phase was washed twice with water and once with brine, and finally concentrated. The crude material was purified by flash chromatoghrphy on silica gel (eluent:ethyl acetate/n-heptane), yielding the subtitle compound (96 mg, 36%) as colourless oil.
¹H-NMR (CDCl₃, 400 MHz): δ 8.45 (d, J=8.5 Hz, 1H), 8.12 (s, 1H), 7.69 (dd, J=8.5, 1.6 Hz, 1H), 7.54 (d, J=1.7 Hz, 1H), 4.43 (dd, J=11.3, 2.3 Hz, 1H), 3.96 (dd, J=11.3, 6.3 Hz, 1H), 3.89 (s, 3H), 3.41 (m, 1H), 2.96 (t, J=4.5 Hz, 1H), 2.79 (dd, J=4.7, 2.6 Hz, 1H), 2.24 (s, 3H) APCI-MS: m/z 266 (MH⁺).

Step III:
Methyl 4-(acetylamino)-3-{[(2S)-3-(5-chloro-1'H,3H-spiro [1-benzofuran-2,4'-piperidin]-1'-yl)-2-hydroxypropyl] oxy}benzoate trifluoroacetate (salt)
A solution of 5-chloro-3H-spiro[1-benzofuran-2,4'-piperidine] (81 mg, 0.36 mmol) and methyl 4-(acetylamino)-3-[(2S)-oxiran-2-ylmethoxy]benzoate (96 mg, 0.36 mmol) in ethanol (5 mL) was refluxed for 5 h. The solvent was distilled off under reduced pressure. The residue was purified by HPLC (eluent: [acetonitrile/water+0.1% TFA]) to afford a colourless solid (177 mg, 82%).
¹H-NMR (acetone-d₆, 400 MHz): δ 8.97 (s, 1H), 8.49 (d, J=8.5 Hz, 1H), 7.64 (dd, J=8.6, 1.7 Hz, 1H), 7.57 (d, J=1.4 Hz, 1H), 7.24 (s, 1H), 7.13 (dd, J=8.5, 2.0 Hz, 1H), 6.76 (d, J=8.5 Hz, 1H), 4.60 (m, 1H), 4.22 (m, 2H), 3.93-3.69 (m, 6H), 3.85 (s, 3H), 3.21 (s, 2H), 2.44-2.22 (m, 4H), 2.20 (s, 3H) APCI-MS: m/z 489 (MH⁺).

Example 122

4-(acetylamino)-3-{[(2S)-3-(5-chloro-1'H,3H-spiro [1-benzofuran-2,4'-piperidin]-1'-yl)-2-hydroxypropyl]oxy)benzoic acid trifluoroacetate (salt)

To a stirred solution of methyl 4-(acetylamino)-3-{[(2S)-3-(5-chloro-1'H,3H-spiro[1-benzofuran-2,4'-piperidin]-1'-yl)-2-hydroxypropyl]oxy}benzoate trifluoroacetate salt (175 mg, 0.29 mmol) in ethanol (4 ml) was added 2 M aq. NaOH (4 ml). The reaction mixture was stirred at room temperature overnight. Then pH was adjusted to 5 by addition of TFA.
The mixture was concentrated in vacuo and purified by HPLC (eluent: [acetonitrile/water +0.1% TFA]) to afford colourless solid (114 mg, 67%).
¹H-NMR (acetone-d₆, 400 MHz): δ 8.96 (s, 1H), 8.48 (d, J=8.4 Hz, 1H), 7.67 (dd, J=8.5, 1.6 Hz, 1H), 7.58 (d, J=1.1 Hz, 1H), 7.24 (s, 1H), 7.13 (dd, J=8.5, 2.1 Hz, 1H), 6.76 (d, J=8.5 Hz, 1H), 4.61 (m, 1H), 4.23 (m, 2H), 3.96-3.42 (m, 6H), 3.21 (s, 2H), 2.48-2.21 (m, 4H), 2.20 (s, 3H) APCI-MS: m/z 475 (MH⁺).

Example 123

N-(2-{[(2S)-3-(5-chloro-3'-fluoro-1'H,3H-spiro[1-benzofuran-2,4'-piperidin]-1'-yl)-2-hydroxypropyl] oxy}-4-hydroxyphenyl)acetamide The title compound was prepared as described in Example 27 from 5-chloro-3'-fluoro-3H-spiro(1-benzofuran-2,4'-piperidine) (57.3 mg, 0.212 mmol) and 4-{(acetylamino)-3-(2S)-oxiran-2-ylmethoxy]phenyl acetate (51.2 mg, 0.216 mmol) and to give 18 mg (18%) of the title compound.
APCI-MS: m/z 465 (M+H)⁺

Example 124

2-{[(2S)-3-(5-chloro-1'H,3H-spiro[1-benzofuran-2,4'-piperidin]-1'-yl)-2-hydroxypropyl]oxy}-4-hydroxy-N-(2-hydroxypropyl)benzamide Resin-bound carbodiimide (60 mg, 0.08 mmol) was allowed to swell in dichloromethane (0.5 mL) for 30 minutes. 2-{[(2S)-3-(5-chloro-1'H,3H-spiro[1-benzofuran-2,4'-piperidin]-1'-yl)-2-hydroxypropyl]oxy}-4-[(4-methoxybenzyl) oxy]benzoic acid (24.7 mg, 0.045 mmol, 0.3 M in 1-methyl-2-pyrrolidinone) was added and after additionally 30 minutes 1-aminopropan-2-ol (0.21 ml, 0.3 M in 1-methyl-2-pyrrolidinone) was added. After reaction over night at room temperature the resin was filtered off, and washed with several portions of dichloromethane. The organic layers were combined and evaporated. The crude material of 2-{[(2S)-3-(5-chloro-1'H,3H-spiro[1-benzofuran-2,4'-piperidin]-1'-yl)-2-hydroxypropyl]oxy}-N-(2-hydroxypropyl)-4-[(4-methoxybenzyl)oxy]benzamide was dissolved in trifluoroacetic acid/dichloromethane (1.2 mL 70/30) and stirred over night at room temperature. The solvents were evaporated and the resulting crude material was purified on C18 with acetonitrile/water 0.1% trifluoroacetic acid as mobile phase. Pure fractions were collected, pooled and evaporated to give the title compound as the trifluoroacetate.

APCI-MS m/z: 490 [MH$^+$]

The following compounds in Examples 125 to 166 were prepared by methods analogous to the method described in Example 124.

Example 125

2-{[(2S)-3-(5-chloro-1'H,3H-spiro[1-benzofuran-2, 4'-piperidin]-1'-yl)-2-hydroxypropyl]oxy}-4-hydroxy-N-(2-hydroxy-1,1-dimethylethyl)benzamide APCI-MS m/z: 505 [MH$^+$]

Example 126

2-{[(2S)-3-(5-chloro-1'H,3H-spiro[1-benzofuran-2, 4'-piperidin]-1'-yl)-2-hydroxypropyl]oxy}-N-cyclopentyl-4-hydroxybenzamide APCI-MS m/z: 501 [MH$^+$]

Example 127

2-{1[(2S)-3-(5-chloro-1'H,3H-spiro[1-benzofuran-2, 4'-piperidin]-1'-yl)-2-hydroxypropyl]oxy}-4-hydroxy-N-(2-methoxyethyl)benzamide APCI-MS m/z: 491 [MH$^+$]

Example 128

2-{[(2S)-3-(5-chloro-1'H,3H-spiro[1-benzofuran-2, 4'-piperidin]-1'-yl)-2-hydroxypropyl]oxy}-4-hydroxy-N{2-hydroxyphenyl)benzamide APCI-MS m/z: 525 [MH$^+$]

Example 129

N-(tert-butyl)-2-{[(2S)-3-(5-chloro-1'H,3H-spiro[1-benzofuran-2,4'-piperidin]-1'-yl)-2-hydroxypropyl]oxy})-hydroxybenzamide APCI-MS m/z: 489 [MH$^+$]

Example 130

2-{[(2S)-3-(5-chloro-1'H,3H-spiro[1-benzofuran-2, 4'-piperidin]-1'-yl)-2-hydroxypropyl]oxy}-4-hydroxy-N-(2-hydroxy-1-methylethyl)benzamide APCI-MS m/z: 491 [MH$^+$]

Example 131

2-{[(2S)-3-(5-chloro-1'H,3H-spiro[1-benzofuran-2, 4'-piperidin]-1'-yl)-2-hydroxypropyl]oxy}-4-hydroxy-N-isobutylbenzamide APCI-MS m/z: 489 [MH$^+$]

Example 132

2-{[(2S)-3-(5-chloro-1'H,3H-spiro[1-benzofuran-2, 4-piperidin]-1'-yl)-2-hydroxypropyl]oxy}-4-hydroxy-N-(4-hydroxycyclohexyl)benzamide APCI-MS m/z: 530 [MH$^+$]

Example 133

2-{[(2S)-3-(5-chloro-1'H,3H-spiro[1-benzofuran-2, 4'-piperidin]-1'-yl)-2-hydroxypropyl]oxy}-N-(2,3-dihydroxypropyl)-4-hydroxybenzamide APCI-MS m/z: 507 [MH$^+$]

Example 134

2-{[(2S)-3-(5-chloro-1'H,3H-spiro[1-benzofuran-2, 4'-piperidin]-1'-yl)-2-hydroxypropyl]oxy}+hydroxy-N-(2-hydroxyethyl)-N-methylbenzamide APCI-MS m/z: 491 [MH$^+$]

Example 135 methyl N-(2-{[(2S)-3-(5-chloro-1'H,3H-spiro[1-benzofuran-2,4'-piperidin]-1'-yl)-2-hydroxypropyl]oxy}-4-hydroxybenzoyl)serinate APCI-MS m/z: 535 [MH$^+$]

Example 136

2-{[(2S)-3-(5-chloro-1'H,3H-spiro[1-benzofuran-2, 4'-piperidin]-1'-yl)-2-hydroxypropyl]oxy}-N-(1-ethylpropyl)-4-hydroxybenzamide APCI-MS m/z: 503 [MH$^+$]

Example 137

2-{[(2S)-3-(5-chloro-1'H,3H-spiro[1-benzofuran-2, 4'-piperidin]-1'-yl)-2-hydroxypropyl]oxy}-4-hydroxy-N-(tetrahydrofuran-2-ylmethyl)benzamide APCI-MS m/z: 517 [MH$^+$]

Example 138

2-{[(2S)-3-(5-chloro-1'H,3H-spiro[1-benzofuran-2, 4'-piperidin-1'-yl)-2-hydroxypropyl]oxy}-4-hydroxy-N-[1-(hydroxymethyl)-2,2-dimethylpropyl]benzamide APCI-MS m/z: 533 [MH$^+$]

Example 139

2-{[(2S)-3-(5-chloro-1'H,3H-spiro[1-benzofuran-2, 4'-piperidin]-1'-yl)-2-hydroxypropyl]oxy}-N-{[(1S, 2R,5S)-6,6-dimethylbicyclo[3.1.1]hept-2-yl]methyl}-4-hydroxybenzamide APCI-MS m/z: 569 [MH$^+$]

Example 140

2-{[(2S)-3-(5-chloro-1'H,3H-spiro[1-benzofuran-2,4'-piperidin]-1'-yl)-2-hydroxypropyl]oxy}-4-hydroxy-N-[1-(hydroxymethyl)-2-methylpropyl]benzamide APCI-MS m/z: 519 [MH$^+$]

Example 141

3-{[(2S)-3-(5-chloro-1'H,3H-spiro[1-benzofuran-2,4'-piperidin]-1'-yl)-2-hydroxypropyl]oxy}-4-{[4-(2-hydroxyethyl)piperazin-1-yl]carbonyl}phenol APCI-MS m/z: 546 [MH$^+$]

Example 142

3-{[(2S)-3-(5-chloro-1'H,3H-spiro[1-benzofuran-2,4'-piperidin]-1'-yl)-2-hydroxypropyl]oxy}){[3-(hydroxymethyl)piperidin-1-yl]carbonyl)phenol APCI-MS m/z: 531 [MH$^+$]

Example 143

2-{[(2S)-3-(5-chloro-1'H,3H-spiro[1-benzofuran-2,4'-piperidin]-1'-yl)-2-hydroxypropyl]oxy}-N-[5-(1,1-dimethylpropyl)-2-hydroxyphenyl]4-hydroxybenzamide APCI-MS m/z: 595 [MH$^+$]

Example 144

2-{[(2S)-3-(5-chloro-1'H,3H-spiro[1-benzofuran-2,41-piperidin]-1'-yl)-2-hydroxypropyl]oxy}-4-hydroxy-N-[3-(1-hydroxyethyl)phenyl]benzamide APCI-MS m/z: 553 [MH$^+$]

Example 145

2-{[(2S)-3-(5-chloro-1'H,3H-spiro[1-benzofuran-2,4'-piperidin]-1'-yl)-2-hydroxypropyl]oxy}-N-(cyclopropylmethyl)-4-hydroxybenzamide APCI-MS m/z: 487 [MH$^+$]

Example 146

2-{[(2S)-3-(5-chloro-1'H,3H-spiro[1-benzofuran-2,4'-piperidin]-1'-yl)-2-hydroxypropyl]oxy}-4-hydroxy-N-pyrrolidin-1-ylbenzamide APCI-MS m/z: 502 [MH$^+$]

Example 147

N-[(1R,4S)-bicyclo[2.2.1]hept-2-yl]-2-{[(2S)-3-(5-chloro-1'H,3H-spiro[1-benzofuran-2,4'-piperidin]-1'-yl)-2-hydroxypropyl]oxy}-4-hydroxybenzamide APCI-MS m/z: 527 [MH$^+$]

Example 148

4-(4-chlorophenyl)-1-(2-{[(2S)-3-(5-chloro-1'H,3H-spiro[1-benzofuran-2,4'-piperidin]-1'-yl)-2-hydroxypropyl]oxy)-4-hydroxybenzoyl)piperidin-4-ol APCI-MS m/z: 627 [MH$^+$]

Example 149

2-{[(2S)-3-(5-chloro-1'H,3H-spiro[1-benzofuran-2,4'-piperidin]-1'-yl)-2-hydroxypropyl]oxy}-4-hydroxy-N-(2-hydroxy-1-phenylethyl)benzamide APCI-MS m/z: 553 [MH$^+$]

Example 150

1-(2-{[(2S)-3-(5-chloro-1'H,3H-spiro[1-benzofuran-2,4'-piperidin]-1'-yl)-2-hydroxypropyl]oxy}-4-hydroxybenzoyl)-4-phenylpiperidin-4-ol APCI-MS m/z: 593 [MH$^+$]

Example 151

3-{[(2S)-3-(5-chloro-1'H,3H-spiro[1-benzofuran-2,4'-piperidin]-1'-yl)-2-hydroxypropyl]oxy}-4-(3,4-dihydroisoquinolin-2(1H)-ylcarbonyl)phenol APCI-MS m/z: 549 [MH$^+$]

Example 152

3-{[(2S)-3-(5-chloro-1'H,3H-spiro[1-benzofuran-2,4'-piperidin-1'-yl)-2-hydroxypropyl]oxy}-4-{[2-(hydroxymethyl)piperidin-1-yl]carbonyl)phenol APCI-MS m/z: 531 [MH$^+$]

Example 153

1-(2-1[(2S)-3-(5-chloro-1'H,3H-spiro[1-benzofuran-2,41-piperidin]-1'-yl)-2-hydroxypropyl]oxy}-4-hydroxybenzoyl)-N,N-dimethylprolinamide APCI-MS m/z: 558 [MH$^+$]

Example 154 methyl(4R)-1-(2-{[(2S)-3-(5-chloro-1'H,3H-spiro[1-benzofuran-2,4'-piperidin]-1'-yl)-2-hydroxypropyl]oxy}-4-hydroxybenzoyl)-4-hydroxyprolinate APCI-MS m/z: 561 [MH$^+$]

Example 155

(3R)-1-(2-{[(2S-3-(5-chloro-1'H,3H-spiro[1-benzofuran-2,4'-piperidin]-1-yl)-2-hydroxypropyl]oxy)-4-hydroxybenzoyl)piperidin-3-ol APCI-MS m/z: 517 [MH$^+$]

Example 156

2-{[(2S)-3-(5-chloro-1'H,3H-spiro[1-benzofuran-2,4'-piperidin]-1'-yl)-2-hydroxypropyl]oxy}-4-hydroxy-N-(2-hydroxycyclohexyl)benzamide APCI-MS m/z: 531 [MH+]

Example 157

3-{[(2S)-3-(5-chloro-1'H,3H-spiro[1-benzofuran-2,4'-piperidin]-1'-yl)-2-hydroxypropyl]oxy}1[(4-phenylpiperidin-1-yl)carbonyl]phenol APCI-MS m/z: 577 [MH+]

Example 158

3-{[(2S)-3-(5-chloro-1'H,3H-spiro[1-benzofuran-2,4'-piperidin]-1'-yl)-2-hydroxypropyl]oxy}-4-(thiomorpholin-4-ylcarbonyl)phenol APCI-MS m/z: 519 [MH+]

Example 159

1-(2-{[(2S)-3-(5-chloro-1'H,3H-spiro[1-benzofuran-2,4'-piperidin]-1'-yl)-2-hydroxypropyl]oxy)}hydroxybenzoyl)piperidin-3-ol APCI-MS m/z: 517 [MH+]

Example 160

2-{[(2S)-3-(5-chloro-1'H,3H-spiro[1-benzofuran-2,4'-piperidin]-1'-yl)-2-hydroxypropyl]oxy}-N-(cyclopropylmethyl)-4-hydroxy-N-propylbenzamide APCI-MS m/z: 529 [MH+]

Example 161

2-{[(2S)-3-(5-chloro-1'H,3H-spiro[1-benzofuran-2,4'-piperidin]-1'-yl)-2-hydroxypropyl]oxy}-4-hydroxy-N,N-diisobutylbenzamide APCI-MS m/z: 545 [MH+]

Example 162

3-{[(2S)-3-(5-chloro-1'H,3H-spiro[1-benzofuran-2,4'-piperidin]-1'-yl)-2-hydroxypropyl]oxy)-4-(1,3-dihydro-2H-isoindol-2-ylcarbonyl)phenol APCI-MS m/z: 535 [MH+]

Example 163

N-(2-tert-butoxyethyl)-2-{[(2S)-3-(5-chloro-1'H,3H-spiro[1-benzofuran-2,4'-piperidin]-1'-yl)-2-hydroxypropyl]oxy}-4-hydroxy-N-isobutylbenzamide APCI-MS m/z: 589 [MH+]

Example 164

3-{[(2S)-3-(5-chloro-1'H,3H-spiro[1-benzofuran-2,4'-piperidin]-1'-yl)-2-hydroxypropyl]oxy}-4-[(4-fluoropiperidin-1-yl)carbonyl]phenol APCI-MS m/z: 519 [MH+]

Example 165

3-{[(2S)-3-(5-chloro-1'H,3H-spiro[1-benzofuran-2,4'-piperidin]-1'-yl)-2-hydroxypropyl]oxy)-4-[(4,4-difluoropiperidin-1-yl)carbonyl]phenol APCI-MS m/z: 537 [MH+]

Example 166

2-{[(2S)-3-(5-chloro-1'H,3H-spiro [1-benzofuran-2,4'-piperidin]-1'-yl)-2-hydroxypropyl]oxy}-N-phenylbenzamide APCI-MS m/z: 493 [MH+]

The following compounds in Examples 167 to 211 were prepared as described in Example 124 using 6-Chloro-3H-spiro[2-benzofuran-1,4'-piperidine] as starting material

Example 167

3-{[(2S)-3-(5-chloro-1'H,3H-spiro[2-benzofuran-1,4'-piperidin]-1'-yl)-2-hydroxypropyl]oxy}-4-({(2R)-2-[hydroxy(diphenyl)methyl]pyrrolidin-1-yl}carbonyl)phenol APCI-MS m/z: 669 [MH+]

Example 168

2-{[(2S)-3-(5-chloro-1'H,3H-spiro[2-benzofuran-1,4'-piperidin]-1'-yl)-2-hydroxypropyl]oxy}-4-hydroxy-N-(2-hydroxyethyl)-N-methylbenzamide APCI-MS m/z: 491 [MH+]

Example 169

3-{[(2S)-3-(5-chloro-1'H,3H-spiro[2-benzofuran-1,4'-piperidin]-1'-yl)-2-hydroxypropyl]oxy}-4-(pyrrolidin-1-ylcarbonyl)phenol APCI-MS m/z: 487 [MH+]

Example 170

3-{[(2S)-3-(5-chloro-1'H,3H-spiro(2-benzofuran-1,4'-piperidin]-1'-yl)-2-hydroxypropyl]oxy}-4-{[4-(2-hydroxyethyl)piperazin-1-yl]carbonyl}phenol APCI-MS m/z: 546 [MH+]

Example 171

3-{[(2S)-3-(5-chloro-1'H,3H-spiro[2-benzofuran-1,4'-piperidin]-1'-yl)-2-hydroxypropyl]oxy}-4-{[3-(hydroxymethyl)piperidin-1-yl]carbonyl)phenol APCI-MS m/z: 531 [MH+]

Example 172

4-(4-chlorophenyl)-1-(2-{[(2S)-3-(5-chloro-1'H,3H-spiro[2-benzofuran-1,4'-piperidin]-1'-yl)-2-hydroxypropyl]oxy}-4-hydroxybenzoyl)piperidin-4-ol APCI-MS m/z: 627 [MH⁺]

Example 173

3-{[(2S)-3-(5-chloro-1'H,3H-spiro[2-benzofuran-1,4'-piperidin]-1'-yl)-2-hydroxypropyl]oxy}-4-{[4-(hydroxymethyl)piperidin-1-yl]carbonyl)phenol APCI-MS m/z: 531 [MH⁺]

Example 174

1-(2-{[(2S)-3-(5-chloro-1'H,3H-spiro[2-benzofuran-1,4'-piperidin]-1'-yl)-2-hydroxypropyl]oxy}-4-hydroxybenzoyl)-4-phenylpiperidin-4-ol APCI-MS m/z: 593 [MH⁺]

Example 175

3-{[(2S)-3-(5-chloro-1'H,3H-spiro 12-benzofuran-1,4'-piperidin]-1'-yl)-2-hydroxypropyl]oxy}-4-(3,4-dihydroisoquinolin-2(1H)-ylcarbonyl)phenol APCI-MS m/z: 549 [MH⁺]

Example 176

3-{[(2S)-3-(5-chloro-1'H,3H-spiro[2-benzofuran-1,4'-piperidin]-1'-yl)-2-hydroxypropyl]oxy}-4-{[2-(hydroxymethyl)piperidin-1-yl]carbonyl}phenol APCI-MS m/z: 531 [MH⁺]

Example 177

3-{[(2S)-3-(5-chloro-1'H,3H-spiro[2-benzofuran-1,4'-piperidin]-1'-yl)-2-hydroxypropyl]oxy}-4-{[3-(dimethylamino)pyrrolidin-1-yl]carbonyl}phenol APCI-MS m/z: 530 [MH⁺]

Example 178

1-(2-{[(2S)-3-(5-chloro-1'H,3H-spiro[2-benzofuran-1,4'-piperidin]-1'-yl)-2-hydroxypropyl]oxy}-4-hydroxybenzoyl)-N,N-dimethylprolinamide APCI-MS m/z: 558 [MH⁺]

Example 179

2-{[(2S)-3-(5-chloro-1'H,3H-spiro[2-benzofuran-1,4'-piperidin]-1'-yl)-2-hydroxypropyl]oxy}-N-cyclohexyl-4-hydroxy-N-(2-hydroxyethyl)benzamide APCI-MS m/z: 559 [MH⁺]

Example 180 methyl(4R)-1-(2-{[(2S)-3-(5-chloro-1'H,3H-spiro[2-benzofuran-1,4'-piperidin]-1'-yl)-2-hydroxypropyl]oxy}-4-hydroxybenzoyl}-4-hydroxyprolinate APCI-MS m/z: 561 [MH⁺]

Example 181

(3R)-1-(2-{[(2S)-3-(5-chloro-1'H,3H-spiro[2-benzofuran-1,4'-piperidin-1'-yl)-2-hydroxypropyl]oxy}-4-hydroxybenzoyl)piperidin-3-ol APCI-MS m/z: 517 [MH⁺]

Example 182

3-{[(2S)-3-(5-chloro-1'H,3H-spiro[2-benzofuran-1,4'-piperidin]-1'-yl)-2-hydroxypropyl]oxy)-4-[(4-phenylpiperidin-1-yl)carbonyl]phenol APCI-MS m/z: 577 [MH⁺]

Example 183

3-{[(2S)-3-(5-chloro-1'H,3H-spiro[2-benzofuran-1,4'-piperidin]-1'-yl)-2-hydroxypropyl]oxy}-4-(thiomorpholin-4-ylcarbonyl)phenol APCI-MS m/z: 519 [MH⁺]

Example 184

1-(2-{[(2S)-3-(5-chloro-1'H,3H-spiro[2-benzofuran-1,4'-piperidin]-1'-yl)-2-hydroxypropyl]oxy}-4-hydroxybenzoyl)piperidin-3-ol APCI-MS m/z: 517 [MH⁺]

Example 185

2-{[(2S)-3-(5-chloro-1'H,3H-spiro[2-benzofuran-1,41-piperidin]-1'-yl)-2-hydroxypropyl]oxy}-N-(cyclopropylmethyl)-4-hydroxy-N-propylbenzamide APCI-MS m/z: 529 [MH⁺]

Example 186

2-{[(2S)-3-(5-chloro-1'H,3H-spiro[2-benzofuran-1,4'-piperidin]-1'-yl)-2-hydroxypropyl]oxy}-4-hydroxy-N,N-diisobutylbenzamide APCI-MS m/z: 545 [MH⁺]

Example 187

3-{[(2S)-3-(5-chloro-1'H,3H-spiro[2-benzofuran-1,4'-piperidin)-1'-yl)-2-hydroxypropyl]oxy}-4-(1,3-dihydro-2H-isoindol-2-ylcarbonyl)phenol APCI-MS m/z: 535 [MH⁺]

Example 188

N-(2-tert-butoxyethyl)-2-{[(2S)-3-(5-chloro-1'H,3H-spiro[2-benzofuran-1,4'-piperidin]-1'-yl)-2-hydroxypropyl]oxy}-4-hydroxy-N-isobutylbenzamide APCI-MS m/z: 589 [MH$^+$]

Example 189

3-{[(2S)-3-(5-chloro-1'H,3H-spiro[2-benzofuran-1,4'-piperidin]-1'-yl)-2-hydroxypropyl]oxy}-4-[(4-fluoropiperidin-1-yl)carbonyl]phenol APCI-MS m/z: 519 [MH$^+$]

Example 190

3-{[(2S)-3-(5-chloro-1'H,3H-spiro[2-benzofuran-1,4'-piperidin]-1'-yl)-2-hydroxypropyl]oxy}-4-[(4,4-difluoropiperidin-1-yl)carbonyl]phenol APCI-MS m/z: 537 μM

Example 191

2-{[(2S)-3-(5-chloro-1'H,3H-spiro[2-benzofuran-1,4'-piperidin]-1'-yl)-2-hydroxypropyl]oxy}-4-hydroxy-N-(2-hydroxypropyl)benzamide APCI-MS m/z: 491 [MH$^+$]

Example 192

2-{[(2S)-3-(5-chloro-1'H,3H-spiro[2-benzofuran-1,4'-piperidin]-1'-yl)-2-hydroxypropyl]oxy}-4-hydroxy-N-(2-hydroxy-1,1-dimethylethyl)benzamide APCI-MS m/z: 505 [MH$^+$]

Example 193

2-{[(2S)-3-(5-chloro-1'H,3H-spiro[2-benzofuran-1,4'-piperidin]-1'-yl)-2-hydroxypropyl]oxy}-N-cyclopentyl-4-hydroxybenzamide APCI-MS m/z: 501 [MH$^+$]

Example 194

2-{[(2S)-3-(5-chloro-1'H,3H-spiro[2-benzofuran-1,4'-piperidin]-1'-yl)-2-hydroxypropyl]oxy}-4-hydroxy-N-(2-methoxyethyl)benzamide APCI-MS m/z: 491 [MH$^+$]

Example 195

2-{[(2S)-3-(5-chloro-1'H,3H-spiro[2-benzofuran-1,4'-piperidin]-1'-yl)-2-hydroxypropyl]oxy}-4-hydroxy-N-(2-hydroxyphenyl)benzamide APCI-MS m/z: 525 [MH$^+$]

Example 196

2-{[(2S)-3-(5-chloro-1'H,3H-spiro[2-benzofuran-1,4'-piperidin]-1'-yl)-2-hydroxypropyl]oxy}-4-hydroxy-N-(2-hydroxy-1-methylethyl)benzamide APCI-MS m/z: 491 [MH$^+$]

Example 197

2-{[(2S)-3-(5-chloro-1'H,3H-spiro[2-benzofuran-1,4'-piperidin]-1'-yl)-2-hydroxypropyl]oxy}-4-hydroxy-N-isobutylbenzamide APCI-MS m/z: 489 [MH$^+$]

Example 198

2-{[(2S)-3-(5-chloro-1'H,3H-spiro[2-benzofuran-1,4'-piperidin]-1'-yl)-2-hydroxypropyl]oxy}-4-hydroxy-N-(2-hydroxyethyl)benzamide APCI-MS m/z: 477 [MH$^+$]

Example 199

2-{[(2S)-3-(5-chloro-1'H,3H-spiro[2-benzofuran-1,4'-piperidin]-1'-yl)-2-hydroxypropyl]oxy}-4-hydroxy-N-(4-hydroxycyclohexyl)benzamide APCI-MS m/z: 531 [MH$^+$]

Example 200

2-{[(2S)-3-(5-chloro-1'H,3H-spiro[2-benzofuran-1,4'-piperidin]-1'-yl)-2-hydroxypropyl]oxy}-N-(2,3-dihydroxypropyl)-4-hydroxybenzamide APCI-MS m/z: 507 [MH$^+$]

Example 201 methyl N-(2-{[(2S)-3-(5-chloro-1'H,3H-spiro[2-benzofuran-1,4'-piperidin]-1'-yl)-2-hydroxypropyl]oxy}-4-hydroxybenzoyl)serinate APCI-MS m/z: 535 [MH$^+$]

Example 202

2-{[(2S)-3-(5-chloro-1'H,3H-spiro[2-benzofuran-1,4'-piperidin]-1'-yl)-2-hydroxypropyl]oxy}-N-(1-ethylpropyl)-4-hydroxybenzamide APCI-MS m/z: 503 [MH$^+$]

Example 203

2-{[(2S)-3-(5-chloro-1'H,3H-spiro[2-benzofuran-1,4'-piperidin]-1'-yl)-2-hydroxypropyl]oxy}-4-hydroxy-N-(tetrahydrofuran-2-ylmethyl)benzamide APCI-MS m/z: 517 [MH$^+$]

Example 204

2-{[(2S)-3-(5-chloro-1'H,3H-spiro[2-benzofuran-1,4'-piperidin]-1'-yl)-2-hydroxypropyl]oxy}-4-hydroxy-N-[1-(hydroxymethyl)-2,2-dimethylpropyl]benzamide APCI-MS m/z: 533 [MH$^+$]

Example 205

2-{[(2S)-3-(5-chloro-1'H,3H-spiro[2-benzofuran-1,4'-piperidin]-1'-yl)-2-hydroxypropyl]oxy}-4-hydroxy-N-[1-(hydroxymethyl)-2-methylpropyl]benzamide APCI-MS m/z: 519 [MH$^+$]

Example 206

2-{[(2S)-3-(5-chloro-1'H,3H-spiro[2-benzofuran-1,4'-piperidin]-1'-yl)-2-hydroxypropyl]oxy}-4-hydroxy-N-[3-(1-hydroxyethyl)phenyl]benzamide APCI-MS m/z: 553 [MH$^+$]

Example 207

2-{[(2S)-3-(5-chloro-1'H,3H-spiro[2-benzofuran-1,4'-piperidin]-1'-yl)-2-hydroxypropyl]oxy}-N-(cyclopropylmethyl)-4-hydroxybenzamide APCI-MS m/z: 487 [MH$^+$]

Example 208

2-{[(2S)-3-(5-chloro-1'H,3H-spiro[2-benzofuran-1,4'-piperidin]-1'-yl)-2-hydroxypropyl]oxy}-4-hydroxy-N-pyrrolidin-1-ylbenzamide APCI-MS m/z: 502 [MH$^+$]

Example 209

N-[(1R,4S)-bicyclo[2.2.11 hept-2-yl]-2-{[(2S)-3-(5-chloro-1'H,3H-spiro[2-benzofuran-1,4'-piperidin]-1'-yl)-2-hydroxypropyl]oxy}-4-hydroxybenzamide APCI-MS m/z: 527 [MH$^+$]

Example 210

2-{[(2S)-3-(5-chloro-1'H,3H-spiro[2-benzofuran-1,4'-piperidin]-1'-yl)-2-hydroxypropyl]oxy}-4-hydroxy-N-(2-hydroxy-1-phenylethyl)benzamide APCI-MS m/z: 553 [MH$^+$]

Example 211

2-{[(2S)-3-(5-chloro-1'H,3H-spiro[2-benzofuran-1,4'-piperidin]-1'-yl)-2-hydroxypropyl]oxy}+hydroxy-N-(2-hydroxycyclohexyl)benzamide APCI-MS m/z: 531 [MH$^+$]

Example 212

1-(2-{[(2S)-3-(5-chloro-1'H,3H-spiro[1-benzofuran-2,4'-piperidin]-1'-yl)-2-hydroxypropyl]oxy}-4-hydroxybenzoyl)pyrrolidine-3-carboxamide trifluoroacetate Step I:

1-{2-{[(2S)-3-(5-chloro-1'H,3H-spiro[1-benzofuran-2,4'-piperidin]-1'-yl)-2-hydroxypropyl]oxy}-4-[(4-methoxybenzyl)oxy]benzoyl}pyrrolidine-3-carboxamide A mixture of PS-carbodiimide (425 mg, 0.54 mmol) and dichloromethane (5 mL) was stirred at room temperature for 15 minutes, a solution of 2-{[(2S)-3-(5-chloro-1'H,3H-spiro[1-benzofuran-2,4'-piperidin]-1'-yl)-2-hydroxypropyl]oxy}-4-[(4-methoxybenzyl)oxy]benzoic acid hydrochloride (160 mg, 0.27 mmol) in NMP (2.5 mL) and dichloromethane (2.5 mL) was added. The mixture was stirred for 30 minutes, and a mixture of pyrrolidine-3-carboxamide hydrochloride (73 mg, 0.48 mmol) and triethylamine (73 μL, 52 mmol) in dichloromethane (2.5 mL) was added. The mixture was stirred at room tempertaure overnight and filtrated. Volatiles were removed in vacuo, the residue was purified by HPLC (acetonitrile/water, 0.025% ammonium hydroxid) and gave (55 mg, yield 31%) of the subtitle compound.

APCI-MS: m/z 650 (MH$^+$)

Step II:

1-{2-{[(2S)-3-(5-chloro-1'H,3H-spiro[1-benzofuran-2,4'-piperidin]-1'-yl)-2-hydroxypropyl]oxy}-4-hydroxybenzoyl)pyrrolidine-3-carboxamide trifluoroacetate To a solution of 1-{2-{[(2S)-3-(5-chloro-1'H,3H-spiro(1-benzofuran-2,4'-piperidin]-1'-yl)-2-hydroxypropyl]oxy}-4-[(4-methoxybenzyl)oxy]benzoyl}pyrrolidine-3-carboxamide (55 mg, 0.084 mmol) in dichloromethane (3 mL) was added trifluoroacetic acid (0.3 mL). The mixture was stirred at room tempertaure for 1 h, volatiles were removed, the residue was purified by HPLC (acetonitrile/water, 0.1% trifluoroacetic acid) to give 23 mg (42%) of the title compound.

$^1$H-NMR (acetone-d$_6$, 400 MHz): δ 7.28-7.22 (m, 1H); 7.18-7.07 (m, 2H); 6.83-6.75 (m, 1H); 6.67-6.57 (m, 1H); 6.56-6.48 (m, 1H); 4.62-4.46 (m, 1H); 4.21-3.92 (m, 2H); 3.91-3.44 (m, 8H); 3.44-3.26 (m, 2H); 3.26-3.06 (m, 3H); 2.50-2.01 (m, 6H). APCI-MS: m/z 530 (MH$^+$)

Example 213

1-(2-{[(2S)-3-(5-chloro-1'H,3H-spiro[1-benzofuran-2,4'-piperidin]-1'-yl)-2-hydroxypropyl]oxy}-4-hydroxybenzoyl)-L-prolinamide trifluoroacetate Step I:

1-{2-{[(2S)-3-(5-chloro-1'H,3H-spiro[1-benzofuran-2,4'-piperidin]-1'-yl)-2-hydroxypropyl]oxy}-4-[(4-methoxybenzyl)oxy]benzoyl}-L-prolinamide A mixture of PS-carbodiimide (425 mg, 0.54 mmol) and dichloromethane (3 mL) was stirred at room temperature for 15 minutes, a solution of 2-{[(2S)-3-(5-chloro-1'H,3H-spiro[1-benzofuran-2,4'-piperidin]-1'-yl)-2-hydroxypropyl]oxy}-4-[(4-methoxybenzyl)oxy]benzoic acid hydrochloride (160 mg, 0.27 mmol) in NMP (1.5 mL) and dichloromethane (2 mL) was added. The mixture was stirred for 30 minutes, and a mixture of L-prolinamide (46 mg, 0.40 mmol) in dichloromethane (2 mL) was added. The mixture was stirred at room tempertaure overnight and filtrated. Volatiles were removed in vacuo, the residue was purified by HPLC (acetonitrile/water, 0.025% ammonium hydroxid) and gave 85 mg (48%) of the subtitle compound.
APCI-MS: m/z 650 (MH$^+$)

Step II:

1-(2-{[(2S)-3-(5-chloro-1'H,3H-spiro[1-benzofuran-2,4'-piperidin]-1'-yl)-2-hydroxypropyl]oxy)}hydroxybenzoyl)-L-prolinamide trifluoroacetate To a solution of 1-{2-{[(2S)-3-(5-chloro-1'H,3H-spiro[1-benzofuran-2,4'-piperidin]-1'-yl)-2-hydroxypropyl]oxy}-4-[(4-methoxybenzyl)oxy]benzoyl}-L-prolinamide (85 mg, 0.13 mmol) in dichloromethane (3 mL) was added trifluoroacetic acid (0.3 mL). The mixture was stirred at room temperature for 1 h, volatiles were removed, the residue was purified by HPLC (acetonitrile/water, 0.1% trifluoroacetic acid) and gave 37 mg (44%) of the title compound.
$^1$H-NMR (acetone-d$_6$, 400 MHz): δ 7.23 (s, 1H); 7.19-7.10, 7.06-7.03 and 6.61-6.54 (m, 5H); 6.77 (d, J=8.3 Hz, 1H); 6.53-6.48 and 6.46-6.42 (m, 1H); 4.61-4.55 (m, 1H); 4.55-4.47 (m, 1H); 4.17-4.08 (m, 1H); 4.05-3.94 (m, 1H); 3.88-3.70 (m, 2H); 3.70-3.28 (m, 6H); 3.16 (br. s, 2H); 2.47-2.14 (m, 4H); 2.10-1.77 (m, 4H). The compound exists in solution as a mixture of 2 rotamers. APCI-MS: m/z 530 (MH$^+$)

Example 214

2-chloro-5-{[(2S)-3-(5-chloro-1'H,3H-spiro[1-benzofuran-2,4'-piperidin]-1'-yl)-2-hydroxypropyl]oxy}-4-{[(3R)-3-(dimethylamino)pyrrolidin-1-yl]carbonyl}phenol bis(trifluoroacetate)

Step I:

methyl 5-chloro-2-hydroxy-4-[(4-methoxybenzyl)oxy]benzoate

A mixture of 1-(chloromethyl)-4-methoxybenzene (1.53 g, 9.8 mmol), methyl 5-chloro-2,4-dihydroxybenzoate (1.98 g, 9.8 mmol) and potassiumcarbonate (1.35 g, 9.8 mmol) in acetone (15 mL) was stirred at reflux overnight. The mixture was filtered, solvent was removed in vacuo, the residue was dissolved in ethyl acetate and was washed with brine two times. The organic layer was dried over sodium sulphate, solvent was removed in vacuo and the residue was purified by recrystillaziation from methanol. (1.46 g, 46%) of the title compound was obtained.
$^1$H-NMR (CDCl$_3$, 400 MHz): δ 10.90 (s, 1H); 7.84 (s, 1H); 7.39 (d, J=8.5 Hz, 2H); 6.94 (d, J=8.7 Hz, 2H); 6.57 (s, 1H); 5.10 (s, 2H); 3.93 (s, 3H); 3.83 (s, 3H).

Step II:

methyl 5-chloro-4-[(4-methoxybenzyl)oxy]-2-[(2S)-oxiran-2-ylmethoxy]benzoate

A mixture of methyl 5-chloro-2-hydroxy-4-[(4-methoxybenzyl)oxy]benzoate (1.78 g, 5.5 mmol), (2S)-oxiran-2-ylmethyl 3-nitrobenzenesulfonate (1.43 g, 5.5 mmol) and cesiumcarbonate (2.15 g, 6.6 mmol) in NMP (15 mL) was stirred at room temperature overnight. Water was added to the mixture and it was then extracted with with ethyl acetate three times. The combined organinc layers was washed with water, dried over sodium sulphate and solvent was removed in vacuo. The residue was purified by silica gel flash chromatography (ethyl acetate/heptane 10-30%), (1.66 g, 79%) of the title compound was obtained.
$^1$H-NMR (CDCl$_3$, 300 MHz): δ 7.92 (s, 1H); 7.39 (d, J=8.8 Hz, 2H); 6.93 (d, J=8.7 Hz, 2H); 6.67 (s, 1H); 5.15 (s, 2H); 4.35 (dd, J=2.5, 11.5 Hz, 1H); 4.02-3.96 (m, 1H); 3.87 (s, 1H); 3.83 (s, 3H); 3.41-3.35 (m, 1H); 2.95-2.88 (m, 2H). APCI-MS: m/z 379 (MH$^+$)

Step III:

methyl 5-chloro-2-{[(2S)-3-(5-chloro-1'H,3H-spiro[1-benzofuran-2,4'-piperidin]-1'-yl)-2-hydroxypropyl]oxy}-4-[(4-methoxybenzyl)oxy]benzoate A mixture of 5-chloro-3H-spiro[1-benzofuran-2,4'-piperidine] (420 mg, 1.9 mmol) and methyl 5-chloro-4-[(4-methoxybenzyl)oxy]-2-[(2S)-oxiran-2-ylmethoxy]benzoate (710 mg, 1.9 mmol) in ethanol (15 mL) was stirred and heated at reflux overnight. Solvent was removed in vacuo, the residue required no further purification, (1.13 g, 100%) of the title compound was obtained.
APCI-MS: m/z 602 (MH$^+$)

Step IV:

5-chloro-2-{[(2S)-3-(5-chloro-1'H,3H-spiro[1-benzofuran-2,4'-piperidin]-1'-yl)-2-hydroxypropyl]oxy}-4-[(4-methoxybenzyl)oxy]benzoic acid hydrochloride A mixture of methyl 5-chloro-2-{[(2S)-3-(5-chloro-1'H,3H-spiro[1-benzofuran-2,4'-piperidin]-1'-yl)-2-hydroxypropyl]oxy}-4-[(4-methoxybenzyl)oxy]benzoate (1.13 g, 1.9 mmol), potassium hydroxide (15 g), water (15 mL) and ethanol (50 mL) was stirred att room tempertue for two hours. Ethanol was removed in vacuo, aqueous hydrochloric acid (37%) was added until pH=1, the mixture was extracted with ethyl acetate, washed with brine and dried with sodium sulphate. Solvent was removed in vacuo, no further purification was needed, (1.05 g, 89%) of the title compound was obtained.
APCI-MS: m/z 588 (MH$^+$)

Step V:

(2S)-1-{4-chloro-2-{[(3R)-3-(dimethylamino)pyrrolidin-1-yl]carbonyl}-5-[(4-methoxybenzyl)oxy]phenoxy)-3-(5-chloro-1'H,3H-spiro[1-benzofuran-2,4'-piperidin]-1'-yl)propan-2-ol A mixture of PS-carbodiimide (380 mg, 0.49 mmol) and dichloromethane (3 mL) was stirred at room temperature for 15 minutes, a solution of 5-chloro-2-{[(2S)-3-(5-chloro-1'H,3H-spiro[1-benzofuran-2,4'-piperidin]-1'-yl)-2-hydroxypropyl]oxy}-4-[(4-methoxybenzyl)oxy]benzoic acid hydrochloride (150 mg, 0.24 mmol) in NMP (0.5 mL) and dichloromethane (2.5 mL) was added. The mixture was stirred for 30 minutes, and a mixture of (3R)-N,N-dimethylpyrrolidin-3-amine (56 mg, 0.49 mmol) in dichloromethane (2.5 mL) was added. The mixture was stirred at room tempterture overnight and filtrated. Volatiles were removed in vacuo, the residue was purified by HPLC (acetonitrile/water, 0.025% ammonium hydroxid) and gave 110 mg, (67%) of the subtitle compound.
APCI-MS: m/z 684 (MH$^+$)

Step VI:

2-chloro-5-{[(2S)-3-(5-chloro-1'H,3H-spiro[1-benzofuran-2,4'-piperidin]-1'-yl)-2-hydroxypropyl]oxy}-4-{[(3R)-3-(dimethylamino)pyrrolidin-1-yl]carbonyl}phenol bis(trifluoroacetate)

To a solution of (2S)-1-{4-chloro-2-{[(3R)-3-(dimethylamino)pyrrolidin-1-yl]carbonyl}-5-[(4-methoxybenzyl)oxy]phenoxy)-3-(5-chloro-1'H,3H-spiro[1-benzofuran-2,4'-piperidin]-1'-yl)propan-2-ol (10 mg, 0.16 mmol) in dichloromethane (3 mL) was added trifluoroacetic acid (0.3 mL). The mixture was stirred at room temperature for 1 hour, volatiles were removed, the residue was purified by HPLC (acetonitrile/water, 0.1% trifluoroacetic acid) and gave 45 mg (35%) of the title compound.

$^1$H-NMR (acetone-$d_6$, 400 MHz,): δ 7.24-7.21 (m, 2H); 7.13 (d, J=8.9 Hz, 1H); 7.07 and 6.98 (m, 1H); 6.77 (d, J=8.5 Hz, 1H); 4.66-4.50 (m, 1H); 4.20-3.96 (m, 2H); 3.94-3.70 (m, 2H); 3.68-3.46 (m, 4H); 3.44-3.35 (m, 1H); 3.19 (br. s, 2H); 2.97 (s, 3H); 2.93 (s, 3H); 2.58-2.19 (m, 6H). The compound exists in solution as a mixture of 2 rotamers. APCI-MS: m/z 564 (MH$^+$)

Example 215

2-chloro-5-{[(2S)-3-(5-chloro-1'H,3H-spiro[1-benzofuran-2,4'-piperidin]-1'-yl)-2-hydroxypropyl]oxy}-4-{[(3R)-3-(hydroxymethyl)pyrrolidin-1-yl]carbonyl}phenol trifluoroacetate Step I:

(2S)-1-(4-chloro-2-{[(3R)-3-(hydroxymethyl)pyrrolidin-1-yl]carbonyl)-5-[(4-methoxybenzyl)oxy]phenoxy)-3-(5-chloro-1'H,3H-spiro[1-benzofuran-2,4'-piperidin]-1'-yl)propan-2-ol A mixture of PS-carbodiimide (380 mg, 0.49 mmol) and dichloromethane (3 mL) was stirred at room temperature for 15 minutes, a solution of 5-chloro-2-{[(2S)-3-(5-chloro-1'H,3H-spiro(1-benzofuran-2,4'-piperidin]-1'-yl)-2-hydroxypropyl]oxy}-4-[(4-methoxybenzyl)oxy]benzoic acid hydrochloride (150 mg, 0.24 mmol) in NMP (1 mL) and dichloromethane (2.5 mL) was added. The mixture was stirred for 30 minutes, and a mixture of (3R)-pyrrolidin-3-ylmethanol (82 mg, 0.59 mmol) and triethylamine (85 µL, 61 mmol) in dichloromethane (2.5 mL) was added. The mixture was stirred at room temperature for 48 h and was then filtered. Volatiles were removed in vacuo, the residue was purified by HPLC (acetonitrile/water, 0.025% ammonium hydroxid) and gave 87 mg (54%) of the subtitle compound.

APCI-MS: m/z 671 (MH$^+$)

Step II:

2-chloro-5-{[(2S)-3-(5-chloro-1'H,3H-spiro[1-benzofuran-2,4'-piperidin]-1'-yl)-2-hydroxypropyl]oxy}-4-{[(3R)-3-(hydroxymethyl)pyrrolidin-1-yl]carbonyl}phenol trifluoroacetate To a solution of (2S)-1-{4-chloro-2-{[(3R)-3-(hydroxymethyl)pyrrolidin-1-yl]carbonyl}-5-[(4-methoxybenzyl)oxy]phenoxy}-3-(5-chloro-1'H,3H-spiro[1-benzofuran-2,4'-piperidin]-1'-yl)propan-2-ol (87 mg, 0.13 mmol) in dichloromethane (3 mL) was added trifluoroacetic acid (0.3 mL). The mixture was stirred at room temperature for 1 hour, volatiles were removed, the residue was purified by HPLC (acetonitrile/water, 0.1% trifluoroacetic acid) and gave 23 mg (26%) of the title compound.

$^1$H-NMR (acetone-$d_6$, 300 MHz): δ 7.24-7.21 (m, 2H); 7.13 (dd, J=2.4, 8.6 Hz, 1H); 6.97-6.92 (m, 1H); 6.77 (dd, J=1.2, 8.6 Hz, 1H); 4.57-4.46 (m, 1H); 4.18-4.04 (m, 2H); 3.92-3.70 (m, 2H); 3.70-3.30 (m, 10H); 3.29-3.12 (m, 3H); 2,52-2.16 (m, 4H); 2.10-1.68 (m, 2H). APCI-MS: m/z 551 (MH$^+$)

Example 216

2-chloro-5-{(2S)-3-(5-chloro-1'H,3H-spiro[1-benzofuran-2,4'-piperidin]-1'-yl)-2-hydroxypropyl]oxy}-4-{[(3S)-3-(hydroxymethyl)pyrrolidin-1-yl]carbonyl}phenol trifluoroacetate The title compound was prepared using (3S)-pyrrolidin-3-ylmethanol as described in Example 215.

$^1$H-NMR (acetone-$d_6$, 300 MHz): δ 7.26-7.21 (m, 2H); 7.13 (dd, J=2.3, 8.5 Hz, 1H); 6.97-6.90 (m, 1H); 6.77 (dd, J=1.2, 8.4 Hz, 1H); 4.56-4.46 (m, 1H); 4.17-4.03 (m, 2H); 3.92-3.70 (m, 2H); 3.70-3.33 (m, 10H); 3.30-3.22 (m, 1H); 3.17 (br. s, 2H); 2.52-2.16 (m, 4H); 2.10-1.68 (m, 2H). APCI-MS: m/z 551 (MH$^+$)

Example 217

2-chloro-5-{[(2S)-3-(5-fluoro-1'H,3H-spiro[1-benzofuran-2,4'-piperidin]-1'-yl}2-hydroxypropyl]oxy}-4-(pyrrolidin-1-ylcarbonyl)phenol trifluoroacetate Step I:

methyl 5-chloro-2-{[(2S)-3-(5-fluoro-1'H,3H-spiro[1-benzofuran-2,4'-piperidin]-1'-yl)-2-hydroxypropyl]oxy}-4-[(4-methoxybenzyl)oxy]benzoate A mixture of 5-fluoro-3H-spiro[1-benzofuran-2,4'-piperidine] (390 mg, 1.9 mmol) and methyl 5-chloro-4-[(4-methoxybenzyl)oxy]-2-[(2S)-oxiran-2-ylmethoxy]benzoate (710 mg, 1.9 mmol) in ethanol (15 mL) was stirred and heated at reflux overnight. Solvent was removed in vacuo, the residue was purified by silica gel flash chromatography (dichloromethane/methanol 0-3%), and gave the subtitle compound.

APCI-MS: m/z 586 (MH$^+$)

Step II:

5-chloro-2-{[(2S)-3-(5-fluoro-1'H,3H-spiro[1-benzofuran-2,4'-piperidin]-1'-yl)-2-hydroxypropyl]oxy}-4-[(4-methoxybenzyl)oxy]benzoic acid hydrochloride A mixture of methyl 5-chloro-2-{[(2S)-3-(5-fluoro-1'H,3H-spiro[1-benzofuran-2,4'-piperidin]-1'-yl)-2-hydroxypropyl]oxy}-4-[(4-methoxybenzyl)oxy]benzoate (910 mg, 1.5 mmol), potassium hydroxide (15 g), water (15 mL) and ethanol (50 mL) was stirred att room temperture for three hours. Ethanol was removed in vacuo, aqueous hydrochloric acid (37%) was added until pH=1, the mixture was extracted with ethyl acetate, washed with brine and dried with sodium sulphate. Solvent was removed in vacuo, no further purification was needed. 0.91 g (80% overall yield for Steps I-II) of the title compound were obtained.

APCI-MS: m/z 572 (MH$^+$)

Step III:

(2S)-1-[4-chloro-5-[(4-methoxybenzyl)oxy]-2-(pyrrolidin-1-ylcarbonyl)phenoxy]-3-(5 fluoro-1'H,3H-spiro[1-benzofuran-2,4'-piperidin]-1'-yl)propan-2-ol A mixture of PS-carbodiimide (380 mg, 0.49 mmol) and dichloromethane (3 mL) was stirred at room temperature for 15 minutes, a solution of 5-chloro-2-{[(2S)-3-(5-fluoro-1'H,3H-spiro[1-benzofuran-2,4'-piperidin]-1'-yl)-2-hydroxypropyl]oxy}-4-[(4-methoxybenzyl)oxy]benzoic acid hydrochloride (150 mg, 0.25 mmol) in NMP (0.5 mL) and dichloromethane (2.5 mL) was added. The mixture was stirred for 30 minutes, and a mixture of pyrrolidine (56 mg, 0.49 mmol) in dichloromethane (2.5 mL) was added. The mixture was stirred at room temperture for 48 hours and was then filtrated. Volatiles were removed in vacuo, the residue was purified by HPLC (acetonitrile/water, 0.025% ammonium hydroxid) and gave (45 mg, yield 29%) of the subtitle compound.

APCI-MS: m/z 625 (MH$^+$)

Step IV:

2-chloro-5-{[(2S)-3-(5-fluoro-1'H,3H-spiro[1-benzofuran-2,4'-piperidin-1'-yl)-2-hydroxypropyl]oxy}-4-(pyrrolidin-1-ylcarbonyl)phenol trifluoroacetate To a solution of (2S)-1-[4-chloro-5-[(4-methoxybenzyl)oxy]-2-(pyrrolidin-1-ylcarbonyl)phenoxy]-3-(5-fluoro-1'H,3H-spiro[1-benzofuran-2,4'-piperidin]-1'-yl)propan-2-ol (45 mg, 0.07 mmol) in dichloromethane (3 mL) was added trifluoroacetic acid (0.3 mL). The mixture was stirred at room tempertaure for 1 hour, volatiles were removed, the residue was purified by HPLC (acetonitrile/water, 0.1% trifluoroacetic acid) and gave 38 mg (87%) of the title compound.

$^1$H-NMR (acetone-d$_6$, 300 MHz): δ 7.24 (s, 1H); 7.04-6.98 (m, 1H); 6.97-6.94 (m, 1H); 6.94-6.84 (m, 1H); 6.77-6.72 (m, 1H); 4.56-4.45 (m, 1H); 4.17-4.06 (m, 2H); 3.90-3.69 (m, 2H); 3.60-3.44 (m, 4H); 3.44-3.28 (m, 4H); 3.16 (br. s, 2H); 2.46-2.14 (m, 4H); 2.00-1.82 (m, 4H). APCI-MS: m/z 505 (MH$^+$)

Example 218

N-(2-{[(2R)-3-(5-Fluoro-1'H,3H-spiro[1-benzofuran-2,4'-piperidin]-1'-yl)-2-hydroxypropyl]oxy}-4-methoxyphenyl)acetamide Step I (2R)-2-[(5-Methoxy-2-nitrophenoxy)methyl]oxirane To a mixture of (2S)-oxiran-2-ylmethanol (296.3 mg, 4.0 mmol), 5-methoxy-2-nitrophenol (676.6 mg, 4.0 mmol) and triphenyl phosphine (1.05 g, 4.0 mmol) in THF (10 mL) was added diethyl azodicarboxylate (DEAD, 704.6 mg, 4.0 mmol) in THF (5 mL) dropwise at room temperature. After addition was completed the reaction mixture was stirred at room temperature overnight. The volatiles were removed in vacuo and the residue was purified by silica gel flash chromatography (040% ethyl acetate in petroleum spirit) to give the subtitled compound (650 mg).

$^1$H-NMR (CDCl$_3$, 400 MHz): δ 8.00 (d, J=9.0 Hz, 1H), 6.60 (d, J=2.5 Hz, 1H); 6.55 (dd, J=2.5, 9.2 Hz, 1H); 4.41 (dd, J=2.7, 11.3 Hz, 1H); 4.12 (dd, J=5.0, 11.3 Hz, 1H); 3.90 (s, 3H); 3.41 (m, 1H); 2.93 (m, 2H).

Step 11

N-(4-Methoxy-2-[(2R)-oxiran-2-ylmethoxy]phenyl)acetamide

A mixture of (2R)-2-[(5-methoxy-2-nitrophenoxy)methyl]oxirane (620 mg, 2.75 mmol), Pd on charcoal (10%) (250 mg), N-ethyldiisopropylamine (0.941 mL), acetic anhydride (0.52 mL, 5.5 mmol) in ethyl acetate (25 mL) was hydrogenated at normal pressure for 40 min. The catalyst was filtered off and the filtrate was concentrated. The residue was purified by silica gel flash chromatography (0-60% ethyl acetate in petroleum spirit) to give the subtitled compound (155 mg).

$^1$H-NMR (CDCl$_3$, 400 MHz): δ 8.21 (d, J=8.7 Hz, 1H); 6.52 (m, 2H); 4.35 (dd, J=2.5, 11.4 Hz, 1H); 3.93 (dd, J=6.0, 11.4 Hz, 1H); 3.80 (s, 3H); 3.40 (m, 1H); 2.96 (t, J=4.6 Hz, 1H); 2.78 (dd, J=2.7, 4.8 Hz, 1H). APCI-MS: m/z 238 (MH$^+$).

Step III

N-(2-{[(2R)-3-(5-Fluoro-1'H,3H-spiro[1-benzofuran-2,4'-piperidin]-1'-yl)-2-hydroxypropyl]oxy}-4-methoxyphenyl)acetamide A mixture of 5-fluoro-3H-spiro[1-benzofuran-2,4'-piperidine]hydrochloride (154 mg, 0.632 mmol), N-{4-Methoxy-2-[(2R)-oxiran-2-ylmethoxy]phenyl}acetamide (150 mg, 0.632 mmol) and K$_2$CO$_3$ (87 mg, 0.632 mmol) in ethanol (3 mL) was stirred at 80° C. for 3 h. The reaction mixture was partitioned between ethyl acetate and H$_2$O. The organic layer was dried over Na$_2$SO$_4$, filtered and concentrated in vacuo. The residue was purified by silica gel flash chromatography (0-1.5% methanol in dichloromethane, 0.2% NH$_4$OH) to to give the titled compound (100 mg).

$^1$H-NMR (CDCl$_3$, 400 MHz): δ 8.18 (d, J=8.6 Hz, 1H); 8.02 (br.s, 1H); 6.87 (m, 1H); 6.80 (m, 1H); 6.66 (dd, J=4.2, 8.7 Hz, 1H); 6.56-6.51 (m, 2H); 4.18 (m, 1H); 4.04 (dd, J=3.3, 10.1 Hz, 1H); 3.96 (dd, J=5.7, 10.1 Hz, 1H); 3.79 (s, 3H); 3.01 (s, 2H); 2.91 (m, 2H); 2.78-2.57 (m, 4H); 2.20 (s, 3H); 2.07-1.84 (m, 4H). APCI-MS: m/z 445 (MH$^+$).

Example 219

Methyl 2-{[(2S)-3-(5-fluoro-1'H,3H-spiro[1-benzofuran-2,4'-piperidin]-1'-yl)-2-hydroxypropyl]oxy}benzoate A mixture of 5-fluoro-3H-spiro[1-benzofuran-2,4'-piperidine] (155.4 mg, 0.75 mmol) and methyl 2-[(2S)-oxiran-2-ylmethoxy]benzoate (157 mg, 0.75 mmol) in methanol (4 mL) was stirred at 80° C. overnight. The volatiles were removed in vacuo and the residue was purified by silica gel flash chromatography (0-1% methanol in dichloromethane, 0.1% NH$_4$OH) to give the titled compound (250 mg).

$^1$H-NMR (CDCl$_3$, 400 MHz): δ 7.83 (dd, J=1.9, 4.1 Hz, 1H); 7.48 (m, 1H); 7.02 (m, 2H); 6.86 (m, 1H); 6.79 (m, 1H); 6.66 (dd, J=4.2, 8.7 Hz, 1H); 4.26-4.16 (m, 2H); 4.09 (dd, J=5.7, 9.2 Hz, 1H); 3.90 (s, 3H); 3.00 (s, 2H); 2.90-2.68 (m, 6H); 2.00 (m, 2H); 1.90 (m, 2H). APCI-MS: m/z 416 (MH$^+$).

Example 220

2-{[(2S)-3-(5-Fluoro-1'H,3H-spiro[1-benzofuran-2,4'-piperidin]-1'-yl)-2-hydroxypropyl]oxy}benzoic acid (hydrochloride)

Methyl 2-{[(2S)-3-(5-fluoro-1'H,3H-spiro[1-benzofuran-2,4'-piperidin]-1'-yl)-2-hydroxypropyl]oxy}benzoate (240 mg, 0.58 mmol) was dissolved in THF (4 mL), aqueous KOH (67 mg KOH in 1 mL H$_2$O) was added and the reaction mixture was stirred at room temperature overnight. The pH of the reaction mixture was adjusted to 2.0 by addition of aqueous HCl, extrated with ethyl acetate. The organic layer was washed with H$_2$O, dried over Na$_2$SO$_4$, filtered and concentrated to give the titled compound (210 mg).

$^1$H-NMR (CD$_3$OD, 400 MHz): δ 7.93 (dd, J=1.8, 7.8 Hz, 1H); 7.57 (m, 1H); 7.18 (d, J=8.4 Hz, 1H); 7.10 (t, J=7.6 Hz, 1H); 6.97 (dd, J=2.6, 8.1 Hz, 1H); 6.85 (m, 1H); 6.73 (dd, J=4.2, 8.8 Hz, 1H); 4.46 (m, 1H); 4.31 (dd, J=4.0, 9.5 Hz, 1H); 4.15 (dd, J=5.4, 9.5 Hz, 1H); 3.76-3.40 (m, 6H); 3.16 (s, 2H); 2.30 (m, 2H); 2.19 (m, 2H). APCI-MS: m/z 403 (MH$^+$).

Example 221

(3S)-1-(2-{[(2S)-3-(5-Fluoro-1'H,3H-spiro[1-benzofuran-2,4'-piperidin)-1'-yl)-2-hydroxypropyl]oxy}benzoyl)pyrrolidin-3-ol A mixture of 2-{[(2S)-3-(5-fluoro-1'H,3H-spiro[1-benzofuran-2,4'-piperidin]-1'-yl)-2-hydroxypropyl]oxy}benzoic acid (hydrochloride) (200 mg, 0.456 mmol) and N,N-carbonyldiimidazole (89 mg, 0.548 mmol) in DMF (3 mL) was stirred at room temperature for 40 min, a solution of 3(S)-pyrrolidin-3-ol (199 mg, 2.28 mmol) in DMF (1 mL) was added and the reaction mixture was stirred at room temperature overnight. The mixture was partitioned between ethyl acetate and $H_2O$, organic layer was dried over $Na_2SO_4$, filtered and concentrated. The residue was purified by silica gel flash chromatography (0-2% methanol in dichloromethane, 0.2% $NH_4OH$) to give the titled compound (96 mg).

$^1$H-NMR (CD$_3$OD, 400 MHz): δ 7.42 (m, 1H); 7.27 (d, J=7.4 Hz, 1H); 7.11 (dd, J=2.8, 8.4 Hz, 1H); 7.04 (t, J=7.4 Hz, 1H); 6.90 (dd, J=2.5, 8.0 Hz, 1H); 6.78 (m, 1H); 6.63 (dd, J=4.2, 8.7 Hz, 1H); 4.50 (m, 0.5H); 4.38 (m, 0.5H); 4.17-4.00 (m, 3H); 3.72 (m 1H); 3.63 (m, 1H); 3.50 (m, 1H); 3.373.18 (m, 1H, under methanol peak); 3.02 (s, 2H); 2.77-2.54 (m, 6H); 2.18-1.78 (m, 6H). APCI-MS: m/z 471 (MH$^+$).

Example 222

3-{[(2S)-3-(5-Fluoro-1'H,3H-spiro[1-benzofuran-2,4'-piperidin]-1'-yl)-2-hydroxypropyl]oxy}-4-(pyrrolidin-1-ylcarbonyl)phenol Step I Methyl 2-{[(2S)-3-(5-fluoro-1'H,3H-spiro[1-benzofuran-2,4'-piperidin]-1'-yl)-2-hydroxypropyl]oxy}-4-[(4-methoxybenzyl)oxy]benzoate A mixture of 5-fluoro-3H-spiro[1-benzofuran-2,4'-piperidine] (119 mg, 0.577 mmol) and methyl 4-[(4-methoxybenzyl)oxy]-2-[(2S)-oxiran-2-ylmethoxy]benzoate (199 mg, 0.577 mmol) in methanol (3 mL) was stirred at 80° C. overnight. The volatiles were removed in is vacuo and the residue was purified by silica gel flash chromatography (0-1.5% methanol in dichloromethane, 0.2% $NH_4OH$) to give the sub titled compound (228 mg).

$^1$H-NMR (CDCl$_3$, 400 MHz): δ 7.85 (d, J=8.6 Hz, 1H); 7.36 (d, J=8.6 Hz, 1H); 6.94 (m, 2H); 6.89-6.77 (m, 2H); 6.66 (dd, J=4.1, 8.7 Hz, 1H); 6.62-6.57 (m, 2H); 4.28 (m, 1H); 4.12 (dd, J=4.7, 9.3 Hz, 1H); 4.06 (dd, J=5.9, 9.3 Hz, 1H); 3.88 (s, 3H); 3.85 (s, 3H); 3.00 (s, 2H); 2.98-2.74 (m, 6H); 2.00 (br,s, 4H). APCI-MS: m/z 552 (MH$^+$).

Step II

2-{[(2S)-3-(5-Fluoro-1'H,3H-spiro[1-benzofuran-2,4' piperidin]-1'-yl)-2-hydroxypropyl]oxy}-4-[(4-methoxybenzyl)oxy]benzoicacid (hydrochloride)

Methyl 2-{[(2S)-3-(5-fluoro-1'H,3H-spiro[1-benzofuran-2,4'-piperidin]-1'-yl)-2-hydroxypropyl]oxy}-4-[(4-methoxybenzyl)oxy]benzoate (220 mg, 0.398 mmol) was taken in ethanol (3 mL), aqueous KOH (224 mg, KOH in 1 mL $H_2O$) was added and the mixture was stirred at reflux temperature overnight, cooled to 0° C., aqueous HCl was added until pH became 2.0, extracted with ethyl acetate, washed with $H_2O$, dried over $Na_2SO_4$, filtered and concentrated to give the sub titled compound (180 mg).

$^1$H-NMR (CD$_3$OD, 400 MHz): δ 7.90 (d, J=9.1 Hz, 1H); 7.36 (d, J=8.7 Hz, 2H); 6.98-6.91 (m, 3H); 6.83 (m, 1H); 6.74-6.68 (m, 3H); 5.10 (s, 2H); 4.44 (m, 1H); 4.27 (dd, J=4.0, 9.4 Hz, 1H); 4.10 (dd, J=5.4, 9.4 Hz, 1H); 3.80 (s, 3H); 3.77-3.40 (m, 6H); 3.12 (s, 2H); 2.30 (m, 2H); 2.15 (m, 2H). APCI-MS: m/z 538 (MH$^+$).

Step III (2S)-1-(5-Fluoro-1'H,3H-spiro[1-benzofuran-2,4'-piperidin]-1'-yl)-3-[5-[(4-methoxybenzyl)oxy]-2-(pyrrolidin-1-ylcarbonyl)phenoxy]propan-2-ol 2-{[(2S)-3-(5-Fluoro-1'H,3H-spiro[1-benzofuran-2,4' piperidin]-1'-yl)-2-hydroxypropyl]oxy}-4-[(4-methoxybenzyl)oxy]benzoicacid (hydrochloride) (136 mg, 0.237 mmol) and N,N-carbonyldiimidazole (46 mg, 0.284 mmol) was taken in DMF (3 mL) and stirred at room temperature for 55 min, pyrrolidine (168.5 mg, 2.37 mmol) was added and stirred at room temperature overnight. The reaction mixture was partitioned between ethyl acetate and $H_2O$. The organic layer was dried over $Na_2SO_4$, filtered and concentrated. The residue was purified by silica gel flash chromatography (0-1.5% methanol in dichloromethane, 0.2% $NH_4OH$) to give the sub titled compound (70 mg).

APCI-MS: m/z 552 (MH$^+$).

Step IV

3-{[(2S)-3-(5-Fluoro-1'H,3H-spiro[1-benzofuran-2,4'-piperidin]-1'-yl)-2-hydroxypropyl]oxy}-4-(pyrrolidin-1-ylcarbonyl)phenol (2S)-1-(5-Fluoro-1'H,3H-spiro[1-benzofuran-2,4'-piperidin]-1'-yl)-3-[5-[(4-methoxybenzyl)oxy]-2-(pyrrolidin-1-ylcarbonyl)phenoxy]propan-2-ol (65 mg, 0.11 mmol) was treated with 10% CF$_3$CO$_2$H in CH$_2$Cl$_2$ (3 mL) for 25 min at room temperature. The volatiles were removed in vacuo and the residue was purified by silica gel flash chromatography (0-2.5% methanol in dichloromethane, 0.2% $NH_4OH$) to give the titled compound (28 mg).

$^1$H-NMR (CD$_3$OD, 400 MHz): δ 7.07 (d, J=8.2 Hz, 1H); 6.90 (dd, J=2.6, 8.2 Hz, 1H); 6.77 (m, 1H); 6.63 (dd, J=4.2, 8.7 Hz, 1H); 6.50 (d, J=2.1 Hz, 1H); 6.44 (dd, J=2.1, 8.3 Hz, 1H); 4.10 (m, 1H); 4.03 (dd, J=4.3, 9.7 Hz, 1H); 3.96 (dd, J=5.6, 9.7 Hz, 1H); 3.56 (t, J=7.0 Hz, 2H); 3.34 (m, 2H, inside methanol peak); 3.01 (s, 2H); 2.70 (br.s, 4H); 2.56 (m, 2H); 2.01-1.78 (m, 8H). APCI-MS: m/z 471 (MH$^+$).

Example 223

N-(4-fluoro-2-{[(2S)-3-(5-fluoro-1'H,3H-spiro[1-benzofuran-2,4'-piperidin]-1'-yl)-2-hydroxypropyl]oxy}phenyl)acetamide The title compound was prepared using 5-fluoro-3H-spiro[1-benzofuran-2,4'-piperidine] as described in Example 2.

$^1$H-NMR (acetone-d$_6$, 300 MHz): δ 8.63 (br. s, 1H); 8.26-8.17 (m, 1H); 6.99-6.88 (m, 2H); 6.87-6.76 (m, 1H); 6.74-6.62 (m, 2H); 4.25-4.19 (m, 1H); 4.19-4.09 (m, 1H); 4.07-3.99 (m, 1H); 3.03 (s, 2H); 2.85 (br. s, 1H); 2.78-2.60 (m, 4H); 2.60-2.54 (m, 2H); 2.10 (s, 3H); 1.97-1.76 (m, 4H). APCI-MS: m/z 433 (MH$^+$)

Example 224

N-(5-chloro-2-[3-(5-chloro-1'H,3H-spiro[1-benzofuran-2,4 '-piperidin]-1 '-yl)-2-hydroxypropoxy]-4-hydroxyphenyl]cyclopentanecarboxamide Step I:

5-chloro-6-[(triisopropylsilyl)oxy]-1,3-benzoxazol-2(3H)-one 5-chloro-6-hydroxy-1,3-benzoxazol-2(3H)-one (0.93 g, 5 mmol) and imidazole (1.00 g, 15 mmol) were dissolved in dimethylformamide (10 mL) with stirring under inert atmosphere. Triisopropylsilylchloride (1.15 g, 6 mmol) was added and the resulting solution was stirred for 3 days. The reaction mixture was partitioned between water and heptane. The organic layer was washed with water and dried over magnesium sulphate, filtrated and concentrated, to give 1.45 g (85%) of the subtitled compound as a grey solid.

APCI-MS: m/z 342 [MH$^+$]

Step II:

N-{5-chloro-2-hydroxy-4-[(triisopropylsilyl)oxy]phenyl}cyclopentanecarboxamide

Bromo(cyclopentyl)magnesium (0.58 mL, 1.16 mmol, 2 M in diethylether) was added under inert atmosphere to a solution of 5-chloro-6-[(triisopropylsilyl)oxy]-1,3-benzoxazol-2(3H)-one (66 mg, 0.19 mmol) in tetrahydrofuran (3 mL). After stirring over night at 70° C., the solution was evaporated and dissolved in ethylacetate. The organic layer was washed with water and 1M hydrochloric acid, dried and finally concentrated to give 68 mg (89%) of the subtitled compound as a brown solid.

APCI-MS: m/z 412 [MH$^+$]

Step III;

N-{5-chloro-2-(oxiran-2-ylmethoxy)-4-[(triisopropylsilyl)oxy]phenyl}-cyclopentanecarboxamide N-{5-chloro-2-hydroxy-4-[(triisopropylsilyl)oxy]phenyl}cyclopentanecarboxamide (140 mg, 0.3 mmol) was dissolved in 1,4-dioxane (20 mL). Caesium carbonate (170 mg, 0.5 mmol) was added, followed by (2S)-oxiran-2-y-methyl 3-nitrobenzenesulfonate (90 mg, 0.3 mmol). After stirring over night at room temperature the mixture was partitioned between ethyl acetate and water. The organic layer was washed with water and concentrated. Purification by HPLC on C18 (Xterra, 5 um, 19×50 mm; acetonitrile/water 60/40 to 100/0 over 15 min) yielded 25 mg (17%) of the titled intermediate compound.

$^1$H-NMR (300 MHz, (CDCl$_3$) δ: 8.45 (1H, s); 7.70 (1H, bs); 6.51 (1H, s); 4.27 (1H, dd); 3.88 (1H, dd); 3.39-3.34 (1H, m); 2.98-2.95 (1H, m); 2.80 (1H, dd); 2.79-2.67 (1H, m); 2.02-1.61 (8H, m); 1.36-1.22 (3H, m); 1.17-1.05 (18H, m) APCI-MS: m/z 468 [MH$^+$]

Step IV:

N-{5-chloro-2-[3-(5-chloro-1'H,3H-spiro[1-benzofuran-2,4'-piperidin]-1'-yl)-2-hydroxypropoxy]4-hydroxyphenyl)cyclopentanecarboxamide A solution of 5-chloro-3H-spiro[1-benzofuran-2,4'-piperidine] (11 mg, 0.05 mmol) and N-{5-chloro-2-(oxiran-2-ylmethoxy)-4-[(triisopropylsilyl)oxy]phenyl}cyclopentanecarboxamide (25 mg, 0.05 mmol) in isopropanol (15 mL) was stirred over night at 65° C., and then concentrated to give 34 mg (98%) of N-{5-chloro-2-[3-(5-chloro-1'H,3H-spiro[1-benzofuran-2,4'-piperidin]-1'-yl)-2-hydroxypropoxy]-4-[(triisopropylsilyl)oxy]phenyl}-cyclopentanecarboxamide as a light brown solid, which was dissolved in dimethylformamide (15 mL) and water (1.5 mL). Caesium carbonate (32 mg, 0.10 mmol) was added. The solution was stirred over night at room temperature, and then partitioned between water and ethyl acetate. The organic layer was washed several times with water, dried and concentrated. The residue was purified by HPLC on C18 (Kromasil, 5 um, acetonitrile/water 10/90 to 60/40 over 20 min) to give the titled compound.

APCI-MS: m/z 535 [MH$^+$]

Example 225

N-{5-chloro-2-[3-(5-fluoro-1'H,3H-spiro[1-benzofuran-2,4'-piperidin]-1'-yl)-2-hydroxypropoxy]4-hydroxyphenyl}cyclopentanecarboxamide The title compound was prapered as described in Example 224 using 5-fluoro-3H-spiro[1-benzofuran-2,4'-piperidine].
APCI-MS: m/z 519 [MH$^+$]

Example 226

N-{5-chloro-4-hydroxy-2-12-hydroxy-3-1'H,3H-spiro[1-benzofuran-2,4'-piperidin]-1'-yl)propoxy]phenyl}cyclopentanecarboxamide The title compound was prapered as described in Example 224 using 3H-spiro[1-benzofuran-2,4'-piperidine].
APCI-MS: m/z 501 [MH$^+$]

Example 227

N-(5-Chloro-2-{[(2S)-3-(5-chloro-1'H,3H-spiro[1-benzofuran-2,4'-piperidin]-1'-yl)-2-hydroxypropyl]oxy}-4-hydroxyphenyl)benzamide trifluoroacetate (salt)

Step I:

N-(5-Chloro-2,4-dimethoxyphenyl)benzamide

To a stirred solution of (5-chloro-2,4-dimethoxyphenyl)amine (1.88 g, 10 mmol) and triethylamine (2.1 mL, 15 mmol) in DCM (50 mL)benzoylchloride (1.3 mL, 11 mmol) was added dropwise while cooled. The reaction was complete in 5. The solution was washed consecutively with 1M sodium hydrogencarbonate solution (10 mL) and water (3×10 mL), dried and concentrated in vacuo leaving a solid, which was recrystallized from ethylacetate (25 mL) to give a pale gray solid (1.975 g, 67%).

APCI-MS: m/z 292 (MH$^+$)

Step II:

N-(5-Chloro-2,4-dihydroxyphenyl)benzamide

To a stirred solution of N-(5-chloro-2,4-dimethoxyphenyl)benzamide (292 mg, 1 mmol) in DCM (10 mL) 1M boron tribromide in DCM (3 mL, 3 mmol) was added dropwise at ambient temperature. A precipitate was formed after 30 min. The stirring was continued over night. The mixture was quenched with methanol (5 mL) and concentrated in vacuo leaving an oil which was used without further purification.

APCI-MS: m/z 264 (MH$^+$)

Step III:

4-(Benzoylamino)-2-chloro-5-hydroxyphenyl benzoate

To crude N-(5-chloro-2,4-dihydroxyphenyl)benzamide (1 mmol) in acetone (10 mL) potassium carbonate (280 mg, 2 mmol) and benzoylchloride (140 mg, 1 mmol) was added. The mixture was stirred at ambient tempearature over night. The solvent was removed in vacuo and the residue purified by flash chromatography on silica using DCM and methanol in gradient. The pure compound was obtained as a white solid (153 mg, 42%).

$^1$H-NMR (Aceton-d$_6$, 400 MHz): δ 9.81 (bs, 1H); 9.39 (bs, 1H); 8.21 (d, J=7.3 Hz, 2H); 8.16 (s, 1H); 8.06 (d, J=7.3 Hz, 2H); 7.77 (t, J=7.6 Hz, 1H); 7.68-7.55 (m, 5H); 7.07 (s, 1H) APCI-MS: m/z 368 (MH$^+$)

Step IV:

4-(Benzoylamino)-2-chloro-5-[(2S)-oxiran-2-ylmethoxy] phenyl benzoate

To a stirred solution of 4-(benzoylamino)-2-chloro-5-hydroxyphenyl benzoate (103 mg, 0.28 mmol) and [(2S)-2-methyloxiran-2-yl]methyl 3-nitrobenzenesulfonate (73 mg, 0.28 mmol) in DMF (3 mL) cesium carbonate (98 mg, 0.3 mmol) was added. The stirring was continued at ambient temperature over night. The mixture was poured into water and partitioned between water and ethylacetate. The organic phase was washed with water, dried and concentrated in vacuo to give a white solid (117 mg, 98%). The solid was used without further purification.

$^1$H-NMR (Aceton-d$_6$, 400 MHz): δ 9.06 (bs, 1H); 8.66 (s, 1H); 8.22 (d, J=7.5 Hz, 2H); 8.02 (d, J=7.5 Hz, 2H); 7.77 (t, J=7.7 Hz, 1H); 7.64 (t, J=7.7 Hz, 2H); 7.57 (t, J=7.7 Hz, 2H); 7.30 (s, 1H); 4.57 (dd, J=2.4, 11.5 Hz, 1H); 4.11 (dd, J=6.2, 11.5 Hz, 1H); 3.49-3.43 (m, 1H); 2.90-2.87 (m, 1H); 2.81-2.78 (m, 2H) APCI-MS: m/z 424 (MH$^+$)

Step V:

N-(5-Chloro-2-{[(2S)-3-(5-chloro-1'H,3H-spiro[1-benzofuran-2,4'-piperidin]-1'-yl)-2-hydroxypropyl]oxy}-4-hydroxyphenyl)benzamide trifluoroacetate (salt)

A solution of 5-chloro-3H-spiro[1-benzofuran-2,4'-piperidine (29 mg, 0.13 mmol) and 4-(benzoylamino)-2-chloro-5-[(2S)-oxiran-2-ylmethoxy]phenyl benzoate (55 mg, 0.13 mmol) in ethanol (3 mL) was stirred at 80° C. for 2 h. 1M NaOH (0.15 mL, 0.15 mmol) was added and the stirring continued at 80° C. for 1 h. The solvent was evaporated in vacuo and the crude product purified by flash chromatography (silica, DCM and methanol in gradient) leaving an oil (32 mg), which was dissolved in acetic acid and acified with TFA. After freeze drying the titled compound was obtained as an amorphous solid (36 mg, 42%).

$^1$H-NMR (Aceton-d$_6$, 400 MHz): δ 9.01 (s, 1H); 8.95 (bs, 1H); 8.24 (s, 1H); 8.23 (s, 1H); 8.03-7.98 (m, 2H); 7.59-7.49 (m, 3H); 7.24-7.22 (m, 1H); 7.14 (dd, J=8.5, 2.3 Hz, 1H); 6.92 (s, 1H); 6.76 (d, J=8.5 Hz, 1H); 4.66-4.58 (m, 1H); 4.21-4.12 (m, 2H); 3.80-3.53 (m, 3H); 3.53-3.36 (m, 3H); 3.17 (s, 2H); 2.38-2.16 (m, 4H) APCI-MS: m/z 543 (MH$^+$)

Example 228

N-(5-Chloro-2-{[(2S)-3-(5-fluoro-1'H,3H-spiro[1-benzofuran-2,4'-piperidin]-1'-yl)-2-hydroxypropyl]oxy}-4-hydroxyphenyl)benzamide trifluoroacetate (salt)

The compound was prepared using 5-fluoro-3H-spiro[1-benzofuran-2,4'-piperidine] as described in Example 227.

$^1$H-NMR (Aceton-d$_6$, 400 MHz): δ 9.02 (bs, 2H); 8.23 (s, 1H); 8.22 (s, 1H); 8.01 (d, J=7.3 Hz, 2H); 7.59-7.49 (m, 3H); 7.01 (d, J=8.3 Hz, 1H); 6.94 (s, 1H); 6.88 (ddd, J=9.0, 2.3 Hz, 1H); 6.73 (dd, J=8.7, 4.2 Hz, 1H); 4.69-4.59 (m, 1H); 4.21-4.12 (m, 2H); 3.86-3.57 (m, 3H); 3.57-3.36 (m, 3H); 3.17 (s, 2H); 2.40-2.14 (m, 4H) APCI-MS: m/z 527 (MH$^+$)

Example 229

N-(5-Chloro-2-{[(2S)-3-(5-chloro-1'H,3H-spiro[1-benzofuran-2,4'-piperidin)-1'-yl)-2-hydroxypropyl]oxy}-4-hydroxyphenyl)urea trifluoroacetate (salt)

Step I:

5-Chloro-2-{[(2S)-3-(5-chloro-1'H,3H-spiro[1-benzofuran-2,4'-piperidin]-1'-yl)-2-hydroxypropyl]oxy}-4-[(4-methoxybenzyl)oxy]benzoyl azide To a stirred slurry of 5-chloro-2-{[(2S)-3-(5-chloro-1'H, 3H-spiro[1-benzofuran-2,4'-piperidin]-1'-yl)-2-hydroxypropyl]oxy}-4-[(4-methoxybenzyl)oxy)benzoic acid hydrochloride (235 mg, 0.4 mmol) in DCM (10 mL) triethylamine (60 uL, 0.4 mL) was added to obtain a solution. To the solution diphenyl phosphoryl azide (90 μL, 0.4 mmol) and triethylamine (60 μL, 0.4 mmol) were added. The mixture was stirred at ambient temperature over night. The solvent was evaporated in vacuo and the residue purified by flash chromatography (silica, DCM) leaving the subtitled compound as an impure colourless oil (235 mg), which was used in the next step without wurther purification.

APCI-MS: m/z 585 (MH$^+$, isocyanate)

Step II:

N-(5-Chloro-2-{[(2S)-3-(5-chloro-1'H,3H-spiro[1-benzofuran-2,4'-piperidin]-1'-yl)-2-hydroxypropyl]oxy}-4-hydroxyphenyl)urea trifluoroacetate (salt)

Crude 5-chloro-2-{[(2S)-3-(5-chloro-1'H,3H-spiro[1-benzofuran-2,4'-piperidin]-1'-yl)-2-hydroxypropyl]oxy}-4-[(4-methoxybenzyl)oxy]benzoyl azide (235 mg, <0.4 mmol) was dissolved in toluene (3 mL) and heated while stirred for 3 h. The yellow solution was cooled to ambient temperature and 0.5M ammonia in dioxane (1.6 mL, 0.8 mmol) was added and the mixture was left over night. The solvent was evaporated in vacuo and the residue dissolved in 10% TFA in DCM (5 mL) and left for 1 h. The solvent was evaporated in vacuo and the dark residue purified by preparative HPLC using acetonitrile/water containing 0.1% TFA as mobile phase. The titled compound was obtained as a white amorphous solid after freeze drying (6 mg, 2.5%).

$^1$H-NMR (Aceton-d$_6$,400 MHz): δ 8.35 (s, 1H), 7.70 (br. s, 1H), 7.25 (s, 1H), 7.14 (dd, J=8.5, 2.0 Hz, 1H), 6.77 (d, J=8.5 Hz, 1H), 6.65 (s, 1H), 5.92 (br. s, 2H), 4.54 (m, 1H), 4.14 (d, J=9.7 Hz, 1H), 4.02 (dd, J=9.4, 5.1 Hz, 1H), 3.95-3.65 (m, 2H), 3.60-3.39 (m, 4H), 3.21 (s, 2H), 2.43-2.18 (m, 4H) APCI-MS: m/z 482 (MH$^+$)

Example 230

N-(5-Chloro-2-{[(2S)-3-(5-fluoro-1'H,3H-spiro[1-benzofuran-2,4'-piperidin]-1'-yl)-2-hydroxypropyl]oxy}-4-hydroxyphenyl)urea trifluoroacetate (salt)

The compound was prepared from 5-chloro-2-{[(2S)-3-(5-chloro-1'H,3H-spiro[1-benzofuran-2,4'-piperidin]-1'-yl)-2-hydroxypropyl]oxy}-4-[(4-methoxybenzyl)oxy]-benzoic acid as described in Example 229.

APCI-MS: m/z 466 (MH$^+$)

Example 231

N-(5-chloro-2-{[(2S)-3-(5-fluoro-1'H,3H-spiro[1-benzofuran-2,4'-piperidin]-1'-yl)-2-hydroxypropyl]oxy}phenyl)urea Step I:

N-(5-chloro-2-hydroxyphenyl)urea 2-amino-4-chlorophenol (1.3 g, 8.9 mmol) was dissolved in 1M HCl (10 mL). Ammonium acetate was added to the solution to adjust pH to 5. The stirred mixture was treated with a suspension of potassium cyanate (0.80 mg, 9.8 mmol) in water, and than kept overnight at room temperature. Water was removed by evaporation and the residue was recrystallized from water to afford pink precipitate (0.9 g, 55%).

APCI-MS: m/z 187 [MH$^+$]

Step II:

N-{5-chloro-2-[(2S)-oxiran-2-ylmethoxy]phenyl}urea

A solution of N-(5-chloro-2-hydroxyphenyl)urea (0.9 g, 4.9 mmol) and (2S)-oxiran-2-ylmethyl 3-nitrobenzenesulfonate (1.0 g, 3.8 mmol) in dimethylformamide were stirred under nitrogen. Cesium carbonate (1.9 g, 5.7 mmol) was added to the mixture and the reaction was stirred under nitrogen at room temperature over night. The mixture was partitioned between water and dichloromethane, and the organic phase was washed with water. After drying, filtration and evaporation of the solvent 0.48 g, (52%) of subtitle compound was obtained.

APCI-MS: m/z 243 [MH$^+$].

Step III:

N-(5-chloro-2-{[(2S)-3-(5-fluoro-1'H,3H-spiro[1-benzofuran-2,4'-piperidin]-1'-yl)-2-hydroxypropyl]oxy}phenyl)urea N-{5-chloro-2-[(2S)-oxiran-2-ylmethoxy]phenyl}urea (0.48 g, 2.0 mmol) and 5-fluoro-3H-spiro[1-benzofuran-2,4'-piperidine] (0.49 g, 2.0 mmol) were dissolved in 3 mL ethanol. The reaction mixture was stirred at 80° C. over night. Ethanol was removed by evaporation and the mixture was purified by column chromatography (dichloromethane/methanol) and HPLC on C18 (Xterra) to afford 35 mg (39%) of the title compound.

$^1$H-NMR (DMSO-d$_6$, 400 MHz): δ 8.18 (d, J=2.6 Hz, 1H); 7.92 (s, 1H); 7.07-6.97 (m, 2H); 6.91-6.84 (m, 2H); 6.73-6.68 (m, 1H); 6.33 (s, 2H); 4.88 (br.s, 1H); 4.15-3.98 (m, 2H); 3.97-3.85 (m, 1H); 3.00 (s, 2H); 2.76-2.30 (br.m, 6H, partially covered with the signal of solvent); 1.94-1.65 (br.m, 4H). APCI-MS: m/z 450 [MH$^+$]

Example 232

N-(5-chloro-2-{[(2S)-3-(5-chloro-1'H,3H-spiro[1-benzofuran-2,4'-piperidin]-1'-yl)-2-hydroxypropyl]oxy}phenyl)urea The title compound was prepared using 5-chloro-3H-spiro[1-benzofuran-2,4'-piperidine] as described in Example 231.

APCI-MS: m/z 466 [MH$^+$]

Example 233

N-(2-{[(2S)-3-(5-fluoro-1'H,3H-spiro 1-benzofuran-2,4'-piperidin]-1'-yl)-2-hydroxypropyl]oxy}phenyl)urea The title compound was prepared from 2-aminophenol as according to the procedure described in Example 231.

$^1$H-NMR (DMSO-d$_6$, 400 MHz): δ 8.08-8.01 (m, 1H); 7.77 (s, 1H); 7.08-7.03 (m, 1H); 7.00-6.95 (m, 1H); 6.92-6.80 (m, 3H); 6.75-6.69 (m, 1H); 6.16 (s, 2H); 4.90 (br.s, 1H); 4.20-4.00 (br.m, 2H); 3.97-3.86 (m, 1H); 3.02 (s, 2H); 2.86-2.35 (br.m, 6H, partially covered with the signal of solvent); 2.02-1.67 (br.m, 4H). APCI-MS: m/z 416.2 [MH$^+$]

Example 234

N-(2-{[(2S)-2-hydroxy-3-(1'H,3H-spiro[1-benzofuran-2,4'-piperidin]-1'-yl)propyl]oxy}phenyl)urea The title compound was prepared from 2-aminophenol and 3H-spiro[1-benzofuran-2,4'-piperidine] according to the procedure described in Example 231.

$^1$H-NMR (acetone-d$_6$, 400 MHz): δ 8.25-8.21 (m, 1H); 7.81 (br.s, 1H); 7.17-7.13 (m, 1H); 7.10-7.04 (m, 1H); 7.02-6.96 (m, 1H); 6.92-6.84 (m, 2H); 6.81-6.75 (m, 1H); 6.69 (d, J=7.6 Hz, 1H); 5.60 (br.s, 2H); 4.18-4.09 (m, 2H); 4.02-3.94 (m, 1H); 3.01 (s, 2H); 2.82-2.53 (m, 6H, partially covered with the signal of solvent); 1.95-1.77 (m, 4H). APCI-MS: m/z 398 [MH$^+$]

Example 235

N-(4-fluoro-2-{[(2S)-3-(5-fluoro-1'H,3H-spiro[1-benzofuran-2,4'-piperidin]-1'-yl}-2-hydroxypropyl]oxy)phenyl)urea The title compound was prepared from 2-amino-5-fluorophenol and 5-fluoro-3H-spiro[1-benzofuran-2,4'-piperidine] according to the procedure described in Example 231.

$^1$H-NMR (acetone-d$_6$, 400 MHz): δ 8.17 (dd, J=9.0, 6.4 Hz, 1H); 7.75 (br.s, 1H); 6.97-6.92 (m, 1H); 6.87-6.79 (m, 2H); 6.69-6.60 (m, 2H); 5.68 (br.s, 2H); 4.21-4.12 (m, 2H); 4.06-3.97 (m, 1H); 3.04 (s, 2H); 2.81-2.55 (m, 6H, partially covered with the signal of solvent); 1.97-1.79 (m, 4H). APCI-MS: m/z 434.2 [MH$^+$]

Example 236

N-(4-fluoro-2-{[(2S)-2-hydroxy-3-(1'H,3H-spiro[1-benzofuran-2,4'-piperidin]-1'-yl)propyl]oxy}phenyl)urea The title compound was prepared from 2-amino-5-fluorophenol and 3H-spiro[1-benzofuran-2,4'-piperidine] according to the procedure described in Example 231.

$^1$H-NMR (acetone-d$_6$, 400 MHz): δ 8.21-8.15 (m, 1H); 7.71 (br.s, 1H); 7.15 (d, J=7.3 Hz, 1H); 7.07 (t, J=7.7 Hz, 1H); 6.88-6.82 (m, 2H); 6.79 (t, J=7.4 Hz, 1H); 6.69 (d, J=7.9 Hz, 1H); 6.67-6.60 (m, 1H); 5.64 (br.s, 2H); 4.22-4.11 (m, 3H); 4.05-4.00 (m, 1H); 3.02 (s, 2H); 2.90-2.57 (m, 6H, partially covered with the signal of solvent); 1.97-1.79 (m, 4H). APCI-MS: m/z 416.2 [MH$^+$]

THP-1 Chemotaxis Assay

Introduction

The assay measured the chemotactic response elicited by MIP-1α chemokine in the human monocytic cell line THP-1. The compounds of the Examples were evaluated by their ability to depress the chemotactic response to a standard concentration of MIP-1α chemokine.

Methods

Culture of THP-1 Cells

Cells were thawed rapidly at 37° C. from frozen aliquots and resuspended in a 25 cm flask containing 5 ml of RPMI-1640 medium supplemented with Glutamax and 10% heat inactivated fetal calf serum without antibiotics (RPMI+10% HIFCS). At day 3 the medium is discarded and replaced with fresh medium.

THP-1 cells are routinely cultured in RPMI-1640 medium supplemented with 10% heat inactivated fetal calf serum and glutamax but without antibiotics. Optimal growth of the cells requires that they are passaged every 3 days and that the minimum subculture density is 4×10$^5$ cells/ml.

Chemotaxis Assay

Cells were removed from the flask and washed by centrifugation in RPMI+10% HIFCS+glutamax. The cells were then resuspended at $2 \times 10^7$ cells/ml in fresh medium (RPMI+10% HIFCS+glutamax) to which was added calcein-AM (5 µl of stock solution to 1 ml to give a final concentration of $5 \times 10^{-6}$ M). After gentle mixing the cells were incubated at 37° C. in a $CO_2$ incubator for 30 minutes. The cells were then diluted to 50 ml with medium and washed twice by centrifugation at 400×g. Labelled cells were then resuspended at a cell concentration of $1 \times 10^7$ cells/ml and incubated with an equal volume of MIP-1α antagonist ($10^{-10}$ M to $10^{-6}$ M final concentration) for 30 minutes at 37° C. in a humidified $CO_2$ incubator.

Chemotaxis was performed using Neuroprobe 96-well chemotaxis plates employing 8 µm filters (cat no. 101-8). Thirty microlitres of chemoattractant supplemented with various concentrations of antagonists or vehicle were added to the lower wells of the plate in triplicate. The filter was then carefully positioned on top and then 25111 of cells preincubated with the corresponding concentration of antagonist or vehicle were added to the surface of the filter. The plate was then incubated for 2 hours at 37° C. in a humidified $CO_2$ incubator. The cells remaining on the surface were then removed by adsorption and the whole plate was centrifuged at 2000 rpm for 10 minutes. The filter was then removed and the cells that had migrated to the lower wells were quantified by the fluorescence of cell associated calcein-AM. Cell migration was then expressed in fluorescence units after subtraction of the reagent blank and values were standardized to % migration by comparing the fluorescence values with that of a known number of labelled cells. The effect of antagonists was calculated as % inhibition when the number of migrated cells were compared with vehicle.

The invention claimed is:
1. A compound of formula

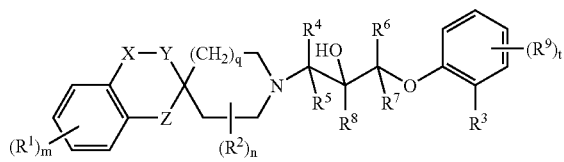

(I)

wherein
m is 0, 1, 2, 3 or 4;
each $R^1$ independently represents halogen, cyano, hydroxyl, $C_1$-$C_6$ alkyl, $C_1$-$C_6$ haloalkyl, $C_1$-$C_6$ alkoxy or sulphonamido;
either X represents a bond, —$CH_2$—, —O— or —C(O)— and Y represents a bond, —$CH_2$—, —O— or —C(O)—, or X and Y together represent a group —CH=C($CH_3$)— or —C($CH_3$)=CH—, and Z represents a bond, —O—, —NH— or —$CH_2$—, provided that only one of X, Y and Z can represent a bond at any one time and provided that X and Y do not both simultaneously represent —O— or —C(O)—;
n is 0, 1 or 2;
each $R^2$ independently represents halogen or $C_1$-$C_6$ alkyl;
q is 0 or 1;
$R^3$ represents —C(O)$NR^{11}R^{12}$ or —$COOR^{12a}$;
$R^4$, $R^5$, $R^6$, $R^7$ and $R^8$ each independently represent a hydrogen atom or a $C_1$-$C_6$ alkyl group;
t is 0, 1 or 2;
each $R^9$ independently represents halogen, cyano, hydroxyl, carboxyl, $C_1$-$C_6$ alkoxy, $C_1$-$C_6$ alikoxycarbonyl, $C_1$-$C_6$ haloalkyl, or $C_1$-$C_6$ alkyl optionally substituted by at least one substituent selected from carboxyl and $C_1$-$C_6$ alkoxycarbonyl;
$R^{11}$ and $R^{12}$ each independently represent (i) a hydrogen atom, (ii) a 3- to 6-membered saturated or unsaturated ring optionally comprising at least one ring heteroatom selected from nitrogen, oxygen and sulphur and optionally further comprising a bridging group, the ring being optionally substituted with at least one substituent selected from halogen, hydroxyl, $C_1$-$C_6$ alkyl, $C_1$-$C_6$ hydroxyalkyl and $C_1$-$C_6$ haloalkyl, (iii) a $C_1$-$C_6$ alkyl group optionally substituted by at least one substituent selected from halogen, amino, hydroxyl, $C_1$-$C_6$ haloalkyl, carboxyl, $C_1$-$C_6$ alkoxy, $C_1$-$C_6$ alkoxycarbonyl, $C_1$-$C_6$ alkylcarbonylamino and a 3- to 6-membered saturated or unsaturated ring optionally comprising at least one ring heteroatom selected from nitrogen, oxygen and sulphur and optionally further comprising a bridging group, the ring being optionally substituted with at least one substituent selected from halogen, hydroxyl, oxo (=O), $C_1$-$C_6$ alkyl, $C_1$-$C_6$ hydroxyalkyl and $C_1$-$C_6$ haloalkyl, or (iv) $C_1$-$C_6$ alkylsulphonyl, or $R^{11}$ and $R^{12}$ together with the nitrogen atom to which they are attached form a 4- to 7-membered saturated heterocyclic ring that optionally further comprises a ring nitrogen, oxygen or sulphur atom and that is optionally fused to a benzene ring to form a 8- to 11-membered ring system, the heterocyclic ring or ring system being optionally substituted with at least one substituent selected from halogen, hydroxyl, amido, $C_1$-$C_6$ alkyl, $C_1$-$C_6$ hydroxyalkyl, $C_1$-$C_6$ alkoxy, $C_1$-$C_6$ alkoxycarbonyl, $C_1$-$C_6$ haloalkyl, $C_1$-$C_6$ alkylamino, di-$C_1$-$C_6$ alkylamino, $C_1$-$C_6$ alkylcarbonyl, $C_1$-$C_6$ alkylcarbonylamino, $C_1$-$C_6$ alkylaminocarbonyl, di-$C_1$-$C_6$ alkylaminocarbonyl, phenyl, halophenyl, phenylcarbonyl, phenylcarbonyloxy and hydroxydiphenylmethyl;
$R^{12a}$ represents a hydrogen atom or a $C_1$-$C_6$ alkyl group;
or a pharmaceutically acceptable salt thereof.

2. A compound according to claim 1, wherein
m is 0, 1, 2, 3 or 4;
each $R^1$ independently represents halogen, cyano, hydroxyl, $C_1$-$C_6$ alkyl, $C_1$-$C_6$ alkoxy or sulphonamido;
either X represents a bond, —$CH_2$—, —O— or —C(O)— and Y represents a bond, —$CH_2$—, —O— or —C(O)—, or X and Y together represent a group —CH=C($CH_3$)— or —C($CH_3$)=CH—, and Z represents a bond, —O—, —NH— or —$CH_2$—, provided that only one of X, Y and Z can represent a bond at any one time and provided that X and Y do not both simultaneously represent —O— or —C(O)—;
n is 0, 1 or 2;
each $R^2$ independently represents halogen or $C_1$-$C_6$ alkyl;
q is 0 or 1;
$R^3$ represents —C(O)$NR^{11}R^{12}$ or —$COOR^{12a}$;
$R^4$, $R^5$, $R^6$, $R^7$ and $R^8$ each independently represent a hydrogen atom or a $C_1$-$C_6$ alkyl group;
t is 0, 1 or 2;
each $R^9$ independently represents halogen, cyano, hydroxyl, $C_1$-$C_6$ alkoxy, $C_1$-$C_6$ haloalkyl, or $C_1$-$C_6$ alkyl optionally substituted by at least one substituent selected from carboxyl and $C_1$-$C_6$ alkoxycarbonyl;
$R^{11}$ and $R^{12}$ each independently represent (i) a hydrogen atom, (ii) a 3- to 6-membered saturated or unsaturated ring optionally comprising at least one ring heteroatom selected from nitrogen, oxygen and sulphur, the ring being optionally substituted with at least one substituent selected from halogen, methyl and trifluoromethyl, or (iii) a $C_1$-$C_6$ alkyl group optionally substituted by at least one substituent selected from halogen, amino, hydroxyl, trifluoromethyl, carboxyl, $C_1$-$C_6$ alkoxycarbonyl and a 3- to 6-membered saturated or unsaturated ring optionally comprising at least one ring heteroatom selected from nitrogen, oxygen and sulphur, the ring being optionally substituted with at least one substituent selected from halogen, methyl and trifluoromethyl, or $R^{11}$ and $R^{12}$ together with the nitrogen atom to which they are attached form a 4- to 7-membered saturated heterocyclic ring optionally further comprising a ring oxygen atom, the heterocyclic ring being optionally substituted with at least one substituent selected from hydroxyl and $C_1$-$C_6$ alkoxy;

$R^{12a}$ represents a hydrogen atom or a $C_1$-$C_6$ alkyl group; or a pharmaceutically acceptable salt thereof.

3. A compound according to claim 1, wherein X and Y have the meanings shown in the following table:

| X | Y |
|---|---|
| bond | O |
| O | bond |
| $CH_2$ | bond |
| bond | $CH_2$ |
| $CH_2$ | O |
| O | $CH_2$ |
| C(O) | O |
| O | C(O) |
| $CH_2$ | $CH_2$ |
| —CH=C($CH_3$)— | |

4. A compound according to claim 1, wherein Z represents a bond, —O— or —$CH_2$—.

5. A compound according to claim 1, wherein represents —C(O)$NR^{11}R^{12}$.

6. A compound according to claim 1, wherein t is 0, 1 or 2.

7. A compound according to claim 1, wherein each $R^9$ independently represents halogen, hydroxyl, carboxyl, $C_1$-$C_4$ alkoxy, $C_1$-$C_4$ alkoxycarbonyl, $C_1$-$C_4$ haloalkyl or $C_1$-$C_4$ alkyl.

8. A compound according to claim 1 selected from:

2-{[(2S)-3-(5-Chloro-1'H,3H-spiro[1-benzofuran-2,4'-piperidin]-1'-yl)-2-hydroxypropyl]oxy}-N-cyclopropyl-benzamide, 2-{[(2S)-3-(5-Chloro-1'H,3H-spiro[1-benzofuran-2,4'-piperidin]-1'-yl)-2-hydroxypropyl]oxy}-N-cyclopropyl-4-fluorobenzamide, 2-{[(2S)-3-(5-Chloro-1'H,3H-spiro[1-benzofuran-2,4'-piperidin]-1'-yl)-2-hydroxypropyl]oxy}-N-cyclopropyl-4-methoxybenzamide, 2-{[(2S)-3-(6-Chloro-1'H,3H-spiro[2-benzofuran-1,4'-piperidin]-1'-yl)-2-hydroxypropyl]oxy}-N-cyclopropyl-4-fluorobenzamide, N-Cyclopropyl-2-{[(2S)-2-hydroxy-3-(1'H,3H-spiro[2-benzofuran-1,4'-piperidin]-1'-yl)propyl]oxy}benzamide, 2-{[(2S)-3-(5-Chloro-1'H,3H-spiro[1-benzofuran-2,4'-piperidin]-1'-yl)-2-hydroxypropyl]oxy}-N-cyclopropyl-4-hydroxybenzamide, 2-{[(2S)-3-(5-Chloro-1'H,3H-spiro[1-benzofuran-2,4'-piperidin]-1'-yl)-2-hydroxy-2-methylpropyl]oxy}-N-cyclopropyl-4-hydroxybenzamide, 2-{[(2S)-3-(5-Chloro-1'H,3H-spiro[1-benzofuran-2,4'-piperidin]-1'-yl)-2-hydroxy-2-methylpropyl]oxy}-4-hydroxy-N-methylbenzamide (trifluoroacetate), 2-{[(2S)-3-(5-Chloro-1'H,3H-spiro[1-benzofuran-2,4'-piperidin]-1'-yl)-2-hydroxy]oxy}-4-hydroxy-N-methylbenzamide, 2-{[(2S)-3-(5-Chloro-1'H,3H-spiro[2-benzofuran-1,4'-piperidin]-1'-yl)-2-hydroxypropyl]oxy}-4-hydroxy-N-methylbenzamide, 2-{[(2S)-3-(5-Chloro-1'H,3H-spiro[1-benzofuran-2,4'-piperidin]-1'-yl)-2-hydroxy-2-methoxypropyl]oxy}-N-cyclopropyl-4-hydroxybenzamide, 2-{[(2S)-3-(5-Chloro-1'H,3H-spiro[1-benzofuran-2,4'-piperidin]-1'-yl)-2-hydroxypropyl]oxy}-4-hydroxy-N-(2-hydroxyethyl)benzamide, N-(2-Aminoethyl)-2-{[(2S)-3-(5-chloro-1'H,3H-spiro[1-benzofuran-2,4'-piperidin]-1'-yl)-2-hydroxypropyl]oxy}-4-hydroxybenzamide, 2-{[(2S)-3-(5-Fluoro-1'H,3H-spiro[1-benzofuran-2,4'-piperidin]-1'-yl)-2-hydroxypropyl]oxy}-4-hydroxy-N-methylbenzamide, 2-{[(2S)-3-(5-Chloro-1'H,3H-spiro[1-benzofuran-2,3'-pyrrolidin]-1'-yl)-2-hydroxypropyl]oxy}-4-hydroxy-N-methylbenzamide, 2-{[(2S)-3-(5-Chloro-1'H,3H-spiro[1-benzofuran-2,4'-piperidin]-1'-yl)-2-hydroxypropyl]oxy}-4-hydroxybenzoic acid (trifluoroacetate), 3(S)-1-(2-{[(2S)-3-(5-Chloro-1'H,3H-spiro[1-benzofuran-2,4'-piperidin]-1'-yl)-2-hydroxypropyl]oxy}-4-hydroxybenzoyl)pyrrolidin-3-ol, 3(R)-1-(2-{[(2S)-3-(5-Chloro-1'H,3H-spiro[1-benzofuran-2,4'-piperidin]-1'-yl)-2-hydroxypropyl]oxy}-4-hydroxybenzoyl)pyrrolidin-3-ol, 3-{[(2S)-3-(5-Chloro-1'H,3H-spiro[1-benzofuran-2,4'-piperidin]-1'-yl)-2-hydroxypropyl]oxy}-4-(morpholin-4-ylcarbonyl)phenol, and pharmaceutically acceptable salts of any one thereof.

9. A compound according to claim 1 selected from:

2-{[(2S)-3-(5-Chloro-1'H,3H-spiro[1-benzofuran-2,4'-piperidin]-1'-yl)-2-hydroxypropyl]oxy}-N-cyclopropyl-benzamide, 2-{[(2S)-3-(5-Chloro-1'H,3H-spiro[1-benzofuran-2,4'-piperidin]-1'-yl)-2-hydroxypropyl]oxy}-N-cyclopropyl-4-fluorobenzamide, 2-{[(2S)-3-(5-Chloro-1'H,3H-spiro[1-benzofuran-2,4'-piperidin]-1'-yl)-2-hydroxypropyl]oxy}-N-cyclopropyl-4-methoxybenzamide, 2-{[(2S)-3-(6-Chloro-1'H,3H-spiro[2-benzofuran-1,4'-piperidin]-1'-yl)-2-hydroxypropyl]oxy}-N-cyclopropyl-4-fluorobenzamide, N-Cyclopropyl-2-{[(2S)-2-hydroxy-3-(1'H,3H-spiro[2-benzofuran-1,4'-piperidin]-1'-yl)propyl]oxy}benzamide, 2-{[(2S)-3-(5-Chloro-1'H,3H-spiro[1-benzofuran-2,4'-piperidin]-1'-yl)-2-hydroxypropyl]oxy}-N-cyclopropyl-4-hydroxybenzamide, 2-{[(2S)-3-(5-Chloro-1'H,3H-spiro[1-benzofuran-2,4'-piperidin]-1'-yl)-2-hydroxy-2-methylpropyl]oxy}-N-cyclopropyl-4-hydroxybenzamide, 2-{[(2S)-3-(5-Chloro-1'H,3H-spiro[1-benzofuran-2,4'-piperidin]-1'-yl)-2-hydroxy-2-methylpropyl]oxy}-4-hydroxy-N-methylbenzamide (trifluoroacetate), 2-{[(2S)-3-(5-Chloro-1'H,3H-spiro[1-benzofuran-2,4'-piperidin]-1'-yl)-2-hydroxy]oxy}-4-hydroxy-N-methylbenzamide, 2-{[(2S)-3-(5-Chloro-1'H,3H-spiro[2-benzofuran-1,4'-piperidin]-1'-yl)-2-hydroxypropyl]oxy}-4-hydroxy-N-methylbenzamide,
2-{[(2S)-3-(5-Chloro-1'H,3H-spiro[2-benzofuran-1,4'-piperidin]-1'-yl)-2-hydroxy-2-methoxypropyl]oxy}-N-cyclopropyl-4-hydroxybenzamide,
2-{[(2S)-3-(5-Chloro-1'H,3H-spiro[1-benzofuran-2,4'-piperidin]-1'-yl)-2-hydroxypropyl]oxy}-4-hydroxy-N-(2-hydroxyethyl)benzamide,
N-(2-Aminoethyl)-2-{[(2S)-3-(5-chloro-1'H,3H-spiro[1-benzofuran-2,4'-piperidin]-1'-yl)-2-hydroxypropyl]oxy}-4-hydroxybenzamide,
2-{[(2S)-3-(5-Chloro-1'H,3H-spiro[1-benzofuran-2,4'-piperidin]-1'-yl)-2-hydroxypropyl]oxy}-4-hydroxy-N-(2-hydroxyethyl)benzamide,
2-{[(2S)-3-(5-Chloro-1'H,3H-spiro[1-benzofuran-2,3'-pyrrolidin]-1'-yl)-2-hydroxypropyl]oxy}-4-hydroxy-N-methylbenzamide,
2-{[(2S)-3-(5-Chloro-1'H,3H-spiro[1-benzofuran-2,4'-piperidin]-1'-yl)-2-hydroxypropyl]oxy}-4-hydroxybenzoic acid (trifluoroacetate),
3(S)-1-(2-{[(2S)-3-(5-Chloro-1'H,3H-spiro[1-benzofuran-2,4'-piperidin]-1'-yl)-2-hydroxypropyl]oxy}-4-hydroxybenzoyl)pyrrolidin-3-ol,
3(R)-1-(2-{[(2S)-3-(5-Chloro-1'H,3H-spiro[1-benzofuran-2,4'-piperidin]-1'-yl)-2-hydroxypropyl]oxy}-4-hydroxybenzoyl)pyrrolidin-3-ol,
3-{[(2S)-3-(5-Chloro-1'H,3H-spiro[1-benzofuran-2,4'-piperidin]-1'-yl)-2-hydroxypropyl]oxy}-4-(morpholin-4-ylcarbonyl)phenol,
2-{[(2S)-3-(5-chloro-1'H-spiro[1,3-benzodioxole-2,4'-piperidin]-1'-yl)-2-hydroxypropyl]oxy}-N-methylbenzamide trifluoro acetate,
2-{[(2S)-3-(6-chloro-3,4-dihydro-1'H-spiro[chromene-2,4'-piperidin]-1'-yl)-2-hydroxypropyl]oxy}-N-methylbenzamide trifluoroacetate,
3-{[(2S)-3-(5-Chloro-1'H,3H-spiro[1-benzofuran-2,4'-piperidin]-1'-yl)-2-hydroxypropyl]oxy}-4-(pyrrolidin-1-ylcarbonyl)phenol,
1-(2-{[(2S)-3-(5-Chloro-1'H,3H-spiro[1-benzofuran-2,4'-piperidin]-1'-yl)-2-hydroxypropyl]oxy}-4-hydroxybenzoyl)piperidin-4-ol,
(3S)-1-(2-{[(2S)-3-(5-Chloro-1'H,3H-spiro[1-benzofuran-2,4'-piperidin]-1'-yl)-2-hydroxypropyl]oxy}benzoyl)pyrrolidin-3-ol,
3-{[(2S)-3-(5-Chloro-1'H,3H-spiro[1-benzofuran-2,4'-piperidin]-1'-yl)-2-hydroxypropyl]oxy}-4-(piperidin-1-ylcarbonyl)phenol,
(3S)-1-(2-{[(2S)-3-(5-Chloro-1'H,3H-spiro[2-benzofuran-1,4'-piperidin]-1'-yl)-2-hydroxypropyl]oxy}-4-hydroxybenzoyl)pyrrolidin-3-ol,
1-(2-{[(2S)-3-(5-Chloro-1'H,3H-spiro[2-benzofuran-1,4'-piperidin]-1'-yl)-2-hydroxypropyl]oxy}-4-hydroxybenzoyl)piperidin-4-ol,
(3S)-1-(2-{[(2S)-3-(5-Chloro-1'H,3H-spiro[1-benzofuran-2,4'-piperidin]-1'-yl)-2-hydroxypropyl]oxy}-4-hydroxybenzoyl)pyrrolidin-3-ylbenzoate,
(3S)-1-(2-{[(2S)-3-(5-Chloro-1'H,3H-spiro[1-benzofuran-2,4'-piperidin]-1'-yl)-2-hydroxypropyl]oxy}-4-fluorobenzoyl)pyrrolidin-3-ol,
(3S)-1-[4-Hydroxy-2-({(2S)-2-hydroxy-3-[5-(trifluoromethyl)-1'H,3H-spiro[1-benzofuran-2,4'-piperidin]-1'-yl]propyl}oxy)benzoyl]pyrrolidin-3-ol,
(3S)-1-(4-Fluoro-2-{[(2S)-2-hydroxy-3-(1'H,3H-spiro[1-benzofuran-2,4'-piperidin]-1'-yl)propyl]oxy}benzoyl)pyrrolidin-3-ol,
4-Fluoro-2-{[(2S)-3-(5-fluoro-1'H,3H-spiro[1-benzofuran-2,4'-piperidin]-1'-yl)-2-hydroxypropyl]oxy}benzoic acid (hydrochloride),
(3S)-1-(4-Fluoro-2-{[(2S)-3-(5-fluoro-1'H,3H-spiro[1-benzofuran-2,4'-piperidin]-1'-yl)-2-hydroxypropyl]oxy}benzoyl)pyrrolidin-3-ol,
N-[(3S)-1-(2-{[(2S)-3-(5-Chloro-1'H,3H-spiro[1-benzofuran-2,4'-piperidin]-1'-yl)-2-hydroxypropyl]oxy}-4-hydroxybenzoyl)pyrrolidin-3-yl]acetamide,
2-{[(2S)-3-(5-Chloro-1'H,3H-spiro[1-benzofuran-2,4'-piperidin]-1'-yl)-2-hydroxypropyl]oxy}-4-methylbenzoic acid hydrochloride,
(3S)-1-(2-{[(2S)-3-(5-Chloro-1'H,3H-spiro[1-benzofuran-2,4'-piperidin]-1'-yl)-2-hydroxypropyl]oxy]}-4-methylbenzoyl)pyrrolidin-3-ol,
2-{[(2S)-3-(5-Fluoro-1'H,3H-spiro[1-benzofuran-2,4'-piperidin]-1'-yl)-2-hydroxypropyl]oxy}-4-methylbenzoic acid hydrochloride,
(2S)-1-(5-Chloro-1'H,3H-spiro[1-benzofuran-2,4'-piperidin]-1'-yl)-3-(2-{[2-(hydroxymethyl)morpholin-4-yl]carbonyl}-5-methylphenoxy)propan-2-ol,
(3S)-1-(2-{[(2S)-3-(5-Fluoro-1'H,3H-spiro[1-benzofuran-2,4'-piperidin]-1'-yl)-2-hydroxypropyl]oxy}-4-methylbenzoyl)pyrrolidin-3-ol,
2-{[(2S)-3-(5-Chloro-1'H,3H-spiro[1-benzofuran-2,4'-piperidin]-1'-yl)-2-hydroxypropyl]oxy}-N-{[(4R)-2,5-dioxoimidazolidin-4-yl]methyl}-4-hydroxybenzamide,
1-(2-{[(2S)-3-(5-Chloro-1'H,3H-spiro[1-benzofuran-2,4'-piperidin]-1'-yl)-2-hydroxypropyl]oxy}-4-hydroxybenzoyl)-3-(trifluoromethyl)pyrrolidin-3-ol,
3-{[(2S)-3-(5-Chloro-1'H,3H-spiro[1-benzofuran-2,4'-piperidin]-1'-yl)-2-hydroxypropyl]oxy}-4-{[3-(trifluoromethyl)pyrrolidin-1-yl]carbonyl}phenol,
N-[2-(Acetylamino)ethyl]-2-{[(2S)-3-(5-chloro-1'H,3H-spiro[1-benzofuran-2,4'-piperidin]-1'-yl)-2-hydroxypropyl]oxy}-4-hydroxybenzamide,
(4S)-2-(2-{[(2S)-3-(5-Chloro-1'H,3H-spiro[1-benzofuran-2,4'-piperidin]-1'-yl)-2-hydroxypropyl]oxy}-4-hydroxybenzoyl)isoxazolidin-4-ol trifluoro acetate,
(4R)-2-(2-{[(2S)-3-(5-Chloro-1'H,3H-spiro[1-benzofuran-2,4'-piperidin]-1'-yl)-2-hydroxypropyl]oxy}-4-hydroxybenzoyl)isoxazolidin-4-ol trifluoroacetate,
(4S)-2-(2-{[(2S)-3-(5-Chloro-1'H,3H-spiro[1-benzofuran-2,4'-piperidin]-1'-yl)-2-hydroxypropyl]oxy}-4-hydroxybenzoyl)-4-methylisoxazolidin-4-ol trifluoroacetate,
(4R)-2-(2-{[(2S)-3-(5-Chloro-1'H,3H-spiro[1-benzofuran-2,4'-piperidin]-1'-yl)-2-hydroxypropyl]oxy}-4-hydroxybenzoyl)-4-methylisoxazolidin-4-ol trifluoroacetate,
2-{[(2S)-3-(5-chloro-1'H,3H-spiro[1-benzofuran-2,4'-piperidin]-1'-yl)-2-hydroxypropyl]oxy}-N-(methylsulfonyl)benzamide trifluoro acetate,
2-{[(2S)-3-(5-chloro-1'H,3H-spiro[1-benzofuran-2,4'-piperidin]-1'-yl)-2-hydroxypropyl]oxy}-N-1H-tetrazol-5-ylbenzamide bis(trifluoroacetate),
3-{[(2S)-3-(5-chloro-1'H,3H-spiro[1-benzofuran-2,4'-piperidin]-1'-yl)-2-hydroxypropyl]oxy}-4-{[(3R)-3-(dimethylamino)pyrrolidin-1-yl]carbonyl}phenol bis(trifluoroacetate),
3-{[(2S)-3-(5-chloro-1'H,3H-spiro[1-benzofuran-2,4'-piperidin]-1'-yl)-2-hydroxypropyl]oxy}-4-{[(3S)-3-(dimethylamino)pyrrolidin-1-yl]carbonyl}phenol bis(trifluoroacetate), (3S)-1-(5-chloro-2-{[(2S)-3-(5-chloro-1'H,3H-spiro[1-benzofuran-2,4'-piperidin]-1'-yl)-2-hydroxypropyl]oxy}-4-hydroxybenzoyl)pyrrolidin-3-ol trifluoro acetate, 3-{[(2S)-3-(5-chloro-1'H,3H-spiro[1-benzofuran-2,4'-piperidin]-1'-yl)-2-hydroxypropyl]oxy}-4-{[(3S)-3-methoxypyrrolidin-1-yl]carbonyl}phenol trifluoroacetate, 3-{[(2S)-3-(5-chloro-1'H,3H-spiro[1-benzofuran-2,4'-piperidin]-1'-yl)-2-hydroxypropyl]oxy}-4-{[(2R)-2-(hydroxymethyl)pyrrolidin-1-yl]carbonyl}phenol trifluoroacetate, 3-{[(2S)-3-(5-chloro-1'H,3H-spiro[1-benzofuran-2,4'-piperidin]-1'-yl)-2-hydroxypropyl]oxy}-4-{[(2S)-2-(hydroxymethyl)pyrrolidin-1-yl]carbonyl}phenol trifluoroacetate, 3-{[(2S)-3-(5-chloro-1'H,3H-spiro[1-benzofuran-2,4'-piperidin]-1'-yl)-2-hydroxypropyl]oxy}-4-{[3-(hydroxymethyl)pyrrolidin-1-yl]carbonyl}phenol trifluoroacetate, 1-(2-{[(2S)-3-(5-chloro-1'H,3H-spiro[1-benzofuran-2,4'-piperidin]-1'-yl)-2-hydroxypropyl]oxy}-4-hydroxybenzoyl)-D-prolinamide trifluoroacetate, (3S)-1-(4-hydroxy-2-{[(2S)-2-hydroxy-3-(1'H,3H-spiro[1-benzofuran-2,4'-piperidin]-1'-yl)propyl]oxy}benzoyl)pyrrolidin-3-ol trifluoroacetate, 2-{[(2S)-3-(5-chloro-1'H,3H-spiro[1-benzofuran-2,4'-piperidin]-1'-yl)-2-hydroxypropyl]oxy}-3-methylbenzoic acid hydrochloride, 2-{[(2S)-3-(5-chloro-1'H,3H-spiro[1-benzofuran-2,4'-piperidin]-1'-yl)-2-hydroxypropyl]oxy}-4-methoxybenzoic acid hydrochloride, (3S)-1-(2-{[(2S)-3-(5-chloro-1'H,3H-spiro[1-benzofuran-2,4'-piperidin]-1'-yl)-2-hydroxypropyl]oxy}-3-methylbenzoyl)pyrrolidin-3-ol trifluoroacetate, (3S)-1-(2-{[(2S)-3-(5-chloro-1'H,3H-spiro[1-benzofuran-2,4'-piperidin]-1'-yl)-2-hydroxypropyl]oxy}-4-methoxybenzoyl)pyrrolidin-3-ol trifluoroacetate, 5-chloro-2-{[(2S)-3-(5-chloro-1'H,3H-spiro[1-benzofuran-2,4'-piperidin]-1'-yl)-2-hydroxypropyl]oxy}benzoic acid hydrochloride, (3S)-1-(5-chloro-2-{[(2S)-3-(5-chloro-1'H,3H-spiro[1-benzofuran-2,4'-piperidin]-1'-yl)-2-hydroxypropyl]oxy}benzoyl)pyrrolidin-3-ol trifluoroacetate, 2-{[(2S)-3-(5-chloro-1'H,3H-spiro[1-benzofuran-2,4'-piperidin]-1'-yl)-2-hydroxypropyl]oxy}-3-fluorobenzoic acid hydrochloride, (3S)-1-(2-{[(2S)-3-(5-chloro-1'H,3H-spiro[1-benzofuran-2,4'-piperidin]-1'-yl)-2-hydroxypropyl]oxy}-3-fluorobenzoyl)pyrrolidin-3-ol trifluoroacetate, 2-{[(2S)-3-(5-chloro-1'H,3H-spiro[1-benzofuran-2,4'-piperidin]-1'-yl)-2-hydroxypropyl]oxy}-4-hydroxy-N-(2-hydroxypropyl)benzamide, 2-{[(2S)-3-(5-chloro-1'H,3H-spiro[1-benzofuran-2,4'-piperidin]-1'-yl)-2-hydroxypropyl]oxy}-4-hydroxy-N-(2-hydroxy-1,1-dimethylethyl)benzamide, 2-{[(2S)-3-(5-chloro-1'H,3H-spiro[1-benzofuran-2,4'-piperidin]-1'-yl)-2-hydroxypropyl]oxy}-N-cyclopentyl-4-hydroxybenzamide, 2-{[(2S)-3-(5-chloro-1'H,3H-spiro[1-benzofuran-2,4'-piperidin]-1'-yl)-2-hydroxypropyl]oxy}-4-hydroxy-N-(2-methoxyethyl)benzamide, 2-{[(2S)-3-(5-chloro-1'H,3H-spiro[1-benzofuran-2,4'-piperidin]-1'-yl)-2-hydroxypropyl]oxy}-4-hydroxy-N-(2-hydroxyphenyl)benzamide, N-(tert-butyl)-2-{[(2S)-3-(5-chloro-1'H,3H-spiro[1-benzofuran-2,4'-piperidin]-1'-yl)-2-hydroxypropyl]oxy}-4-hydroxybenzamide, 2-{[(2S)-3-(5-chloro-1'H,3H-spiro[1-benzofuran-2,4'-piperidin]-1'-yl)-2-hydroxypropyl]oxy}-4-hydroxy-N-(2-hydroxy-1-methylethyl)benzamide, 2-{[(2S)-3-(5-chloro-1'H,3H-spiro[1-benzofuran-2,4'-piperidin]-1'-yl)-2-hydroxypropyl]oxy}-4-hydroxy-N-isobutylbenzamide, 2-{[(2S)-3-(5-chloro-1'H,3H-spiro[1-benzofuran-2,4'-piperidin]-1'-yl)-2-hydroxypropyl]oxy}-4-hydroxy-N-(4-hydroxycyclohexyl)benzaniide, 2-{[(2S)-3-(5-chloro-1'H,3H-spiro[1-benzofuran-2,4'-piperidin]-1'-yl)-2-hydroxypropyl]oxy}-N-(2,3-dihydroxypropyl)-4-hydroxybenzamide, 2-{[(2S)-3-(5-chloro-1'H,3H-spiro[1-benzofaran-2,4'-piperidin]-1'-yl)-2-hydroxypropyl]oxy}-4-hydroxy-N-(2-hydroxyethyl)-N-methylbenzamide, Methyl N-(2-{[(2S)-3-(5-chloro-1'H,3H-spiro[1-benzofuran-2,4'-piperidin]-1'-yl)-2-hydroxypropyl]oxy}-4-hydroxybenzoyl)serinate, 2-{[(2S)-3-(5-chloro-1'H,3H-spiro[1-benzofuran-2,4'-piperidin]-1'-yl)-2-hydroxypropyl]oxy}-N-(1-ethylpropyl)-4-hydroxybenzamide, 2-{[(2S)-3-(5-chloro-1'H,3H-spiro[1-benzofuran-2,4'-piperidin]-1'-yl)-2-hydroxypropyl]oxy}-4-hydroxy-N-(tetrahydrofuran-2-ylmethyl)benzamide, 2-{[(2S)-3-(5-chloro-1'H,3H-spiro[1-benzofuran-2,4'-piperidin]-1'-yl)-2-hydroxypropyl]oxy}-4-hydroxy-N-[1-(hydroxymethyl)-2,2-dimethylpropyl]benzamide, 2-{[(2S)-3-(5-chloro-1'H,3H-spiro[1-benzofuran-2,4'-piperidin]-1'-yl)-2-hydroxypropyl]oxy}-N-{[(1S,2R,3S)-6,6-dimethylbicyclo[3.1.1]hept-2-yl]methyl}-4-hydroxybenzamide, 2-{[(2S)-3-(5-chloro-1'H,3H-spiro[1-benzofuran-2,4'-piperidin]-1'-yl)-2-hydroxypropyl]oxy}-4-hydroxy-N-[1-(hydroxymethyl)-2-methylpropyl]benzamide, 3-{[(2S)-3-(5-chloro-1'H,3H-spiro[1-benzofuran-2,4'-piperidin]-1'-yl)-2-hydroxypropyl]oxy}-4-{[4-(2-hydroxyethyl)piperazin-1-yl]carbonyl}phenol, 3-{[(2S)-3-(5-chloro-1'H,3H-spiro[1-benzofuran-2,4'-piperidin]-1'-yl)-2-hydroxypropyl]oxy}-4-{[3-(hydroxymethyl)piperidin-1-yl]carbonyl}phenol, 2-{[(2S)-3-(5-chloro-1'H,3H-spiro[1-benzofuran-2,4'-piperidin]-1'-yl)-2-hydroxypropyl]oxy}-N-[3-(1,1-dimethylpropyl)-2-hydroxyphenyl]-4-hydroxybenzamide, 2-{[(2S)-3-(5-chloro-1'H,3H-spiro[1-benzofuran-2,4'-piperidin]-1'-yl)-2-hydroxypropyl]oxy}-4-hydroxy-N-[3-(1-hydroxyethyl)phenyl]benzamide, 2-{[(2S)-3-(5-chloro-1'H,3H-spiro[1-benzofuran-2,4'-piperidin]-1'-yl)-2-hydroxypropyl]oxy}-N-(cyclopropylmethyl)-4-hydroxybenzamide, 2-{[(2S)-3-(5-chloro-1'H,3H-spiro[1-benzofuran-2,4'-piperidin]-1'-yl)-2-hydroxypropyl]oxy}-4-hydroxy-N-pyrrolidin-1-ylbenzamide, N-[(1R,4S)-bicyclo[2.2.1]hept-2-yl]-2-{[(2S)-3-(5-chloro-1'H,3H-spiro[1-benzofuran-2,4'-piperidin]-1'-yl)-2-hydroxypropyl]oxy}-4-hydroxybenzamide, 4-(4-chlorophenyl)-1-(2-{[(2S)-3-(5-chloro-1'H,3H-spiro[1-benzofuran-2,4'-piperidin]-1'-yl)-2-hydroxypropyl]oxy}-4-hydroxybenzoyl)piperidin-4-ol, 2-{[(2S)-3-(5-chloro-1'H,3H-spiro[1-benzofuran-2,4'-piperidin]-1'-yl)-2-hydroxypropyl]oxy}-4-hydroxy-N-(2-hydroxy-1-phenylethyl)benzamide, 1-(2-{[(2S)-3-(5-chloro-1'H,3H-spiro[1-benzofuran-2,4'-piperidin]-1'-yl)-2-hydroxypropyl]oxy}-4-hydroxybenzoyl)-4-phenylpiperidin-4-ol, 3-{[(2S)-3-(5-chloro-1'H,3H-spiro[1-benzofuran-2,4'-piperidin]-1'-yl)-2-hydroxypropyl]oxy}-4-(3,4-dihydroisoquinolin-2(1H)-ylcarbonyl)phenol, 3-{[(2S)-3-(5-chloro-1'H,3H-spiro[1-benzofuran-2,4'-piperidin]-1'-yl)-2-hydroxypropyl]oxy}-4-{[2-(hydroxymethyl)piperidin-1-yl]carbonyl}phenol, 1-(2-{[(2S)-3-(5-chloro-1'H,3H-spiro[1-benzofuran-2,4'-piperidin]-1'-yl)-2-hydroxypropyl]oxy}-4-hydroxybenzoyl)-N,N-dimethylprolinamide, Methyl (4R)-1-(2-{[(2S)-3-(5-chloro-1'H,3H-spiro[1-benzofuran-2,4'-piperidin]-1'-yl)-2-hydroxypropyl]oxy}-4-hydroxybenzoyl)-4-hydroxyprolinate, (3R)-1-(2-{[(2S)-3-(5-chloro-1'H,3H-spiro[1-benzofuran-2,4'-piperidin]-1'-yl)-2-hydroxypropyl]oxy}-4-hydroxybenzoyl)piperidin-3-ol, 2-{[(2S)-3-(5-chloro-1'H,3H-spiro[1-benzofuran-2,4'-piperidin]-1'-yl)-2-hydroxypropyl]oxy}-4-hydroxy-N-(2-hydroxycyclohexyl)benzamide, 3-{[(2S)-3-(5-chloro-1'H,3H-spiro[1-benzofuran-2,4'-piperidin]-1'-yl)-2-hydroxypropyl]oxy}-4-[(4-phenylpiperidin-1-yl)carbonyl]phenol, 3-{[(2S)-3-(5-chloro-1'H,3H-spiro[1-benzofuran-2,4'-piperidin]-1'-yl)-2-hydroxypropyl]oxy}-4-(thiomorpholin-4-ylcarbonyl)phenol, 1-(2-{[(2S)-3-(5-chloro-1'H,3H-spiro[1-benzofuran-2,4'-piperidin]-1'-yl)-2-hydroxypropyl]oxy}-4-hydroxybenzoyl)piperidin-3-ol, 2-{[(2S)-3-(5-chloro-1'H,3H-spiro[1-benzofuran-2,4'-piperidin]-1'-yl)-2-hydroxypropyl]oxy}-N-(cyclopropylmethyl)-4-hydroxy-N-propylbenzamide, 2-{[(2S)-3-(5-chloro-1'H,3H-spiro[1-benzofuran-2,4'-piperidin]-1'-yl)-2-hydroxypropyl]oxy}-4-hydroxy-N,N-diisobutylbenzamide, 3-{[(2S)-3-(5-chloro-1'H,3H-spiro[1-benzofuran-2,4'-piperidin]-1'-yl)-2-hydroxypropyl]oxy}-4-(1,3-dihydro-2H-isoindol-2-ylcarbonyl)phenol, N-(2-tert-butoxyethyl)-2-{[(2S)-3-(5-chloro-1'H,3H-spiro[1-benzofuran-2,4'-piperidin]-1'-yl)-2-hydroxypropyl]oxy}-4-hydroxy-N-isobutylbenzamide, 3-{[(2S)-3-(5-chloro-1'H,3H-spiro[1-benzofuran-2,4'-piperidin]-1'-yl)-2-hydroxypropyl]oxy}-4-[(4-fluoropiperidin-1-yl)carbonyl]phenol, 3-{[(2S)-3-(5-chloro-1'H,3H-spiro[1-benzofuran-2,4'-piperidin]-1'-yl)-2-hydroxypropyl]oxy}-4-[(4,4-difluoropiperidin-1-yl)carbonyl]phenol, 2-{[(2S)-3-(5-chloro-1'H,3H-spiro[1-benzofuran-2,4'-piperidin]-1'-yl)-2-hydroxypropyl]oxy}-N-phenylbenzamide, 3-{[(2S)-3-(5-chloro-1'H,3H-spiro[2-benzofuran-1,4'-piperidin]-1'-yl)-2-hydroxypropyl]oxy}-4-({(2R)-2-[hydroxy(diphenyl)methyl]pyrrolidin-1-yl}carbonyl)phenol, 2-{[(2S)-3-(5-chloro-1'H,3H-spiro[2-benzofuran-1,4'-piperidin]-1'-yl)-2-hydroxypropyl]oxy}-4-hydroxy-N-(2-hydroxyethyl)-N-methylbenzamide, 3-{[(2S)-3-(5-chloro-1'H,3H-spiro[2-benzofuran-1,4'-piperidin]-1'-yl)-2-hydroxypropyl]oxy}-4-(pyrrolidin-1-ylcarbonyl)phenol, 3-{[(2S)-3-(5-chloro-1'H,3H-spiro[2-benzofuran-1,4'-piperidin]-1'-yl)-2-hydroxypropyl]oxy}-4-{[4-(2-hydroxyethyl)piperazin-1-yl]carbonyl}phenol, 3-{[(2S)-3-(5-chloro-1'H,3H-spiro[2-benzofuran-1,4'-piperidin]-1'-yl)-2-hydroxypropyl]oxy}-4-{[3-(hydroxymethyl)piperidin-1-yl]carbonyl}phenol, 4-(4-chlorophenyl)-1-(2-{[(2S)-3-(5-chloro-1'H,3H-spiro[2-benzofuran-1,4'-piperidin]-1'-yl)-2-hydroxypropyl]oxy}-4-hydroxybenzoyl)piperidin-4-ol, 3-{[(2S)-3-(5-chloro-1'H,3H-spiro[2-benzofuran-1,4'-piperidin]-1'-yl)-2-hydroxypropyl]oxy}-4-{[4-(hydroxymethyl)piperidin-1-yl]carbonyl}phenol, 1-(2-{[(2S)-3-(5-chloro-1'H,3H-spiro[2-benzofuran-1,4'-piperidin]-1'-yl)-2-hydroxypropyl]oxy}-4-hydroxybenzoyl)-4-phenylpiperidin-4-ol, 3-{[(2S)-3-(5-chloro-1'H,3H-spiro[2-benzofuran-1,4'-piperidin]-1'-yl)-2-hydroxypropyl]oxy}-4-(3,4-dihydroisoquinolin-2(1R)-ylcarbonyl)phenol, 3-{[(2S)-3-(5-chloro-1'H,3H-spiro[2-benzofuran-1,4'-piperidin]-1'-yl)-2-hydroxypropyl]oxy}-4-{[2-(hydroxymethyl)piperidin-1-yl]carbonyl}phenol, 3-{[(2S)-3-(5-chloro-1'H,3H-spiro[2-benzofuran-1,4'-piperidin]-1'-yl)-2hydroxypropyl]oxy}-4-{[3-(dimethylamino)pyrrolidin-1-yl]carbonyl}phenol, 1-(2-{[(2S)-3-(5-chloro-1'H,3H-spiro[2-benzofuran-1,4'-piperidin]-1'-yl)-2-hydroxypropyl]oxy}-4-hydroxybenzoyl)-N,N-dimethylprolinamide, 2-{[(2S)-3-(5-chloro-1'H,3H-spiro[2-benzofuran-1,4'-piperidin]-1'-yl)-2-hydroxypropyl]oxy}-N-cyclohexyl-4-hydroxy-N-(2-hydroxyethyl)benzamide, Methyl (4R)-1-(2-{[(2S)-3-(5-chloro-1'H,3H-spiro[2-benzofuran-1,4'-piperidin]-1'-yl)-2-hydroxypropyl]oxy}-4-hydroxybenzoyl)-4-hydroxyprolinate, (3R)-1-(2-{[(2S)-3-(5-chloro-1'H,3H-spiro[2-benzofuran-1,4'-piperidin]-1'-yl)-2-hydroxypropyl]oxy}-4-hydroxybenzoyl)piperidin-3-ol, 3-{[(2S)-3-(5-chloro-1'H,3H-spiro[2-benzofuran-1,4'-piperidin]-1'-yl)-2-hydroxypropyl]oxy}-4-[(4-phenylpiperidin-1-yl)carbonyl]phenol, 3-{[(2S)-3-(5-chloro-1'H,3H-spiro[2-benzofuran-1,4'-piperidin]-1'-yl)-2-hydroxypropyl]oxy}-4-(thiomorpholin-4-ylcarbonyl)phenol, 1-(2-{[(2S)-3-(5-chloro-1'H,3H-spiro[2-benzofuran-1,4'-piperidin]-1'-yl)-2-hydroxypropyl]oxy}-4-hydroxybenzoyl)piperidin-3-ol, 2-{[(2S)-3-(5-chloro-1'H,3H-spiro[2-benzofuran-1,4'-piperidin]-1'-yl)-2-hydroxypropyl]oxy}-N-(cyclopropylmethyl)-4-hydroxy-N-propylbenzamide, 2-{[(2S)-3-(5-chloro-1'H,3H-spiro[2-benzofuran-1,4'-piperidin]-1'-yl)-2-hydroxypropyl]oxy}-4-hydroxy-N,N-diisobutylbenzamide, 3-{[(2S)-3-(5-chloro-1'H,3H-spiro[2-benzofuran-1,4'-piperidin]-1'-yl)-2-hydroxypropyl]oxy}-4-(1,3-dihydro-2H-isoindol-2-ylcarbonyl)phenol, N-(2-tert-butoxyethyl)-2-{[(2S)-3-(5-chloro-1'H,3H-spiro[2-benzofiiran-1,4'-piperidin]-1'-yl)-2-hydroxypropyl]oxy}-4-hydroxy-N-isobutylbenzamide, 3-{[(2S)-3-(5-chloro-1'H,3H-spiro[2-benzofuran-1,4'-piperidinl-1'-yl)-2-hydroxypropyl]oxy}-4-[(4-fluoropiperidin-1-yl)carbonyl]phenol, 3-{[(2S)-3-(5-chloro-1'H,3H-spiro[2-benzofuran-1,4'-piperidin]-1'-yl)-2-hydroxypropyl]oxy}-4-[(4,4-difluoropiperidin-1-yl)carbonyl]phenol, 2-{[(2S)-3-(5-chloro-1'H,3H-spiro[2-benzofuran-1,4'-piperidin]-1'-yl)-2-hydroxypropyl]oxy}-4-hydroxy-N-(2-hydroxypropyl)benzamide, 2-{[(2S)-3-(5-chloro-1'H,3H-spiro[2-benzofuran-1,4'-piperidin]-1'-yl)-2-hydroxypropyl]oxy}-4-hydroxy-N-(2-hydroxy-1,1-dimethylethyl)benzamide, 2-{[(2S)-3-(5-chloro-1'H,3H-spiro[2-benzofuran-1,4'-piperidin]-1'-yl)-2-hydroxypropyl]oxy}-N-cyclopentyl-4-hydroxybenzamide, 2-{[(2Y)-3-(5-chloro-1'H,3H-spiro[2-benzofuran-1,4'-piperidin]-1'-yl)-2-hydroxypropyl]oxy}-4-hydroxy-N-(2-methoxyethyl)benzamide, 2-{[(2S)-3-(5-chloro-1'H,3H-spiro[2-benzofuran-1,4'-piperidin]-1'-yl)-2-hydroxypropyl]oxy}-4-hydroxy-N-(2-hydroxyphenyl)benzamide,
2-{[(2S)-3-(5-chloro-1'H,3H-spiro[2-benzofuran-1,4'-piperidin]-1'-yl)-2-hydroxypropyl]oxy}-4-hydroxy-N-(2-hydroxy-1-methylethyl)benzamide,
2-{[(2S)-3-(5-chloro-1'H,3H-spiro[2-benzofuran-1,4'-piperidin]-1'-yl)-2-hydroxypropyl]oxy}-4-hydroxy-N-isobutylbenzamide,
2-{[(2S)-3-(5-chloro-1'H,3H-spiro[2-benzofuran-1,4'-piperidin]-1'-yl)-2-hydroxypropyl]oxy}-4-hydroxy-N-(2-hydroxyethyl)benzamide,
2-{[(2S)-3-(5-chloro-1'H,3H-spiro[2-benzofuran-1,4'-piperidin]-1'-yl)-2-hydroxypropyl]oxy}-4-hydroxy-N-(4-hydroxycyclohexyl)benzamide,
2-{[(2S)-3-(5-chloro-1'H,3H-spiro[2-benzofuran-1,4'-piperidin]-1'-yl)-2-hydroxypropyl]oxy}-N-(2,3-dihydroxypropyl)-4-hydroxybenzamide,
Methyl N-(2-{[(2S)-3-(5-chloro-1'H,3H-spiro[2-benzofuran-1,4'-piperidin]-1'-yl)-2-hydroxypropyl]oxy}-4-hydroxybenzoyl)serinate,
2-{[(2S)-3-(5-chloro-1'H,3H-spiro[2-benzofuran-1,4'-piperidin]-1'-yl)-2-hydroxypropyl]oxy}-N-(1-ethylpropyl)-4-hydroxybenzamide,
2-{[(2S)-3-(5-chloro-1'H,3H-spiro[2-benzofuran-1,4'-piperidin]-1'-yl)-2-hydroxypropyl]oxy}-4-hydroxy-N-(tetrahydrofuran-2-ylmethyl)benzamide,
2-{[(2S)-3-(5-chloro-1'H,3H-spiro[2-benzofuran-1,4'-piperidin]-1'-yl)-2-hydroxypropyl]oxy}-4-hydroxy-N-[1-(hydroxymethyl)-2,2-dimethylpropyl]benzamide,
2-{[(2S)-3-(5-chloro-1'H,3H-spiro[2-benzofuran-1,4'-piperidin]-1'-yl)-2-hydroxypropyl]oxy}-4-hydroxy-N-[1-(hydroxymethyl)-2-methylpropyl]benzamide,
2-{[(2S)-3-(5-chloro-1'H,3H-spiro[2-benzofuran-1,4'-piperidin]-1'-yl)-2-hydroxypropyl]oxy}-4-hydroxy-N-[3-(1-hydroxyethyl)phenyl]benzamide,
2-{[(2S)-3-(5-chloro-1'H,3H-spiro[2-benzofuran-1,4'-piperidin]-1'-yl)-2-hydroxypropyl]oxy}-N-(cyclopropylmethyl)-4-hydroxybenzamide,
2-{[(2S)-3-(5-chloro-1'H,3H-spiro[2-benzofUran-1,4'-piperidin]-1'-yl)-2-hydroxypropyl]oxy}-4-hydroxy-N-pyrrolidin-1-ylbenzamide,
N-[(1R,4S)-bicyclo[2.2.1]hept-2-yl]-2-{[(2S)-3-(5-chloro-1'H,3H-spiro[2-benzofuran -1,4'-piperidin]-1'-yl)-2-hydroxypropyl]oxy}-4-hydroxybenzamide,
2-{[(2S)-3-(5-chloro-1'H,3H-spiro[2-benzofuran-1,4'-piperidin]-1'-yl)-2-hydroxypropyl]oxy}-4-hydroxy-N-(2-hydroxy-1-phenylethyl)benzamide,
2-{[(2S)-3-(5-chloro-1'H,3H-spiro[2-benzofuran-1,4'-piperidin]-1'-yl)-2-hydroxypropyl]oxy}-4-hydroxy-N-(2-hydroxycyclohexyl)benzamide,
1-(2-{[(2S)-3-(5-chloro-1'H,3H-spiro[1-benzofuran-2,4'-piperidin]-1'-yl)-2-hydroxypropyl]oxy}-4-hydroxybenzoyl)pyrrolidine-3-carboxamide trifluoroacetate,
1-(2-{[(2S)-3-(5-chloro-1'H,3H-spiro[1-benzofuran-2,4'-piperidin]-1'-yl)-2-hydroxypropyl]oxy}-4-hydroxybenzoyl)-L-prolinamide trifluoroacetate,
2-chloro-5-{[(2S)-3-(5-chloro-1'H,3H-spiro[1-benzofuran-2,4'-piperidin]-1'-yl)-2-hydroxypropyl]oxy}-4-{[(3R)-3-(dimethylamino)pyrrolidin-1-yl]carbonyl}phenol bis(trifluoroacetate),
2-chloro-5-{[(2S)-3-(5-chloro-1'H,3H-spiro[1-benzofuran-2,4'-piperidinl-1'-yl)-2-hydroxypropyl]oxy}-4-{[(3R)-3-(hydroxymethyl)pyrrolidin-1-yl]carbonyl}phenol trifluoroacetate,
2-chloro-5-{[(2S)-3-(5-chloro-1'H,3H-spiro[1-benzofuran-2,4'-piperidin]-1'-yl)-2-hydroxypropyl]oxy}-4-{[(3S)-3-(hydroxymethyl)pyrrolidin-1-yl]carbonyl}phenol trifluoroacetate,
2-chloro-5-{[(2S)-3-(5-fluoro-1'H,3H-spiro[1-benzofuran-2,4'-piperidin]-1'-yl)-2-hydroxypropyl]oxy}-4-(pyrrolidin-1-ylcarbonyl)phenol trifluoroacetate,
Methyl 2-{[(2S)-3-(5-fluoro-1'H,3H-spiro[1-benzofuran-2,4'-piperidin]-1'-yl)-2-hydroxypropyl]oxy}benzoate,
2-{[(2S)-3-(5-Fluoro-1'H,3H-spiro[1-benzofuran-2,4'-piperidin]-1'-yl)-2-hydroxypropyl]oxy}benzoic acid (hydrochloride),
(3S)-1-(2-{[(2S)-3-(5-Fluoro-1'H,3H-spiro[1-benzofuran-2,4'-piperidin]-1'-yl)-2-hydroxypropyl]oxy}benzoyl)pyrrolidin-3-ol,
3-{[(2S)-3-(5-Fluoro-1'H,3H-spiro[1-benzofuran-2,4'-piperidin]-1'-yl)-2-hydroxypropyl]oxy}-4-(pyrrolidin-1-ylcarbonyl)phenol,
and pharmaceutically acceptable salts of any one thereof.

10. A process for the preparation of a compound of formula (I) or a pharmaceutically acceptable salt thereof as defined in claim 1 which comprises, (a) reacting a compound of formula

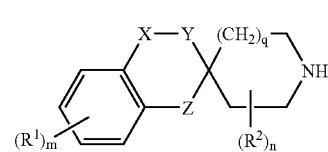

(II)

wherein m, $R^1$, n, $R^2$, q, X, Y and Z are as defined in claim 1, with a compound of formula

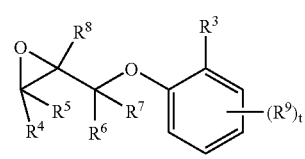

(III)

wherein $R^3$, $R^4$, $R^5$, $R^6$, $R^7$, $R^8$, t and $R^9$ are as defined in claim 1; or (b) reacting a compound of formula

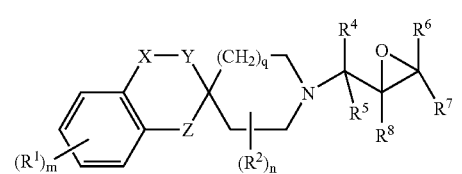

(IV)

wherein m, $R^1$, n, $R^2$, q, X, Y, Z, $R^4$, $R^5$, $R^6$, $R^7$ and $R^8$ are as defined in claim 1, with a compound of formula

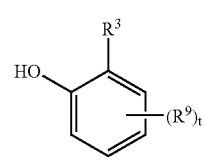

(V)

wherein R³, t and R⁹ are as defined in claim 1, in the presence of a suitable base; or (c) when R³ represents —C(O)NR¹¹R¹², reacting a compound of formula

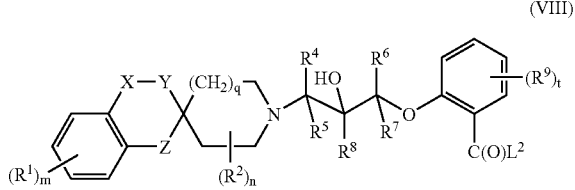

(VIII)

wherein L² represents a leaving group and m, R¹, n, R², q, X, Y, Z, R⁴, R⁵, R⁶, R⁷, R⁸, t and R⁹ are as defined in formula (I), with a compound of formula (IX), NHR¹¹R¹², wherein R¹¹ and R¹² are as defined in formula (I);

and optionally after (a), (b), or (c) forming a pharmaceutically acceptable salt.

11. A pharmaceutical composition comprising a compound of formula (I) or a pharmaceutically acceptable salt thereof as claimed in claim 1 in association with a pharmaceutically acceptable adjuvant, diluent or carrier.

12. A process for the preparation of a pharmaceutical composition comprising a compound of formula (I) or a pharmaceutically acceptable salt thereof in association with a pharmaceutically acceptable adjuvant, diluent or carrier which comprises mixing a compound of formula (I)

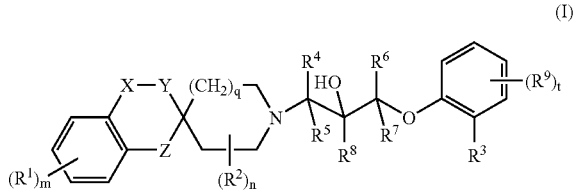

(I)

wherein
m is 0, 1, 2, 3 or 4;
each R¹ independently represents halogen, cyano, hydroxyl, $C_1$-$C_6$ alkyl, $C_1$-$C_6$ haloalkyl, $C_1$-$C_6$ alkoxy or sulphonamido;
either X represents a bond, —CH₂—, —O— or —C(O)— and Y represents a bond, —CH₂—, —O— or —C(O)—, or X and Y together represent a group —CH═C(CH₃)— or —C(CH₃)═CH—, and Z represents a bond, —O—, —NH— or —CH₂—, provided that only one of X, Y and Z can represent a bond at any one time and provided that X and Y do not both simultaneously represent O— or —C(O)—;
n is 0, 1 or 2;
each R² independently represents halogen or $C_1$-$C_6$ alkyl;
q is 0 or 1;
R³ represents —C(O)NR¹¹R¹² or —COOR¹²ᵃ;
R⁴, R⁵, R⁶, R⁷ and R⁸ each independently represent a hydrogen atom or a $C_1$-$C_6$ alkyl group;
t is 0, 1 or 2;
each R⁹ independently represents halogen, cyano, hydroxyl, carboxyl, $C_1$-$C_6$ alkoxy, $C_1$-$C_6$ alkoxycarbonyl, $C_1$-$C_6$ haloalkyl, or $C_1$-$C_6$ alkyl optionally substituted by at least one substituent selected from carboxyl and $C_1$-$C_6$ alkoxycarbonyl;
R¹¹ and R¹² each independently represent (i) a hydrogen atom, (ii) a 3- to 6-membered saturated or unsaturated ring optionally comprising at least one ring heteroatom selected from nitrogen, oxygen and sulphur and optionally further comprising a bridging group, the ring being optionally substituted with at least one substituent selected from halogen, hydroxyl, $C_1$-$C_6$ alkyl, $C_1$-$C_6$ hydroxyalkyl and $C_1$-$C_6$ haloalkyl, (iii) a $C_1$-$C_6$ alkyl group optionally substituted by at least one substituent selected from halogen, amino, hydroxyl, $C_1$-$C_6$ haloalkyl, carboxyl, $C_1$-$C_6$ alkoxy, $C_1$-$C_6$ alkoxycarbonyl, $C_1$-$C_6$ alkylcarbonylamino and a 3- to 6-membered saturated or unsaturated ring optionally comprising at least one ring heteroatom selected from nitrogen, oxygen and sulphur and optionally further comprising a bridging group, the ring being optionally substituted with at least one substituent selected from halogen, hydroxyl, oxo (═O), $C_1$-$C_6$ alkyl, $C_1$-$C_6$ hydroxyalkyl and $C_1$-$C_6$ haloalkyl, or (iv) $C_1$-$C_6$ alkylsulphonyl, or R¹¹ and R¹² together with the nitrogen atom to which they are attached form a 4- to 7-membered saturated heterocyclic ring that optionally further comprises a ring nitrogen, oxygen or sulphur atom and that is optionally fused to a benzene ring to form a 8- to 11-membered ring system, the heterocyclic ring or ring system being optionally substituted with at least one substituent selected from halogen, hydroxyl, amido, $C_1$-$C_6$ alkyl, $C_1$-$C_6$ hydroxyalkyl, $C_1$-$C_6$ alkoxy, $C_1$-$C_6$ alkoxycarbonyl, $C_1$-$C_6$ haloalkyl, $C_1$-$C_6$ alkylamino, di-$C_1$-$C_6$ alkylamino, $C_1$-$C_6$ alkylcarbonyl, $C_1$-$C_6$ alkylcarbonylamino, $C_1$-$C_6$ alkylaminocarbonyl, di-$C_1$-$C_6$ alkylaminocarbonyl, phenyl, halophenyl, phenylcarbonyl, phenylcarbonyloxy and hydroxydiphenylmethyl;

R¹²ᵃ represents a hydrogen atom or a $C_1$-$C_6$ alkyl group;

or a pharmaceutically acceptable salt thereof with a pharmaceutically acceptable adjuvant, diluent or carrier.

* * * * *

UNITED STATES PATENT AND TRADEMARK OFFICE
CERTIFICATE OF CORRECTION

| | | |
|---|---|---|
| PATENT NO. | : 7,449,475 B2 | Page 1 of 1 |
| APPLICATION NO. | : 10/520699 | |
| DATED | : November 11, 2008 | |
| INVENTOR(S) | : Hossain et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 178 days.

Signed and Sealed this

Seventeenth Day of May, 2011

David J. Kappos
*Director of the United States Patent and Trademark Office*